US011638755B2

(12) United States Patent
van Dijk et al.

(10) Patent No.: US 11,638,755 B2
(45) Date of Patent: May 2, 2023

(54) ANTI-CTLA-4 ANTIBODIES AND METHODS OF USE THEREOF

(71) Applicants: Agenus Inc., Lexington, MA (US); Ludwig Institute for Cancer Research Ltd., Zurich (CH); Memorial Sloan Kettering Cancer Center, New York, NY (US)

(72) Inventors: Marc van Dijk, Bosch en Duin (NL); Cornelia Anne Mundt, Lörrach (DE); Gerd Ritter, New York, NY (US); David Schaer, Mamaroneck, NY (US); Jedd David Wolchok, New York, NY (US); Taha Merghoub, Jersey City, NJ (US); Nicholas Stuart Wilson, San Carlos, CA (US); David Adam Savitsky, Boxford, MA (US); Mark Arthur Findeis, Belmont, MA (US); Dennis John Underwood, Boston, MA (US); Jean-Marie Cuillerot, Somerville, MA (US); Igor Proscurshim, Carlisle, MA (US); Olga Shebanova, Somerville, MA (US)

(73) Assignees: Agenus Inc., Lexington, MA (US); Ludwig Institute for Cancer Research Ltd., Zurich (CH); Memorial Sloan-Kettering Cancer Center, New York, NY (US)

( * ) Notice: Subject to any disclaimer, the term of this patent is extended or adjusted under 35 U.S.C. 154(b) by 310 days.

(21) Appl. No.: 17/121,229

(22) Filed: Dec. 14, 2020

(65) Prior Publication Data

US 2021/0205451 A1 Jul. 8, 2021

Related U.S. Application Data

(62) Division of application No. 17/030,650, filed on Sep. 24, 2020, now Pat. No. 10,912,831, which is a division of application No. 15/834,290, filed on Dec. 7, 2017, now Pat. No. 11,013,802.

(60) Provisional application No. 62/431,272, filed on Dec. 7, 2016.

(51) Int. Cl.
*A61K 39/395* (2006.01)
*C07K 16/28* (2006.01)
*A61P 35/04* (2006.01)
*A61P 11/00* (2006.01)
*A61K 39/00* (2006.01)

(52) U.S. Cl.
CPC ........ *A61K 39/39558* (2013.01); *A61P 11/00* (2018.01); *A61P 35/04* (2018.01); *C07K 16/2818* (2013.01); *A61K 2039/505* (2013.01); *A61K 2039/507* (2013.01); *A61K 2039/572* (2013.01); *C07K 2317/21* (2013.01); *C07K 2317/52* (2013.01); *C07K 2317/55* (2013.01); *C07K 2317/732* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| 5,811,097 | A | 9/1998 | Allison et al. |
|---|---|---|---|
| 5,977,318 | A | 11/1999 | Linsley et al. |
| 6,207,156 | B1 | 3/2001 | Kuchroo et al. |
| 6,383,492 | B1 | 5/2002 | Srivastava et al. |
| 6,391,306 | B1 | 5/2002 | Srivastava et al. |
| 6,403,095 | B1 | 6/2002 | Srivastava et al. |
| 6,410,026 | B1 | 6/2002 | Srivastava |
| 6,436,404 | B1 | 8/2002 | Srivastava et al. |
| 6,447,780 | B1 | 9/2002 | Srivastava et al. |
| 6,447,781 | B1 | 9/2002 | Srivastava |
| 6,610,659 | B1 | 8/2003 | Pramod |
| 6,682,736 | B1 | 1/2004 | Hanson et al. |
| 6,719,972 | B1 | 4/2004 | Gribben et al. |
| 6,808,710 | B1 | 10/2004 | Wood et al. |
| 7,034,121 | B2 | 4/2006 | Carreno et al. |
| 7,332,582 | B2 | 2/2008 | Hardy et al. |
| 7,452,535 | B2 | 11/2008 | Davis et al. |
| 7,465,446 | B2 | 12/2008 | Lowy et al. |
| 7,488,802 | B2 | 2/2009 | Collins et al. |
| 7,605,238 | B2 | 10/2009 | Korman et al. |
| 7,943,743 | B2 | 5/2011 | Korman et al. |

(Continued)

FOREIGN PATENT DOCUMENTS

| CN | 101074264 A | 11/2007 |
|---|---|---|
| CN | 102134276 A | 7/2011 |

(Continued)

OTHER PUBLICATIONS (1997a) "Guidance for Industry: S6 Preclinical Safety Evaluation of Biotechnology-Derived Pharmaceuticals", US Food and Drug Administration (FDA), Center for Drug Evaluation and Research (CDER) and Center for Biologies Evaluation and Research (CBER).
(1997b) "Points to Consider in the Manufacture and Testing of Monoclonal Antibody Products for Human Use", US Food and Drug Administration, Center for Biologies Evaluation and Research (CBER).

(Continued)

*Primary Examiner* — Julie Wu
*Assistant Examiner* — Cheom-Gil Cheong
(74) *Attorney, Agent, or Firm* — Dechert LLP; Andrew T Wilkins; Victoria E. Pedanou

(57) ABSTRACT

The instant disclosure provides antibodies that specifically bind to CTLA-4 (e.g., human CTLA-4) and antagonize CTLA-4 function. Also provided are pharmaceutical compositions comprising these antibodies, nucleic acids encoding these antibodies, expression vectors and host cells for making these antibodies, and methods of treating a subject using these antibodies.

20 Claims, 20 Drawing Sheets

Figure 2:
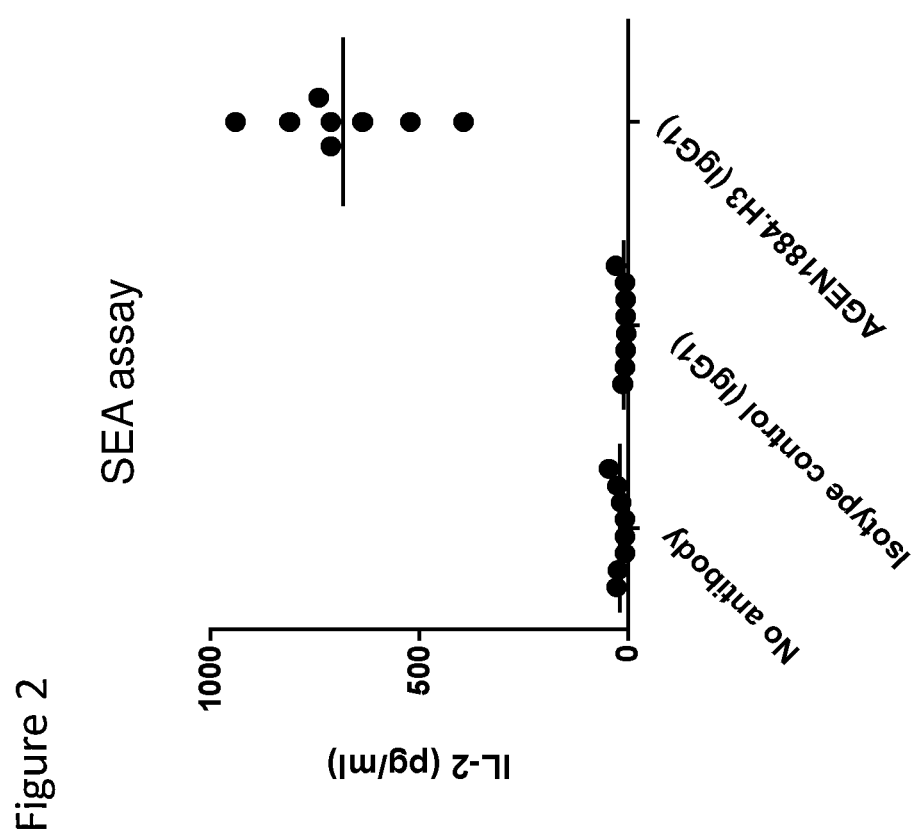

Specification includes a Sequence Listing.

(56) References Cited

U.S. PATENT DOCUMENTS

| | | |
|---|---|---|
| 8,008,449 B2 | 8/2011 | Korman et al. |
| 8,039,592 B2 | 10/2011 | Lazar et al. |
| 8,114,845 B2 | 2/2012 | Langermann et al. |
| 8,119,129 B2 | 2/2012 | Jure-Kunkel et al. |
| 8,168,179 B2 | 5/2012 | Honjo et al. |
| 8,168,757 B2 | 5/2012 | Finnefrock et al. |
| 8,217,149 B2 | 7/2012 | Irving et al. |
| 8,263,073 B2 | 9/2012 | Korman et al. |
| 8,354,509 B2 | 1/2013 | Carven et al. |
| 8,388,955 B2 | 3/2013 | Lazar et al. |
| 8,449,886 B2 | 5/2013 | Jure-Kunkel |
| 8,552,154 B2 | 10/2013 | Freeman et al. |
| 8,686,119 B2 | 4/2014 | Rotem-Yehudar et al. |
| 8,697,845 B2 | 4/2014 | Ward et al. |
| 8,728,474 B2 | 5/2014 | Honjo et al. |
| 8,735,553 B1 | 5/2014 | Li et al. |
| 8,747,847 B2 | 6/2014 | Rotem-Yehudar et al. |
| 8,779,105 B2 | 7/2014 | Korman et al. |
| 8,779,108 B2 | 7/2014 | Queva et al. |
| 8,927,697 B2 | 1/2015 | Davis et al. |
| 8,981,063 B2 | 3/2015 | Chen |
| 8,993,731 B2 | 3/2015 | Tyson |
| 9,102,727 B2 | 8/2015 | Freeman et al. |
| 9,119,839 B2 | 9/2015 | Huang et al. |
| 9,132,281 B2 | 9/2015 | Zeng et al. |
| 9,175,082 B2 | 11/2015 | Zhou et al. |
| 9,205,148 B2 | 12/2015 | Langermann et al. |
| 9,241,992 B2 | 1/2016 | Ponte et al. |
| 9,244,059 B2 | 1/2016 | Triebel et al. |
| 9,273,135 B2 | 3/2016 | Korman et al. |
| 9,358,289 B2 | 6/2016 | Korman et al. |
| 9,457,080 B2 | 10/2016 | Freeman et al. |
| 9,714,290 B2 | 7/2017 | Jones et al. |
| 9,758,583 B2 | 9/2017 | Wang et al. |
| 9,856,320 B2 | 1/2018 | Cogswell et al. |
| 10,144,779 B2 | 12/2018 | van Dijk et al. |
| 10,196,445 B1 | 2/2019 | Engelhardt et al. |
| 10,479,833 B2 | 11/2019 | van Dijk et al. |
| 10,912,831 B1 | 2/2021 | van Dijk et al. |
| 2003/0086930 A1 | 5/2003 | Mueller et al. |
| 2005/0277173 A1 | 12/2005 | Chin et al. |
| 2006/0034844 A1 | 2/2006 | Allison et al. |
| 2006/0093612 A1 | 5/2006 | Srivastava |
| 2006/0240006 A1 | 10/2006 | Chu et al. |
| 2009/0123477 A1 | 5/2009 | Hanke et al. |
| 2009/0214553 A1 | 8/2009 | Chin et al. |
| 2010/0203056 A1 | 8/2010 | Irving et al. |
| 2011/0150892 A1 | 6/2011 | Thudium et al. |
| 2013/0202623 A1 | 8/2013 | Chomont et al. |
| 2013/0291136 A1 | 10/2013 | Freeman et al. |
| 2013/0323249 A1 | 12/2013 | Zhou et al. |
| 2014/0044738 A1 | 2/2014 | Langermann et al. |
| 2014/0093511 A1 | 4/2014 | Lonberg et al. |
| 2014/0220021 A1 | 8/2014 | Shibayama et al. |
| 2014/0286935 A1 | 9/2014 | Hamblin et al. |
| 2014/0341917 A1 | 11/2014 | Nastri et al. |
| 2014/0356363 A1 | 12/2014 | Zhou et al. |
| 2015/0203580 A1 | 7/2015 | Papadopoulos et al. |
| 2015/0225483 A1 | 8/2015 | Lo |
| 2015/0259420 A1 | 9/2015 | Triebel et al. |
| 2015/0273033 A1 | 10/2015 | Bosch et al. |
| 2015/0283237 A1 | 10/2015 | Felder et al. |
| 2015/0346208 A1 | 12/2015 | Couto et al. |
| 2015/0352206 A1 | 12/2015 | Gajewski et al. |
| 2015/0355184 A1 | 12/2015 | Pierce et al. |
| 2016/0060344 A1 | 3/2016 | Narwal et al. |
| 2016/0075753 A1 | 3/2016 | Altman et al. |
| 2016/0075783 A1 | 3/2016 | King et al. |
| 2016/0185870 A1 | 6/2016 | Van Eenennaam et al. |
| 2016/0193239 A1 | 7/2016 | Baylin et al. |
| 2016/0200814 A1 | 7/2016 | Smythe |
| 2016/0222121 A1 | 8/2016 | Johnson et al. |
| 2016/0237154 A1 | 8/2016 | Gray et al. |
| 2016/0243225 A1 | 8/2016 | Ioffe et al. |
| 2016/0272708 A1 | 9/2016 | Chen |
| 2016/0289327 A1 | 10/2016 | Hermans et al. |
| 2016/0347848 A1 | 12/2016 | Hammond et al. |
| 2016/0362492 A1 | 12/2016 | Freeman et al. |
| 2016/0375115 A1 | 12/2016 | Binder et al. |
| 2016/0376367 A1 | 12/2016 | Yuan et al. |
| 2017/0037132 A1 | 2/2017 | Manekas et al. |
| 2017/0088626 A1 | 3/2017 | Jure-Kunkel et al. |
| 2017/0114364 A9 | 4/2017 | Allison et al. |
| 2017/0157188 A1 | 6/2017 | Silvestre et al. |
| 2017/0158776 A1 | 6/2017 | Feltquate et al. |
| 2017/0209574 A1 | 7/2017 | Cao et al. |
| 2017/0210806 A1 | 7/2017 | Liu |
| 2017/0216433 A1 | 8/2017 | Li et al. |
| 2017/0224734 A1 | 8/2017 | Chapman et al. |
| 2017/0233476 A1 | 8/2017 | Zhou et al. |
| 2017/0253655 A1 | 9/2017 | Bakacs et al. |
| 2017/0296659 A1 | 10/2017 | Lebwohl et al. |
| 2017/0340733 A1 | 11/2017 | Cao |
| 2018/0051347 A1 | 2/2018 | Ribas et al. |
| 2018/0118836 A1 | 5/2018 | Bernett et al. |
| 2018/0127501 A1 | 5/2018 | Bernett et al. |
| 2018/0185481 A1 | 7/2018 | van Dijk et al. |
| 2019/0048096 A1 | 2/2019 | Hermann et al. |
| 2019/0216818 A1 | 7/2019 | Woody |
| 2019/0241660 A1 | 8/2019 | Giroir et al. |
| 2019/0292260 A1 | 9/2019 | Tschaika |
| 2019/0315865 A1 | 10/2019 | Tschaika |
| 2019/0382490 A1 | 12/2019 | Loffredo et al. |
| 2020/0048358 A1 | 2/2020 | Ellmark et al. |

FOREIGN PATENT DOCUMENTS

| | | |
|---|---|---|
| EP | 1137436 A1 | 10/2001 |
| EP | 1262193 A1 | 12/2002 |
| EP | 2100615 A1 | 9/2009 |
| EP | 3206711 A1 | 8/2017 |
| EP | 3218 408 A1 | 9/2017 |
| EP | 3218004 A1 | 9/2017 |
| EP | 3233123 A2 | 10/2017 |
| EP | 3240551 A1 | 11/2017 |
| EP | 3625255 A1 | 3/2020 |
| EP | 3626745 A1 | 3/2020 |
| JP | 2006327937 A | 12/2006 |
| WO | WO-1999047558 A2 | 9/1999 |
| WO | WO-2001079300 A1 | 10/2001 |
| WO | WO-2004029069 A2 | 4/2004 |
| WO | WO-2005092380 A2 | 10/2005 |
| WO | WO-2006028999 A2 | 3/2006 |
| WO | WO-2006029219 A2 | 3/2006 |
| WO | WO-2006096491 A2 | 9/2006 |
| WO | WO-2006121168 A1 | 11/2006 |
| WO | WO-2007056539 A2 | 5/2007 |
| WO | WO-2007067959 A2 | 6/2007 |
| WO | WO-2007076354 A2 | 7/2007 |
| WO | WO-2007113648 A2 | 10/2007 |
| WO | WO-2007126805 A2 | 11/2007 |
| WO | WO-2008083174 A2 | 7/2008 |
| WO | WO-2008100562 A2 | 8/2008 |
| WO | WO-2009019312 A2 | 2/2009 |
| WO | WO-2009089260 A2 | 7/2009 |
| WO | WO-2009100140 A1 | 8/2009 |
| WO | WO-2011020024 A2 | 2/2011 |
| WO | WO-2011061487 A1 | 5/2011 |
| WO | WO-2011120135 A1 | 10/2011 |
| WO | WO-2012120125 A1 | 9/2012 |
| WO | WO-2012162277 A1 | 11/2012 |
| WO | WO-2013022091 A1 | 2/2013 |
| WO | WO-2013043569 A1 | 3/2013 |
| WO | WO-2013126809 A1 | 8/2013 |
| WO | WO-2013142796 A2 | 9/2013 |
| WO | WO-2013169388 A1 | 11/2013 |
| WO | WO-2013173223 A1 | 11/2013 |
| WO | WO-2014022758 A1 | 2/2014 |
| WO | WO-2014055897 A2 | 4/2014 |
| WO | WO-2014066532 A1 | 5/2014 |
| WO | WO-2014089113 A1 | 6/2014 |
| WO | WO-2014100079 A1 | 6/2014 |
| WO | WO-2014144960 A2 | 9/2014 |
| WO | WO-2014179664 A2 | 11/2014 |

(56) References Cited

FOREIGN PATENT DOCUMENTS

| | | |
|---|---|---|
| WO | WO-2014206107 A1 | 12/2014 |
| WO | WO-2014209804 A1 | 12/2014 |
| WO | WO-2015009856 A2 | 1/2015 |
| WO | WO-2015036394 A1 | 3/2015 |
| WO | WO-2015042246 A1 | 3/2015 |
| WO | WO-2015058573 A1 | 4/2015 |
| WO | WO-2015061668 A1 | 4/2015 |
| WO | WO-2015085847 A1 | 6/2015 |
| WO | WO-2015109124 A2 | 7/2015 |
| WO | WO-2015116539 A1 | 8/2015 |
| WO | WO-2015176033 A1 | 11/2015 |
| WO | WO-2015195163 A1 | 12/2015 |
| WO | WO-2015200119 A1 | 12/2015 |
| WO | WO-2016000619 A1 | 1/2016 |
| WO | WO-2016015685 A1 | 2/2016 |
| WO | WO-2016020856 A2 | 2/2016 |
| WO | WO-2016028672 A1 | 2/2016 |
| WO | WO-2016030350 A1 | 3/2016 |
| WO | WO-2016149387 A1 | 9/2016 |
| WO | WO-2016168809 A1 | 10/2016 |
| WO | WO-2016179576 A1 | 11/2016 |
| WO | WO-2016183469 A1 | 11/2016 |
| WO | WO-2016196237 A1 | 12/2016 |
| WO | WO-2016196389 A1 | 12/2016 |
| WO | WO-2016197067 A1 | 12/2016 |
| WO | WO-2017021913 A1 | 2/2017 |
| WO | WO-2017025871 A1 | 2/2017 |
| WO | WO-2017040790 A1 | 3/2017 |
| WO | WO-2017062615 A2 | 4/2017 |
| WO | WO-2017079303 A1 | 5/2017 |
| WO | WO-2017106372 A1 | 6/2017 |
| WO | WO-2017120612 A1 | 7/2017 |
| WO | WO-2017129790 A1 | 8/2017 |
| WO | WO-2017149150 A1 | 9/2017 |
| WO | WO-2017156349 A1 | 9/2017 |
| WO | WO-2017160717 A2 | 9/2017 |
| WO | WO-2017198212 A1 | 11/2017 |
| WO | WO-2017201502 A1 | 11/2017 |
| WO | WO-2018035413 A1 | 2/2018 |
| WO | WO-2018071824 A1 | 4/2018 |
| WO | WO-2018102567 A1 | 6/2018 |
| WO | WO-2018106862 A1 | 6/2018 |
| WO | WO-2018106864 A1 | 6/2018 |
| WO | WO-2018156250 A1 | 8/2018 |
| WO | WO-2018160536 A1 | 9/2018 |
| WO | WO-2018165895 A1 | 9/2018 |
| WO | WO-2018178989 A1 | 10/2018 |
| WO | WO-2018183408 A1 | 10/2018 |
| WO | WO-2018202649 A1 | 11/2018 |
| WO | WO-2018204343 A1 | 11/2018 |
| WO | WO-2018237173 A1 | 12/2018 |
| WO | WO-2018237326 A1 | 12/2018 |
| WO | WO-2019042168 A1 | 3/2019 |
| WO | WO-2019056281 A1 | 3/2019 |
| WO | WO-2019070834 A1 | 4/2019 |
| WO | WO-2019094352 A1 | 5/2019 |

OTHER PUBLICATIONS (2012) "Guidance for Industry: S6 Addendum to Preclinical Safety Evaluation of Biotechnology-Derived Pharmaceuticals", US Food and Drug Administration (FDA), Center for Drug Evaluation and Research (CDER) and Center for Biologics Evaluation and Research (CBER).
(2016) "Targeting TNFR Family Members: Therapeutic Opportunities in Immuno-Oncology and Immune-Inflammation", PEGS Boston.
(2017) "Keytruda® (pembrolizumab) Package Insert", Merck Sharp & Dohme USA.
(2018) "Agenus News", vol. 1, Issue 1.
(2018) "Agenus News", vol. 1, Issue 2.
(2018) "Agenus News", vol. 1, Issue 3.
(Apr. 18, 2016) "Agenus Presents Posters on Checkpoint Antibody Product Candidates at the American Association for Cancer Research (AACR) 2016 Annual Meeting".
(Apr. 2016) "Integrated Solutions in Immuno-Oncology".
(Apr. 27, 2016) "Agenus Commences Phase 1 Clinical Trial of its CTLA-4 Checkpoint Antibody to Treat Solid Tumors".
(Aug. 3, 2017) "Q2 2017 Results", Earnings Call Transcript.
(Feb. 28, 2016) "Q4 2015 Results", Earnings Call Transcript.
(Jan. 21, 2016) "Agenus Announces Clearance of Investigational New Drug Applications by the FDA for anti-CTLA-4 and anti-GITR Antibodies", Business Wire.
(Mar. 2016) "A comprehensive immune-oncology Ecosystem", Cowen and Company 36th Annual Health Care Conference.
(Mar. 27, 2014) "Immuno-Oncology", RBS Immunotherapy Conference.
(Mar. 31, 2016) "Integrated Approach to Immuno-Oncology", Integrated Approach to Immuno-Oncology.
(May 15, 2015) "Agenus Investor Relations Deck".
(May 2016) "Integrated Solutions in Immuno-Oncology".
(May 8, 2015) "Agonist Checkpoint Modulators: Challenges and Opportunities", PEGS Boston.
(Nov. 7, 2017) "Q3 2017 Results", Earnings Call Transcript.
(Nov. 19, 2015) "Agenus R&D Day", New York, NY.
(Nov. 2015) "Emerging Leader In Immuno-Oncology", Lexington, MA.
(Sep. 2015) "Rodman & Renshaw Annual Global Investment Conference".
Abdallah et al. (Jun. 2016) "Ipilimumab-Induced Necrotic Myelopathy in a Patient with Metastatic Melanoma: A Case Report and Review of Literature", Journal of Oncology Pharmacy Practice, vol. 22, No. 3, pp. 537-542.
Acuto et al. (Dec. 2003) "CD28-Mediated Co-Stimulation: A Quantitative Support for TCR Signaling", Nature Reviews Immunology, vol. 3, No. 12, pp. 939-951.
Alegre et al., (2001) "T-cell regulation by CD28 and CTLA-4" Nat Rev Immunol 1(3):220-8.
Ampie et al. (Jul. 2015) "Heatshock Protein Vaccines Against Glioblastoma: from Bench to Bedside", Journal of Neuro-Oncology, vol. 123, No. 3, pp. 441-448.
Arnold et al. (Aug. 4, 1997) "Influences of Transporter Associated with Antigen Processing (Tap) on The Repertoire of Peptides Associated with The Endoplasmic Reticulum-Resident Stress Protein gp96", Journal of Experimental Medicine, vol. 186, No. 3, pp. 461-466.
Arnold-Schild et al. (Aug. 1, 2000) "One-Step Single-Chain Fv Recombinant Antibody-based Purification of gp96 for Vaccine Development", Cancer Research, vol. 60, pp. 4175-4178.
Azuma et al. (Nov. 4, 1993) B70 Antigen is a Second Ligand for CTLA-4 and CD28, Nature, vol. 366, No. 6450, pp. 76-79.
Ban-Hoefen et al. (Jul.-Sep. 2016) "Ipilimumab-Induced Neutropenia in Melanoma", Journal of Investigative Medicine High Impact Case Reports, vol. 4, No. 3, pp. 1-5.
Barthelemy et al. (2008) "Comprehensive Analysis of the Factors Contributing to the Stability and Solubility of Autonomous Human VH Domains", J. Biol. Chem., 283(6):3639-3654.
Bartkowiak et al. (Sep. 22, 2015) "Unique Potential of 4-1 BB Agonist Antibody to Promote Durable Regression of HPV+ Tumors When Combined with an E6/E7 Peptide Vaccine", Proceedings of the National Academy of Sciences of the United States of America, vol. 112, No. 38, pp. E5290-E5299.
Beiboer et al. (2000) "Guided Selection of a Pan Carcinoma Specific Antibody Reveals Similar Binding Characteristics yet Structural Divergence Between the Original Murine Antibody and its Human Equivalent", J. Mol. Bio., 296:833-849.
Binder et al. (Dec. 15, 2014) "Functions of Heat Shock Proteins in Pathways of the Innate and Adaptive Immune System", Journal of Immunology, vol. 193, No. 12, pp. 5765-5771.
Binder et al. (Jun. 2005) "Peptides Chaperoned by Heat-Shock Proteins are a Necessary and Sufficient Source of Antigen in the Cross-Priming of CD8+ T cells", Nature Immunology, vol. 6, No. 6, pp. 593-599.

(56) References Cited

OTHER PUBLICATIONS

Blachere et al. (Nov. 1993) "Heat Shock Protein Vaccines Against Cancer", Journal of Immunotherapy with Emphasis on Tumor Immunology, vol. 14, No. 4, pp. 352-356.
Boise et al. (Jul. 1995) "CD28 Costimulation Can Promote T Cell Survival By Enhancing The Expression of Bcl-XL", Immunity, vol. 3, No. 1, pp. 87-98.
Bouchez et al. (Jun. 2012) "Development of a Delayed-Type Hypersensitivity (DTH) Model in the Cynomolgus Monkey", Journal of Toxicologic Pathology, vol. 25, No. 2, pp. 183-188.
Boussiotis et al. (Dec. 4, 2014) "Somatic Mutations and Immunotherapy Outcome with CTLA-4 Blockade in Melanoma", The New England Journal of Medicine, vol. 371, No. 23, pp. 2230-2232.
Boutros et al. (Aug. 2016) "Safety Profiles of Anti-CTLA-4 and Anti-PD-1 Antibodies Alone and in Combination", Nature Reviews Clinical Oncology, vol. 13, No. 8, pp. 473-486.
Bowes et al. (Dec. 2012) "Reducing Safety-Related Drug Attrition: The Use Of In Vitro Pharmacological Profiling", Nature Reviews Drug Discovery, vol. 11, No. 12, pp. 909-922.
Braster et al. (Jan. 1, 2014) "Myeloid Cells as Effector Cells for Monoclonal Antibody Therapy of Cancer", Methods, vol. 65, No. 1, pp. 28-37.
Brem et al. (Apr. 22, 1995) "Placebo-Controlled Trial of Safety and Efficacy of Intraoperative Controlled Delivery by Biodegradable Polymers of Chemotherapy for Recurrent Gliomas", Lancet, vol. 345, No. 8956, pp. 1008-1012.
Brennan et al. (May-Jun. 2010) "Safety and Immunotoxicity Assessment of Immunomodulatory Monoclonal Antibodies", MAbs, vol. 2, No. 3, pp. 233-255.
Breous-Nystrom et al. (Jan. 1, 2014) "Retrocyte Display® Technology: Generation and Screening of a High Diversity Cellular Antibody Library", Methods, vol. 65, No. 1, pp. 57-67.
Bretscher, (1999) "A two-step, two-signal model for the primary activation of precursor helper T cells" Proc. Natl. Acad. Sci. USA 96:185-90.
Brown et al. (May 2014) "Neo-Antigens Predicted By Tumor Genome Meta-Analysis Correlate With Increased Patient Survival", Genome Research, vol. 24, No. 5, pp. 743-750.
Bruhns et al. (Apr. 16, 2009) "Specificity and Affinity of Human Fcgamma Receptors and their Polymorphic Variants for Human IgG Subclasses", Blood, vol. 113, No. 16, pp. 3716-3725.
Brunet et al. (Jul. 16-22, 1987) "A New Member of the Immunoglobulin Superfamily-CTLA-4", Nature, vol. 328, No. 6127, pp. 267-270.
Bryceson et al. (Dec. 2006) "Activation, Coactivation, and Costimulation of Resting Human Natural Killer Cells", Immunological Reviews, vol. 214, pp. 73-91.
Buchbinder et al. (Feb. 2016) "CTLA-4 and PD-1 Pathways: Similarities, Differences, and Implications of Their Inhibition", American Journal of Clinical Oncology, vol. 39, No. 1, pp. 98-106.
Bukau, et al. (Feb. 6, 1998) "The Hsp70 and Hsp60 Chaperone Machines", Cell, vol. 92, No. 3, pp. 351-366.
Bulliard et al. (Aug. 26, 2013) "Activating Fcγ Receptors Contribute to The Antitumor Activities of Immunoregulatory Receptor-Targeting Antibodies", Journal of Experimental Medicine, vol. 210, No. 9, pp. 1685-1693.
Bulliard et al. (Jul. 2014)"0X40 Engagement Depletes Intratumoral Tregs via Activating FcγRs, Leading to Antitumor Efficacy", Immunology and Cell Biology, vol. 92, No. 6, pp. 475-480.
Callahan et al. (Jan. 15, 2015) "CTLA-4 and PD-1 Pathway Blockade: Combinations in the Clinic", Frontiers in Oncology, vol. 4, No. 385, pp. 1-6.
Callahan et al. (Oct. 2010) "Anti-CTLA-4 Antibody Therapy: Immune Monitoring During Clinical Development of a Novel Immunotherapy", Seminars in Oncology, vol. 37, No. 5, pp. 473-484.
Camacho, L. (May 2015) "CTLA-4 Blockade with Ipilimumab: Biology, Safety, Efficacy, and Future Considerations", Cancer Medicine, vol. 4, No. 5, pp. 661-672.
Caravella et al. (2010) "Structure-Guided Design of Antibodies," Current Computer-Aided Drug Design. 6(2):128-138.
Carthon et al. (May 15, 2010) "Preoperative CTLA-4 Blockade: Tolerability and Immune Monitoring in the Setting of a Presurgical Clinical Trial", Clinical Cancer Research, vol. 16, No. 10, pp. 2861-2871.
Cartron et al. (Feb. 1, 2002) "Therapeutic Activity of Humanized Anti-CD20 Monoclonal Antibody and Polymorphism in IgG Fc Receptor FcgammaRIIIa Gene", Blood, vol. 99, No. 3, pp. 754-758.
Castle et al. (2014) "Immunomic, Genomic and Transcriptomic Characterization of CT26 Colorectal Carcinoma", BMC Genomics, vol. 15, No. 190, 11 Pages.
Caudill et al. (2001) "HSPPC-96: a personalized cancer vaccine," Exp. Opin. Biol. Ther. 1(3):539-547.
Ceuppens et al. (Dec. 1, 1988) "Human T cell activation with phytohemagglutinin. The function of IL-6 as an accessory signal", Journal of Immunology, vol. 141, No. 11, pp. 3868-3874.
Chaft, J. (Mar. 30, 2017) "Immunotherapy for Lung Cancer and the Landscape of Combinations", Thoracis Oncology Service Memorial Sloan Kettering Cancer Center.
Chang et al. (May 11, 2013) "Blockade of the negative co-stimulatory molecules PD-1 and CTLA-4 improves survival in primary and secondary fungal sepsis", Critical care, vol. 17, No. 3, pp. R85.
Chapman et al. (Feb. 2007) "Preclinical Safety Testing of Monoclonal Antibodies: The Significance of Species Relevance", Nature Reviews Drug Discovery, vol. 6, No. 2, pp. 120-126.
Chen et al. (Jul. 25, 2013) "Oncology Meets Immunology: The Cancer-Immunity Cycle", Immunity, vol. 39, No. 1, pp. 1-10.
Cheng et al. (Dec. 1, 2014) "Development of a Robust Reporter-Based ADCC Assay with Frozen, Thaw-And-Use Cells to Measure Fc Effector Function of Therapeutic Antibodies", Journal of Immunological Methods, vol. 414, pp. 69-81.
Choe et al. (Oct. 8, 2016) "Autoimmune Meningoencephalitis in a Melanoma Patient Treated with Ipilimumab", Immunotherapy, vol. 8, No. 10, pp. 1163-1167.
Choi et al. (2011) "Predicting antibody complementarity determining region structures without classification.", Molecular Biosystems, 7:3327-3334.
Choueiri et al. (Aug. 2015) "Abstract 1306: Biomarker Results from a Clinical Trial of Nivolumab in Patients (pts) With Metastatic Renal Cell Carcinoma (mRCC) (CA209-009): Gene Expression, Serum Profiling for Immune Markers, and Multiplex Tissue Immunohistochemistry (IHC)", Cancer Research, vol. 75, No. 15.
Chung, C. (Jun. 2008) "Managing Premedications and the Risk for Reactions to Infusional Monoclonal Antibody Therapy", The Oncologist, vol. 13, No. 6, pp. 725-732.
Coiffier, B. (May 2007) "Rituximab Therapy in Malignant Lymphoma", Oncogene, vol. 26, No. 25, pp. 3603-3613.
Collins et al. (Aug. 2002) "The Interaction Properties of Costimulatory Molecules Revisited", Immunity, vol. 17, No. 2, pp. 201-210.
Curran et al. (Mar. 2, 2010) "PD-1 and CTLA-4 Combination Blockade Expands Infiltrating T Cells and Reduces Regulatory T and Myeloid Cells within B16 Melanoma Tumors", Proceedings of the National Academy of Sciences of the United States of America, vol. 107, No. 9, pp. 4725-4780.
Curti et al. (Dec. 15, 2013) "0X40 is a Potent Immune-Stimulating Target in Late-Stage Cancer Patients", Cancer Research, vol. 73, No. 24, pp. 7189-7198.
Dangl et al. (Jul. 1988) "Segmental Flexibility and Complement Fixation of Genetically Engineered Chimeric Human, Rabbit and Mouse Antibodies", The EMBO Journal, vol. 7, No. 7, pp. 1989-1994.
Dariavach et al. (Dec. 1988) "Human Ig Superfamily CTLA-4 Gene: Chromosomal Localization and Identity of Protein Sequence Between Murine and Human CTLA-4 Cytoplasmic Domains", European Journal of Immunology, vol. 18, No. 12, pp. 1901-1905.
Das et al. (Feb. 1, 2015) "Combination Therapy with Anti-Ctla-4 and Anti-Pd-1 Leads to Distinct Immunologic Changes In Vivo", Journal of Immunology, vol. 194, No. 3, pp. 950-959.
Dasanu et al. (Apr. 2017) "Late-Onset Pericardial Tamponade, Bilateral Pleural Effusions and Recurrent Immune Monoarthritis

(56) References Cited

OTHER PUBLICATIONS

Induced By Ipilimumab Use for Metastatic Melanoma", Journal of Oncology Pharmacy Practice, vol. 23, No. 3, pp. 231-234.
Davis et al. (May 18-21, 2002) "MDX-010 (human anti-CTLA4): a phase 1 trial in hormone refractory prostate carcinoma (HRPC)", ASCO 38th Annual Meeting, Orlando FL.
Dick et al. (Aug. 15, 2008) "C-terminal Lysine Variants in Fully Human Monoclonal Antibodies: Investigation of Test Methods and Possible Causes", Biotechnology and Bioengineering, vol. 100, No. 6, pp. 1132-1143.
Drouin et al. (Apr. 16-20, 2016) "AGEN1884 and AGEN2041: Two functionally distinct anti-CTLA-4 antagonist antibodies," Poster No. 5005. Presented at the American Association for Cancer Research Annual Meeting 2016, New Orleans, LA, USA, Apr. 16-20, 2016.
Duraiswamy, et al. (Jun. 15, 2013) "Dual Blockade of PD-1 and CTLA-4 Combined with Tumor Vaccine Effectively Restores T-Cell Rejection Function in Tumors", Cancer Research, vol. 73, No. 12, pp. 3591-3603.
Edwards et al. (Nov. 14, 2003) "The Remarkable Flexibility of the Human Antibody Repertoire; Isolation of Over One Thousand Different Antibodies to a Single Protein, BLyS", Journal of Molecular Biology, vol. 334, No. 1, pp. 103-118.
Ehrenstein et al. (Nov. 2010) "The Importance of Natural IgM: Scavenger, Protector and Regulator", Nature Reviews Immunology, vol. 10, No. 11, pp. 778-786.
Eisenhauer et al. (Jan. 2009) "New Response Evaluation Criteria in Solid Tumours: Revised RECIST Guideline (Version 1.1)", European Journal of Cancer, vol. 45, No. 2, pp. 228-247.
Epstein et al. (Apr. 1971) "The Interaction of Human Macrophages and Lymphocytes in the Phytohemagglutinin-Stimulated Production of Interferon", Journal of Clinical Investigation, vol. 50, No. 4, pp. 744-753.
Finco et al. (Apr. 2014) "Cytokine Release Assays: Current Practices and Future Directions", Cytokine, vol. 66, No. 2, pp. 143-155.
Freedman et al. (Oct. 15, 1991) "Selective Induction of B7/BB-1 on Interferon-Gamma Stimulated Monocytes: A Potential Mechanism for Amplification of T Cell Activation Through the CD28 Pathway", Cellular Immunology, vol. 137, No. 2, pp. 429-437.
Friedman et al. (Aug. 2009) "Bevacizumab Alone and in Combination With Irinotecan in Recurrent Glioblastoma", Journal of Clinical Oncology, vol. 27, No. 28, pp. 4733-4740.
Furness et al. (Jul. 2014) "Impact of Tumour Microenvironment and Fc Receptors on The Activity of Immunomodulatory Antibodies", Trends in Immunology, vol. 35, No. 7, pp. 290-298.
Genst et al. (2005) "Antibody repertoire development in camelids", Developmental and Comparative Immunology, 30:187-198.
Gombos et al. (Apr. 4, 2018) "Toxicological and Pharmacological Assessment of AGEN1884, a Novel Human IgG1 Anti-CTLA-4 Antibody", PLoS One, vol. 13, No. 4, pp. 1-28.
Griffiths et al. (1993) "Human anti-self antibodies with high specificity from phage display libraries", EMBO, 12(2):725-734.
Grosso et al. (Feb. 2013) "CTLA-4 Blockade in Tumor Models: An Overview of Preclinical and Translational Research", Cancer Immunity, vol. 13, No. 1, 14 Pages.
Guilliams et al. (Feb. 2014) "The Function of Fcγ Receptors in Dendritic Cells and Macrophages", Nature Reviews Immunology, vol. 14, No. 2, pp. 94-108.
Hahn et al. (Dec. 2016) "Bilateral Neuroretinitis and Anterior Uveitis Following Ipilimumab Treatment for Metastatic Melanoma", Journal of Ophthalmic Inflammation and Infection, vol. 6, No. 1, 14 Pages.
Hall et al. (2008) "Tissue Cross-Reactivity Studies for Monoclonal Antibodies: Predictive Value and Use for Selection of Relevant Animal Species for Toxicity Testing", edited by J.A.Cavagnaro, John Wiley Sons, Inc., pp. 208-240.
Hanahan et al., (2011) "Hallmarks of cancer: the next generation" Cell 144:646-674.
Hathcock et al. (Nov. 5, 1993) "Identification of an Alternative CTLA-4 Ligand Costimulatory for T Cell Activation", Science, vol. 262, No. 5135, pp. 905-907.
Heemskerk et al. (Jan. 23, 2013) "The Cancer Antigenome", The EMBO Journal, vol. 32, No. 2, pp. 194-203.
Heinzerling et al. (Aug. 16, 2016) "Cardiotoxicity Associated with CTLA4 and PD1 Blocking Immunotherapy", Journal for ImmunoTherapy of Cancer, vol. 4, 50 Pages.
Hellmann et al. (2016) "CheckMate 012: safety and efficacy of first-line nivolumab and ipilimumab in advanced NSCLC", In American Society of Clinical Oncology Annual Meeting, Chicago.
Herrero-Beaumont et al. (Mar.-Apr. 2012) "Abatacept Mechanism of Action: Concordance with its Clinical Profile", Reumatologia Clinica, vol. 8, No. 2, pp. 78-83.
Hodi et al. (Aug. 19, 2010) "Improved Survival with Ipilimumab in Patients with Metastatic Melanoma", The New England Journal of Medicine, vol. 363, No. 8, pp. 711-723.
Hogarth et al. (Mar. 30, 2012) "Fc Receptor-Targeted Therapies for the Treatment of Inflammation, Cancer and Beyond", Nature Reviews Drug Discovery, vol. 11, No. 4, pp. 311-331.
Hurwitz et al. (May 1, 2000) "Combination Immunotherapy of Primary Prostate Cancer in a Transgenic Mouse Model Using CTLA-4 Blockade", Cancer Research, vol. 60, No. 9, pp. 2444-2448.
Hurwitz, (Aug. 18, 1998) "CTLA-4 Blockade Synergizes with Tumor-Derived Granulocyte-Macrophage Colony-Stimulating Factor for Treatment of an Experimental Mammary Carcinoma", Proceedings of the National Academy of Sciences of the United States of America, vol. 95, No. 17, pp. 10067-10071.
Idusogie (Apr. 15, 2000) "Mapping of the C1q Binding Site on Rituxan, a Chimeric Antibody with a Human IgG1 Fc", Journal of Immunology, vol. 168, No. 8, pp. 4178-4184.
Ikemizu et al. (Jan. 2000) "Structure and Dimerization of a Soluble Form of B7-1", Immunity, vol. 12, No. 1, pp. 51-60.
International Search Report and Written Opinion received for PCT Patent Application No. PCT/US2017/065014, dated Feb. 13, 2018, 15 Pages.
International Search Report with Written Opinion corresponding to International Patent Application No. PCT/US2016/034508, dated Aug. 5, 2016.
International Search Report with Written Opinion corresponding to International Patent Application No. PCT/US2017/065011, dated Mar. 13, 2018.
Jacobsen (Jan. 1, 2011) "Molecular and Functional Characterization of Cynomolgus Monkey IgG Subclasses", Journal of Immunology, vol. 186, No. 1, pp. 341-349.
Jiang et al. (May 15, 2015) "Elevated Chronic Inflammatory Factors and Myeloid-Derived Suppressor Cells Indicate Poor Prognosis in Advanced Melanoma Patients", International Journal of Cancer, vol. 136, No. 10, pp. 2352-2360.
Keler (Dec. 2003) "Activity and Safety of CTLA-4 Blockade Combined with Vaccines in Cynomolgus Macaques", Journal of Immunology, vol. 171, No. 11, pp. 6251-6259.
Kesari et al. (2007) "Phase II Study of Metronomic Chemotherapy for Recurrent Malignant Gliomas in Adults", Neuro-Oncology, vol. 9, pp. 354-363.
Kim et al. (Aug. 26, 2013) "Fcγ Receptors Enable Anticancer Action of Proapoptotic and Immune-Modulatory Antibodies", Journal of Experimental Medicine, vol. 210, No. 9, pp. 1647-1651.
Kirchberger et al. (Aug. 6, 2016) "Combined low-dose ipilimumab and pembrolizumab after sequential ipilimumab and pembrolizumab failure in advanced melanoma", European Journal of Cancer, vol. 65, pp. 182-184.
Klimka et al. (2000) "Human anti-CD30 recombinant antibodies by guided phage antibody selection using cell panning", Br. J. Cancer, 83(2):252-260.
Koene et al. (Aug. 1, 1997) "Fc gammaRIIIa-158V/F Polymorphism Influences the Binding of IgG by Natural Killer Cell Fc gammaRIIIa, Independently of the Fc gammaRIIIa-48L/R/H Phenotype", Blood, vol. 90, No. 3, pp. 1109-1114.
Kreisl, et al. (Feb. 10, 2009) "Phase II Trial of Single-Agent Bevacizumab Followed by Bevacizumab Plus Irinotecan at Tumor Progression in Recurrent Glioblastoma", Journal of Clinical Oncology, vol. 27, No. 5, pp. 740-745.
Krummel et al., (1995) "CD28 and CTLA-4 have opposing effects on the response of T cells to stimulation" J. Exp. Med. 182:459-465.

(56) References Cited

OTHER PUBLICATIONS

Kuehn et al. (Sep. 26, 2014) "Immune Dysregulation in Human Subjects with Heterozygous Germline Mutations in CTLA", Science, vol. 345, No. 6204, pp. 1623-1627.
Kuiper (Aug. 15, 1995) "Activated T Cells Can Induce High Levels of CTLA-4 Expression on B Cells", Journal of Immunology, vol. 155, No. 4, pp. 1776-1783.
Kumaraguru et al. (Jan. 2002) "Immunization with Chaperone-Peptide Complex Induces Low-Avidity Cytotoxic T Lymphocytes Providing Transient Protection Against Herpes Simplex Virus Infection", Journal of Virology, vol. 76, No. 1, pp. 136-141.
Lammert et al. (Apr. 1997) "The Endoplasmic Reticulum-Resident Stress Protein gp96 Binds Peptides Translocated by TAP", European Journal of Immunology, vol. 27, No. 4, pp. 923-927.
Langer et al. (Nov. 2016) "Carboplatin and Pemetrexed With or Without Pembrolizumab for Advanced, Non-Squamous Non-Small-Cell Lung Cancer: A Randomised, Phase 2 Cohort of The Open-Label KEYNOTE-021 Study", The Lancet Oncology, vol. 17, No. 11, pp. 1497-1508.
Larkin et al. (Jul. 2, 2015) "Combined Nivolumab and Ipilimumab or Monotherapy in Untreated Melanoma", New England Journal of Medicine, vol. 373, pp. 23-34.
Leach et al. (Dec. 2010) "Use of Tissue Cross-reactivity Studies in the Development of Antibody-based Biopharmaceuticals: History, Experience, Methodology, and Future Directions", Toxicologic Pathology, vol. 38, No. 7, pp. 1138-1166.
Leach et al. (Mar. 22, 1996) "Enhancement of Antitumor Immunity by CTLA-4 Blockade", Science, vol. 271, No. 5256, pp. 1734-1736.
Lee et al. (2019) "Molecular Interactions of Antibody Drugs Targeting PD-1, PD-L1, and CTLA-4 in Immuno-Oncology", Molecules, 24, 1190.
Li et al. (Aug. 1993) "Tumor Rejection Antigen gp96/grp94 is an ATPase: Implications for Protein Folding and Antigen Presentation", The EMBO Journal, vol. 12, No. 8, pp. 3143-3151.
Lindquist et al. (1986) "The Heat-Shock Response", Annual Review of Biochemistry, vol. 55, pp. 1151-1191.
Lindsley (Dec. 1992) "Coexpression and Functional Cooperation of CTLA-4 and CD28 on Activated T Lymphocytes", Journal of Experimental Medicine, vol. 176, No. 6, pp. 1595-1604.
Lindsley et al. (Jun. 1996) "Intracellular Trafficking of CTLA-4 and Focal Localization Towards Sites of TCR Engagement", Immunity, vol. 4, No. 6, pp. 535-543.
Lindsten et al. (Oct. 1, 1993) "Characterization of CTLA-4 Structure and Expression on Human T Cells", Journal of Immunology, vol. 151, No. 7, pp. 3489-3499.
Lloyd et al. (2009) "Protein Engineering, Design & Selection", vol. 22, No. 3, pp. 159-168.
Long et al. (May 20, 2016) "Pembrolizumab (Pembro) Plus Ipilimumab (Ipi) for Advanced Melanoma: Results of the KEYNOTE-029 Expansion Cohort", Journal of Clinical Oncology, vol. 34, No. 15, pp. 9506-9506.
Malia et al. (2016) "Epitope mapping and structure basis for the recognition of phosphorylated tau by the anti-tau antibody ATB", Proteins, 84:427-434.
Mangsbo et al. (Apr. 2010) "Enhanced Tumor Eradication by Combining CTLA-4 or PD-1 Blockade With CpG Therapy", Journal of Immunotherapy, vol. 33, No. 3, pp. 225-235.
Marabelle (Jun. 2013) "Depleting Tumor-Specific Tregs at a Single Site Eradicates Disseminated Tumors", Journal of Clinical Investigation, vol. 123, No. 6, pp. 2447-2463.
Marrack et al. (Feb. 1, 1990) "The Toxicity of Staphylococcal Enterotoxin B in Mice is Mediated by T Cells", Journal of Experimental Medicine, vol. 171, No. 2, pp. 455-464.
McCoy et al. (Feb. 1999) "The Role of CTLA-4 in the Regulation of T Cell Immune Responses", Immunology and Cell Biology, vol. 77, No. 1, pp. 1-10.
Metzler et al. (Aug. 1997) "Solution Structure of Human CTLA-4 and Delineation of a CD80/CD86 Binding Site Conserved in CD28", Nature Structural Biology, vol. 4, No. 7, pp. 527-531.
Moreau et al. (Mar. 1996) "Transient Increase in Symptoms Associated with Cytokine Release in Patients with Multiple Sclerosis", Brain, vol. 119, No. 1, pp. 225-237.
Newton (Nov. 1, 1996) "Mutations in the MHC class II Binding Domains of Staphylococcal Enterotoxin A Differentially Affect T Cell Receptor Vbeta Specificity", The Journal of Immunology, vol. 157, No. 9, pp. 3988-3994.
Nimmerjahn et al. (Apr. 2007) "Antibodies, Fc Receptors and Cancer", Current Opinion in Immunology, vol. 19, No. 2, pp. 239-245.
Nimmerjahn et al. (Jan. 2006) "Fcγ Receptors: Old Friends and New Family Members", Immunity, vol. 24, No. 1, pp. 19-28.
Nimmerjahn et al. (Jan. 2008) "Fcgamma Receptors as Regulators of Immune Responses", Nature Reviews Immunology, vol. 8, No. 1, pp. 34-47.
Nimmerjahn et al. (May 1, 2012) "Translating Basic Mechanisms of IgG Effector Activity into Next Generation Cancer Therapies", Cancer Immunity, vol. 12, No. 13, 7 Pages.
Okada et al. (Nov. 2015) "Immunotherapy Response Assessment in Neuro-Oncology (iRANO): A Report of the RANO Working Group", The Lancet Oncology, vol. 16, No. 15, pp. e534-e542.
Oken et al. (Dec. 1982) "xicity and response criteria of the Eastern Cooperative Oncology Group", American Journal of Clinical Oncology, vol. 5, No. 6, pp. 649-655.
Ostrom et al. (Nov. 2013) "CBTRUS Statistical Report: Primary Brain and Central Nervous System Tumors Diagnosed in the United States in 2006-2010", Neuro-Oncology, vol. 15, No. 2, pp. ii1-ii56.
Ott et al. (Oct. 1, 2013) "CTLA-4 and PD-1/PD-L1 Blockade: New Immunotherapeutic Modalities with Durable Clinical Benefit in Melanoma Patients", Clinical Cancer Research, vol. 19, No. 19, pp. 5300-5309.
Page et al. (Oct. 2013) "Checkpoint Modulation in Melanoma: An Update on Ipilimumab and Future Directions", Current Oncology Reports, vol. 15, No. 5, pp. 500-508.
Parekh et al. (May-Jun. 2012) "Development and Validation of an Antibody-Dependent Cell-Mediated Cytotoxicity-Reporter Gene Assay", MAbs, vol. 4, No. 3, pp. 310-318.
Peggs et al. (Aug. 2008) "Cell Intrinsic Mechanisms of T-Cell Inhibition and Application to Cancer Therapy", Immunological Reviews, vol. 224, pp. 141-165.
Peggs et al. (Jul. 2009) "Cancer Immunotherapy: Co-Stimulatory Agonists and Co-Inhibitory Antagonists", Clinical and Experimental Immunology, vol. 157, No. 1, pp. 9-19.
Peggs, et al. (Apr. 2006) "Principles and Use of Anti-CTLA4 Antibody in Human Cancer Immunotherapy", Current Opinion in Immunology, vol. 18, No. 2, pp. 206-213.
Petersson et al. (Dec. 2002) "Crystal Structure of a SEA Variant in Complex with MHC Class II Reveals the Ability of SEA to Crosslink MHC Molecules", Structure, vol. 10, No. 12, pp. 1619-1626.
Phan et al. (Jul. 8, 2003) "Cancer Regression and Autoimmunity Induced by Cytotoxic T Lymphocyte-Associated Antigen 4 Blockade in Patients with Metastatic Melanoma", Proceedings of the National Academy of Sciences of the United States of America, vol. 100, No. 14, pp. 8372-8377.
Postow et al. (May 21, 2015) "Nivolumab and Ipilimumab versus Ipilimumab in Untreated Melanoma", The New England Journal of Medicine, vol. 372, No. 21, pp. 2006-2017.
Presta (Aug. 2008) "Molecular Engineering and Design of Therapeutic Antibodies", Current Opinion in Immunology, vol. 20, No. 4, pp. 460-470.
Preusser et al. (Sep. 2015) "Prospects of Immune Checkpoint Modulators in the Treatment of Glioblastoma", Nature Reviews Neurology, vol. 11, No. 9, pp. 504-514.
Qureshi et al., (2011) "Trans-endocytosis of CD80 and CD86: a molecular basis for the cell-extrinsic function of CTLA-4" Science 332:600-603.
Regnault et al. (Feb. 2017) "Tumour Lysis Syndrome: An Unexpected Adverse Event Associated with Ipilimumab", Journal of the European Academy of Dermatology and Venereology, vol. 31, No. 2, pp. e73-e74.

(56) References Cited

OTHER PUBLICATIONS

Reuben et al. (Jun. 1, 2006) "Biologic and Immunomodulatory Events after CTLA-4 Blockade with Ticilimumab in Patients with Advanced Malignant Melanoma", Cancer, vol. 106, No. 11, pp. 2437-2444.
Riley et al. (Jan. 1, 2005) "The CD28 Family: A T-Cell Rheostat for Therapeutic Control of T-Cell Activation", Blood, vol. 105, No. 1, pp. 13-21.
Robert et al. (Jun. 2014) "Distinct Immunological Mechanisms of CTLA-4 and PD-1 Blockade Revealed by Analyzing TCR Usage in Blood Lymphocytes", Oncoimmunology, vol. 3, pp. e29244-1-e29244-2.
Robert et al. (Jun. 25, 2015) "Pembrolizumab versus Ipilimumab in Advanced Melanoma", The New England Journal of Medicine, vol. 327, No. 26, pp. 2521-2532.
Robert et al. (Jun. 30, 2011) "Ipilimumab plus Dacarbazine for Previously Untreated Metastatic Melanoma", New England Journal of Medicine, vol. 264, No. 26, pp. 2517-2526.
Rogers (Aug. 2014) "Complement in Monoclonal Antibody Therapy of Cancer", Immunologic Research, vol. 59, No. 1-3, pp. 203-210.
Romano et al. (May 12, 2015) "Ipilimumab-Dependent Cell-Mediated Cytotoxicity of Regulatory T Cells Ex Vivo by Nonclassical Monocytes in Melanoma Patients", Proceedings of the National Academy of Sciences of the United States of America, vol. 112, No. 19, pp. 6140-6145.
Roth et al. (Nov./Dec. 2016) "Left Ventricular Dysfunction After Treatment With Ipilimumab for Metastatic Melanoma", American Journal of Therapeutics, vol. 23, No. 6, pp. e1925-1928.
Rothstein et al. (Dec. 2003) "T-Cell Costimulatory Pathways in Allograft Rejection and Tolerance", Immunological Reviews, vol. 196, pp. 85-108.
Sampson et al. (Nov. 1, 2010) "Immunologic Escape After Prolonged Progression-Free Survival with Epidermal Growth Factor Receptor Variant III Peptide Vaccination in Patients With Newly Diagnosed Glioblastoma", Journal of Clinical Oncology, vol. 28, No. 1, pp. 4722-4729.
Sarma et al. (Jan. 2011) "The Complement System", Cell and Tissue Research, vol. 343, No. 1, pp. 227-235.
Sathornsumetee et al. (Dec. 2010) "Phase II Trial of Bevacizumab and Erlotinib in Patients with Recurrent Malignant Glioma", Neuro-Oncology, vol. 12, No. 12, pp. 1300-1310.
Schandendorf et al. (Jun. 10, 2015) "Pooled Analysis of Long-Term Survival Data From Phase II and Phase III Trials of Ipilimumab in Unresectable or Metastatic Melanoma", Journal of Clinical Oncology, vol. 33, No. 17, pp. 1889-1894.
Seeking Alpha (Oct.-Nov. 2017) "Agenus1 (AGEN) CEO Garo Armen on Q3 2017 Results-Earnings Call Transcript," Quarters Earnings Summary and Earning Conference Call for Agenus, 3 pgs.
Selby et al. (Jul. 2013) "Anti-CTLA-4 Antibodies of IgG2a Isotype Enhance Antitumor Activity Through Reduction of Intratumoral Regulatory T Cells", Cancer Immunology Research, vol. 1, No. 1, pp. 32-42.
Selby et al. (Sep. 9, 2016) "Preclinical Development of Ipilimumab and Nivolumab Combination Immunotherapy: Mouse Tumor Models, In Vitro Functional Studies, and Cynomolgus Macaque Toxicology", PLoS One, vol. 11, No. 9, p. e0161779.
Sharma et al. (Apr. 3, 2015) "The Future of Immune Checkpoint Therapy", Science, vol. 348, No. 6230, pp. 56-61.
Sharpe et al. (Feb. 2002) "The B7-CD28 Superfamily", Nature Reviews Immunology, pp. 116-126.
Sheridan (Apr. 7, 2015): "IDO inhibitors move center stage in immuno-oncology," Nat. Biotechnol. 33(4):321-322.
Shields et al., (2002) "High resolution mapping of the binding site on human IgG1 for Fcgamma RI, Fc gamma RII, Fcgamma RIII, and FcRn and design of IgG1 variants with improved binding to the Fc gamma R." The Journal of Biological Chemistry 276:6591-6604.
Sica et al. (Jun. 2003) "B7-H4, a Molecule of the B7 Family, Negatively Regulates T Cell Immunity", Immunity, vol. 18, No. 6, pp. 849-861.

Simpson et al. (Aug. 26, 2013) "Fc-Dependent Depletion of Tumor-Infiltrating Regulatory T Cells Co-Defines the Efficacy of Anti-Ctla-4 Therapy Against Melanoma", Journal of Experimental Medicine, vol. 210, No. 9, pp. 1695-1710.
Snyder et al. (Dec. 4, 2014) "Genetic Basis for Clinical Response to CTLA-4 Blockade in Melanoma", The New England Journal of Medicine, vol. 371, No. 23, pp. 2189-2199.
Srivastava (Feb. 2009) "Treating Human Cancers with Heat Shock Protein-Peptide Complexes: The Road Ahead", Expert Opinion on Biological Therapy, vol. 9, No. 2, pp. 179-186.
Stamper et al. (Mar. 29, 2001) "Crystal Structure of The B7-1/CTLA-4 Complex That Inhibits Human Immune Responses", Nature, vol. 410, No. 68, pp. 608-611.
Stebbings et al. (Sep. 1, 2007) "Cytokine storm" in the phase I trial of monoclonal antibody TGN1412: better understanding the causes to improve preclinical testing of immunotherapeutics, Journal of Immunology, vol. 179, No. 5, pp. 3325-3331.
Stupp et al. (Mar. 10, 2005) "Radiotherapy plus Concomitant and Adjuvant Temozolomide for Glioblastoma", The New England Journal of Medicine, vol. 352, No. 10, pp. 987-996.
Tai et al. (May 31, 2012) "Basis of CTLA-4 Function in Regulatory and Conventional CD4+ T Cells", Blood, vol. 119, No. 22, pp. 5155-5163.
Tamura et al. (Oct. 3, 1997) "Immunotherapy of Tumors with Autologous Tumor-Derived Heat Shock Protein Preparations", Science, vol. 278, No. 5335, pp. 117-120.
Tivol et al. (Nov. 1995) "Loss of CTLA-4 Leads to Massive Lymphoproliferation and Fatal Multiorgan Tissue Destruction, Revealing A Critical Negative Regulatory Role of CTLA-4", Immunity, vol. 3, No. 5, pp. 541-547.
Topalian et al. (Apr. 13, 2015) "Immune Checkpoint Blockade: A Common Denominator Approach to Cancer Therapy", Cancer Cell, vol. 27, No. 4, pp. 450-461.
Udono et al. (Apr. 12, 1994) "Cellular Requirements for Tumor-Specific Immunity Elicited by Heat Shock Proteins: Tumor Rejection Antigen gp96 Primes CD8+ T Cells In Vivo", Proceedings of the National Academy of Sciences of the United States of America, vol. 91, No. 8, pp. 3077-3081.
Udono et al. (Oct. 1, 1993) "Heat Shock Protein 70-Associated Peptides Elicit Specific Cancer Immunity", Journal of Experimental Medicine, vol. 178, No. 4, pp. 1391-1396.
Van Den Bent (Mar. 10, 2009) "Randomized Phase II Trial of Erlotinib Versus Temozolomide or Carmustine in Recurrent Glioblastoma: EORTC Brain Tumor Group Study 26034", Journal of Clinical Oncology, vol. 27, Nos. pp. 1268-1274.
Van Der Merwe et al. (Feb. 3, 1997) "CD80 (B7-1) Binds Both CD28 and CTLA-4 with a Low Affinity and Very Fast Kinetics", Journal of Experimental Medicine, vol. 185, No. 3, pp. 393-403.
Van Elsas et al. (Aug. 2, 1999) "Combination Immunotherapy of B16 Melanoma Using Anti Cytotoxic T Lymphocyte Associated Antigen 4 (CTLA4) and Granulocyte/Macrophage Colony Stimulating Factor (Gm Csf) Producing Vaccines Induces Rejection of Subcutaneous and Metastatic Tumors Accompanied by", Journal of Experimental Medicine, vol. 190, No. 3, pp. 355-366.
Vessillier (Sep. 2015) "Cytokine Release Assays for the Prediction of Therapeutic mAb Safety in First-In Man Trials — Whole Blood Cytokine Release Assays Are Poorly Predictive for TGN1412 Cytokine Storm", Journal of Immunological Methods, vol. 424, pp. 43-52.
Victor (Apr. 16, 2015) "Radiation and Dual Checkpoint Blockade Activate Non-Redundant Immune Mechanisms in Cancer", Nature, vol. 520, No. 7547, pp. 373-377.
Vidal et al. (Aug. 2010) "In Vitro Cytokine Release Assays for Predicting Cytokine Release Syndrome: The Current State-of-the-Science", Report of a European Medicines Agency Workshop, Cytokine, vol. 51, No. 2, pp. 213-215.
Vidarsson et al. (Oct. 20, 2014) "IgG Subclasses and Allotypes: From Structure to Effector Functions", Frontiers in Immunology, vol. 5, No. 520, pp. 1-17.
Vredenburgh et al. (Oct. 20, 2007) "Bevacizumab plus Irinotecan in Recurrent Glioblastoma Multiforme", Journal of Clinical Oncology, vol. 25, No. 30, pp. 4722-4729.

(56) References Cited

OTHER PUBLICATIONS

Waight (Jun. 11, 2018) "Selective FcyR Co-engagement on APCs Modulates the Activity of Therapeutic Antibodies Targeting T Cell Antigens", Cancer Cell, vol. 33, No. 6, pp. 1033-1047.
Waight et al. (Feb. 1, 2015) "Cutting Edge: Epigenetic Regulation of Foxp3 Defines a Stable Population of CD4+ Regulatory T cells in Tumors from Mice and Humans", Journal of Immunology, vol. 194, No. 3, pp. 878-882.
Waldhauer et al. (Oct. 6, 2008) "NK Cells and Cancer Immunosurveillance", Oncogene, vol. 27, No. 45, pp. 5932-5943.
Walker (Feb. 2015) "Confusing Signals: Recent Progress in CTLA-4 Biology", Trends in Immunology, vol. 36, No. 2, pp. 63-70.
Wang et al. (Jul. 12, 2012) "Biomarkers on Melanoma Patient T Cells Associated with Ipilimumab Treatment", Journal of Translational Medicine, vol. 10, No. 146, pp. 1-12.
Wang et al. (Sep. 2014) "In Vitro Characterization of the Anti-PD-1 Antibody Nivolumab, BMS-936558, and In Vivo Toxicology in Non-Human Primates", Cancer Immunology Research, vol. 2, No. 9, pp. 846-856.
Ward et al. (1989) "Binding activities of a repertoire of single immunoglobulin variable domains secreted from *Escherichia coli*", Nature, 341:544-546.
Warncke et al. (May 1, 2012) "Different Adaptations of IgG Effector Function in Human and Nonhuman Primates and Implications for Therapeutic Antibody Treatment", Journal of Immunology, vol. 188, No. 9, pp. 4405-4411.
Waterhouse et al. (Nov. 10, 1995) "Lymphoproliferative Disorders with Early Lethality in Mice Deficient in Ctla-4", Science, vol. 270, No. 5238, pp. 985-988.
Weber et al. (Jul. 20, 2012) "Management of Immune-Related Adverse Events and Kinetics of Response With Ipilimumab", Journal of Clinical Oncology, vol. 30, No. 21, pp. 2691-2697.
Weng et al. (Dec. 1, 2004) "Clinical Outcome of Lymphoma Patients After Idiotype Vaccination Is Correlated With Humoral Immune Response and Immunoglobulin G Fc Receptor Genotype", Journal of Clinical Oncology, vol. 22, No. 23, pp. 4717-4724.
Weng et al. (Nov. 1, 2003) "Two Immunoglobulin G Fragment C Receptor Polymorphisms Independently Predict Response to Rituximab in Patients With Follicular Lymphoma", Journal of Clinical Oncology, vol. 21, No. 21, pp. 3940-3947.
Willman et al. (May 2001) "Multiplex Analysis of Heterophil Antibodies in Patients With Indeterminate HIV Immunoassay Results", American Journal of Clinical Pathology, vol. 115, No. 5, pp. 764-769.
Wilson et al. (2005) "Regulation of Antigen Presentation and Cross-Presentation in the Dendritic Cell Network: Facts, Hypothesis, and Immunological Implications", Advances in Immunology, vol. 86, 2005, pp. 241-305.
Wilson et al. (Jan. 18, 2011) "An Fcy Receptor-Dependent Mechanism Drives Antibody-Mediated Target-Receptor Signaling in Cancer Cells", Cancer Cell, vol. 19, No. 1, pp. 101-113.
Wing et al. (Oct. 10, 2008) "CTLA-4 Control over Foxp3+ Regulatory T Cell Function", Science, vol. 322, No. 5899, pp. 271-275.
Wolchok (2016) "Updated Results from a Phase III Trial of Nivolumab (NIVO) Combined with Ipilimumab (IPI) in Treatment-Naive Patients (pts) with Advanced Melanoma (MEL) (CheckMate 067)", Journal of Clinical Oncology, vol. 34, No. 15, p. 9505.
Wolchok et al. (Dec. 2009) "Guidelines for the Evaluation of Immune Therapy Activity in Solid Tumors: Immune-Related Response Criteria", Clinical Cancer Research, vol. 15, No. 23, pp. 7412-7420.
Wolchok et al. (Feb. 2010) "Ipilimumab Monotherapy in Patients with Pretreated Advanced Melanoma: A Randomised, Double-Blind, Multicentre, Phase 2, Dose-Ranging Study", The Lancet Oncology, vol. 11, No. 2, pp. 155-164.
Wolchok et al. (Jul. 11, 2013) "Nivolumab plus Ipilimumab in Advanced Melanoma", New England Journal of Medicine, vol. 369, No. 2, pp. 122-133.
Wong (Aug. 1999) "Outcomes and Prognostic Factors in Recurrent Glioma Patients Enrolled Onto Phase II Clinical Trials", Journal of Clinical Oncology, vol. 17, No. 8, pp. 2572-2578.
Wu et al. (2013) "Eradication of melanoma by intratumoral injection of attenuated vaccinia virus requires CDR+ T cells and combination of anti-CTIA-4 blockade and virotherapy enhances therapeutic efficacy in advanced melanoma", Pigmentation & Melanoma Abstracts, 1415.
Wu et al. (Jan. 1, 2005) "CD28 Regulates the Translation of Bcl-xL via the Phosphatidylinositol 3-Kinase/Mammalian Target of Rapamycin Pathway", The Journal of Immunology, vol. 174, No. 1, pp. 180-194.
Wu et al. (May 1, 2013) "Eradication of melanoma by intratumoral injection of attenuated vaccinia virus requires CD8+ T cells and combination of anti-CTLA-4 blockade and virotherapy enhances therapeutic efficacy in advanced melanoma," J. Invest. Dermatol. 133(Suppl 1):S241. Abstract No. 1415.
Wu et al. (Sep. 1, 1997) "A Novel Polymorphism of FcgammaRIIIa (CD16) Alters Receptor Function and Predisposes to Autoimmune Disease", Journal of Clinical Investigation, vol. 100, No. 5, pp. 1059-1070.
Xu et al. (2012) "Affinity and cross-reactivity engineering of CTLA4-Ig to modulate T cell costimulation," J. Immunol. 189(9):4470-7.
Yamaguchi (Jun. 4, 2013) "Construction of Self-Recognizing Regulatory T cells from Conventional T cells by Controlling CTLA-4 and IL-2 Expression", Proceedings of the National Academy of Sciences of the United States of America, vol. 110, No. 23, pp. E2116-E2125.
Yang et al. (Nov.-Dec. 2007) "Ipilimumab (Anti-CTLA4 Antibody) Causes Regression of Metastatic Renal Cell Cancer Associated With Enteritis and Hypophysitis", Journal of Immunotherapy, vol. 30, No. 8, pp. 825-830.
Yao et al. (Feb. 2013) "Advances in Targeting Cell Surface Signalling Molecules for Immune Modulation", Nature Reviews Drug Discovery, vol. 12, No. 2, pp. 130-146.
Zhang et al. (Mar. 4, 2003) "Crystal Structure of the Receptor-Binding Domain of Human B7-2: Insights Into Organization and Signaling", Proceedings of the National Academy of Sciences of the United States of America, vol. 100, No. 5, pp. 2586-2591.
Zipfel (Oct. 2009) "Complement Regulators and Inhibitory Proteins", Nature Reviews Immunology, vol. 9, No. 10, pp. 729-740.
Zitvogel et al. (Oct. 2006) "Cancer Despite Immunosurveillance: Immunoselection and Immunosubversion", Nature Reviews Immunology, vol. 6, No. 10, pp. 715-727.
Zou et al. (Apr. 2006) "Regulatory T cells, Tumour Immunity and Immunotherapy", Nature Reviews Immunology, vol. 6, No. 4, pp. 295-307.

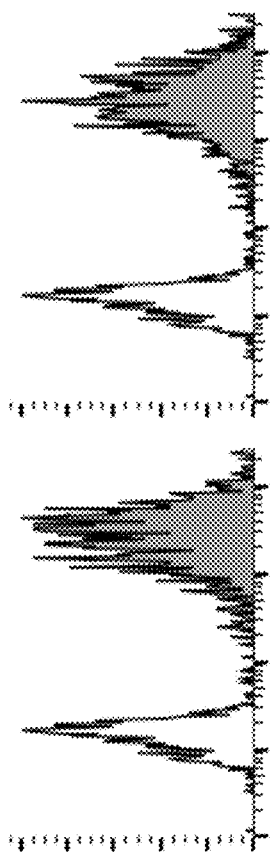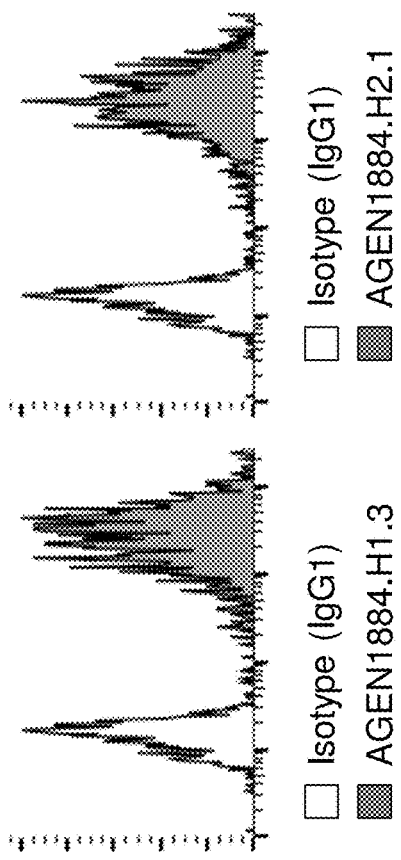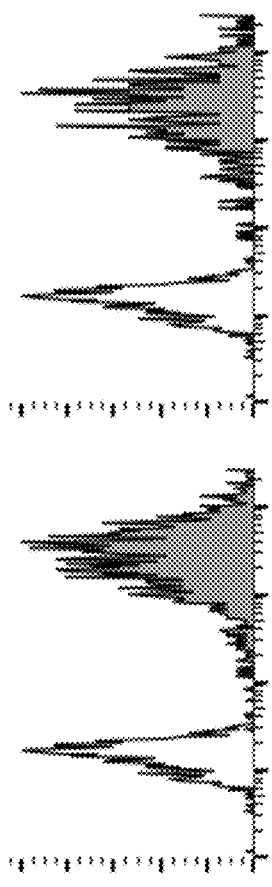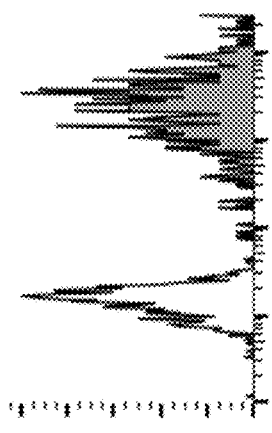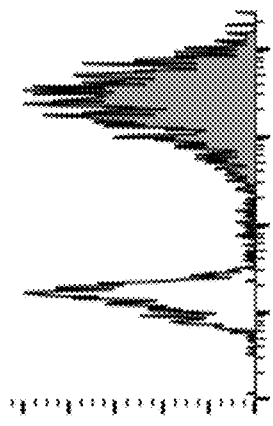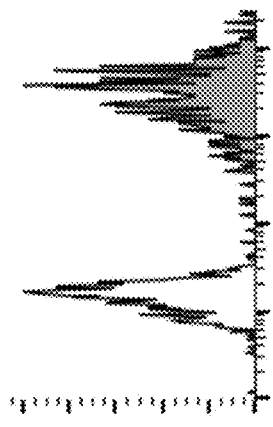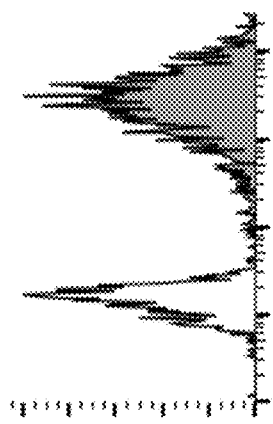

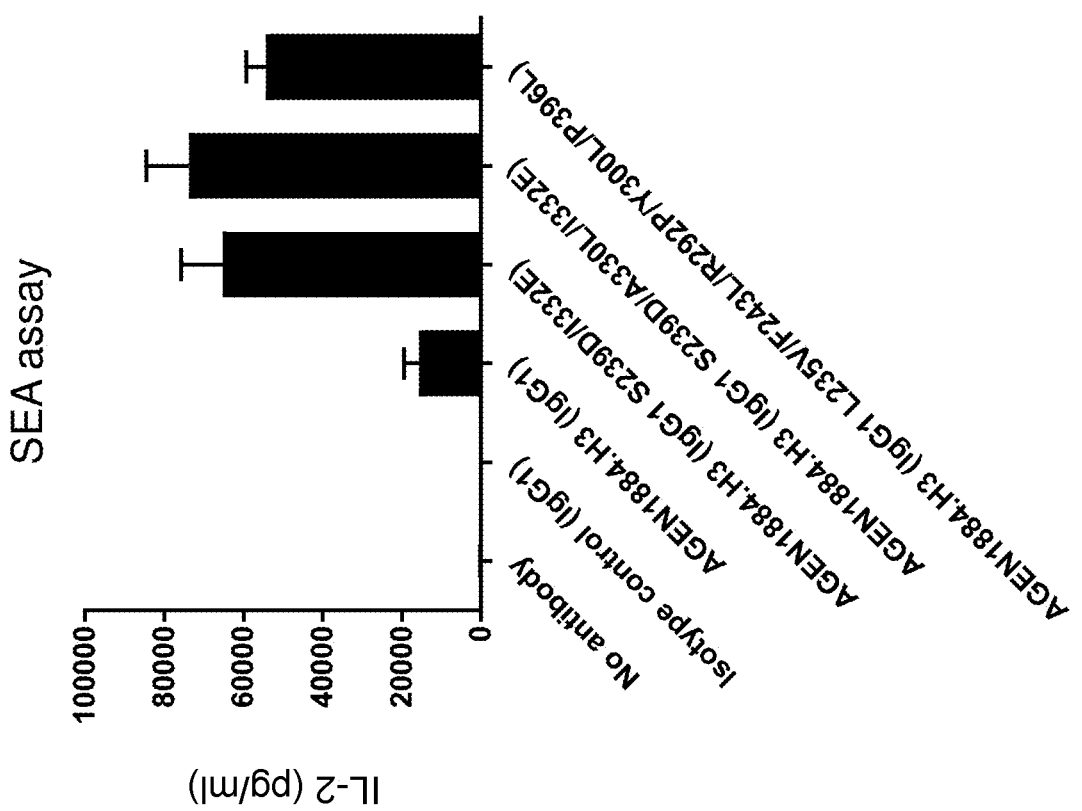

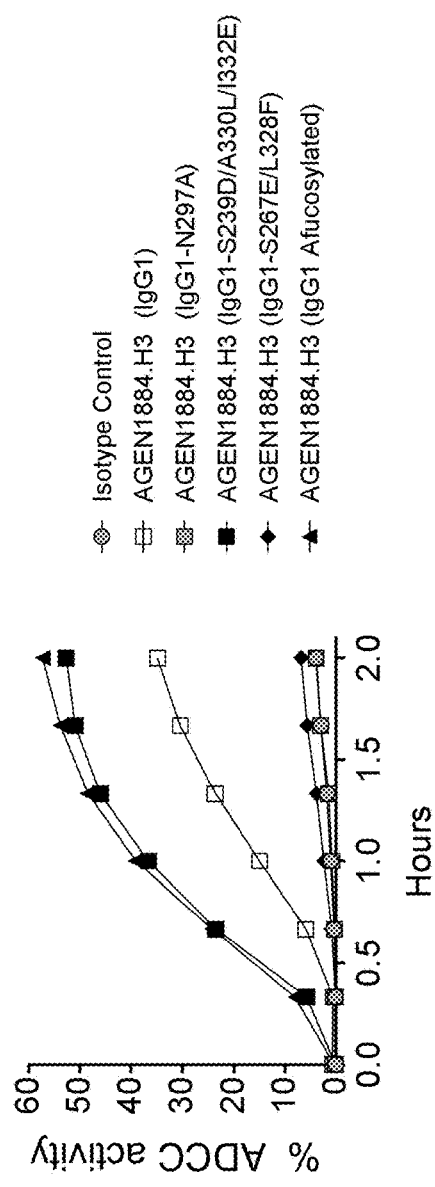
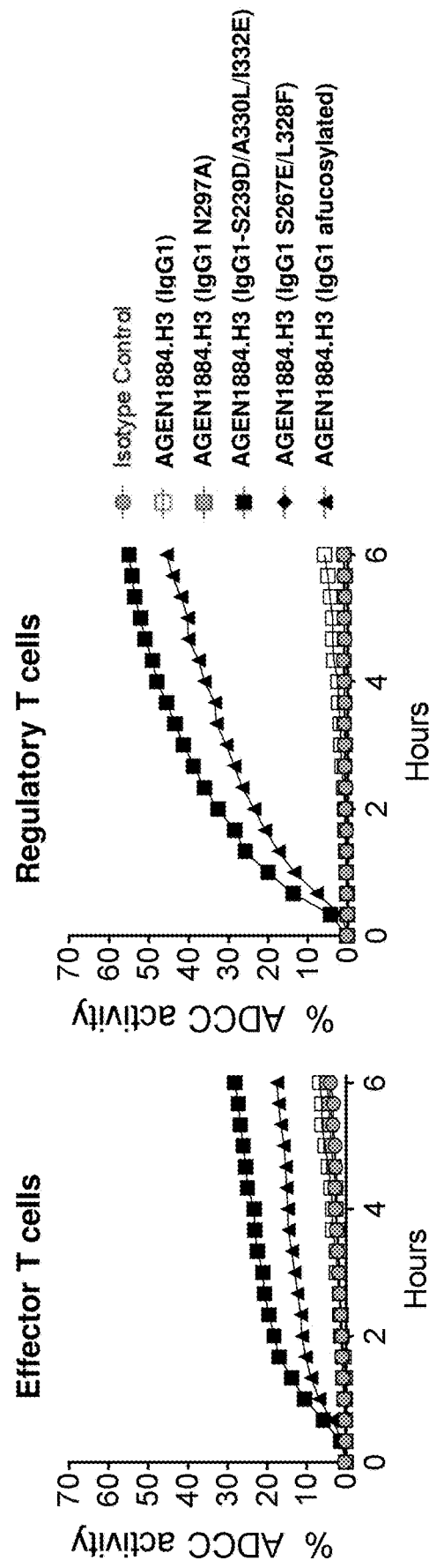
Figure 12A
Figure 12B

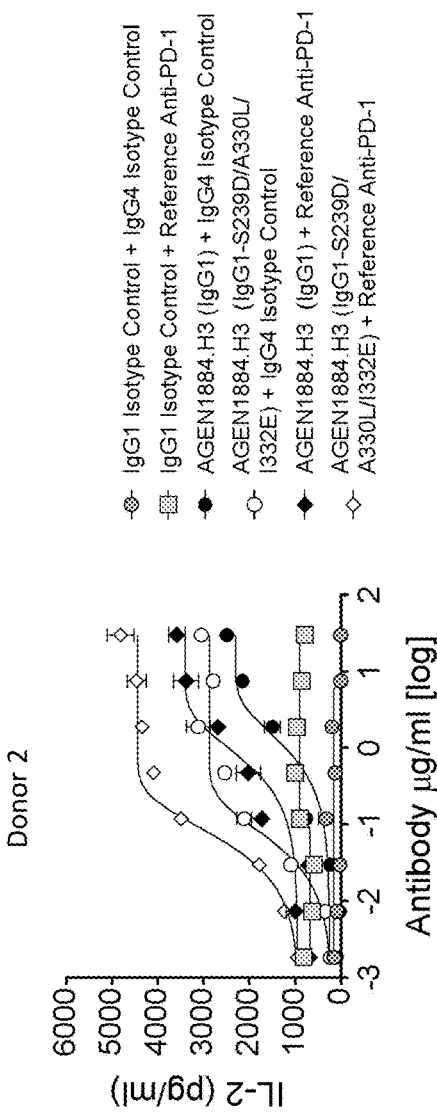
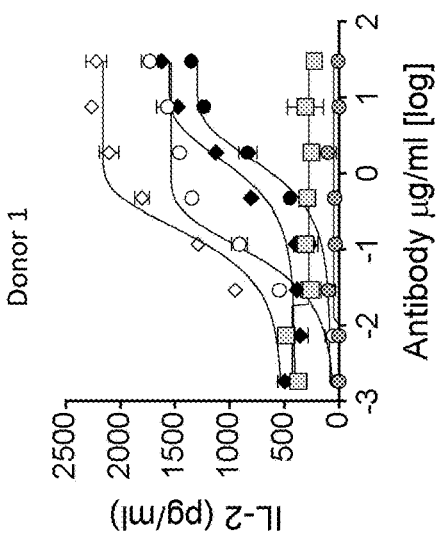
Figure 13A
Figure 13C
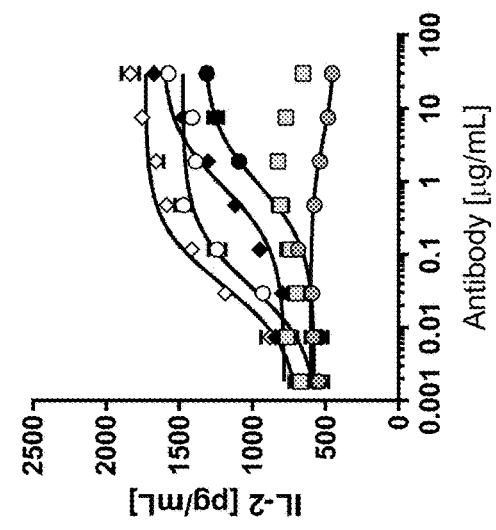
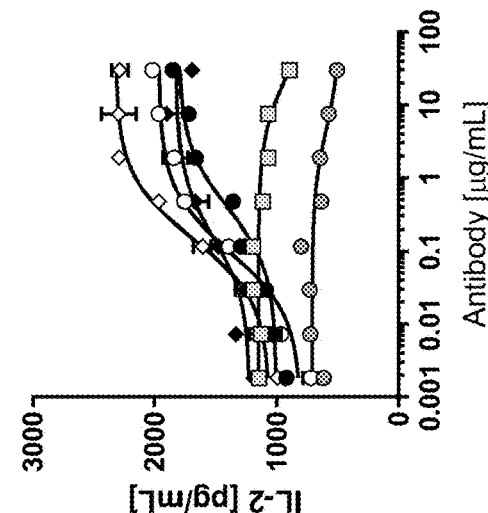
Figure 13B
Figure 13D

Figure 14A

| | | | |
|---|---|---|---|
| P16410 CTLA4_HUMAN | 1 | MACLGFQRHKAQLNLATRTWPCTLLFFLLFIPVFCKAMHVAQPAVVLASSRGIASFVCEY | 60 |
| G7PL88 CTLA4_MACFA | 1 | ..........R.....R.Y....S.................N............... | 60 |
| P09793 CTLA4_MOUSE | 1 | ....LR.Y....Q.PS...FVA.LT......SE.IQ.T..S......H.V...P... | 60 |
| Q62859 CTLA4_RAT   | 1 | ....L..Y.TH.Q.PS....FGV.LS......I.SE.IQ.T..S......H.V...P... | 60 |
| | | ****:*:*:***.*:.********:.*:****:.:*:.*.:*:**::* | |
| P16410 CTLA4_HUMAN | 61 | ASPGKATEVRVTVLRQADSQVTEVCAATYMMGNELTFLDDSICTGTSSGNQVNLTIQGLR | 120 |
| G7PL88 CTLA4_MACFA | 61 | ............................................................ | 120 |
| P09793 CTLA4_MOUSE | 61 | SPSHNTD..............M......T..FTEK..TVG....YPF..S...FNESR.. | 120 |
| Q62859 CTLA4_RAT   | 61 | ..SHNTD..............M......T..FTVK..T.G....PF..S...FNESR.. | 120 |
| | | .:******************:*:*****.*..**.:*:..*:*.:*..*****.:: | |
| P16410 CTLA4_HUMAN | 121 | AMDTGLYICKVELMYPPPYYLGIGNGTQIYVIDPEPCPDSDFLLWILAAVSSGLFFYSFL | 180 |
| G7PL88 CTLA4_MACFA | 121 | ............................................................ | 180 |
| P09793 CTLA4_MOUSE | 121 | .V........L..........................................V...L.. | 180 |
| Q62859 CTLA4_RAT   | 121 | .A........F........M.................................V...L.. | 180 |
| | | .*:******.*.*****.*:***:***********:**.*** | |
| P16410 CTLA4_HUMAN | 181 | LTAVSLSKMLKKRSPLTTGVYVKMPPTEPECEKQFQPYFIPIN | 223 |
| G7PL88 CTLA4_MACFA | 181 | ................................................ | 223 |
| P09793 CTLA4_MOUSE | 181 | VS............................................ | 223 |
| Q62859 CTLA4_RAT   | 181 | .V.....NRT..................................... | 223 |
| | | .:***..:************************ | |

Figure 14B

```
SP|P16410|CTLA4_HUMAN     MACLGFQRHKAQLNLATRTWPCTLLFFLLFIP---VFC-----------KAMHVAQPAVVLA----  48
TR|G7PL88|G7PL88_MACFA    MACLGFQRHKARLNLATRTRPYTLLFSLLFIP---VFS-----------KAMHVAQPAVVLA----  48
SP|P10747|CD28_HUMAN      -----------MLRLLLALN--LFPS-IQVTGNKILVKQSP-MLV---------------------  30
SP|Q9Y6W8|ICOS_HUMAN      ----MKSGLWY-------FF---LFCLRIKVLTGEINGSANYEMFI--------------------  32
SP|Q7Z6A9|BTLA_HUMAN      -----------MKTLPAMLGTGKLFWV--FFLIPYLDIWNIHGKESCDVQLYIK------------  41
SP|Q15116|PDCD1_HUMAN     -----------MQIPQAPWPVVWAVLQLGWRPGWFLDSPD-RPWNPPTFSPALLVV----------  44
                                                        *         ::

SP|P16410|CTLA4_HUMAN     ----------SSRGIASFVCEYASPGKA----TEVRVTVLRQADSQVTEVCAATYMMGNE---LT  96
TR|G7PL88|G7PL88_MACFA    ----------NSRGIASFVCEYASPGKA----TEVRVTVLRQADSQVTEVCAATYMMGNE---LT  96
SP|P10747|CD28_HUMAN      ----------AYDNAVNLSCKYSYNLFS----REFRASLHKGLDSA-VEVCVVYGNYSQQLQVY-  79
SP|Q9Y6W8|ICOS_HUMAN      ----------FHNGGVQILCKYPD---IV----QQFKMQLLKGGQ---ILCDLTKTKGSGNTVS-  76
SP|Q7Z6A9|BTLA_HUMAN      RQSEHSILAGDPFELECPVKYCANRPHVTWCKLN----GT-----TCVKLEDRQ-----------  86
SP|Q15116|PDCD1_HUMAN     ----------TEGDNATFTCSFSNTSESFVLNWYRMSPSNQTDK----LAAFPEDR---------  86
                                      *                   :  :               .

SP|P16410|CTLA4_HUMAN     FLDDSICT-------GTSSGNQVNLTI---QGLRAMDTGLYICKVELMYPPPYYLGIG------- 144
TR|G7PL88|G7PL88_MACFA    FLDDSICT-------GTSSGNQVNLTI---QGLRAMDTGLYICKVELMYPPPYYMGIG------- 144
SP|P10747|CD28_HUMAN      SKTGFNCD-------GKLGNESVIFYL---QNLYVNQTDIYFCKIEVMYPPPYLDNEK------- 127
SP|Q9Y6W8|ICOS_HUMAN      IKSLKFCH-------SQLSNNSVSFFL---YNLDHSHANYYFCNLSIFDPPPFKVTLT------- 124
SP|Q7Z6A9|BTLA_HUMAN      ---------------TSWKEEKNISFFILHFEPVLPNDNGSYRCSANFQSNL----IE------- 125
SP|Q15116|PDCD1_HUMAN     SQPGQDCRFRVTQLPNGRDFHMSV-----VRARRNDSGTYLCGAISLAPKAQIKESLRAELR 143
                                                         :  .                    *  *
```

Figure 14C

```
SP|P16410|CTLA4_HUMAN      -NGTQIYVIDP-------EPCPDS-------DFLLWILAAVSSGLFFYSFLLTAVSL---S-KML 190
TR|G7PL88|G7PL88_MACFA     -NGTQIYVIDP-------EPCPDS-------DFLLWILAAVSSGLFFYSFLLTAVSL---S-KML 190
SP|P10747|CD28_HUMAN       SNGTIIHVKGK-------HLCPSPLFPGPSKPFWVLVVVGGVLACYSLLVTVAFI--IFWVR 180
SP|Q9Y6W8|ICOS_HUMAN       ---GGYLHIYES------QLCCQL-------KFWLPIGCAA---FVVVCILGCIL--ICWLT 165
SP|Q7Z6A9|BTLA_HUMAN       SHSTTLYVTDVKSASERPSKDEMASR-PWLLYRLLPLGG----LPLLITTCFLFCCLRR 180
SP|Q15116|PDCD1_HUMAN      VTERRAEVPTA------HPSPSRPAG-QFQTLVVGVVGGLLGSLVLLVWVLAV--ICSRA 195
                                      :                    .        .              :

SP|P16410|CTLA4_HUMAN      KKRSP-----LTTGVYVKMPPTE-------PEC-EKQFQPYFIPIN------- 223
TR|G7PL88|G7PL88_MACFA     KKRSP-----LTTGVYVKMPPTE-------PEC-EKQFQPYFIPIN------- 223
SP|P10747|CD28_HUMAN       SKRSR-----LLHSDYMNMTPRR-------PGPTRKHYQPYAPPRD--FAAYRS 220
SP|Q9Y6W8|ICOS_HUMAN       KKKYSSSVHDPNGEYMFMRAVN-------TAKKSRLTDVTL----------- 199
SP|Q7Z6A9|BTLA_HUMAN       HQGKQNELSDTAGREINLVDAHLKSEQTEASTRQNSQVLLSETGIYDNDPDLCFRMQEGS 240
SP|Q15116|PDCD1_HUMAN      ARG-------TIG-----ARR-------TGQP-LKEDPSAVPVF--SVDYGELDFQWREKT 234
                                                              :

SP|P16410|CTLA4_HUMAN      ----------------------------------------
TR|G7PL88|G7PL88_MACFA     ----------------------------------------
SP|P10747|CD28_HUMAN       ----------------------------------------
SP|Q9Y6W8|ICOS_HUMAN       ----------------------------------------
SP|Q7Z6A9|BTLA_HUMAN       EVYSNPCLEENKP--GIVYASLNHSVIGPNSRLARNVKEAPTEYASI------CVRS- 289
SP|Q15116|PDCD1_HUMAN      PEPPVPCVPEQTEYATIVFP-----SGMGTSSPARRGSADGPRSAQPLRPEDGHCSWPL 288
```

ANTI-CTLA-4 ANTIBODIES AND METHODS OF USE THEREOF

1. RELATED APPLICATIONS

This application is a division of U.S. patent application Ser. No. 17/030,650, filed Sep. 24, 2020, which is a division of U.S. patent application Ser. No. 15/834,290, filed Dec. 7, 2017, which claims the benefit of U.S. Provisional Application No. 62/431,272, filed Dec. 7, 2016, the entire contents of which are incorporated herein by reference.

2. FIELD

The instant disclosure relates to antibodies that specifically bind to CTLA-4 (e.g., human CTLA-4) and methods of using the same.

3. BACKGROUND

T-lymphocytes are central to the adaptive immune response to antigen. At least two signals are required for full activation of naive T-cells (Bretscher 1999, Proc Natl Acad Sci USA 96:185-90). A first, antigen-specific signal is provided by interaction of the T-cell receptor (TCR) with MHC/peptide complex on an antigen-presenting cell (APC). A second, co-stimulatory signal is provided by the interactions between receptors on the T-cell and their ligands on an antigen presenting cell (APC). Engagement of both TCR/MHC and co-stimulatory interactions leads to T-cell activation via a number of intracellular pathways, including calcium-calcineurin and RAS mitogen-activated protein kinase, and subsequent activation of transcription factors for a number of effector compounds, including cytokines such as IL-2. These events lead to T-cell proliferation, generation of a CD4+ helper T-cell (TH) pool, and expansion of activated CD8+ cytotoxic T-cells. Not only is co-stimulation critical for full T-cell activation, its absence during TCR/MHC engagement results in anergy and/or apoptosis.

Multiple positive and negative co-stimulatory pathways are involved in T-cell regulation; however, the most critical are between CD28 on T-cells and B7-1 (CD80) and B7-2 (CD86) on APCs. CD28 promotes T-cell differentiation into TH1 phenotype cells and enhances antibody production by B cells and activation of T-cells. B7-1 and B7-2, expressed on APCs such as dendritic cells (DC) and B cells, have overlapping but distinct functions. B7-2 is constitutively expressed and is rapidly upregulated on APCs coincident with TCR/MHC engagement (signal 1). B7-1 expression is very low on the resting cell, but is typically induced after prolonged T-cell stimulation. These differences suggest that while B7-2 may be important in initialization of T-cell activation, B7-1 may play a greater role in perpetuating the immune response.

After T-cell activation, the negative regulatory receptor Cytotoxic T-Lymphocyte Antigen 4 (CTLA-4) is upregulated on T-cells (Alegre et al., 2001, Nat Rev Immunol 1:220-8). CTLA-4 is structurally homologous to CD28 but binds more tightly to both B7-1 and B7-2 ligands. CTLA-4 inhibits the immune response in several ways: it competes with CD28 for the B7 ligands and thus blocks co-stimulation; it negatively signals to inhibit T-cell activation; and it can capture CD80 and CD86 from opposing cells by trans-endocytosis, resulting in impaired costimulation via CD28 (Krummel and Allison, 1995, J Exp Med 182:459-465; Walunas et al., 1994, Immunity 1:405-413; Qureshi et al., 2011, Science 332:600-603).

Given the critical role of the B7 co-stimulatory pathway in promoting and maintaining an immune response, therapeutic agents designed to antagonize this pathway are promising for the treatment of autoimmune diseases and disorders.

4. SUMMARY

The instant disclosure provides antibodies that specifically bind to human CTLA-4 and antagonize CTLA-4 function, e.g., CTLA-4-mediated immune suppression. Also provided are pharmaceutical compositions comprising these antibodies, nucleic acids encoding these antibodies, expression vectors and host cells for making these antibodies, and methods of treating a subject using these antibodies. The antibodies described herein are particularly useful for increasing T-cell activation in response to an antigen (e.g., a tumor antigen or an infectious disease antigen) and/or decreasing Treg-mediated immune suppression, and hence for treating cancer in a subject or for treating or preventing an infectious disease in a subject.

Accordingly, in one aspect the instant disclosure provides an isolated antibody comprising a heavy chain variable region comprising complementarity determining regions CDRH1, CDRH2, and CDRH3 and a light chain variable region comprising complementarity determining regions CDRL1, CDRL2, and CDRL3, wherein:

(a) CDRH1 comprises the amino acid sequence of SYSMN (SEQ ID NO: 10);
(b) CDRH2 comprises the amino acid sequence of SISSSSYIYYAXSVKG (SEQ ID NO: 18), wherein X is E or D;
(c) CDRH3 comprises the amino acid sequence of VGLXGPFDI (SEQ ID NO: 19), wherein X is F or M;
(d) CDRL1 comprises the amino acid sequence of RASQSVSRYLG (SEQ ID NO: 15);
(e) CDRL2 comprises the amino acid sequence of GASTRAT (SEQ ID NO: 16); and
(f) CDRL3 comprises the amino acid sequence of QQYGSSPWT (SEQ ID NO: 17), and wherein the CDRH1, CDRH2, and CDRH3 sequences of the antibody are not SEQ ID NOs: 10, 11, and 13, respectively.

In certain embodiments, the CDRH2 comprises the amino acid sequence of SEQ ID NO: 11. In certain embodiments, the CDRH2 comprises the amino acid sequence of SEQ ID NO: 12. In certain embodiments, the CDRH3 comprises the amino acid sequence of SEQ ID NO: 13. In certain embodiments, the CDRH3 comprises the amino acid sequence of SEQ ID NO: 14. In certain embodiments, CDRH1, CDRH2, and CDRH3 comprise the CDRH1, CDRH2, and CDRH3 amino acid sequences set forth in SEQ ID NOs: 10, 11, and 14; 10, 12, and 13; or 10, 12, and 14, respectively. In certain embodiments, CDRH1, CDRH2, and CDRH3 comprise the CDRH1, CDRH2, and CDRH3 amino acid sequences set forth in SEQ ID NOs: 10, 12, and 14, respectively. In certain embodiments, CDRH1, CDRH2, CDRH3, CDRL1, CDRL2, and CDRL3 comprise the amino acid sequences set forth in SEQ ID NOs: 10, 11, 14, 15, 16, and 17; 10, 12, 13, 15, 16, and 17; or 10, 12, 14, 15, 16, and 17, respectively. In certain embodiments, CDRH1, CDRH2, CDRH3, CDRL1, CDRL2, and CDRL3 comprise the amino acid sequences set forth in SEQ ID NOs: 10, 12, 14, 15, 16, and 17, respectively.

In another aspect, the instant disclosure provides an isolated antibody that specifically binds to human CTLA-4, comprising a heavy chain variable region comprising complementarity determining regions CDRH1, CDRH2, and CDRH3 and a light chain variable region comprising complementarity determining regions CDRL1, CDRL2, and CDRL3, wherein:
(a) CDRH1 comprises the amino acid sequence of SYSMN (SEQ ID NO: 10);
(b) CDRH2 comprises the amino acid sequence of SISSSSSYIYYAXSVKG (SEQ ID NO: 18), wherein X is E or D;
(c) CDRH3 comprises the amino acid sequence of VGLXGPFDI (SEQ ID NO: 19), wherein X is F or M;
(d) CDRL1 comprises the amino acid sequence of RASQSVSRYLG (SEQ ID NO: 15);
(e) CDRL2 comprises the amino acid sequence of GASTRAT (SEQ ID NO: 16); and
(f) CDRL3 comprises the amino acid sequence of QQYGSSPWT (SEQ ID NO: 17), and wherein the CDRH1, CDRH2, and CDRH3 sequences of the antibody are not SEQ ID NOs: 10, 11, and 13, respectively.

In certain embodiments, the CDRH2 comprises the amino acid sequence of SEQ ID NO: 11. In certain embodiments, the CDRH2 comprises the amino acid sequence of SEQ ID NO: 12. In certain embodiments, the CDRH3 comprises the amino acid sequence of SEQ ID NO: 13. In certain embodiments, the CDRH3 comprises the amino acid sequence of SEQ ID NO: 14. In certain embodiments, CDRH1, CDRH2, and CDRH3 comprise the CDRH1, CDRH2, and CDRH3 amino acid sequences set forth in SEQ ID NOs: 10, 11, and 14; 10, 12, and 13; or 10, 12, and 14, respectively. In certain embodiments, CDRH1, CDRH2, and CDRH3 comprise the CDRH1, CDRH2, and CDRH3 amino acid sequences set forth in SEQ ID NOs: 10, 12, and 14, respectively. In certain embodiments, CDRH1, CDRH2, CDRH3, CDRL1, CDRL2, and CDRL3 comprise the amino acid sequences set forth in SEQ ID NOs: 10, 11, 14, 15, 16, and 17; 10, 12, 13, 15, 16, and 17; or 10, 12, 14, 15, 16, and 17, respectively. In certain embodiments, CDRH1, CDRH2, CDRH3, CDRL1, CDRL2, and CDRL3 comprise the amino acid sequences set forth in SEQ ID NOs: 10, 12, 14, 15, 16, and 17, respectively.

In another aspect, the instant disclosure provides an isolated antibody that specifically binds to human CTLA-4, comprising a heavy chain variable region comprising complementarity determining regions CDRH1, CDRH2, and CDRH3, and a light chain variable region comprising complementarity determining regions CDRL1, CDRL2, and CDRL3, wherein CDRH1, CDRH2, CDRH3, CDRL1, CDRL2, and CDRL3 comprise the amino acid sequences set forth in SEQ ID NOs: 10, 12, 14, 15, 16, and 17, respectively.

In certain embodiments, the antibody comprises a heavy chain variable region comprising the amino acid sequence of SEQ ID NO: 20. In certain embodiments, the antibody comprises a heavy chain variable region comprising an amino acid sequence which is at least 75%, 80%, 85%, 90%, 95%, 99%, or 100% identical to an amino acid sequence selected from the group consisting of SEQ ID NOs: 2 and 4-8. In certain embodiments, the antibody comprises a heavy chain variable region comprising an amino acid sequence which is at least 75%, 80%, 85%, 90%, 95%, 99%, or 100% identical to an amino acid sequence selected from the group consisting of SEQ ID NOs: 3. In certain embodiments, the heavy chain variable region comprises an amino acid sequence selected from the group consisting of SEQ ID NOs: 2 and 4-8. In certain embodiments, the heavy chain variable region comprises the amino acid sequence of SEQ ID NO: 8. In certain embodiments, the heavy chain variable region comprises the amino acid sequence of SEQ ID NO: 3. In certain embodiments, the antibody comprises a heavy chain comprising the amino acid sequence of SEQ ID NO: 23. In certain embodiments, the antibody comprises a heavy chain comprising the amino acid sequence of SEQ ID NO: 24. In certain embodiments, the antibody comprises a heavy chain comprising the amino acid sequence of SEQ ID NO: 25. In certain embodiments, the antibody comprises a heavy chain comprising the amino acid sequence of SEQ ID NO: 26. In certain embodiments, the antibody comprises a heavy chain variable region having an amino acid sequence derived from a human IGHV3-21 germline sequence (e.g., IGHV3-21*01, e.g., having amino acid sequence of SEQ ID NO: 21).

In certain embodiments, the antibody comprises a light chain variable region comprising an amino acid sequence which is at least 75%, 80%, 85%, 90%, 95%, 99%, or 100% identical to the amino acid sequence of SEQ ID NO: 9. In certain embodiments, the antibody comprises a light chain variable region comprising the amino acid sequence of SEQ ID NO: 9. In certain embodiments, the antibody comprises a light chain comprising the amino acid sequence of SEQ ID NO: 27. In certain embodiments, the antibody comprises a light chain variable region having an amino acid sequence derived from a human IGKV3-20 germline sequence (e.g., IGKV3-20*01, e.g., having amino acid sequence of SEQ ID NO: 22).

In certain embodiments, the instant disclosure provides an isolated antibody that specifically binds to human CTLA-4, the antibody comprising a heavy chain variable region having an amino acid sequence derived from a human IGHV3-21 germline sequence (e.g., IGHV3-21*01, e.g., having amino acid sequence of SEQ ID NO: 21), wherein the heavy chain variable region comprises the amino acid sequence set forth in SEQ ID NO: 14. In certain embodiments, the antibody comprises a light chain variable region having an amino acid sequence derived from a human IGKV3-20 germline sequence (e.g., IGKV3-20*01, e.g., having amino acid sequence of SEQ ID NO: 22).

In another aspect, the instant disclosure provides an isolated antibody that specifically binds to human CTLA-4, comprising a heavy chain variable region comprising an amino acid sequence selected from the group consisting of SEQ ID NOs: 2-8. In certain embodiments, the antibody comprises a heavy chain variable region comprising the amino acid sequence of SEQ ID NO: 8. In certain embodiments, the antibody comprises a heavy chain comprising an amino acid sequence selected from the group consisting of SEQ ID NOs: 23-26. In certain embodiments, the antibody comprises a heavy chain comprising the amino acid sequence of SEQ ID NO: 23. In certain embodiments, the antibody comprises a heavy chain comprising the amino acid sequence of SEQ ID NO: 24. In certain embodiments, the antibody comprises a heavy chain comprising the amino acid sequence of SEQ ID NO: 25. In certain embodiments, the antibody comprises a heavy chain comprising the amino acid sequence of SEQ ID NO: 26.

In another aspect, the instant disclosure provides an isolated antibody that specifically binds to human CTLA-4, comprising a heavy chain variable region and a light chain variable region, wherein the heavy chain variable region and the light chain variable region comprise the amino acid sequences set forth in SEQ ID NOs: 2 and 9; 3 and 9; 4 and 9; 5 and 9; 6 and 9; 7 and 9; or 8 and 9, respectively. In certain embodiments, the antibody comprises a heavy chain variable region comprising the amino acid sequence of SEQ ID NO: 8 and a light chain variable region comprising the amino acid sequence of SEQ ID NO: 9. In certain embodiments, the antibody comprises a heavy chain comprising the amino acid sequence of SEQ ID NO: 23; and a light chain comprising the amino acid sequence of SEQ ID NO: 27. In certain embodiments, the antibody comprises a heavy chain comprising the amino acid sequence of SEQ ID NO: 24; and a light chain comprising the amino acid sequence of SEQ ID NO: 27. In certain embodiments, the antibody comprises a heavy chain comprising the amino acid sequence of SEQ ID NO: 25; and a light chain comprising the amino acid sequence of SEQ ID NO: 27. In certain embodiments, the antibody comprises a heavy chain comprising the amino acid sequence of SEQ ID NO: 26; and a light chain comprising the amino acid sequence of SEQ ID NO: 27.

In another aspect, the instant disclosure provides an isolated antibody that specifically binds to human CTLA-4, comprising a heavy chain variable region having an amino acid sequence derived from a human IGHV3-21*01 germline sequence (e.g., IGHV3-21*01, e.g., having amino acid sequence of SEQ ID NO: 21); and a light chain variable region having an amino acid sequence derived from a human IGKV3-20*01 germline sequence (e.g., IGKV3-20*01, e.g., having amino acid sequence of SEQ ID NO: 22).

In certain embodiments, the antibody comprises a heavy chain constant region selected from the group consisting of human $IgG_1$, $IgG_2$, $IgG_3$, $IgG_4$, $IgA_1$, and $IgA_2$. In certain embodiments, the heavy chain constant region is $IgG_1$. In certain embodiments, the heavy chain constant region is $IgG_2$. In certain embodiments, the antibody comprises a light chain constant region selected from the group consisting of human Igκ and Igλ.

In certain embodiments, the antibody comprises an $IgG_1$ heavy chain constant region. In certain embodiments, the antibody comprises a heavy chain constant region comprising the amino acid sequence of SEQ ID NO: 28. In certain embodiment, the amino acid sequence of the $IgG_1$ heavy chain constant region comprises S239D/I332E mutations, numbered according to the EU numbering system. In certain embodiments, the antibody comprises a heavy chain constant region comprising the amino acid sequence of SEQ ID NO: 29. In certain embodiments, the amino acid sequence of the $IgG_1$ heavy chain constant region comprises S239D/A330L/I332E mutations, numbered according to the EU numbering system. In certain embodiments, the antibody comprises a heavy chain constant region comprising the amino acid sequence of SEQ ID NO: 30. In certain embodiments, the amino acid sequence of the $IgG_1$ heavy chain constant region comprises L235V/F243L/R292P/Y300L/P396L mutations, numbered according to the EU numbering system. In certain embodiments, the antibody comprises a heavy chain constant region comprising the amino acid sequence of SEQ ID NO: 31. In certain embodiments, the $IgG_1$ heavy chain constant region is afucosylated $IgG_1$.

In certain embodiments, the antibody comprises a human IgG heavy chain constant region that is a variant of a wild type human IgG heavy chain constant region, wherein the variant human IgG heavy chain constant region binds to FcγRIIIA with a higher affinity than the wild type human IgG heavy chain constant region binds to FcγRIIIA In certain embodiments, the variant human IgG heavy chain constant region is a variant human $IgG_1$ heavy chain constant region.

In certain embodiments, the antibody comprises a light chain constant region selected from the group consisting of human Igκ and Igλ. In certain embodiments, the antibody comprises an Igκ light chain constant region. In certain embodiments, the antibody comprises a light chain constant region comprising the amino acid sequence of SEQ ID NO: 32.

In another aspect, the instant disclosure provides an isolated antibody that cross-competes for binding to human CTLA-4 with an antibody described herein. In another aspect, the instant disclosure provides an isolated antibody that cross-competes for binding to human CTLA-4 with an antibody comprising the heavy and light chain variable region amino acid sequences set forth in SEQ ID NOs: 8 and 9, respectively.

In another aspect, the instant disclosure provides an isolated antibody that binds to the same epitope on human CTLA-4 as an antibody described herein. In another aspect, the instant disclosure provides an isolated antibody that binds to the same epitope on human CTLA-4 as an antibody comprising the heavy and light chain variable region amino acid sequences set forth in SEQ ID NOs: 8 and 9, respectively.

In another aspect, the instant disclosure provides an isolated antibody that binds, e.g., specifically binds, to an epitope of human CTLA-4. In certain embodiments, the antibody binds to an epitope located within a region of human CTLA-4 consisting of an amino acid sequence selected from the group consisting of SEQ ID NOs: 34-39. In certain embodiments, the antibody binds to an epitope located within a region of human CTLA-4 consisting of the amino acid sequence of SEQ ID NO: 37. In certain embodiments, the antibody binds to an epitope located within a region of human CTLA-4 consisting of the amino acid sequence of SEQ ID NO: 36. In certain embodiments, the antibody binds to an epitope located within a region of human CTLA-4 consisting of the amino acid sequence of SEQ ID NO: 35. In certain embodiments, the antibody binds to an epitope located within a region of human CTLA-4 consisting of the amino acid sequence of SEQ ID NO: 34. In certain embodiments, the antibody binds to an epitope located within a region of human CTLA-4 consisting of the amino acid sequence of SEQ ID NO: 38. In certain embodiments, the antibody binds to an epitope located within a region of human CTLA-4 consisting of the amino acid sequence of SEQ ID NO: 39.

In another aspect, the instant disclosure provides an antibody or isolated antibody that specifically binds to the same epitope of human CTLA-4 as any antibody of the present invention. In certain embodiments, the antibody binds to an epitope located within a region of human CTLA-4 consisting of an amino acid sequence selected from the group consisting of SEQ ID NOs: 34-39. In certain embodiments, the antibody binds to an epitope located within a region of human CTLA-4 consisting of the amino acid sequence of SEQ ID NO: 37. In certain embodiments, the antibody binds to an epitope located within a region of human CTLA-4 consisting of the amino acid sequence of SEQ ID NO: 36. In certain embodiments, the antibody binds to an epitope located within a region of human CTLA-4 consisting of the amino acid sequence of SEQ ID NO: 35. In certain embodiments, the antibody binds to an epitope located within a region of human CTLA-4 consisting of the amino acid sequence of SEQ ID NO: 34. In certain embodiments, the antibody binds to an epitope located within a region of human CTLA-4 consisting of the amino acid sequence of SEQ ID NO: 38. In certain embodiments, the antibody binds to an epitope located within a region of human CTLA-4 consisting of the amino acid sequence of SEQ ID NO: 39.

In another aspect, the instant disclosure provides an antibody that, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 34 relative to hydrogen/deuterium exchange in the region consisting of the amino acid sequence set forth in SEQ ID NO: 34 in the absence of the antibody, as determined by a hydrogen/deuterium assay. In another aspect, the instant disclosure provides an antibody that, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 35 relative to hydrogen/deuterium exchange in the region consisting of the amino acid sequence set forth in SEQ ID NO: 35 in the absence of the antibody, as determined by a hydrogen/deuterium assay. In another aspect, the instant disclosure provides an antibody that, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 36 relative to hydrogen/deuterium exchange in the region consisting of the amino acid sequence set forth in SEQ ID NO: 36 in the absence of the antibody, as determined by a hydrogen/deuterium assay. In another aspect, the instant disclosure provides an antibody that, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 37 relative to hydrogen/deuterium exchange in the region consisting of the amino acid sequence set forth in SEQ ID NO: 37 in the absence of the antibody, as determined by a hydrogen/deuterium assay. In another aspect, the instant disclosure provides an antibody that, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 38 relative to hydrogen/deuterium exchange in the region consisting of the amino acid sequence set forth in SEQ ID NO: 38 in the absence of the antibody, as determined by a hydrogen/deuterium assay. In another aspect, the instant disclosure provides an antibody that, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 39 relative to hydrogen/deuterium exchange in the region consisting of the amino acid sequence set forth in SEQ ID NO: 39 in the absence of the antibody, as determined by a hydrogen/deuterium assay.

In another aspect, the instant disclosure provides an antibody or isolated antibody that specifically binds to the same epitope of human CTLA-4 as any antibody of the present invention. In certain embodiments, the antibody, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 34 relative to hydrogen/deuterium exchange in the region consisting of the amino acid sequence set forth in SEQ ID NO: 34 in the absence of the antibody, as determined by a hydrogen/deuterium assay. In certain embodiments, the antibody, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 35 relative to hydrogen/deuterium exchange in the region consisting of the amino acid sequence set forth in SEQ ID NO: 35 in the absence of the antibody, as determined by a hydrogen/deuterium assay. In certain embodiments, the antibody, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 36 relative to hydrogen/deuterium exchange in the region consisting of the amino acid sequence set forth in SEQ ID NO: 36 in the absence of the antibody, as determined by a hydrogen/deuterium assay. In certain embodiments, the antibody, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 37 relative to hydrogen/deuterium exchange in the region consisting of the amino acid sequence set forth in SEQ ID NO: 37 in the absence of the antibody, as determined by a hydrogen/deuterium assay. In certain embodiments, the antibody, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 38 relative to hydrogen/deuterium exchange in the region consisting of the amino acid sequence set forth in SEQ ID NO: 38 in the absence of the antibody, as determined by a hydrogen/deuterium assay. In certain embodiments, the antibody, when bound to a human CTLA-4 protein or fragment thereof, e.g., comprising the amino acid sequence of residues 37-162 of SEQ ID NO: 33, reduces hydrogen/deuterium exchange in a region consisting of the amino acid sequence set forth in SEQ ID NO: 39 relative to hydrogen/deuterium exchange in the region consisting of the amino acid sequence set forth in SEQ ID NO: 39 in the absence of the antibody, as determined by a hydrogen/deuterium assay.

In certain embodiments, the antibody is a human antibody. In certain embodiment, the antibody is a bispecific antibody.

In certain embodiments, the antibody is antagonistic to human CTLA-4. In certain embodiments, the antibody deactivates, reduces, or inhibits an activity of human CTLA-4. In certain embodiments, the antibody inhibits binding of human CTLA-4 to human CD80 or human CD86. In certain embodiments, the antibody induces IL-2 production by peripheral blood mononuclear cells (PBMCs) stimulated with staphylococcal enterotoxin A (SEA).

In certain embodiments, the antibody is conjugated to a cytotoxic agent, cytostatic agent, toxin, radionuclide, or detectable label.

In certain embodiments, the N-terminal amino acid residue of the heavy chain variable region and/or the light chain variable region of the antibody has been converted to pyroglutamate.

In one embodiment, the present invention relates to an antibody of the present invention for use as a medicament.

In one embodiment, the present invention relates to use of an antibody of the present invention for preparing pharmaceutical compositions or medicaments for immunotherapy. In certain embodiments, the immunotherapy is for increasing T-cell activation in response to an antigen in a subject, optionally for treating cancer, or treating or preventing infectious diseases.

In one embodiment, the present invention relates to an antibody of the present invention for use as a diagnostic.

In one embodiment, the present invention relates to the use of an antibody of the present invention for in vitro detection of human CTLA-4 in a biological sample.

In another aspect, the instant disclosure provides a pharmaceutical composition comprising an anti-CTLA-4 antibody described herein and a pharmaceutically acceptable carrier or excipient.

In another aspect, the instant disclosure provides an isolated polynucleotide encoding a heavy and/or light chain of an antibody described herein. In another aspect, the instant disclosure provides a vector comprising the polynucleotide. In another aspect, the instant disclosure provides a recombinant host cell comprising the polynucleotide or the vector. In another aspect, the instant disclosure provides a method of producing an antibody that binds to human CTLA-4, the method comprising culturing the host cell so that the polynucleotide is expressed and the antibody is produced.

In another aspect, the instant disclosure provides a method of increasing T-cell activation in response to an antigen in a subject, the method comprising administering to the subject an effective amount of an anti-CTLA-4 antibody or pharmaceutical composition described herein. In another aspect, the instant disclosure provides a method of treating cancer in a subject, the method comprising administering to the subject an effective amount of an anti-CTLA-4 antibody or pharmaceutical composition described herein.

In certain embodiments, the subject has cancer. In certain embodiments, the subject has a metastatic or locally advanced tumor (e.g., solid tumor). In certain embodiments, the cancer is treated in accordance with a method described herein as a first cancer therapy after diagnosis of the metastatic or locally advanced tumor (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cancer is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the tumor with a different cancer therapy, optionally wherein the method described herein is provided as the second cancer therapy administered. In certain embodiments, the cancer is treated in accordance with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered. In certain embodiments, the cancer treated in accordance with the methods described herein is a metastatic or locally advanced cancer (e.g., solid tumor) for which no standard therapy is available. In other embodiments, the cancer treated in accordance with the methods described herein is a metastatic or locally advanced cancer (e.g., solid tumor) for which a standard therapy has failed (i.e., the cancer has progressed after the standard therapy). In certain embodiments, a therapy fails if the cancer is refractory to the therapy. In certain embodiments, a therapy fails if the cancer relapses after responding, fully or partially, to the therapy. In certain embodiments, metastatic or locally advanced cancer (e.g., solid tumor) has been confirmed histologically or cytologically.

In certain embodiments, the cancer expresses PD-L1. In certain embodiments, the percentage of tumor cells in a sample of the cancer that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the cancer that exhibit detectable membrane expression (e.g., partial or complete membrane expression) of PD-L1 is at least 1%. In certain embodiments, the percentage of tumor cells in a sample of the cancer that exhibit detectable membrane expression (e.g., partial or complete membrane expression) of PD-L1 is at least 5%. In certain embodiments, the percentage of tumor cells in a sample of the cancer that exhibit detectable membrane expression (e.g., partial or complete membrane expression) of PD-L1 is at least 25%. In certain embodiments, the percentage of tumor cells in a sample of the cancer that exhibit detectable membrane expression (e.g., partial or complete membrane expression) of PD-L1 is at least 50%.

In certain embodiments, the metastatic or locally advanced tumor expresses PD-L1. In certain embodiments, the percentage of tumor cells in a sample of the metastatic or locally advanced tumor that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced tumor that exhibit detectable membrane expression (e.g., partial or complete membrane expression) of PD-L1 is at least 1%. In certain embodiments, the percentage of tumor cells in a sample of the metastatic or locally advanced tumor that exhibit detectable membrane expression (e.g., partial or complete membrane expression) of PD-L1 is at least 5%. In certain embodiments, the percentage of tumor cells in a sample of the metastatic or locally advanced tumor that exhibit detectable membrane expression (e.g., partial or complete membrane expression) of PD-L1 is at least 25%. In certain embodiments, the percentage of tumor cells in a sample of the metastatic or locally advanced tumor that exhibit detectable membrane expression (e.g., partial or complete membrane expression) of PD-L1 is at least 50%.

In certain embodiments, the cancer is a cervical cancer. In certain embodiments, the cancer is a metastatic or locally advanced cancer (e.g., solid tumor). In certain embodiments, the metastatic or locally advanced cancer (e.g., solid tumor) is a metastatic or locally advanced, unresectable squamous cell carcinoma, adenosquamous carcinoma, or adenocarcinoma of the cervix. In certain embodiments, no standard therapy is available for the cancer (e.g., cervical cancer) or metastatic or locally advanced tumor (e.g., solid tumor). In certain embodiments, the cancer (e.g., cervical cancer) or metastatic or locally advanced tumor (e.g., solid tumor) is refractory to a standard therapy. In certain embodiments, the cancer (e.g., cervical cancer) or metastatic or locally advanced tumor (e.g., solid tumor) has relapsed after a standard therapy. In certain embodiments, the standard therapy comprises a platinum-containing chemotherapy. In certain embodiments, the standard therapy is a platinum-containing doublet. In certain embodiments, the cancer (e.g., cervical cancer) is a metastatic or locally advanced, unresectable squamous cell carcinoma, adenosquamous carcinoma, or adenocarcinoma of the cervix that has relapsed after a platinum-containing doublet administered for treatment of advanced (recurrent, unresectable, or metastatic) disease. In certain embodiments, the cancer (e.g., cervical cancer) or metastatic or locally advanced tumor is HPV positive. In certain embodiments, the cancer or metastatic or locally advanced solid tumor is head and neck cancer, melanoma, renal cell carcinoma, urothelial carcinoma, or endometrial carcinoma. In certain embodiments, the cancer (e.g., cervical cancer) or metastatic or locally advanced solid tumor is associated with microsatellite instability.

In certain embodiments, the subject has cervical cancer (e.g., a metastatic or locally advanced, unresectable squamous cell carcinoma, adenosquamous carcinoma, or adenocarcinoma of the cervix), and the method comprises administering to the subject an effective amount of an anti-CTLA-4 antibody described herein, e.g., AGEN1884.H3 (IgG$_1$ S239D/A330L/I332E), or pharmaceutical composition comprising such anti-CTLA-4 antibody as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884.H3 (IgG$_1$ S239D/A330L/I332E), or pharmaceutical composition comprising such anti-CTLA-4 antibody is administered at the dosage and frequency selected from the group consisting of 0.3 mg/kg every four weeks, 1 mg/kg every four weeks, 3 mg/kg every four weeks, 0.3 mg/kg every six weeks, 1 mg/kg every six weeks, 3 mg/kg every six weeks, 0.3 mg/kg every twelve weeks, 1 mg/kg every twelve weeks, and 3 mg/kg every twelve weeks. In certain embodiments, the subject has cervical cancer (e.g., a metastatic or locally advanced, unresectable squamous cell carcinoma, adenosquamous carcinoma, or adenocarcinoma of the cervix), and the method comprises administering to the subject an effective amount of a therapeutic combination comprising an anti-CTLA-4 antibody described herein, e.g., AGEN1884.H3 (IgG$_1$ S239D/A330L/I332E), or pharmaceutical composition comprising such anti-CTLA-4 antibody, and pembrolizumab as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-antibody described herein, e.g., AGEN1884.H3 (IgG$_1$ S239D/A330L/I332E), or pharmaceutical composition comprising such anti-CTLA-4 antibody, is administered at the dosage and frequency selected from the group consisting of 0.3 mg/kg every four weeks, 1 mg/kg every four weeks, 3 mg/kg every four weeks, 0.3 mg/kg every six weeks, 1 mg/kg every six weeks, 3 mg/kg every six weeks, 0.3 mg/kg every twelve weeks, 1 mg/kg every twelve weeks, and 3 mg/kg every twelve weeks, and pembrolizumab is administered at 200 mg every three weeks.

In certain embodiments, the cancer is a non-small cell lung cancer (NSCLC). In certain embodiments, the NSCLC is a Stage IV NSCLC. In certain embodiments, the percentage of tumor cells in a sample of the NSCLC that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the NSCLC that exhibit detectable membrane expression (e.g., partial or complete membrane expression) of PD-L1 is at least 1%. In certain embodiments, the percentage of tumor cells in a sample of the NSCLC that exhibit detectable membrane expression (e.g., partial or complete membrane expression) of PD-L1 is at least 5%. In certain embodiments, the percentage of tumor cells in a sample of the NSCLC that exhibit detectable membrane expression (e.g., partial or complete membrane expression) of PD-L1 is at least 25%. In certain embodiments, the percentage of tumor cells in a sample of the NSCLC that exhibit detectable membrane expression (e.g., partial or complete membrane expression) of PD-L1 is at least 50%. In certain embodiments, the NSCLC has no EGFR or ALK genomic tumor aberrations. In certain embodiments, the metastatic or locally advanced NSCLC has no EGFR sensitizing mutation (e.g., mutation that is amenable to treatment with a tyrosine kinase inhibitor including erlotinib, gefitinib, or afatanib) or ALK translocation. In certain embodiments, the subject has received no prior systemic chemotherapy treatment for NSCLC.

In certain embodiments, the metastatic or locally advanced solid tumor is a metastatic or locally advanced non-small cell lung cancer (NSCLC). In certain embodiments, the metastatic or locally advanced solid tumor is a metastatic non-small cell lung cancer (NSCLC). In certain embodiments, the metastatic or locally advanced solid tumor is a Stage IV, metastatic or locally advanced NSCLC. In certain embodiments, the metastatic or locally advanced solid tumor is a Stage IV, metastatic NSCLC. In certain embodiments, the percentage of tumor cells in a sample of the metastatic or locally advanced NSCLC that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced NSCLC that exhibit detectable membrane expression (e.g., partial or complete membrane expression) of PD-L1 is at least 1%. In certain embodiments, the percentage of tumor cells in a sample of the metastatic or locally advanced NSCLC that exhibit detectable membrane expression (e.g., partial or complete membrane expression) of PD-L1 is at least 5%. In certain embodiments, the percentage of tumor cells in a sample of the metastatic or locally advanced NSCLC that exhibit detectable membrane expression (e.g., partial or complete membrane expression) of PD-L1 is at least 25%. In certain embodiments, the percentage of tumor cells in a sample of the metastatic or locally advanced NSCLC that exhibit detectable membrane expression (e.g., partial or complete membrane expression) of PD-L1 is at least 50%. In certain embodiments, the metastatic or locally advanced NSCLC has no EGFR or ALK genomic tumor aberrations. In certain embodiments, the subject has received no prior systemic chemotherapy treatment for metastatic or locally advanced NSCLC.

In certain embodiments, the subject has NSCLC (e.g., Stage IV, metastatic, or locally advanced NSCLC), optionally wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and the method comprises administering to the subject an effective amount of an anti-CTLA-4 antibody described herein, e.g., AGEN1884.H3 (IgG$_1$ S239D/A330L/I332E), or pharmaceutical composition comprising such anti-CTLA-4 antibody, as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884.H3 (IgG$_1$ S239D/A330L/I332E), or pharmaceutical composition comprising such anti-CTLA-4 antibody, is administered at the dosage and frequency selected from the group consisting of 0.3 mg/kg every four weeks, 1 mg/kg every four weeks, 3 mg/kg every four weeks, 0.3 mg/kg every six weeks, 1 mg/kg every six weeks, 3 mg/kg every six weeks, 0.3 mg/kg every twelve weeks, 1 mg/kg every twelve weeks, and 3 mg/kg every twelve weeks. In certain embodiments, the subject has NSCLC (e.g., Stage IV, metastatic, or locally advanced NSCLC), optionally wherein the percentage of tumor cells in a sample of the NSCLC that exhibit detectable expression (e.g., membrane expression, partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and the method comprises administering to the subject a therapeutic combination comprising an anti-CTLA-4 antibody described herein, e.g., AGEN1884.H3 (IgG$_1$ S239D/A330L/I332E), or pharmaceutical composition comprising such anti-CTLA-4 antibody, and pembrolizumab as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-antibody described herein, e.g., AGEN1884.H3 (IgG$_1$ S239D/A330L/I332E), or pharmaceutical composition comprising such anti-CTLA-4 antibody, is administered at the dosage and frequency selected from the group consisting of 0.3 mg/kg every four weeks, 1 mg/kg every four weeks, 3 mg/kg every four weeks, 0.3 mg/kg every six weeks, 1 mg/kg every six weeks, 3 mg/kg every six weeks, 0.3 mg/kg every twelve weeks, 1 mg/kg every twelve weeks, and 3 mg/kg every twelve weeks, and pembrolizumab is administered at 200 mg every three weeks.

In certain embodiments, the cancer is a cutaneous squamous-cell carcinoma (cSCC). In certain embodiments, the metastatic or locally advanced solid tumor is a Stage IV cutaneous squamous-cell carcinoma (cSCC). In certain embodiments, the cSCC is diagnosed histologically or cytologically according to the eighth edition of the American Joint Committee on Cancer staging manual. In certain embodiments, the cSCC is not curable with radiation therapy. In certain embodiments, the subject has cSCC (e.g., Stage IV cSCC), and the method comprises administering to the subject an effective amount of an anti-CTLA-4 antibody described herein, e.g., AGEN1884.H3 (IgG$_1$ S239D/A330L/I332E), or pharmaceutical composition comprising such anti-CTLA-4 antibody, as a first cancer therapy after diagnosis of the cSCC (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884.H3 (IgG$_1$ S239D/A330L/I332E), or pharmaceutical composition comprising such anti-CTLA-4 antibody, is administered at the dosage and frequency selected from the group consisting of 0.3 mg/kg every four weeks, 1 mg/kg every four weeks, 3 mg/kg every four weeks, 0.3 mg/kg every six weeks, 1 mg/kg every six weeks, 3 mg/kg every six weeks, 0.3 mg/kg every twelve weeks, 1 mg/kg every twelve weeks, and 3 mg/kg every twelve weeks. In certain embodiments, the subject has cSCC (e.g., Stage IV cSCC), and the method comprises administering to the subject an effective amount of a therapeutic combination comprising an anti-CTLA-4 antibody described herein, e.g., AGEN1884.H3 (IgG$_1$ S239D/A330L/I332E), or pharmaceutical composition comprising such anti-CTLA-4 antibody, and pembrolizumab as a first cancer therapy after diagnosis of the cSCC (e.g., within 1, 2, 3, 4, 5, or 6 days; 1, 2, 3, 4, 6, 8, or 12 weeks; or, 1, 2, 3, 4, 6, 8, or 12 months after diagnosis), optionally wherein the anti-CTLA-4 antibody described herein, e.g., AGEN1884.H3 (IgG$_1$ S239D/A330L/I332E), or pharmaceutical composition comprising such anti-CTLA-4 antibody, is administered at the dosage and frequency selected from the group consisting of 0.3 mg/kg every four weeks, 1 mg/kg every four weeks, 3 mg/kg every four weeks, 0.3 mg/kg every six weeks, 1 mg/kg every six weeks, 3 mg/kg every six weeks, 0.3 mg/kg every twelve weeks, 1 mg/kg every twelve weeks, and 3 mg/kg every twelve weeks, and pembrolizumab is administered at 200 mg every three weeks.

In certain embodiments, the anti-CTLA-4 antibody or pharmaceutical composition described herein is administered intravenously. In certain embodiments, the anti-CTLA-4 antibody or pharmaceutical composition described herein is administered intravenously at 0.01 mg/kg, 0.03 mg/kg, 0.1 mg/kg, 0.3 mg/kg, 1 mg/kg, 3 mg/kg, 6 mg/kg, or 10 mg/kg, optionally at an interval of once every two weeks. In certain embodiments, the anti-CTLA-4 antibody or pharmaceutical composition described herein is administered intravenously at 0.01 mg/kg, 0.03 mg/kg, 0.1 mg/kg, 0.3 mg/kg, 1 mg/kg, 3 mg/kg, 6 mg/kg, or 10 mg/kg, optionally at an interval of once every three weeks. In certain embodiments, the anti-CTLA-4 antibody or pharmaceutical composition described herein is administered intravenously at 0.01 mg/kg, 0.03 mg/kg, 0.1 mg/kg, 0.3 mg/kg, 1 mg/kg, 3 mg/kg, 6 mg/kg, or 10 mg/kg, optionally at an interval of once every four weeks. In certain embodiments, the anti-CTLA-4 antibody or pharmaceutical composition described herein is administered intravenously at 0.01 mg/kg, 0.03 mg/kg, 0.1 mg/kg, 0.3 mg/kg, 1 mg/kg, 3 mg/kg, 6 mg/kg, or 10 mg/kg, optionally at an interval of once every six weeks. In certain embodiments, the anti-CTLA-4 antibody or pharmaceutical composition described herein is administered intravenously at 0.01 mg/kg, 0.03 mg/kg, 0.1 mg/kg, 0.3 mg/kg, 1 mg/kg, 3 mg/kg, 6 mg/kg, or 10 mg/kg, optionally at an interval of once every twelve weeks. In certain embodiments, the anti-CTLA-4 antibody or pharmaceutical composition described herein is administered intratumorally. In certain embodiments, the anti-CTLA-4 antibody or pharmaceutical composition described herein is administered intratumorally at 0.01 mg/kg, 0.03 mg/kg, 0.1 mg/kg, 0.3 mg/kg, 1 mg/kg, or 3 mg/kg, optionally at an interval of once every three weeks. In certain embodiments, the anti-CTLA-4 antibody or pharmaceutical composition described herein is administered intratumorally at 0.03 mg/kg, 0.1 mg/kg, or 0.3 mg/kg, optionally at an interval of once every three weeks. In certain embodiments, the anti-CTLA-4 antibody or pharmaceutical composition described herein is administered intratumorally at a dose that is up to 5-fold, 10-fold, 20-fold, 30-fold, 40-fold, 50-fold, 60-fold, 70-fold, 80-fold, 90-fold, 100-fold, or 200-fold lower than a dose given by systemic administration. In certain embodiments, the anti-CTLA-4 antibody or pharmaceutical composition described herein is administered intratumorally at a dose that is up to 10-fold lower than a dose given by systemic administration. In certain embodiments, the anti-CTLA-4 antibody or pharmaceutical composition described herein is administered intratumorally at a dose that is up to 100-fold lower than a dose given by systemic administration. In certain embodiments, the anti-CTLA-4 antibody or pharmaceutical composition described herein is administered (e.g., intratumorally or systemically) as a monotherapy. In certain embodiments, the anti-CTLA-4 antibody or pharmaceutical composition described herein is administered intratumorally and the method further comprises administering an additional therapeutic agent to the subject. In certain embodiments, the additional therapeutic agent is administered systemically. In certain embodiments, the subject has a solid tumor and the additional therapeutic agent is an anti-PD-1 antibody. In certain embodiments, the anti-PD-1 antibody is pembrolizumab or nivolumab. In certain embodiments, the pembrolizumab is administered at a dose of 200 mg every three weeks. In certain embodiments, the subject has head and neck squamous cell carcinoma and the additional therapeutic agent is an anti-EGFR antibody. In certain embodiments, the anti-EGFR antibody is cetuximab. In certain embodiments, the subject has HER2+ breast cancer and the additional therapeutic agent is an anti-HER2 antibody. In certain embodiments, the anti-HER2 antibody is trastuzumab. In certain embodiments, these methods further comprise administering a chemotherapeutic agent to the subject. In certain embodiments, the chemotherapeutic agent is administered systemically. In certain embodiments, the chemotherapeutic agent is gemcitabine. In certain embodiments, the anti-CTLA-4 antibody or pharmaceutical composition described herein is administered intratumorally and the subject has an advanced or metastatic solid tumor. In certain embodiments, the anti-CTLA-4 antibody or pharmaceutical composition described herein is administered intratumorally and the subject has head and neck cancer (e.g., relapsed/refractory head and neck squamous cell carcinoma). In certain embodiments, the anti-CTLA-4 antibody or pharmaceutical composition described herein is administered intratumorally and the subject has breast cancer (e.g., relapsed/refractory HER2+ breast cancer). In certain embodiments, the anti-CTLA-4 antibody or pharmaceutical composition described herein is delivered to a tumor draining lymph node. In certain embodiments, the anti-CTLA-4 antibody or pharmaceutical composition described herein is delivered via a localized administration (e.g., subcutaneous administration). In certain embodiments, the anti-CTLA-4 antibody or pharmaceutical composition described herein is delivered via a localized administration (e.g., subcutaneous administration) at 0.01 mg/kg, 0.03 mg/kg, 0.1 mg/kg, 0.3 mg/kg, 1 mg/kg, or 3 mg/kg. In certain embodiments, the anti-CTLA-4 antibody or pharmaceutical composition described herein is delivered via a localized administration (e.g., subcutaneous administration) at a dose that is up to 5-fold, 10-fold, 20-fold, 30-fold, 40-fold, 50-fold, 60-fold, 70-fold, 80-fold, 90-fold, 100-fold, or 200-fold lower than a dose given by systemic administration. In certain embodiments, the anti-CTLA-4 antibody or pharmaceutical composition described herein is delivered via a localized administration (e.g., subcutaneous administration) at a dose that is up to 10-fold lower than a dose given by systemic administration. In certain embodiments, the anti-CTLA-4 antibody or pharmaceutical composition described herein is delivered via a localized administration (e.g., subcutaneous administration) at a dose that is up to 100-fold lower than a dose given by systemic administration. In certain embodiments, the anti-CTLA-4 antibody or pharmaceutical composition described herein is delivered via a localized administration (e.g., subcutaneous administration) and the method further comprises administering an additional therapeutic agent to the subject. In certain embodiments, the additional therapeutic agent is a vaccine. In certain embodiments, the vaccine comprises a heat shock protein peptide complex (HSPPC) comprising a heat shock protein complexed with an antigenic peptide. In one embodiment, the heat shock protein is gp96 protein and is complexed with a tumor-associated antigenic peptide, wherein the HSPPC is derived from a tumor obtained from a subject. In certain embodiments, the heat shock protein is selected from the group consisting of hsc70, hsp70, hsp90, hsp110, grp170, gp96, calreticulin, a mutant thereof, and combinations of two or more thereof. In certain embodiments, the heat shock protein is hsc70. In certain embodiments, the heat shock protein is hsp70. In certain embodiments, the antigenic peptide is synthetic. In certain embodiments, the subject has cancer. In certain embodiments, the subject has an infectious disease. In certain embodiments, these methods further comprise administering an additional therapeutic agent to the subject. In certain embodiments, the additional therapeutic agent is a chemotherapeutic or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-OX40 antibody, and an agonist anti-CD137 antibody, an agonist anti-DR3 antibody, an agonist anti-TNFSF14 antibody, and an agonist anti-CD27 antibody. In certain embodiments, the additional therapeutic agent is radiotherapy. In certain embodiments, the additional therapeutic agent is an inhibitor of indoleamine-2,3-dioxygenase (IDO). Suitable IDO inhibitors include, without limitation, epacadostat, F001287, indoximod, and NLG919. In certain embodiments, the additional therapeutic agent is a vaccine. In certain embodiments, the vaccine comprises a heat shock protein peptide complex (HSPPC) comprising a heat shock protein complexed with an antigenic peptide. In one embodiment, the heat shock protein is gp96 protein and is complexed with a tumor-associated antigenic peptide, wherein the HSPPC is derived from a tumor obtained from a subject.

In another aspect, the instant disclosure provides a method of treating an infectious disease in a subject, the method comprising administering to the subject an effective amount of an anti-CTLA-4 antibody or pharmaceutical composition described herein. In another aspect, the instant disclosure provides a method of preventing an infectious disease in a subject, the method comprising administering to the subject an effective amount of an anti-CTLA-4 antibody or pharmaceutical composition described herein.

In one embodiment, the present invention relates to an antibody of the present invention, a polynucleotide of the invention, a vector of the invention, and/or a recombinant host cell of the invention, for use as a medicament.

In one embodiment, the present invention relates to an antibody of the present invention, a polynucleotide of the invention, a vector of the invention, and/or a recombinant host cell of the invention, for use as a diagnostic.

In one embodiment, the present invention relates to the use of an antibody of the present invention, a polynucleotide of the invention, a vector of the invention, and/or a recombinant host cell of the invention, for the in vitro detection of human CTLA-4 in a biological sample.

In one aspect, provided herein is a pharmaceutical composition comprising an anti-CTLA-4 antibody described herein and a pharmaceutically acceptable carrier or excipient, for use as a medicament.

In one aspect, provided herein is a pharmaceutical composition comprising an anti-CTLA-4 antibody described herein and a pharmaceutically acceptable carrier or excipient, for use as a diagnostic.

In one aspect, provided herein is a pharmaceutical composition comprising an anti-CTLA-4 antibody described herein, a polynucleotide of the invention, a vector of the invention, and/or a recombinant host cell of the invention, and a pharmaceutically acceptable carrier or excipient. In one aspect, the pharmaceutical composition is for use as a medicament and/or diagnostic.

In one aspect, the present invention relates to an antibody, polynucleotide, vector, recombinant host cell, and/or pharmaceutical composition of the present invention, for use in a method for increasing T-cell activation in response to an antigen.

In one aspect, the present invention relates to an antibody, polynucleotide, vector, recombinant host cell, and/or pharmaceutical composition of the present invention, for use in a method for increasing T-cell activation in response to an antigen in a subject.

In one aspect, the present invention relates to an antibody, polynucleotide, vector, recombinant host cell, and/or pharmaceutical composition of the present invention, for use in a method for increasing T-cell activation in response to an antigen in a subject comprising administering to the subject an effective amount of an antibody, polynucleotide, vector, recombinant host cell, and/or pharmaceutical composition of the invention.

In one aspect, the present invention relates to an antibody, polynucleotide, vector, recombinant host cell, and/or pharmaceutical composition of the present invention, for use in a method for the treatment of cancer.

In one aspect, the present invention relates to an antibody, polynucleotide, vector, recombinant host cell, and/or pharmaceutical composition of the present invention, for use in a method for the treatment of cancer in a subject.

In one aspect, the present invention relates to an antibody, polynucleotide, vector, recombinant host cell, and/or pharmaceutical composition of the present invention, for use in a method for the treatment of cancer in a subject comprising administering to the subject an effective amount of an antibody, polynucleotide, vector, recombinant host cell, and/or pharmaceutical composition of the invention.

In one aspect, the present invention relates to (a) an antibody, polynucleotide, vector, recombinant host cell, and/or pharmaceutical composition of the present invention and (b) an additional therapeutic agent, preferably an anti-PD-1 antibody, for use as a medicament.

In one aspect, the present invention relates to (a) an antibody, polynucleotide, vector, recombinant host cell, and/or pharmaceutical composition of the present invention and (b) an additional therapeutic agent, preferably an anti-PD-1 antibody, for use in a method for the treatment of cancer. In a preferred embodiment, the cancer is a solid tumor. In another preferred embodiment, the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent, preferably an anti-PD-1 antibody.

In one aspect, the present invention relates to (a) an antibody, polynucleotide, vector, recombinant host cell, and/or pharmaceutical composition of the present invention and (b) an anti-EGFR antibody, and optionally (c) a chemotherapeutic agent, for use as a medicament.

In one aspect, the present invention relates to (a) an antibody, polynucleotide, vector, recombinant host cell, and/or pharmaceutical composition of the present invention and (b) an anti-EGFR antibody, and optionally (c) a chemotherapeutic agent, for use in a method for the treatment of cancer. In a preferred embodiment, the cancer is head and neck squamous cell carcinoma. In another preferred embodiment, the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to a pharmaceutical composition, kit or kit-of-parts comprising (a) an antibody, polynucleotide, vector, recombinant host cell, and/or pharmaceutical composition of the present invention and (b) an anti-EGFR antibody, and optionally (c) a chemotherapeutic agent.

In one aspect, the present invention relates to (a) an antibody, polynucleotide, vector, recombinant host cell, and/or pharmaceutical composition of the present invention and (b) an anti-HER2 antibody, and optionally (c) a chemotherapeutic agent, for use as a medicament.

In one aspect, the present invention relates to (a) an antibody, polynucleotide, vector, recombinant host cell, and/or pharmaceutical composition of the present invention and (b) an anti-HER2 antibody, and optionally (c) a chemotherapeutic agent, for use in a method for the treatment of HER2+ breast cancer. In another preferred embodiment, the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to a pharmaceutical composition, kit or kit-of-parts comprising (a) an antibody, polynucleotide, vector, recombinant host cell, and/or pharmaceutical composition of the present invention and (b) an anti-HER2 antibody, and optionally (c) a chemotherapeutic agent.

In one aspect, the present invention relates to an antibody, polynucleotide, vector, recombinant host cell, and/or pharmaceutical composition of the present invention, for use in a method for the treatment of cancer, wherein the antibody, polynucleotide, vector, recombinant host cell, and/or pharmaceutical composition of the present invention is administered intratumorally to the subject, preferably administered intratumorally to the subject at 0.01 mg/kg, 0.03 mg/kg, 0.1 mg/kg, 0.3 mg/kg, 1 mg/kg, or 3 mg/kg, optionally at an interval of once every three weeks.

In one aspect, the present invention relates to an antibody, polynucleotide, vector, recombinant host cell, and/or pharmaceutical composition of the present invention, for use in a method for the treatment of cancer, wherein the antibody, polynucleotide, vector, recombinant host cell, and/or pharmaceutical composition of the present invention is administered subcutaneously or intravenously to the subject, preferably administered intravenously to the subject at 0.01 mg/kg, 0.03 mg/kg, 0.1 mg/kg, 0.3 mg/kg, 1 mg/kg, 3 mg/kg, 6 mg/kg, or 10 mg/kg, optionally at an interval of once every three weeks.

In one aspect, the present invention relates to (a) an antibody, polynucleotide, vector, recombinant host cell, and/or pharmaceutical composition of the present invention and (b) an additional therapeutic agent, for use as a medicament. In a preferred embodiment, the additional therapeutic agent is a chemotherapeutic agent or a checkpoint targeting agent or an inhibitor of indoleamine-2,3-dioxygenase (IDO) or a vaccine.

In one aspect, the present invention relates to (a) an antibody, polynucleotide, vector, recombinant host cell, and/or pharmaceutical composition of the present invention and (b) an additional therapeutic agent, for use in a method for the treatment of cancer. In a preferred embodiment, the additional therapeutic agent is a chemotherapeutic agent or a checkpoint targeting agent or an inhibitor of indoleamine-2,3-dioxygenase (IDO) or a vaccine.

In one aspect, the present invention relates to a pharmaceutical composition, kit or kit-of-parts comprising (a) an antibody, polynucleotide, vector, recombinant host cell, and/or pharmaceutical composition of the present invention and (b) an additional therapeutic agent. In a preferred embodiment, the additional therapeutic agent is a chemotherapeutic agent or a checkpoint targeting agent or an inhibitor of indoleamine-2,3-dioxygenase (IDO) or a vaccine.

In one aspect, the present invention relates to an antibody, polynucleotide, vector, recombinant host cell, and/or pharmaceutical composition of the present invention, for use in a method for the treatment of cancer, and/or for use in a method for increasing T-cell activation in response to an antigen, wherein the antibody, polynucleotide, vector, recombinant host cell, and/or pharmaceutical composition of the present invention is delivered to a tumor draining lymph node.

In one aspect, the present invention relates to the use of an antibody, polynucleotide, vector, recombinant host cell, and/or pharmaceutical composition of the present invention in a method for the treatment of cancer, and/or in a method for increasing T-cell activation in response to an antigen in a subject, wherein the antibody, polynucleotide, vector, recombinant host cell, and/or pharmaceutical composition of the present invention is delivered to a tumor draining lymph node.

In one aspect, the present invention relates to the use of an antibody, polynucleotide, vector, recombinant host cell, and/or pharmaceutical composition of the present invention, for preparing medicaments for immunotherapy, for example, for increasing T-cell activation in response to an antigen in a subject, treating cancer, or treating or preventing infectious diseases.

In one aspect, the present invention relates to the use of an antibody, polynucleotide, vector, recombinant host cell, and/or pharmaceutical composition of the present invention, for preparing medicaments for immunotherapy, for example, for increasing T-cell activation in response to an antigen in a subject, treating cancer, or treating or preventing infectious diseases, wherein the antibody, polynucleotide, vector, recombinant host cell, and/or pharmaceutical composition of the present invention is delivered to a tumor draining lymph node.

In one aspect, the present invention relates to the use of (a) an antibody, polynucleotide, vector, recombinant host cell, and/or pharmaceutical composition of the present invention and (b) an anti-HER2 antibody, and optionally (c) a chemotherapeutic agent, to prepare a medicament for immunotherapy, for example, for increasing T-cell activation in response to an antigen in a subject, treating cancer, or treating or preventing infectious diseases.

In one aspect, the present invention relates to the use of (a) an antibody, polynucleotide, vector, recombinant host cell, and/or pharmaceutical composition of the present invention and (b) an anti-HER2 antibody, and optionally (c) a chemotherapeutic agent, to prepare a medicament for immunotherapy, for example, for increasing T-cell activation in response to an antigen in a subject, treating cancer, or treating or preventing infectious diseases, wherein the antibody, polynucleotide, vector, recombinant host cell, and/or pharmaceutical composition of the present invention is delivered to a tumor draining lymph node.

5. BRIEF DESCRIPTION OF THE DRAWINGS

FIGS. 1A, 1B, 1C, 1D, 1E, 1F, and 1G are flow cytometry histograms showing the binding of anti-CTLA-4 antibodies or an $IgG_1$ isotype control antibody to Jurkat cells engineered to express human CTLA-4 on the cell surface. The anti-CTLA-4 antibodies tested are: AGEN1884.H1.1 (Ig AGEN1884.H1.2 ($IgG_1$), AGEN1884.H1.3 ($IgG_1$), AGEN1884.H2.1 ($IgG_1$), AGEN1884.H2.2 ($IgG_1$), AGEN1884.H2.3 ($IgG_1$), and AGEN1884.H3 ($IgG_1$).

FIG. 2 is a graph showing IL-2 production of primary human PBMCs following incubation under sub-optimal stimulation with the Staphylococcal Enterotoxin A (SEA) superantigen in the absence or presence of the anti-CTLA-4 antibody AGEN1884.H3 ($IgG_1$) or an isotype control antibody ($IgG_1$). Replicates of eight were performed for each group and the mean values of the eight replicates are indicated with a black bar.

Figure 3:
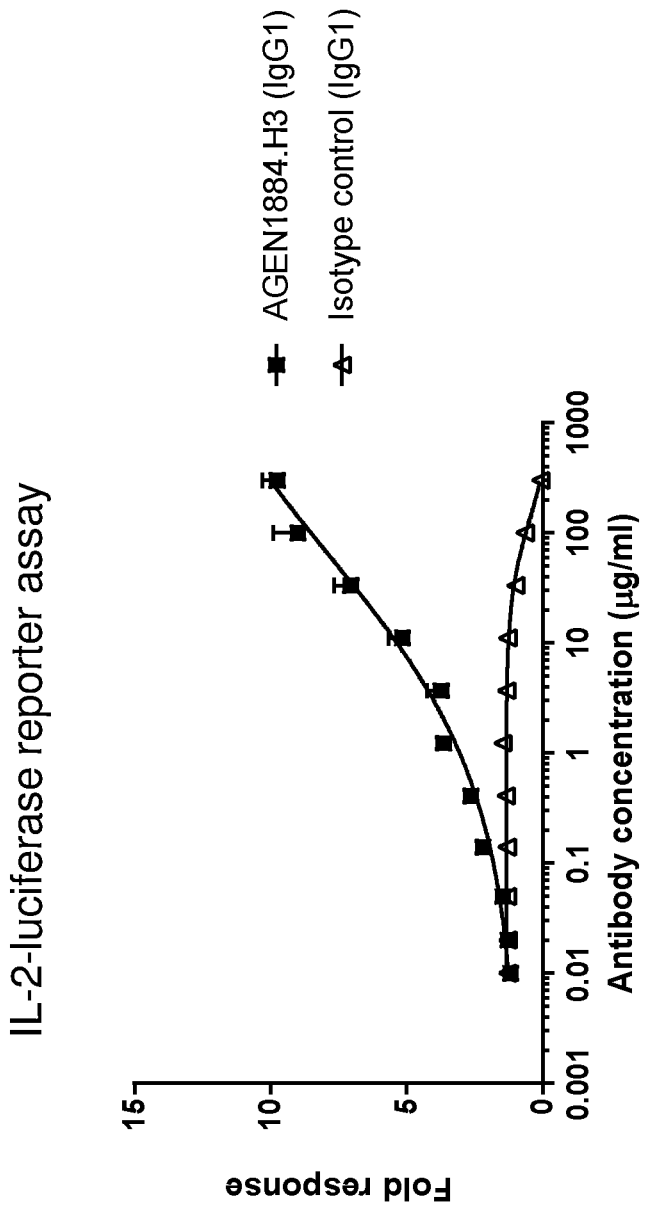

FIG. 3 is a graph showing results from an IL-2-luciferase reporter assay demonstrating that blockade of CTLA-4 leads to T cell activation. Fold response of luciferase expression, a surrogate marker for IL-2 gene activation, is plotted over a range of antibody concentrations for AGEN1884.H3 ($IgG_1$) or an isotype control antibody ($IgG_1$).

Figure 4:
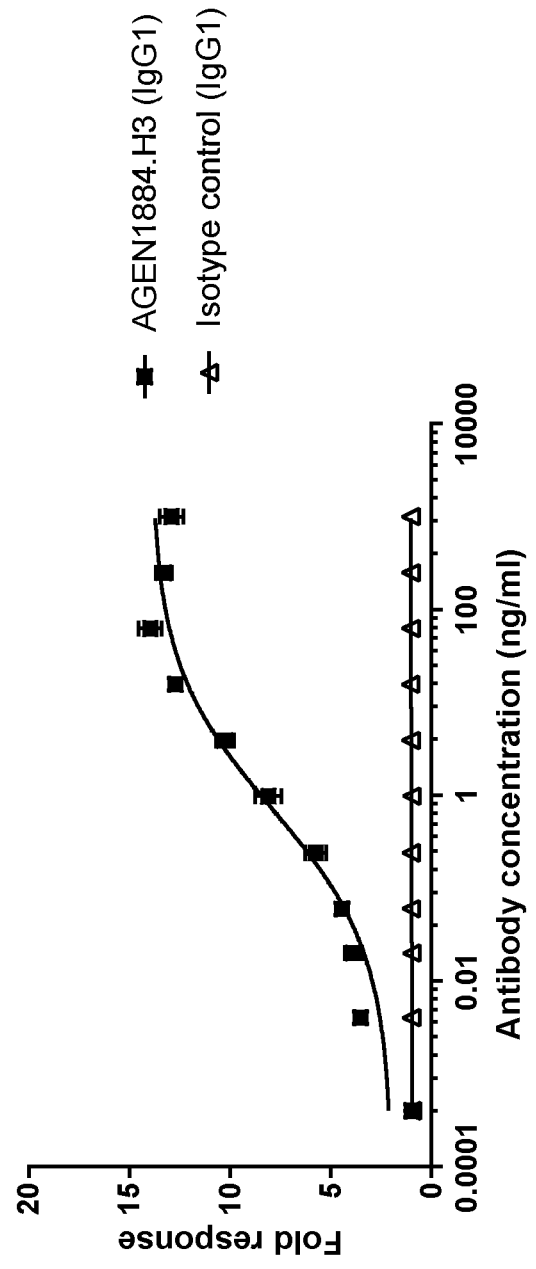
Figure 5A:
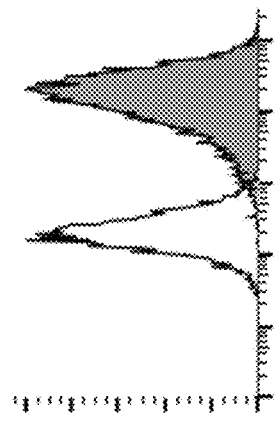
Figure 5B:
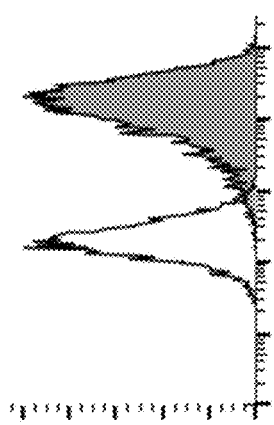
Figure 5C:
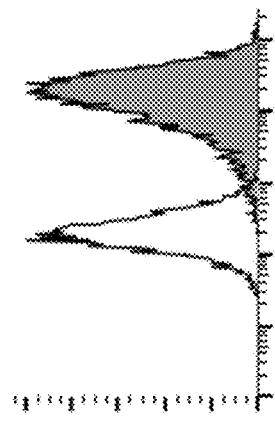
Figure 5D:
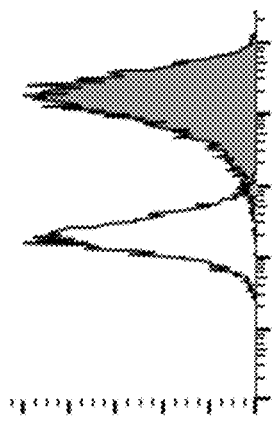

FIG. 4 is a graph showing results from a reporter assay where simultaneous engagement of AGEN1884.H3 ($IgG_1$) to target cells (via CTLA-4 binding) and effector cells (via FcγRIIIA binding) triggers expression of luciferase by the effector cell line. Luciferase activity is a surrogate marker for FcγRIIIA signaling. Fold response of RLU values is plotted against a range of antibody concentrations for AGEN1884.H3 ($IgG_1$) and an isotype control antibody ($IgG_1$).

FIGS. 5A, 5B, 5C, and 5D are flow cytometry histograms showing CTLA-4-expressing Jurkat cells incubated with the anti-CTLA-4 antibody AGEN1884.H3 ($IgG_1$), AGEN1884.H3 ($IgG_1$ S239D/I332E), AGEN1884.H3 ($IgG_1$ S239D/A330L/I332E), or AGEN1884.H3 ($IgG_1$ L235V/F243L/R292P/Y300L/P396L), or an isotype control antibody. Antibody binding was detected using a fluorochrome-conjugated secondary antibody.

Figure 6A:
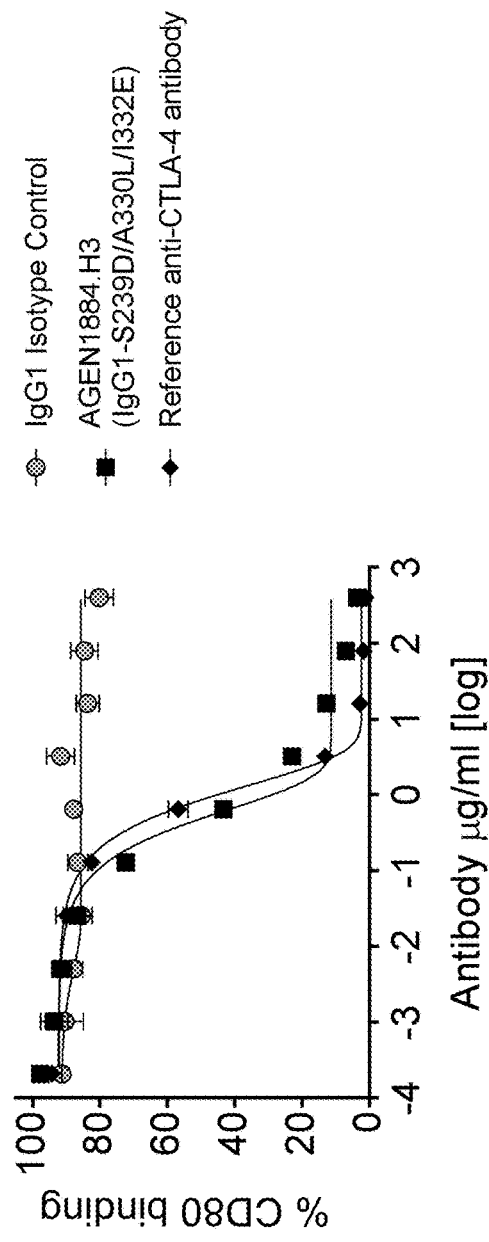
Figure 6B:
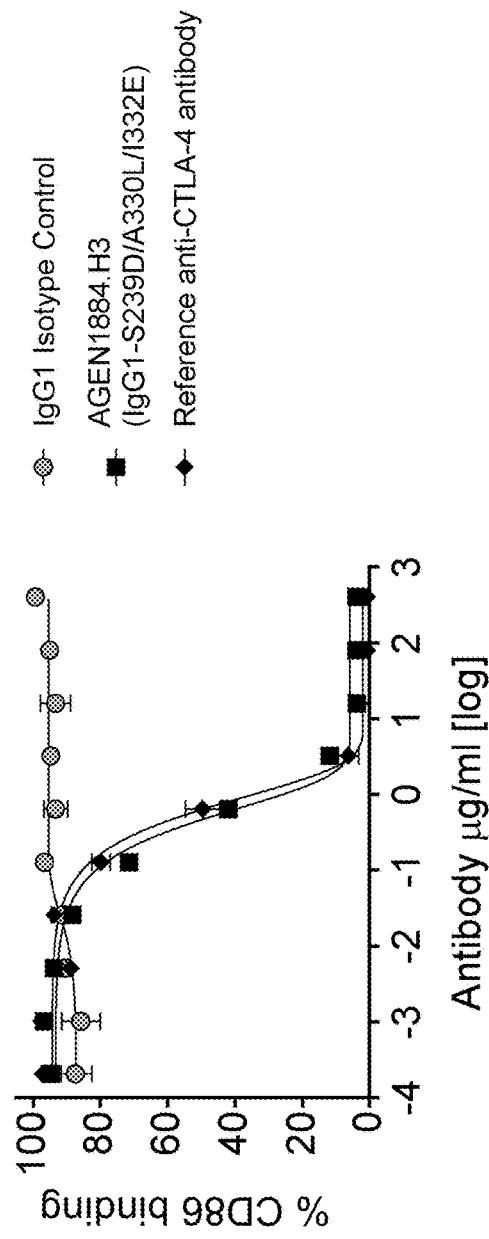

FIGS. 6A and 6B are graphs showing blocking of binding between human CTLA-4 and its ligands, CD80 and CD86, respectively, by AGEN1884.H3 ($IgG_1$ S239D/A330L/I332E). Jurkat cells engineered to constitutively express human CTLA-4 were incubated with anti-CTLA-4 antibody AGEN1884.H3 ($IgG_1$-S239D/A330E/I332E), a reference anti-CTLA-4 antibody, or an isotype control antibody ($IgG_1$), and then stained with the indicated fluorescently labeled ligand. Ligand binding was then assessed by flow cytometry.

Figure 7B:
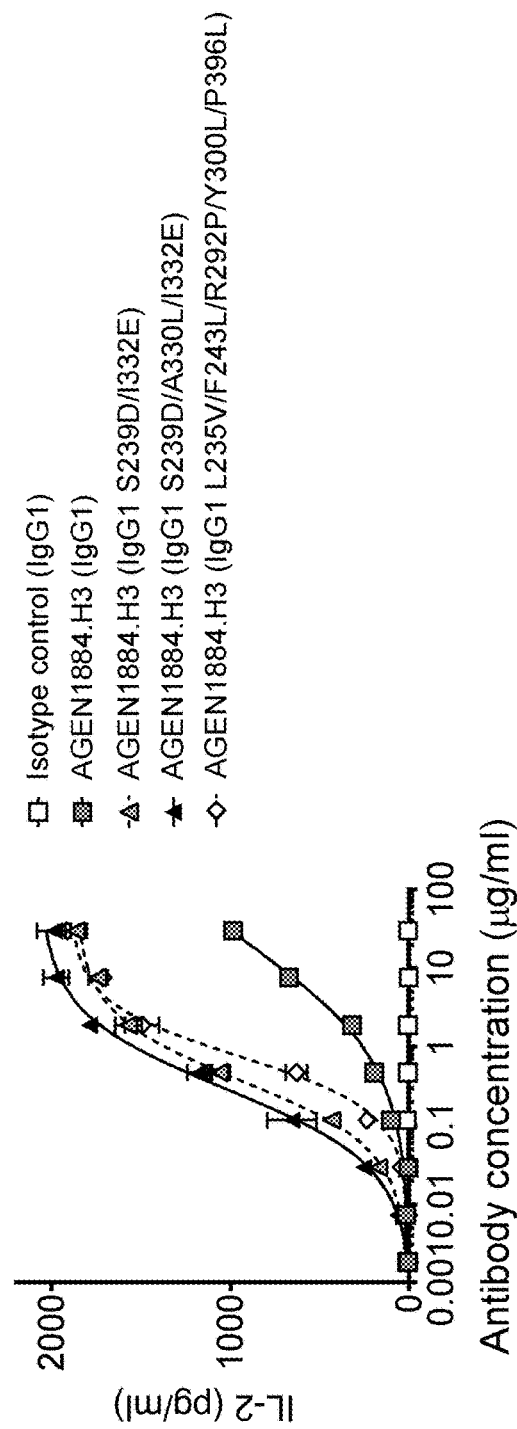
Figure 7C:
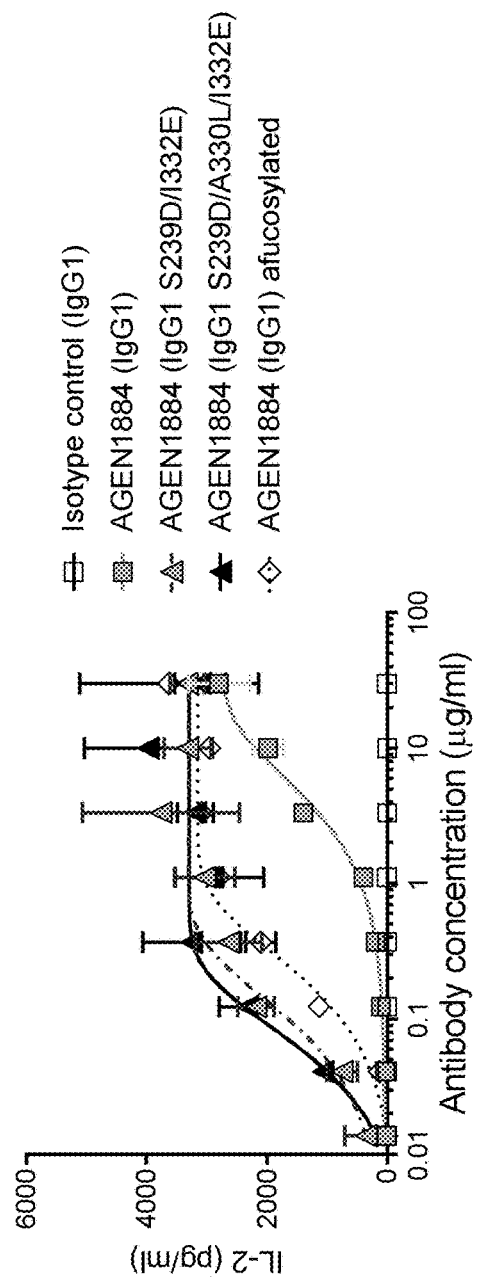

FIGS. 7A, 7B, and 7C are graphs showing IL-2 production of primary human PBMCs cultured under sub-optimal stimulation with the SEA superantigen in the absence or presence of an isotype control antibody ($IgG_1$) or an anti-CTLA-4 antibody. FIGS. 7A and 7B are graphs showing IL-2 production stimulated by either a single dose or a dose titration of the isotype control antibody ($IgG_1$) or the anti-CTLA-4 antibodies AGEN1884.H3 ($IgG_1$), AGEN1884.H3 ($IgG_1$ S239D/I332E), AGEN1884.H3 ($IgG_1$ S239D/A330L/

I332E), and AGEN1884.H3 (IgG$_1$ L235V/F243L/R292P/Y300L/P396L). In the study shown in FIG. 7B, in addition to the isotype control antibody (IgG$_1$) or the anti-CTLA-4 antibody, the cells in each sample were also incubated with an IgG$_4$ S228P isotype control antibody. FIG. 7C is a graph showing IL-2 production stimulated by a dose titration of the isotype control antibody (IgG$_1$) or the anti-CTLA-4 antibodies AGEN1884 (IgG$_1$), AGEN1884 (IgG$_1$ S239D/I332E), AGEN1884 (IgG$_1$ S239D/A330L/I332E), and afucosylated AGEN1884 (IgG$_1$).

Figure 8A:
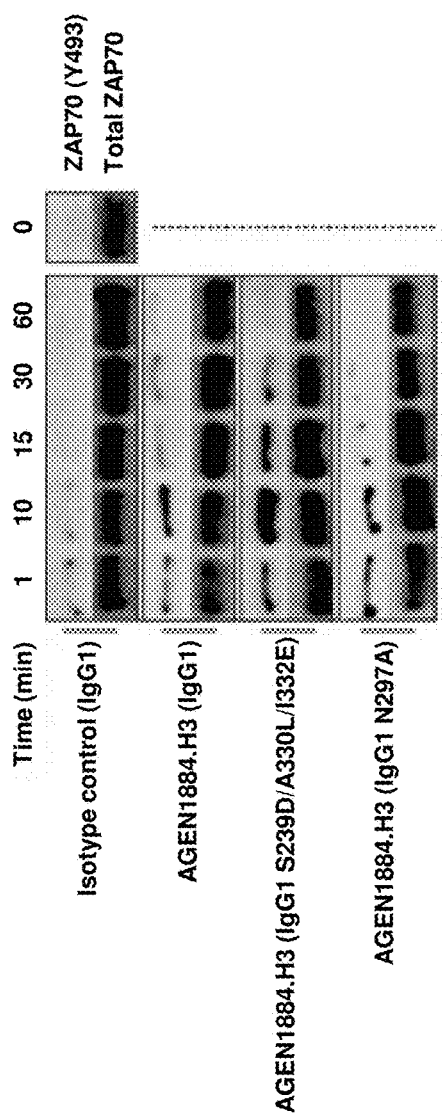
Figure 8B:
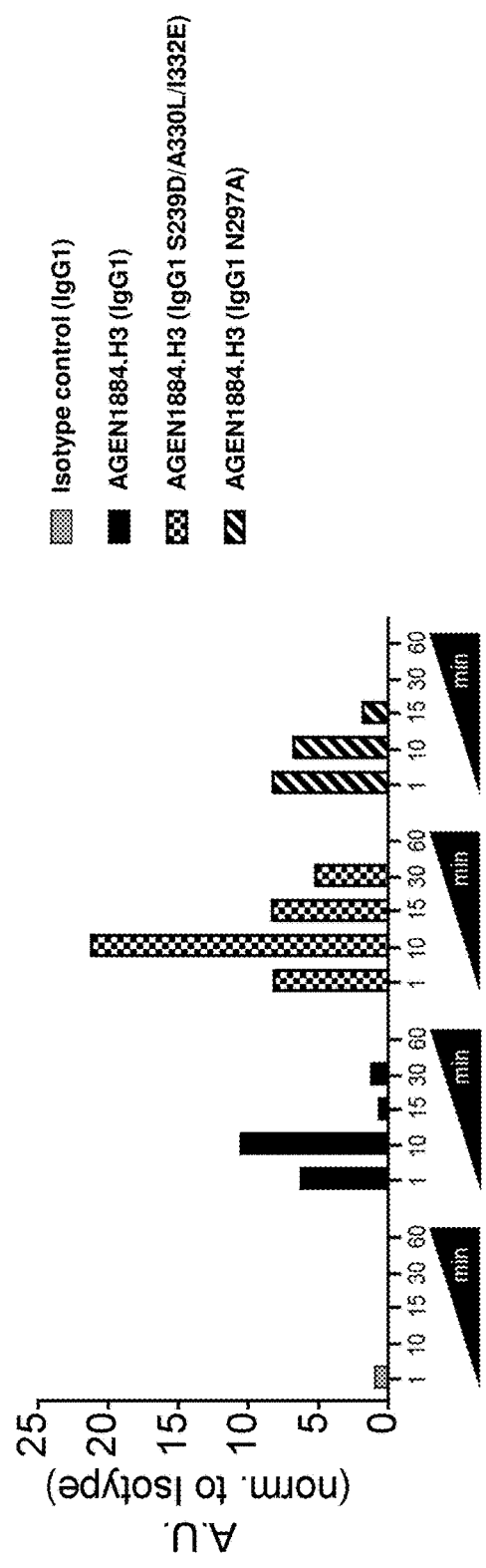

FIG. 8A is an immunoblot analysis for phosphorylated ZAP70 (Y493) in human PBMCs following stimulation with 50 ng/ml of SEA superantigen and 10 μg/ml of isotype control antibody (IgG$_1$) or the anti-CTLA-4 antibodies AGEN1884.H3 (IgG$_1$), AGEN1884.H3 (IgG$_1$ S239D/A330L/I332E), or AGEN1884.H3 (IgG$_1$ N297A). FIG. 8B is a chart showing normalized densitometric analysis of the data shown in FIG. 8A.

Figure 9A:
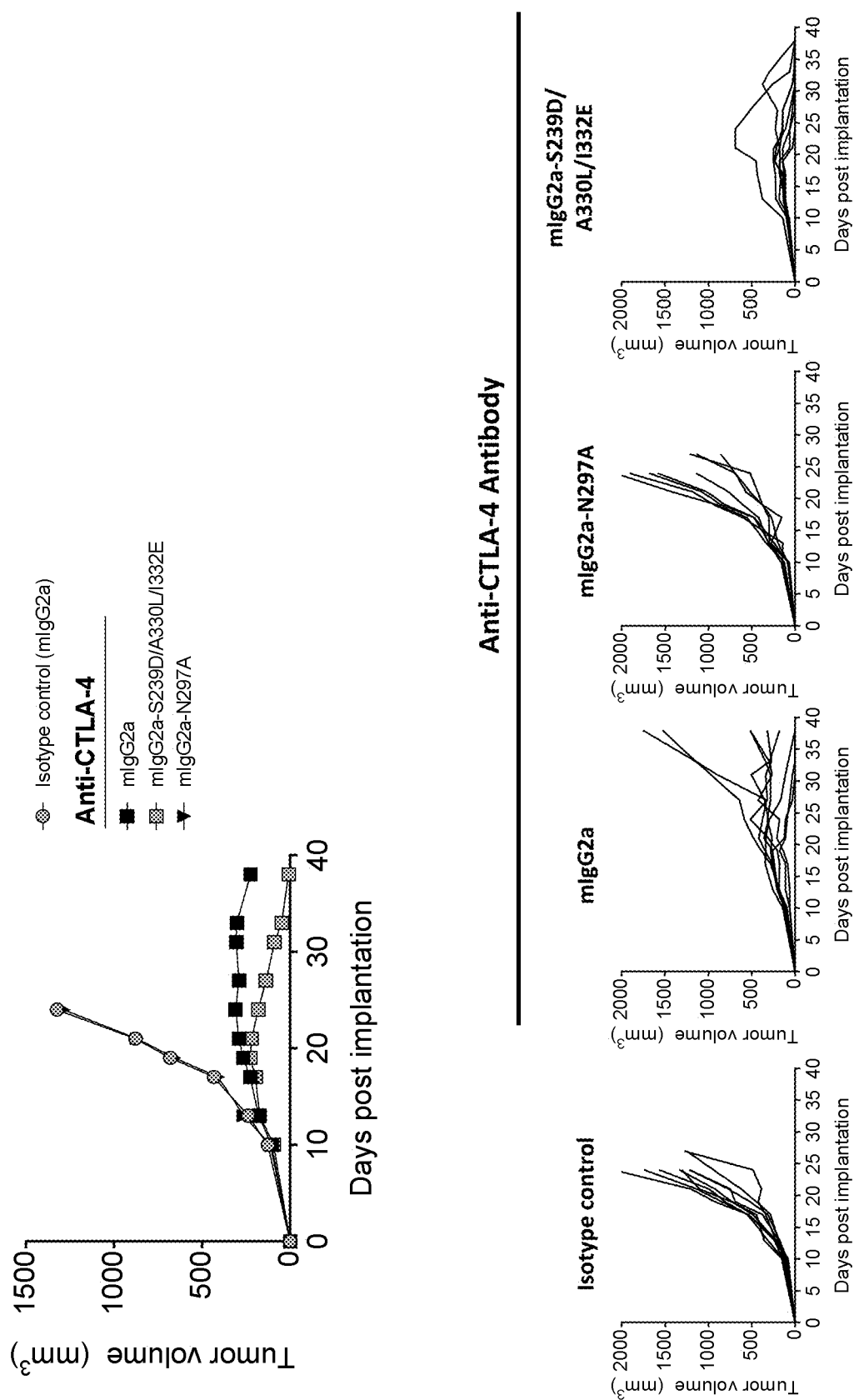
Figure 9B:
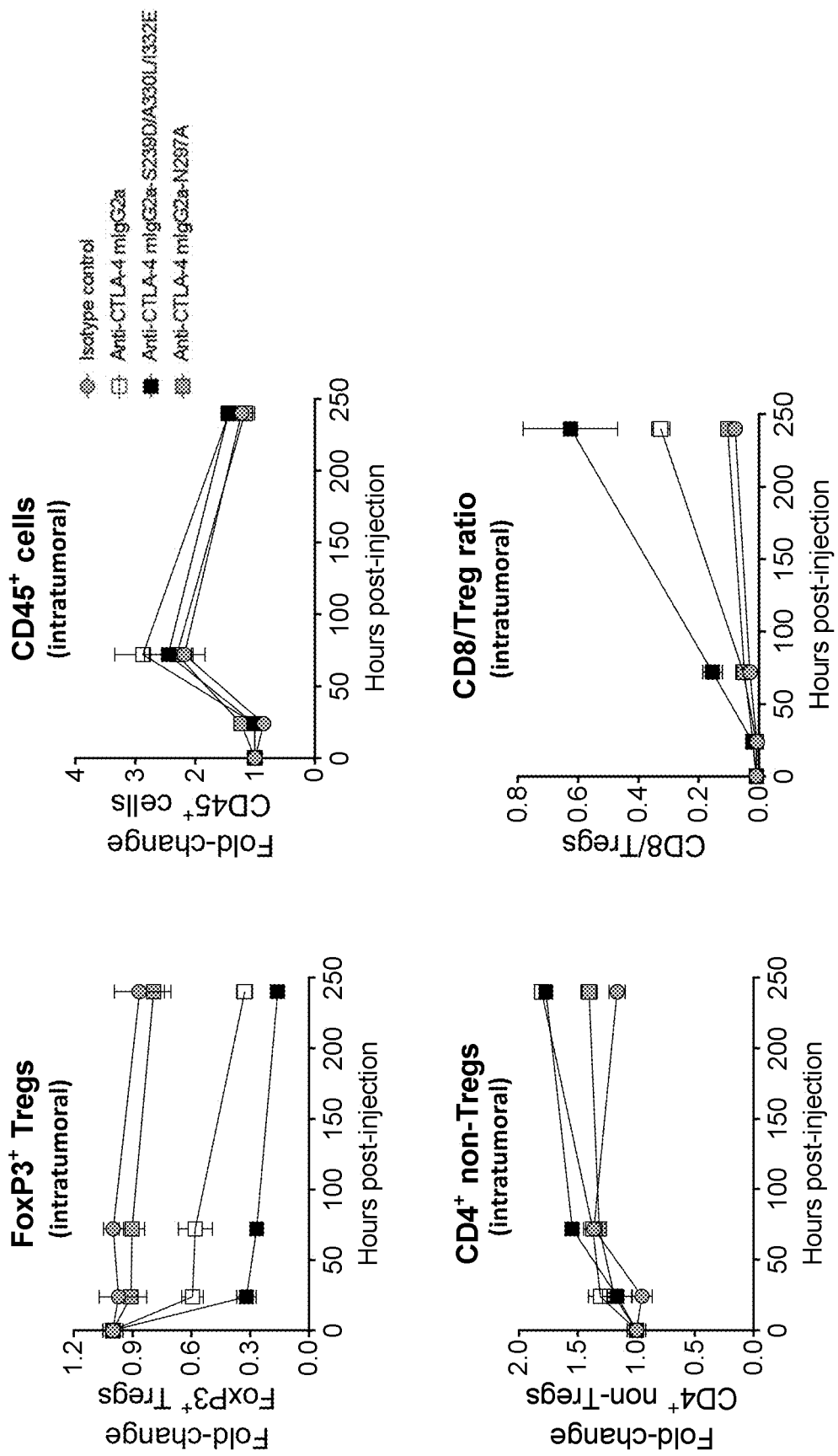
Figure 9C:
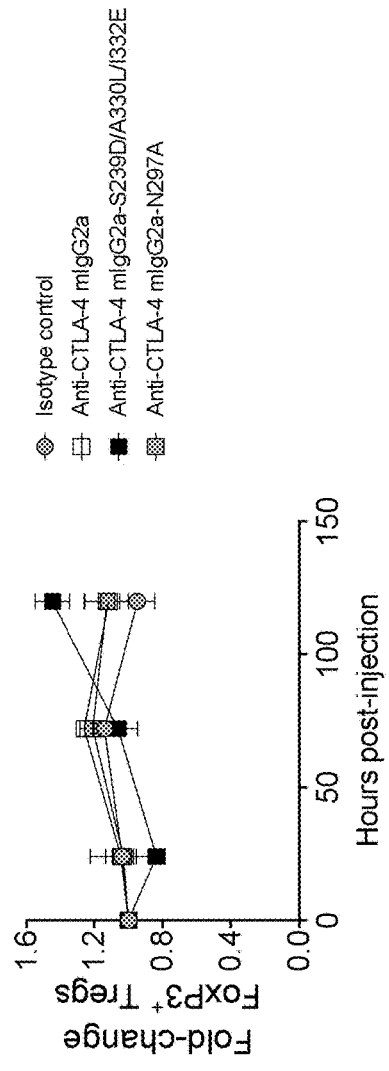
Figure 9D:
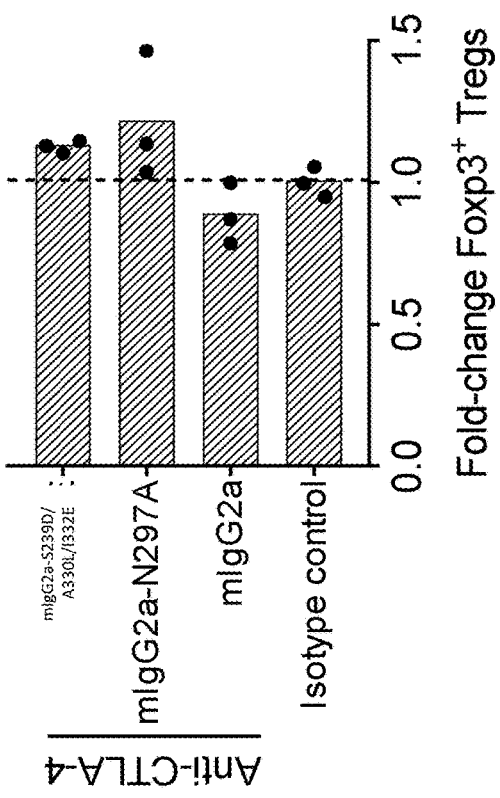

FIGS. 9A, 9B, 9C, and 9D are graphs showing antitumor efficacy and intratumoral regulatory T cell (Treg) depletion induced by Fc variants of murine anti-CTLA-4 antibody 9D9. FIG. 9A shows tumor growth in CT26 mice following single-dose treatment with murine anti-CTLA-4 antibody 9D9 (mIgG2a), an Fc-silent variant of anti-CTLA-4 antibody 9D9 (mIgG2a-N297A), an Fc variant of anti-CTLA-4 antibody 9D9 (mIgG2a-S239D/A330L/I332E), or an isotype control antibody (mIgG2a). The upper panel shows median tumor volume over time for each treatment group. The remaining panels show tumor volume over time for individual animals in each treatment group. FIG. 9B shows the effect of anti-CTLA-4 antibody treatment on T cell populations from tumor infiltrates collected from mice treated with single doses of anti-CTLA-4 antibody 9D9 (mIgG2a), anti-CTLA-4 antibody 9D9 (mIgG2a-N297A), anti-CTLA-4 antibody 9D9 (mIgG2a-S239D/A330L/I332E), or isotype control antibody (mIgG2a). Tumor infiltrates were harvested and analyzed by flow cytometry at indicated time points after injection with antibody. Cell populations analyzed include: FoxP3+ Tregs (upper left panel), CD45+ leukocytes (upper right panel), and CD4+ non-Tregs (lower left panel). The lower right panel shows the ratio of CD8+ T cells to Tregs observed in tumor infiltrates. FIG. 9C shows FoxP3+ Treg populations over time in tumor-draining lymph nodes harvested from mice treated as described for FIG. 9B. FIG. 9D shows fold-change in splenic FoxP3+ Tregs at 72 hours after treatment as described for FIG. 9B.

Figure 10:
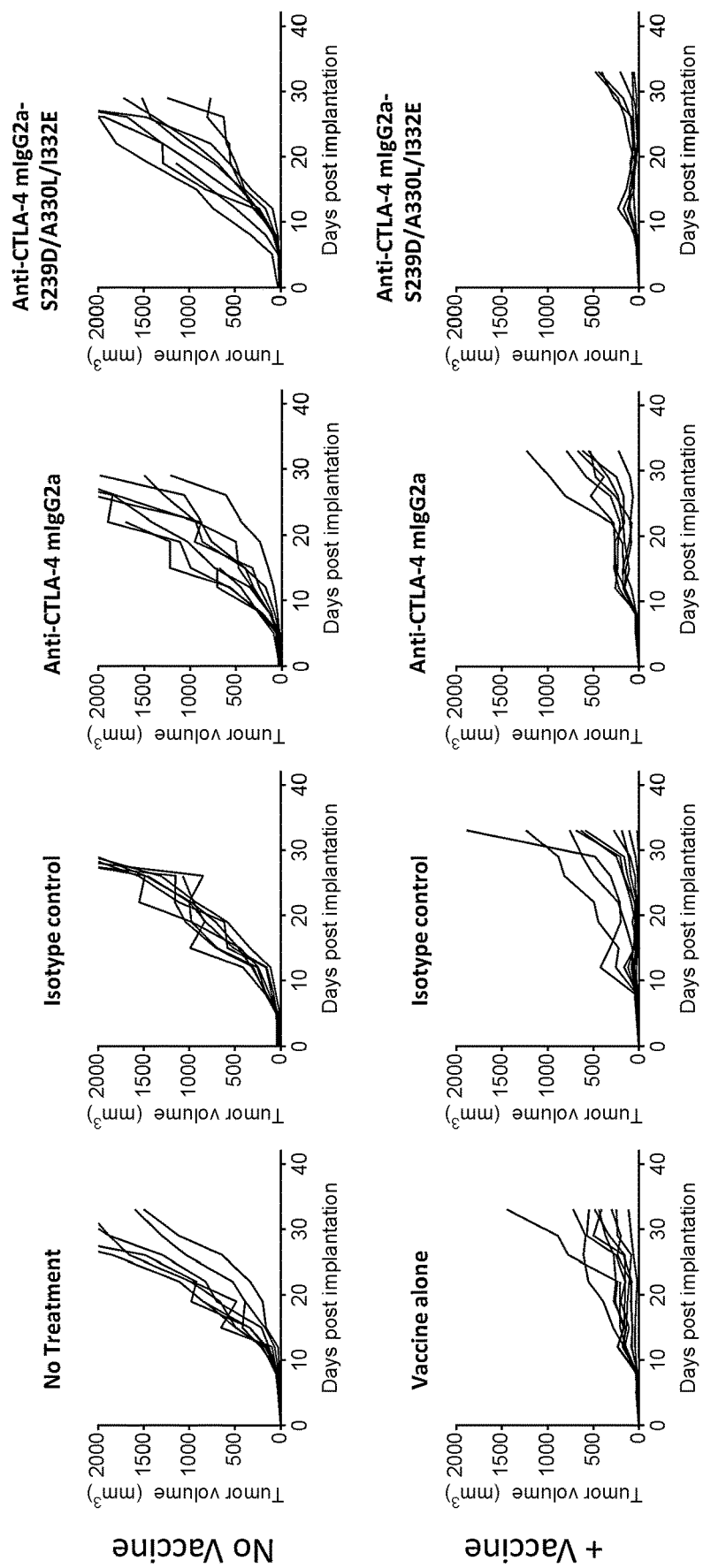

FIG. 10 is a series of graphs showing antitumor efficacy of murine anti-CTLA-4 antibodies when combined with tumor vaccine derived from a HPV+ tumor (viral antigens E6/E7). Shown are tumor volume over time for individual mice receiving no treatment, isotype control antibody (mIgG2a), anti-CTLA-4 antibody 9D9 (mIgG2a), or an Fc variant of anti-CTLA-4 antibody 9D9 (mIgG2a-S239D/A330L/I332E). Graphs in the top row show results for animals that were administered the indicated antibody treatment only. Graphs in the bottom row show results for animals that were administered the indicated antibody treatment in combination with tumor vaccine.

Figure 11A:
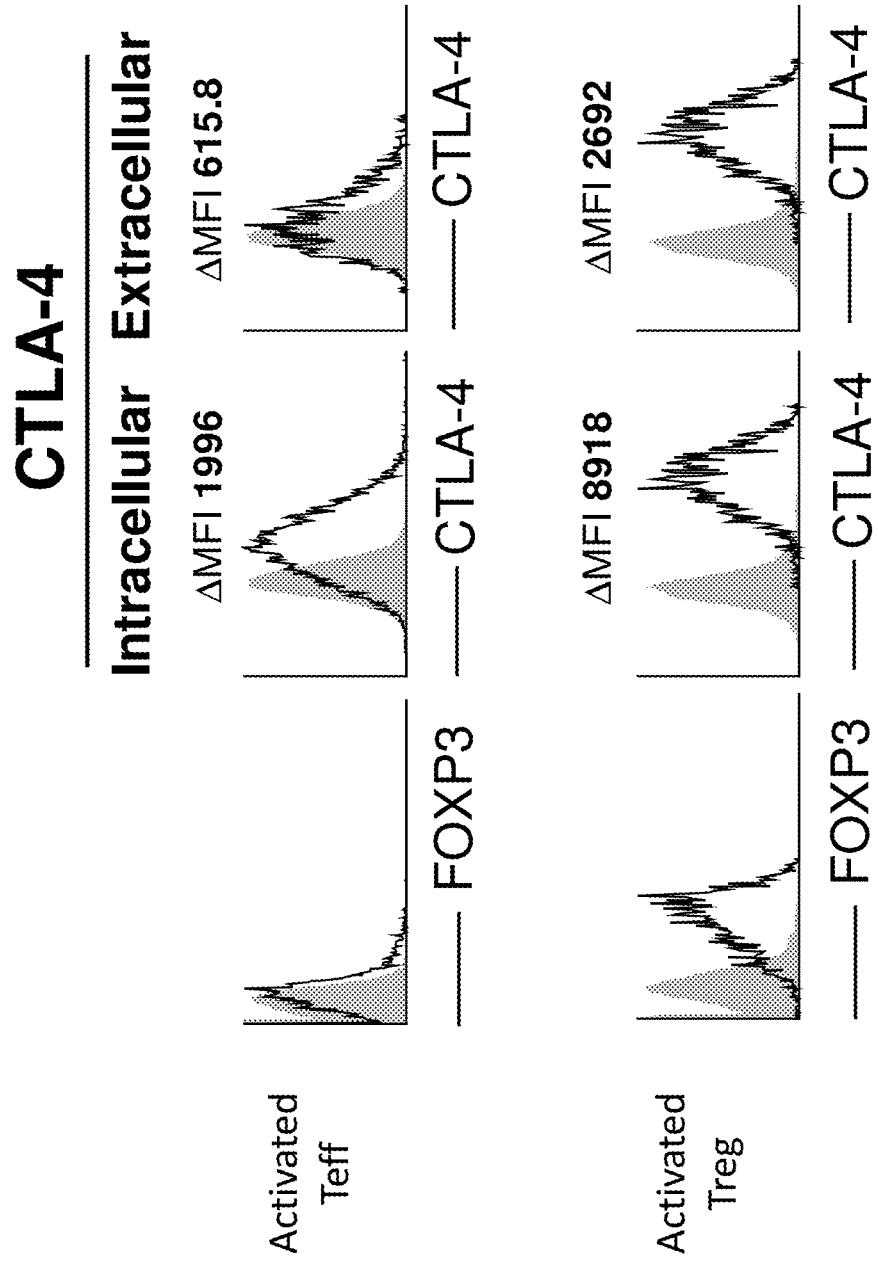
Figure 11B:
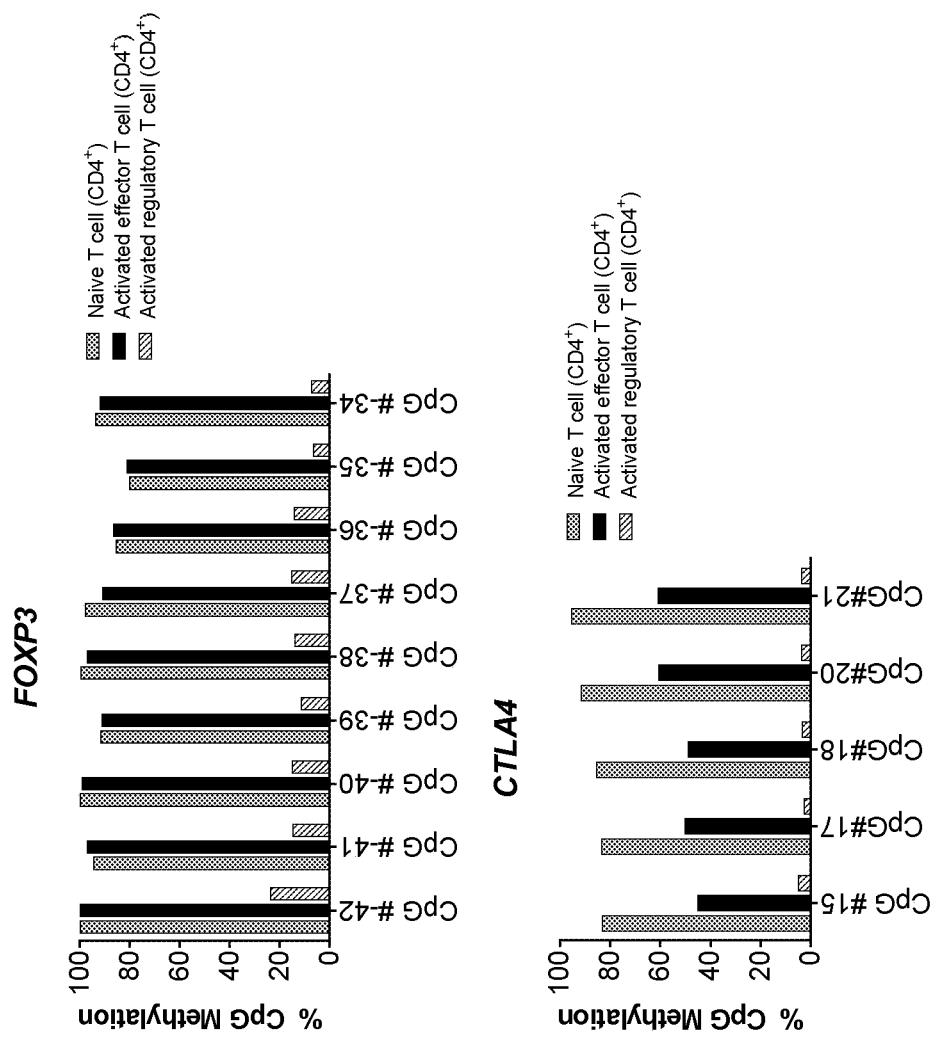

FIGS. 11A and 11B are graphs showing gene expression and CpG methylation of human T cell populations. CD4$^+$ CD25$^{+/-}$ FOXP3$^-$ non-regulatory T cells (Teff) and CD4$^+$ CD25$^+$ FOXP3$^+$ regulatory T cells (Treg) were isolated from peripheral blood of healthy donors, expanded, and activated. FIG. 11A shows FOXP3, intracellular CTLA-4, and membrane CTLA-4 levels in each activated T cell population, as determined by flow cytometry. FIG. 11B shows the level of CpG methylation in CpG regions within the FOXP3 (top panel) and CTLA4 (bottom panel) loci in naïve T cells, activated effector T cells, and activated regulatory T cells, each from the same donor.

FIGS. 12A and 12B are graphs showing time courses of antibody dependent cellular cytotoxicity (ADCC) of human CTLA-4+ target cells after incubation with anti-CTLA-4 antibody AGEN1884.H3 (IgG$_1$) or Fc variants thereof. NK-92 cells (FcγRIIIA V158-expressing) were co-cultured with CTLA-4+ target cells that were incubated with different Fc variants of anti-CTLA-4 antibodies or an IgG$_1$ isotype control (10 μg/ml). High content microscopy of caspase 3/7 activation was then used to quantify ADCC activity. FIG. 12A shows ADCC activity in Jurkat cells engineered to express CTLA-4 on the cell surface, when incubated with AGEN1884.H3 (Ig AGEN1884.H3 (IgG$_1$ N297A), AGEN1884.H3 (IgG$_1$ S239D/A330L/I332E), AGEN1884.H3 (IgG$_1$ S267E/L328F), afucosylated AGEN1884.H3 (IgG$_1$), or an isotype control antibody (IgG$_1$). FIG. 12B shows ADCC activity in primary human activated effector T cells (left panel) or regulatory T cells (right panel) when incubated with these antibodies.

FIGS. 13A, 13B, 13C, and 13D are graphs showing the effects of anti-CTLA-4 antibody variants on T cell function when administered alone or in combination with an anti-PD-1 antibody. Human PBMCs were isolated from two donors and incubated under stimulatory culture conditions with anti-CTLA-4 antibody AGEN1884.H3 (IgG$_1$), an Fc variant anti-CTLA-4 antibody AGEN1884.H3 (IgG$_1$ S239D/A330L/I332E), or an isotype control antibody (IgG$_1$), in combination with a reference anti-PD-1 antibody or an isotype control antibody (IgG$_4$), as indicated. For each treatment condition listed, a dosage titration was used for the first-listed antibody, and a fixed concentration (5 μg/ml) was used for the second-listed antibody. This experiment was performed twice, for a total of two replicates per donor. The levels of IL-2 production induced by each antibody combination on PBMCs collected from the first donor are shown in FIG. 13A (replicate 1) and FIG. 13B (replicate 2). The levels of IL-2 production induced by each antibody combination on PBMCs collected from the second donor are shown in FIG. 13C (replicate 1) and FIG. 13D (replicate 2).

FIGS. 14A, 14B, and 14C are a series of sequence alignments. FIG. 14A is a sequence alignment for human CTLA-4 (SEQ ID NO: 33), cynomolgus monkey CTLA-4 (SEQ ID NO: 40), mouse CTLA-4 (SEQ ID NO: 41), and rat CTLA-4 (SEQ ID NO: 42). Dots represent residues identical to corresponding human residues. An "*" (asterisk) indicates positions which have a single, fully conserved residue. A ":" (colon) indicates conservation between groups of strongly similar properties. A "." (period) indicates conservation between groups of weakly similar properties. FIGS. 14B and 14C are sequence alignments for human CTLA-4 (residues 1-144 and residues 145-223 of SEQ ID NO: 33, respectively), cynomolgus monkey CTLA-4 (residues 1-144 and residues 145-223 of SEQ ID NO: 40, respectively), human CD28 (residues 1-127 and residues 128-220 of SEQ ID NO: 43, respectively), human ICOS (residues 1-124 and residues 125-199 of SEQ ID NO: 44, respectively), human BTLA (residues 1-125 and residues 126-289 of SEQ ID NO: 45, respectively), and human PD-1 (residues 1-143 and residues 144-288 of SEQ ID NO: 46, respectively). The two regions showing strong decrease in deuterium uptake when human CTLA-4 was bound to AGEN1884-Fab are underlined in FIGS. 14A-14C: residues 80-82 (QVT, SEQ ID NO: 39) and residues 135-149 (YPPPYYLGIGNGTQI, SEQ ID NO: 37), numbered according to SEQ ID NO: 33.

6. DETAILED DESCRIPTION

The instant disclosure provides antibodies that specifically bind to CTLA-4 (e.g., human CTLA-4) and antagonize CTLA-4 function, e.g., CTLA-4-mediated immune suppression. Also provided are pharmaceutical compositions comprising these antibodies, nucleic acids encoding these antibodies, expression vectors and host cells for making these antibodies, and methods of treating a subject using these antibodies. The antibodies described herein are particularly useful for increasing T cell activation in response to an antigen (e.g., a tumor antigen or an infectious disease antigen), and hence for treating cancer in a subject or treating or preventing an infectious disease in a subject. All instances of "isolated antibodies" described herein are additionally contemplated as antibodies that may be, but need not be, isolated. All instances of "isolated polynucleotides" described herein are additionally contemplated as polynucleotides that may be, but need not be, isolated. All instances of "antibodies" described herein are additionally contemplated as antibodies that may be, but need not be, isolated. All instances of "polynucleotides" described herein are additionally contemplated as polynucleotides that may be, but need not be, isolated.

The skilled worker will appreciate that a glutamate (E) or glutamine (Q) amino acid residue at the N-terminus of a heavy chain variable region and/or a light chain variable region of any one of the antibodies described herein (e.g., an anti-CTLA4 antibody) can, under certain conditions, spontaneously convert to pyroglutamate by post-translational cyclization of the free amino group to form a lactam. Accordingly, in certain embodiments of each and every one of the methods, uses, pharmaceutical compositions, or kits described herein, the N-terminal amino acid residue of one or more heavy chain variable regions and/or light chain variable regions of the antibody has been converted to pyroglutamate (e.g., as a result of post-translational cyclization of the free amino group of the N-terminal E or Q residue).

6.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "CTLA-4" refers to cytotoxic T-lymphocyte-associated protein 4. As used herein, the term "human CTLA-4" refers to a human CTLA-4 protein encoded by a wild type human CTLA-4 gene, e.g., GenBank™ accession number NM 005214.4 or NM 001037631.2. An exemplary immature amino acid sequence of human CTLA-4 is provided as SEQ ID NO: 33.

As used herein, the terms "antibody" and "antibodies" include full length antibodies, antigen-binding fragments of full length antibodies, and molecules comprising antibody CDRs, VH regions or VL regions. Examples of antibodies include monoclonal antibodies, recombinantly produced antibodies, monospecific antibodies, multispecific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')2 fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., $IgG_1$, $IgG_2$, $IgG_3$, $IgG_4$, $IgA_1$ or $IgA_2$), or any subclass (e.g., $IgG_{2a}$ or $IgG_{2b}$) of immunoglobulin molecule. In certain embodiments, antibodies described herein are IgG antibodies, or a class (e.g., human $IgG_1$ or $IgG_4$) or subclass thereof. In a specific embodiment, the antibody is a humanized monoclonal antibody. In another specific embodiment, the antibody is a human monoclonal antibody.

As used herein, the terms "VH region" and "VL region" refer to single antibody heavy and light chain variable regions, respectively, comprising FR (Framework Regions) 1, 2, 3 and 4 and CDR (Complementarity Determining Regions) 1, 2 and 3 (see Kabat et al., (1991) Sequences of Proteins of Immunological Interest (NIH Publication No. 91-3242, Bethesda), which is herein incorporated by reference in its entirety).

As used herein, the term "CDR" or "complementarity determining region" means the noncontiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), by Chothia et al., J. Mol. Biol. 196:901-917 (1987), and by MacCallum et al., J. Mol. Biol. 262:732-745 (1996), all of which are herein incorporated by reference in their entireties, where the definitions include overlapping or subsets of amino acid residues when compared against each other. In certain embodiments, the term "CDR" is a CDR as defined by Kabat et al., J. Biol. Chem. 252, 6609-6616 (1977) and Kabat et al., Sequences of protein of immunological interest. (1991). In certain embodiments, the term "CDR" is a CDR as defined by Chothia et al., J. Mol. Biol. 196:901-917 (1987). In certain embodiments, the term "CDR" is a CDR as defined by MacCallum et al., J. Mol. Biol. 262:732-745 (1996) and Martin A. "Protein Sequence and Structure Analysis of Antibody Variable Domains," in Antibody Engineering, Kontermann and Dübel, eds., Chapter 31, pp. 422-439, Springer-Verlag, Berlin (2001).

As used herein, the term "framework (FR) amino acid residues" refers to those amino acids in the framework region of an immunoglobulin chain. The term "framework region" or "FR region" as used herein, includes the amino acid residues that are part of the variable region, but are not part of the CDRs (e.g., using the Kabat or Chothia definition of CDRs).

As used herein, the terms "variable region" and "variable domain" are used interchangeably and are common in the art. The variable region typically refers to a portion of an antibody, generally, a portion of a light or heavy chain, typically about the amino-terminal 110 to 125 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody.

The terms "VH" and "VH domain" are used interchangeably to refer to the heavy chain variable region of an antibody.

As used herein, the terms "constant region" and "constant domain" are interchangeable and are common in the art. The constant region is an antibody portion, e.g., a carboxyl terminal portion of a light and/or heavy chain which is not directly involved in binding of an antibody to antigen but which can exhibit various effector functions, such as interaction with an Fc receptor (e.g., Fc gamma receptor). The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\varepsilon$), gamma ($\gamma$), and mu ($\mu$), based on the amino acid sequence of the constant domain, which give rise to IgA, IgD, IgE, IgG, and IgM classes of antibodies, respectively, including subclasses of IgG, e.g., $IgG_1$, $IgG_2$, $IgG_3$, and $IgG_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation rate constant of, e.g., an antibody to an antigen. The $k_{on}$, and $k_{off}$ can be determined by techniques known to one of ordinary skill in the art, such as BIAcore® or KinExA. As used herein, a "lower affinity" refers to a larger $K_D$.

As used herein, the terms "specifically binds," "specifically recognizes," "immunospecifically binds," and "immunospecifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, Id.), or other assays known in the art. In a specific embodiment, molecules that specifically bind to an antigen bind to the antigen with a $K_A$ that is at least 2 logs (i.e., factors of 10), 2.5 logs, 3 logs, 4 logs or greater than the $K_A$ when the molecules bind non-specifically to another antigen.

In another specific embodiment, molecules that specifically bind to an antigen do not cross react with other proteins under similar binding conditions. In another specific embodiment, molecules that specifically bind to CTLA-4 do not cross react with other non-CTLA-4 proteins. In a specific embodiment, provided herein is an antibody that binds to CTLA-4 (e.g., human CTLA-4) with higher affinity than to another unrelated antigen. In certain embodiments, provided herein is an antibody that binds to CTLA-4 (e.g., human CTLA-4) with a 20%, 25%, 30%, 35%, 40%, 45%, 50%, 55%, 60%, 65%, 70%, 75%, 80%, 85%, 90%, 95% or higher affinity than to another, unrelated antigen as measured by, e.g., a radioimmunoassay, surface plasmon resonance, or kinetic exclusion assay. In a specific embodiment, the extent of binding of an anti-CTLA-4 antibody described herein to an unrelated, non-CTLA-4 protein is less than 10%, 15%, or 20% of the binding of the antibody to CTLA-4 protein as measured by, e.g., a radioimmunoassay.

As used herein, the term "afucosylation" or "afucosylated" in the context of an Fc refers to a substantial lack of a fucose covalently attached, directly or indirectly, to residue 297 of the human $IgG_1$ Fc region, numbered according to the EU numbering system, or the corresponding residue in non-$IgG_1$ or non-human $IgG_1$ immunoglobulins. Thus, in a composition comprising a plurality of afucosylated antibodies, at least 70% of the antibodies will not be fucosylated, directly or indirectly (e.g., via intervening sugars) at residue 297 of the Fc region of the antibodies, and in some embodiments at least 80%, 85%, 90%, 95%, or 99% will not be fucosylated, directly or indirectly, at residue 297 of the Fc region.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays (e.g., constraining peptides using CLIPS (Chemical Linkage of Peptides onto Scaffolds) to map discontinuous or conformational epitopes), and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al., U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), all of which are herein incorporated by reference in their entireties. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. CLIPS (Chemical Linkage of Peptides onto Scaffolds) is a technology to present one or more peptides in a structurally constrained configuration to behave as functional mimics of complex protein domains. See, e.g., U.S. Publication Nos. US 2008/0139407 A1 and US 2007/099240 A1, and U.S. Pat. No. 7,972,993, each of which is herein incorporated by reference in its entirety. In a specific embodiment, the epitope of an antibody is determined using alanine scanning mutagenesis studies. In a specific embodiment, the epitope of an antibody is determined using hydrogen/deuterium exchange coupled with mass spectrometry. In a specific embodiment, the epitope of an antibody is determined using CLIPS Epitope Mapping Technology from Pepscan Therapeutics.

As used herein, the term "an epitope located within a region of human CTLA-4" consisting of a particular amino acid sequence or a set of amino acid residues refers to an epitope comprising one or more of the amino acid residues of the specified region, wherein the specified region includes the first specified amino acid residue and the last specified amino acid residue of the region of human CTLA-4. In certain embodiments, the epitope comprises each one of the amino acid residues located within the specified region. In certain embodiments, one or more additional amino acid residues of human CTLA-4 outside the specified region bind to an antibody together with an epitope located within the specified region.

As used herein, the terms "T cell receptor" and "TCR" are used interchangeably and refer to full length heterodimeric αβ or γδ TCRs, antigen-binding fragments of full length TCRs, and molecules comprising TCR CDRs or variable regions. Examples of TCRs include, but are not limited to, full length TCRs, antigen-binding fragments of full length TCRs, soluble TCRs lacking transmembrane and cytoplasmic regions, single-chain TCRs containing variable regions of TCRs attached by a flexible linker, TCR chains linked by an engineered disulfide bond, monospecific TCRs, multi-specific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the terms "major histocompatibility complex" and "MHC" are used interchangeably and refer to an MEW class I molecule and/or an MEW class II molecule.

As used herein, the term "peptide-MHC complex" refers to an MHC molecule (MHC class I or MHC class II) with a peptide bound in the art-recognized peptide binding pocket of the MHC.

As used herein, the term "treat," "treating," and "treatment" refer to therapeutic or preventative measures described herein. The methods of "treatment" employ administration of an antibody to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein with respect to the response of a cancer to a therapy, the terms "refractory" and "resistant" have their art-recognized meaning and are used interchangeably.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., for score=100, wordlength=12 to obtain nucleotide sequences homologous to a nucleic acid molecules described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules (Id.). When utilizing BLAST, Gapped BLAST, and PSI Blast programs, the default parameters of the respective programs (e.g., of) (BLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

6.2 Anti-CTLA-4 Antibodies

In one aspect the instant disclosure provides antibodies that specifically bind to CTLA-4 (e.g., human CTLA-4) and antagonize CTLA-4 function. The amino acid sequences of exemplary antibodies are set forth in Tables 1-4 herein.

TABLE 1

Amino acid sequences of exemplary anti-CTLA-4 antibodies.*

| SEQ ID NO: | Description | Amino acid sequence |
|---|---|---|
| 1 | AGEN1884 VH | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARVGLMGPFDIWGQGTMVTVSS |
| 2 | AGEN1884_M102F VH | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARVGLFGPFDIWGQGTMVTVSS |
| 3 | AGEN1884_M113L VH | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARVGLMGPFDIWGQGTLVTVSS |
| 4 | AGEN1884_D62E VH | EVQLVESGGGLVKPGGSLRLSCAASGFTFSSYSMNWVRQAPGKGLEWVSSISSSSSYIYYAESVKGRFTISRDNAKNSLYLQMNSLRAEDTAVYYCARVGLMGPFDIWGQGTMVTVSS |
| 5 | AGEN1884_M102F_M113L VH | EVQLVESGGGLVKPGGSLRLSCAASGFTFSSYSMNWVRQAPGKGLEWVSSISSSSSYIYYADSVKGRFTISRDNAKNSLYLQMNSLRAEDTAVYYCARVGLFGPFDIWGQGTLVTVSS |
| 6 | AGEN1884_D62E_M102F VH | EVQLVESGGGLVKPGGSLRLSCAASGFTFSSYSMNWVRQAPGKGLEWVSSISSSSSYIYYAESVKGRFTISRDNAKNSLYLQMNSLRAEDTAVYYCARVGLFGPFDIWGQGTMVTVSS |
| 7 | AGEN1884_D62E_M113L VH | EVQLVESGGGLVKPGGSLRLSCAASGFTFSSYSMNWVRQAPGKGLEWVSSISSSSSYIYYAESVKGRFTISRDNAKNSLYLQMNSLRAEDTAVYYCARVGLMGPFDIWGQGTLVTVSS |
| 8 | AGEN1884_D62E_M102F_M113L VH | EVQLVESGGGLVKPGGSLRLSCAASGFTFSSYSMNWVRQAPGKGLEWVSSISSSSSYIYYAESVKGRFTISRDNAKNSLYLQMNSLRAEDTAVYYCARVGLFGPFDIWGQGTLVTVSS |
| 9 | AGEN1884 VL | EIVLTQSPGTLSLSPGERATLSCRASQSVSRYLGWYQQKPGQAPRLLIYGASTRATGIPDRFSGSGSGTDFTLTITRLEPEDFAVYYCQQYGSSPWTFGQGTKVEIK |
| 10 | CDRH1 | SYSMN |
| 11 | CDRH2 | SISSSSSYIYYADSVKG |
| 12 | CDRH2 | SISSSSSYIYYAESVKG |
| 13 | CDRH3 | VGLMGPFDI |
| 14 | CDRH3 | VGLFGPFDI |
| 15 | CDRL1 | RASQSVSRYLG |
| 16 | CDRL2 | GASTRAT |
| 17 | CDRL3 | QQYGSSPWT |
| 18 | CDRH2 consensus sequence | SISSSSSYIYYAXSVKG, wherein: X is E or D |

TABLE 1-continued

Amino acid sequences of exemplary anti-CTLA-4 antibodies.*

| SEQ ID NO: | Description | Amino acid sequence |
|---|---|---|
| 19 | CDRH3 consensus sequence | VGLXGPFDI, wherein:<br>X is F or M |
| 20 | VH consensus sequence | EVQLVESGGGLVKPGGSLRLSCAASGFTFSSYSM<br>NWVRQAPGKGLEWVSSISSSSSYIYYAX$_1$SVKGRF<br>TISRDNAKNSLYLQMNSLRAEDTAVYYCARVGL<br>X$_2$GPFDIWGQGTX$_3$VTVSS, wherein:<br>X$_1$ is E or D,<br>X$_2$ is F or M, and<br>X$_3$ is L or M. |
| 23 | AGEN1884.H3 (IgG$_1$) heavy chain | EVQLVESGGGLVKPGGSLRLSCAASGFTFSSYSM<br>NWVRQAPGKGLEWVSSISSSSSYIYYAESVKGRF<br>TISRDNAKNSLYLQMNSLRAEDTAVYYCARVGLF<br>GPFDIWGQGTLVTVSSASTKGPSVFPLAPSSKSTS<br>GGTAALGCLVKDYFPEPVTVSWNSGALTSGVHTF<br>PAVLQSSGLYSLSSVVTVPSSSLGTQTYICNVNHK<br>PSNTKVDKRVEPKSCDKTHTCPPCPAPELLGGPSV<br>FLFPPKPKDTLMISRTPEVTCVVVDVSHEDPEVKF<br>NWYVDGVEVHNAKTKPREEQYNSTYRVVSVLTV<br>LHQDWLNGKEYKCKVSNKALPAPIEKTISKAKGQ<br>PREPQVYTLPPSREEMTKNQVSLTCLVKGFYPSDI<br>AVEWESNGQPENNYKTTPPVLDSDGSFFLYSKLT<br>VDKSRWQQGNVFSCSVMHEALHNHYTQKSLSLS<br>PG |
| 24 | AGEN1884.H3 (IgG$_1$ S239D/I332E) heavy chain | EVQLVESGGGLVKPGGSLRLSCAASGFTFSSYSM<br>NWVRQAPGKGLEWVSSISSSSSYIYYAESVKGRF<br>TISRDNAKNSLYLQMNSLRAEDTAVYYCARVGLF<br>GPFDIWGQGTLVTVSSASTKGPSVFPLAPSSKSTS<br>GGTAALGCLVKDYFPEPVTVSWNSGALTSGVHTF<br>PAVLQSSGLYSLSSVVTVPSSSLGTQTYICNVNHK<br>PSNTKVDKRVEPKSCDKTHTCPPCPAPELLGGPD<br>VFLFPPKPKDTLMISRTPEVTCVVVDVSHEDPEVK<br>FNWYVDGVEVHNAKTKPREEQYNSTYRVVSVLT<br>VLHQDWLNGKEYKCKVSNKALPAPEEKTISKAK<br>GQPREPQVYTLPPSREEMTKNQVSLTCLVKGFYP<br>SDIAVEWESNGQPENNYKTTPPVLDSDGSFFLYSK<br>LTVDKSRWQQGNVFSCSVMHEALHNHYTQKSLS<br>LSPG |
| 25 | AGEN1884.H3 (IgG$_1$ S239D/A330L/I332E) heavy chain | EVQLVESGGGLVKPGGSLRLSCAASGFTFSSYSM<br>NWVRQAPGKGLEWVSSISSSSSYIYYAESVKGRF<br>TISRDNAKNSLYLQMNSLRAEDTAVYYCARVGLF<br>GPFDIWGQGTLVTVSSASTKGPSVFPLAPSSKSTS<br>GGTAALGCLVKDYFPEPVTVSWNSGALTSGVHTF<br>PAVLQSSGLYSLSSVVTVPSSSLGTQTYICNVNHK<br>PSNTKVDKRVEPKSCDKTHTCPPCPAPELLGGPD<br>VFLFPPKPKDTLMISRTPEVTCVVVDVSHEDPEVK<br>FNWYVDGVEVHNAKTKPREEQYNSTYRVVSVLT<br>VLHQDWLNGKEYKCKVSNKALPLPEEKTISKAK<br>GQPREPQVYTLPPSREEMTKNQVSLTCLVKGFYP<br>SDIAVEWESNGQPENNYKTTPPVLDSDGSFFLYSK<br>LTVDKSRWQQGNVFSCSVMHEALHNHYTQKSLS<br>LSPG |
| 26 | AGEN1884.H3 (IgG$_1$ L235V/F243L/R292P/Y300L/P396L) heavy chain | EVQLVESGGGLVKPGGSLRLSCAASGFTFSSYSM<br>NWVRQAPGKGLEWVSSISSSSSYIYYAESVKGRF<br>TISRDNAKNSLYLQMNSLRAEDTAVYYCARVGLF<br>GPFDIWGQGTLVTVSSASTKGPSVFPLAPSSKSTS<br>GGTAALGCLVKDYFPEPVTVSWNSGALTSGVHTF<br>PAVLQSSGLYSLSSVVTVPSSSLGTQTYICNVNHK<br>PSNTKVDKRVEPKSCDKTHTCPPCPAPELVGGPS<br>VFLLPPKPKDTLMISRTPEVTCVVVDVSHEDPEVK<br>FNWYVDGVEVHNAKTKPPEEQYNSTLRVVSVLT<br>VLHQDWLNGKEYKCKVSNKALPAPIEKTISKAKG<br>QPREPQVYTLPPSREEMTKNQVSLTCLVKGFYPS<br>DIAVEWESNGQPENNYKTTPLVLDSDGSFFLYSK<br>LTVDKSRWQQGNVFSCSVMHEALHNHYTQKSLS<br>LSPG |
| 47 | AGEN1884.H3 (IgG$_1$ N297A) heavy chain | EVQLVESGGGLVKPGGSLRLSCAASGFTFSSYSM<br>NWVRQAPGKGLEWVSSISSSSSYIYYAESVKGRF<br>TISRDNAKNSLYLQMNSLRAEDTAVYYCARVGLF<br>GPFDIWGQGTLVTVSSASTKGPSVFPLAPSSKSTS |

TABLE 1-continued

Amino acid sequences of exemplary anti-CTLA-4 antibodies.*

| SEQ ID NO | Description | Amino acid sequence |
|---|---|---|
| | | GGTAALGCLVKDYFPEPVTVSWNSGALTSGVHTF PAVLQSSGLYSLSSVVTVPSSSLGTQTYICNVNHK PSNTKVDKRVEPKSCDKTHTCPPCPAPELLGGPSV FLFPPKPKDTLMISRTPEVTCVVVDVSHEDPEVKF NWYVDGVEVHNAKTKPREEQYASTYRVVSVLTV LHQDWLNGKEYKCKVSNKALPAPIEKTISKAKGQ PREPQVYTLPPSREEMTKNQVSLTCLVKGFYPSDI AVEWESNGQPENNYKTTPPVLDSDGSFFLYSKLT VDKSRWQQGNVFSCSVMHEALHNHYTQKSLSLS PG |
| 48 | AGEN1884.H3 (IgG$_1$ S267E/L328F) heavy chain | EVQLVESGGGLVKPGGSLRLSCAASGFTFSSYSM NWVRQAPGKGLEWVSSISSSSSYIYYAESVKGRF TISRDNAKNSLYLQMNSLRAEDTAVYYCARVGLF GPFDIWGQGTLVTVSSASTKGPSVFPLAPSSKSTS GGTAALGCLVKDYFPEPVTVSWNSGALTSGVHTF PAVLQSSGLYSLSSVVTVPSSSLGTQTYICNVNHK PSNTKVDKRVEPKSCDKTHTCPPCPAPELLGGPSV FLFPPKPKDTLMISRTPEVTCVVVDVEHEDPEVKF NWYVDGVEVHNAKTKPREEQYNSTYRVVSVLTV LHQDWLNGKEYKCKVSNKAFPAPIEKTISKAKGQ PREPQVYTLPPSREEMTKNQVSLTCLVKGFYPSDI AVEWESNGQPENNYKTTPPVLDSDGSFFLYSKLT VDKSRWQQGNVFSCSVMHEALHNHYTQKSLSLS PG |
| 27 | AGEN1884.H3 light chain | EIVLTQSPGTLSLSPGERATLSCRASQSVSRYLGW YQQKPGQAPRLLIYGASTRATGIPDRFSGSGSGTD FTLTITRLEPEDFAVYYCQQYGSSPWTFGQGTKVE IKRTVAAPSVFIFPPSDEQLKSGTASVVCLLNNFYP REAKVQWKVDNALQSGNSQESVTEQDSKDSTYS LSSTLTLSKADYEKHKVYACEVTHQGLSSPVTKS FNRGEC |
| 28 | IgG$_1$ | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPSVFLFPPKPKDTLMISRT PEVTCVVVDVSHEDPEVKFNWYVDGVEVHNAKT KPREEQYNSTYRVVSVLTVLHQDWLNGKEYKCK VSNKALPAPIEKTISKAKGQPREPQVYTLPPSREE MTKNQVSLTCLVKGFYPSDIAVEWESNGQPENNY KTTPPVLDSDGSFFLYSKLTVDKSRWQQGNVFSC SVMHEALHNHYTQKSLSLSPG |
| 29 | IgG$_1$ S239D/I332E | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPDVFLFPPKPKDTLMISR TPEVTCVVVDVSHEDPEVKFNWYVDGVEVHNAK TKPREEQYNSTYRVVSVLTVLHQDWLNGKEYKC KVSNKALPAPEEKTISKAKGQPREPQVYTLPPSRE EMTKNQVSLTCLVKGFYPSDIAVEWESNGQPENN YKTTPPVLDSDGSFFLYSKLTVDKSRWQQGNVFS CSVMHEALHNHYTQKSLSLSPG |
| 30 | IgG$_1$ S239D/A330L/I332E | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELLGGPDVFLFPPKPKDTLMISR TPEVTCVVVDVSHEDPEVKFNWYVDGVEVHNAK TKPREEQYNSTYRVVSVLTVLHQDWLNGKEYKC KVSNKALPLPEEKTISKAKGQPREPQVYTLPPSRE EMTKNQVSLTCLVKGFYPSDIAVEWESNGQPENN YKTTPPVLDSDGSFFLYSKLTVDKSRWQQGNVFS CSVMHEALHNHYTQKSLSLSPG |
| 31 | IgG$_1$ L235V/F243L/R292P/ Y300L/P396L | ASTKGPSVFPLAPSSKSTSGGTAALGCLVKDYFPE PVTVSWNSGALTSGVHTFPAVLQSSGLYSLSSVV TVPSSSLGTQTYICNVNHKPSNTKVDKRVEPKSC DKTHTCPPCPAPELVGGPSVFLLPPKPKDTLMISR TPEVTCVVVDVSHEDPEVKFNWYVDGVEVHNAK TKPPEEQYNSTLRVVSVLTVLHQDWLNGKEYKC KVSNKALPAPIEKTISKAKGQPREPQVYTLPPSREE MTKNQVSLTCLVKGFYPSDIAVEWESNGQPENNY |

TABLE 1-continued

Amino acid sequences of exemplary anti-CTLA-4 antibodies.*

| SEQ ID NO: | Description | Amino acid sequence |
|---|---|---|
| | | KTTPLVLDSDGSFFLYSKLTVDKSRWQQGNVFSC SVMHEALHNHYTQKSLSLSPG |
| 32 | Light chain constant region | RTVAAPSVFIFPPSDEQLKSGTASVVCLLNNEYPR EAKVQWKVDNALQSGNSQESVTEQDSKDSTYSL SSTLTLSKADYEKHKVYACEVTHQGLSSPVTKSF NRGEC |

*CDRs are defined according to the Kabat numbering system.

TABLE 2

Heavy chain CDR amino acid sequences of exemplary anti-CTLA-4 antibodies.*

| VH (SEQ ID NO:) | CDRH1 (SEQ ID NO:) | CDRH2 (SEQ ID NO:) | CDRH3 (SEQ ID NO:) |
|---|---|---|---|
| AGEN1884 VH (1) | SYSMN (10) | SISSSSSYIYYADSVKG (11) | VGLMGPFDI (13) |
| AGEN1884_M102F VH (2) | SYSMN (10) | SISSSSSYIYYADSVKG (11) | VGLFGPFDI (14) |
| AGEN1884_M113L VH (3) | SYSMN (10) | SISSSSSYIYYADSVKG (11) | VGLMGPFDI (13) |
| AGEN1884_D62E VH (4) | SYSMN (10) | SISSSSSYIYYAESVKG (12) | VGLMGPFDI (13) |
| AGEN1884_M102F_M113L VH (5) | SYSMN (10) | SISSSSSYIYYADSVKG (11) | VGLFGPFDI (14) |
| AGEN1884_D62E_M102F VH (6) | SYSMN (10) | SISSSSSYIYYAESVKG (12) | VGLFGPFDI (14) |
| AGEN1884_D62E_M113L VH (7) | SYSMN (10) | SISSSSSYIYYAESVKG (12) | VGLMGPFDI (13) |
| AGEN1884_D62E_M102F_M113L VH (8) | SYSMN (10) | SISSSSSYIYYAESVKG (12) | VGLFGPFDI (14) |

*Defined according to the Kabat numbering system.

TABLE 3

Light chain CDR amino acid sequences of exemplary anti-CTLA-4 antibodies.*

| VL (SEQ ID NO:) | CDRL1 (SEQ ID NO:) | CDRL2 (SEQ ID NO:) | CDRL3 (SEQ ID NO:) |
|---|---|---|---|
| AGEN1884 VL (9) | RASQSVSRYLG (15) | GASTRAT (16) | QQYGSSPWT (17) |

*Defined according to the Kabat numbering system.

TABLE 4

Exemplary anti-CTLA-4 antibodies.

| Antibody | Heavy chain variable region | SEQ ID NO: | Light chain variable region | SEQ ID NO: |
|---|---|---|---|---|
| AGEN1884 | AGEN1884 VH | 1 | AGEN1884 VL | 9 |
| AGEN1884.H1.1 | AGEN1884_M102F VH | 2 | AGEN1884 VL | 9 |
| AGEN1884.H1.2 | AGEN1884_M113L VH | 3 | AGEN1884 VL | 9 |
| AGEN1884.H1.3 | AGEN1884_D62E VH | 4 | AGEN1884 VL | 9 |
| AGEN1884.H2.1 | AGEN1884_M102F_M113L VH | 5 | AGEN1884 VL | 9 |
| AGEN1884.H2.2 | AGEN1884_D62E_M102F VH | 6 | AGEN1884 VL | 9 |
| AGEN1884.H2.3 | AGEN1884_D62E_M113L VH | 7 | AGEN1884 VL | 9 |
| AGEN1884.H3 | AGEN1884_D62E_M102F_M113L VH | 8 | AGEN1884 VL | 9 |

TABLE 5

Closest germline genes.

| SEQ ID NO: | Closest germline gene | Amino acid sequence |
|---|---|---|
| 21 | IGHV3-21*01 | EVQLVESGGGLVKPGGSLRLSCAASGFTFS SYSMNWVRQAPGKGLEWVSSISSSSSYIYY ADSVKGRFTISRDNAKNSLYLQMNSLRAED TAVYYCAR |
| 22 | IGKV3-20*01 | EIVLTQSPGTLSLSPGERATLSCRASQSVS SSYLAWYQQKPGQAPRLLIYGASSRATGIP DRFSGSGSGTDFTLTISRLEPEDFAVYYCQ QYGSSP |

TABLE 6

Exemplary sequences of CTLA-4 and family members.

| SEQ ID NO: | Description | Amino acid Sequence |
|---|---|---|
| 33 | Human CTLA-4 immature protein (P16410) | MACLGFQRHKAQLNLATRTWPCTLLFFLLFIPVFC KAMHVAQPAVVLASSRGIASFVCEYASPGKATEV RVTVLRQADSQVTEVCAATYMMGNELTFLDDSI CTGTSSGNQVNLTIQGLRAMDTGLYICKVELMYP PPYYLGIGNGTQIYVIDPEPCPDSDFLLWILAAVSS GLFFYSFLLTAVSLSKMLKKRSPLTTGVYVKMPP TEPECEKQFQPYFIPIN |
| 34 | CTLA-4 epitope | YLGI |
| 35 | CTLA-4 epitope | YPPPYYLGI |
| 36 | CTLA-4 epitope | YLGIGNGTQI |
| 37 | CTLA-4 epitope | YPPPYYLGIGNGTQI |
| 38 | CTLA-4 epitope | MYPPPYY |
| 39 | CTLA-4 epitope | QVT |
| 40 | MACFA CTLA-4 (G7PL88) | MACLGFQRHKARLNLATRTRPYTLLFSLLFIPVFS KAMHVAQPAVVLANSRGIASFVCEYASPGKATE VRVTVLRQADSQVTEVCAATYMMGNELTFLDDS ICTGTSSGNQVNLTIQGLRAMDTGLYICKVELMY PPPYYMGIGNGTQIYVIDPEPCPDSDFLLWILAAVS SGLFFYSFLLTAVSLSKMLKKRSPLTTGVYVKMP PTEPECEKQFQPYFIPIN |
| 41 | Mouse CTLA-4 (P09793) | MACLGLRRYKAQLQLPSRTWPFVALLTLLFIPVFS EAIQVTQPSVVLASSHGVASFPCEYSPSHNTDEVR VTVLRQTNDQMTEVCATTFTEKNTVGFLDYPFCS GTFNESRVNLTIQGLRAVDTGLYLCKVELMYPPP YFVGMGNGTQIYVIDPEPCPDSDFLLWILVAVSLG LFFYSFLVSAVSLSKMLKKRSPLTTGVYVKMPPT EPECEKQFQPYFIPIN |
| 42 | Rat CTLA-4 (Q62859) | MACLGLQRYKTHLQLPSRTWPFGVLLSLLFIPIFSE AIQVTQPSVVLASSHGVASFPCEYASSHNTDEVR VTVLRQTNDQVTEVCATTFTVKNTLGFLDDPFCS GTFNESRVNLTIQGLRAADTGLYFCKVELMYPPP YFVGMGNGTQIYVIDPEPCPDSDFLLWILAAVSSG LFFYSFLVTAVSLNRTLKKRSPLTTGVYVKMPPTE PECEKQFQPYFIPIN |
| 43 | Human CD28 (P10747) | MLRLLLALNLFPSIQVTGNKILVKQSPMLVAYDN AVNLSCKYSYNLFSREFRASLHKGLDSAVEVCVV YGNYSQQLQVYSKTGFNCDGKLGNESVTFYLQN LYVNQTDIYFCKIEVMYPPPYLDNEKSNGTIIHVK GKHLCPSPLFPGPSKPFWVLVVVGGVLACYSLLV TVAFIIFWVRSKRSRLLHSDYMNMTPRRPGPTRK HYQPYAPPRDFAAYRS |
| 44 | Human ICOS (Q9Y6W8) | MKSGLWYFFLFCLRIKVLTGEINGSANYEMFIFHN GGVQILCKYPDIVQQFKMQLLKGGQILCDLTKTK GSGNTVSIKSLKFCHSQLSNNSVSFFLYNLDHSHA NYYFCNLSIFDPPPFKVTLTGGYLHIYESQLCCQL KFWLPIGCAAFVVVCILGCILICWLTKKKYSSSVH DPNGEYMFMRAVNTAKKSRLTDVTL |

TABLE 6 -continued

Exemplary sequences of CTLA-4 and family members.

| SEQ ID NO: | Description | Amino acid Sequence |
|---|---|---|
| 45 | Human B TLA (Q7Z6A9) | MKTLPAMLGTGKLFWVFFLIPYLDIWNIHGKESC<br>DVQLYIKRQSEHSILAGDPFELECPVKYCANRPHV<br>TWCKLNGTTCVKLEDRQTSWKEEKNISFFILHFEP<br>VLPNDNGSYRCSANFQSNLIESHSTTLYVTDVKSA<br>SERPSKDEMASRPWLLYRLLPLGGLPLLITTCFCL<br>FCCLRRHQGKQNELSDTAGREINLVDAHLKSEQT<br>EASTRQNSQVLLSETGIYDNDPDLCFRMQEGSEV<br>YSNPCLEENKPGIVYASLNHSVIGPNSRLARNVKE<br>APTEYASICVRS |
| 46 | Human PD-1 (Q15116) | MQIPQAPWPVVWAVLQLGWRPGWFLDSPDRPW<br>NPPTFSPALLVVTEGDNATFTCSFSNTSESFVLNW<br>YRMSPSNQTDKLAAFPEDRSQPGQDCRFRVTQLP<br>NGRDFHMSVVRARRNDSGTYLCGAISLAPKAQIK<br>ESLRAELRVTERRAEVPTAHPSPSPRPAGQFQTLV<br>VGVVGGLLGSLVLLVWVLAVICSRAARGTIGARR<br>TGQPLKEDPSAVPVFSVDYGELDFQWREKTPEPP<br>VPCVPEQTEYATIVFPSGMGTSSPARRGSADGPRS<br>AQPLRPEDGHCSWPL |

In certain embodiments, the instant disclosure provides an isolated antibody that specifically binds to CTLA-4 (e.g., human CTLA-4), the antibody comprising a VH domain comprising one, two, or all three of the CDRs of a VH domain set forth in Table 1 herein. In certain embodiments, the antibody comprises the CDRH1 of one of VH domains set forth in Table 1. In certain embodiments, the antibody comprises the CDRH2 of one of the VH domains set forth in Table 1. In certain embodiments, the antibody comprises the CDRH3 of one of the VH domains set forth in Table 1.

In certain embodiments, the instant disclosure provides an isolated antibody that specifically binds to CTLA-4 (e.g., human CTLA-4), the antibody comprising a VL domain comprising one, two, or all three of the CDRs of a VL domain disclosed in Table 1 herein. In certain embodiments, the antibody comprises the CDRL1 of one of VL domains set forth in Table 1. In certain embodiments, the antibody comprises the CDRL2 of one of the VL domains set forth in Table 1. In certain embodiments, the antibody comprises the CDRL3 of one of the VL domains set forth in Table 1.

In certain embodiments, the CDRs of an antibody can be determined according to Kabat et al., J. Biol. Chem. 252, 6609-6616 (1977) and Kabat et al., Sequences of protein of immunological interest (1991), each of which is herein incorporated by reference in its entirety.

In certain embodiments, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226, all of which are herein incorporated by reference in their entireties). Typically, when using the Kabat numbering convention, the Chothia CDRH1 loop is present at heavy chain amino acids 26 to 32, 33, or 34, the Chothia CDRH2 loop is present at heavy chain amino acids 52 to 56, and the Chothia CDRH3 loop is present at heavy chain amino acids 95 to 102, while the Chothia CDRL1 loop is present at light chain amino acids 24 to 34, the Chothia CDRL2 loop is present at light chain amino acids 50 to 56, and the Chothia CDRL3 loop is present at light chain amino acids 89 to 97. The end of the Chothia CDRH1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In certain embodiments, the instant disclosure provides an isolated antibody that specifically binds to CTLA-4 (e.g., human CTLA-4), the antibody comprising the Chothia VH CDRs of a VH disclosed in Table 1 herein. In certain embodiments, the instant disclosure provides an isolated antibody that specifically binds to CTLA-4 (e.g., human CTLA-4), the antibody comprising the Chothia VL CDRs of a VL disclosed in Table 1 herein. In certain embodiments, the instant disclosure provides an isolated antibody that specifically binds to CTLA-4 (e.g., human CTLA-4), the antibody comprising the Chothia VH CDRs and Chothia VL CDRs of an antibody disclosed in Table 1 herein. In certain embodiments, antibodies that specifically bind to CTLA-4 (e.g., human CTLA-4) comprise one or more CDRs, in which the Chothia and Kabat CDRs have the same amino acid sequence. In certain embodiments, the instant disclosure provides an isolated antibody that specifically binds to CTLA-4 (e.g., human CTLA-4) and comprises combinations of Kabat CDRs and Chothia CDRs.

In certain embodiments, the CDRs of an antibody can be determined according to the IMGT numbering system as described in Lefranc M-P, (1999) The Immunologist 7: 132-136 and Lefranc M-P et al., (1999) Nucleic Acids Res 27: 209-212, each of which is herein incorporated by reference in its entirety.

In certain embodiments, the instant disclosure provides antibodies that specifically bind to CTLA-4 (e.g., human CTLA-4) and comprise CDRs of an antibody disclosed in Table 1 herein, as determined by the IMGT numbering system, for example, as described in Lefranc M-P (1999) supra and Lefranc M-P et al., (1999) supra.

In certain embodiments, the CDRs of an antibody can be determined according to the AbM numbering scheme, which refers to AbM hypervariable regions, which represent a compromise between the Kabat CDRs and Chothia structural loops, and are used by Oxford Molecular's AbM antibody modeling software (Oxford Molecular Group, Inc.), herein incorporated by reference in its entirety. In a particular embodiment, the instant disclosure provides antibodies that specifically bind to CTLA-4 (e.g., human CTLA-4) and comprise CDRs of an antibody disclosed in Table 1 herein as determined by the AbM numbering scheme.

In certain embodiments, the instant disclosure provides an isolated antibody that specifically binds to CTLA-4 (e.g., human CTLA-4), wherein the antibody comprises a heavy chain variable region comprising the CDRH1, CDRH2, and CDRH3 region amino acid sequences of a VH domain set forth in SEQ ID NO: 2, 4, 5, 6, 7, or 8, and a light chain variable region comprising the CDRL1, CDRL2, and CDRL3 region amino acid sequences of a VL domain set forth in SEQ ID NO: 9, wherein each CDR is defined in accordance with the MacCallum definition, the Kabat definition, the Chothia definition, the combination of the Kabat definition and the Chothia definition, the IMGT numbering system, or the AbM definition of CDR.

In certain embodiments, the instant disclosure provides an isolated antibody that specifically binds to CTLA-4 (e.g., human CTLA-4), the antibody comprising:
(a) a CDRH1 comprises the amino acid sequence of SYSMN (SEQ ID NO: 10); and/or
(b) a CDRH2 comprises the amino acid sequence of SISSSSSYIYYAXSVKG (SEQ ID NO: 18), wherein X is E or D; and/or
(c) a CDRH3 comprises the amino acid sequence of VGLXGPFDI (SEQ ID NO: 19), wherein X is F or M; and/or
(d) CDRL1 comprises the amino acid sequence of RASQSVSRYLG (SEQ ID NO: 15); and/or
(e) CDRL2 comprises the amino acid sequence of GASTRAT (SEQ ID NO: 16); and/or
(f) CDRL3 comprises the amino acid sequence of QQYGSSPWT (SEQ ID NO: 17), and wherein the CDRH1, CDRH2, and CDRH3 sequences of the antibody are not SEQ ID NOs: 10, 11, and 13, respectively.

In certain embodiments, CDRH2 comprises the amino acid sequence of SEQ ID NO: 11. In certain embodiments, CDRH2 comprises the amino acid sequence of SEQ ID NO: 12. In certain embodiments, CDRH3 comprises the amino acid sequence of SEQ ID NO: 13. In certain embodiments, CDRH3 comprises the amino acid sequence of SEQ ID NO: 14.

In certain embodiments, the instant disclosure provides an isolated antibody that specifically binds to CTLA-4 (e.g., human CTLA-4), wherein the antibody comprises a VH domain comprising the CDRH1, CDRH2, and CDRH3 amino acid sequences set forth in SEQ ID NOs: 10, 11, and 14; 10, 12, and 13; or 10, 12, and 14, respectively. In certain embodiments, the instant disclosure provides an isolated antibody that specifically binds to CTLA-4 (e.g., human CTLA-4), wherein the antibody comprises a VH domain comprising the CDRH1, CDRH2, and CDRH3 amino acid sequences set forth in SEQ ID NOs: 10, 12, and 14, respectively.

In certain embodiments, the instant disclosure provides an isolated antibody that specifically binds to CTLA-4 (e.g., human CTLA-4), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 10, 11, 14, 15, 16, and 17; 10, 12, 13, 15, 16, and 17; or 10, 12, 14, 15, 16, and 17, respectively. In certain embodiments, the instant disclosure provides an isolated antibody that specifically binds to CTLA-4 (e.g., human CTLA-4), wherein the antibody comprises a heavy chain variable region comprising CDRH1, CDRH2, and CDRH3 regions, and a light chain variable region comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 10, 12, 14, 15, 16, and 17, respectively.

In certain embodiments, the instant disclosure provides an isolated antibody that specifically binds to CTLA-4 (e.g., human CTLA-4), comprising a heavy chain variable region comprising an amino acid sequence of SEQ ID NO: 20. In certain embodiments, the instant disclosure provides an isolated antibody that specifically binds to CTLA-4 (e.g., human CTLA-4), comprising a heavy chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 2, 4, 5, 6, 7, or 8. In certain embodiments, the instant disclosure provides an isolated antibody that specifically binds to CTLA-4 (e.g., human CTLA-4), comprising a heavy chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 3. In certain embodiments, the antibody comprises a heavy chain variable region having the amino acid sequence set forth in SEQ ID NO: 2, 4, 5, 6, 7, or 8. In certain embodiments, the antibody comprises a heavy chain variable region having the amino acid sequence set forth in SEQ ID NO: 2. In certain embodiments, the antibody comprises a heavy chain variable region having the amino acid sequence set forth in SEQ ID NO: 3. In certain embodiments, the antibody comprises a heavy chain variable region having the amino acid sequence set forth in SEQ ID NO: 4. In certain embodiments, the antibody comprises a heavy chain variable region having the amino acid sequence set forth in SEQ ID NO: 5. In certain embodiments, the antibody comprises a heavy chain variable region having the amino acid sequence set forth in SEQ ID NO: 6. In certain embodiments, the antibody comprises a heavy chain variable region having the amino acid sequence set forth in SEQ ID NO: 7. In certain embodiments, the antibody comprises a heavy chain variable region having the amino acid sequence set forth in SEQ ID NO: 8.

In certain embodiments, the instant disclosure provides an isolated antibody that specifically binds to CTLA-4 (e.g., human CTLA-4), comprising a light chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 9. In certain embodiments, the antibody comprises a light chain variable region having the amino acid sequence set forth in SEQ ID NO: 9.

In certain embodiments, the instant disclosure provides an isolated antibody that specifically binds to CTLA-4 (e.g., human CTLA-4), comprising a heavy chain variable region comprising an amino acid sequence of SEQ ID NO: 20, and a light chain variable region comprising an amino acid sequence of SEQ ID NO: 9. In certain embodiments, the instant disclosure provides an isolated antibody that specifically binds to CTLA-4 (e.g., human CTLA-4), comprising a heavy chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 2, 4, 5, 6, 7, or 8, and a light chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 9. In certain embodiments, the instant disclosure provides an isolated antibody that specifically binds to CTLA-4 (e.g., human CTLA-4), comprising a heavy chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 3, and a light chain variable region comprising an amino acid sequence that is at least 75%, 80%, 85%, 90%, 95%, 99%, or 100% (e.g., at least 86, 87, 88, 89, 90, 91, 92, 93, 94, 95, 96, 97, 98 or 99%) identical to the amino acid sequence set forth in SEQ ID NO: 9. In certain embodiments, the antibody comprises a heavy chain variable region and light chain variable region having the amino acid sequences set forth in SEQ ID NO: 2 and 9; 4 and 9; 5 and 9; 6 and 9; 7 and 9; or 8 and 9, respectively. In certain embodiments, the antibody comprises a heavy chain variable region and light chain variable region having the amino acid sequences set forth in SEQ ID NO: 2 and 9, respectively. In certain embodiments, the antibody comprises a heavy chain variable region and light chain variable region having the amino acid sequences set forth in SEQ ID NO: 3 and 9, respectively. In certain embodiments, the antibody comprises a heavy chain variable region and light chain variable region having the amino acid sequences set forth in SEQ ID NO: 4 and 9, respectively. In certain embodiments, the antibody comprises a heavy chain variable region and light chain variable region having the amino acid sequences set forth in SEQ ID NO: 5 and 9, respectively. In certain embodiments, the antibody comprises a heavy chain variable region and light chain variable region having the amino acid sequences set forth in SEQ ID NO: 6 and 9, respectively. In certain embodiments, the antibody comprises a heavy chain variable region and light chain variable region having the amino acid sequences set forth in SEQ ID NO: 7 and 9, respectively. In certain embodiments, the antibody comprises a heavy chain variable region and light chain variable region having the amino acid sequences set forth in SEQ ID NO: 8 and 9, respectively.

In certain embodiments, the instant disclosure provides an isolated antibody that specifically binds to CTLA-4 (e.g., human CTLA-4), comprising a heavy chain variable region having an amino acid sequence derived from a human IGHV3-21 germline sequence (e.g., IGHV3-21*01, e.g., having the amino acid sequence of SEQ ID NO: 21). One or more regions selected from framework 1, framework 2, framework 3, CDRH1, and CDRH2 (e.g., two, three, four or five of these regions) can be derived from a human IGHV3-21 germline sequence (e.g., IGHV3-21*01, e.g., having the amino acid sequence of SEQ ID NO: 21). In one embodiment, framework 1, framework 2, framework 3, CDRH1, and CDRH2 are all derived from a human IGHV3-21 germline sequence (e.g., IGHV3-21*01, e.g., having the amino acid sequence of SEQ ID NO: 21).

In certain embodiments, the instant disclosure provides an isolated antibody that specifically binds to CTLA-4 (e.g., human CTLA-4), comprising a light chain variable region having an amino acid sequence derived from a human germline sequence selected from the group consisting of IGKV3-20 (e.g., IGKV3-20*01, e.g., having the amino acid sequence of SEQ ID NO: 22). One or more regions selected from framework 1, framework 2, framework 3, CDRL1, and CDRL2 (e.g., two, three, four or five of these regions) can be derived from a human germline sequence selected from the group consisting of IGKV3-20 (e.g., IGKV3-20*01, e.g., having the amino acid sequence of SEQ ID NO: 22). In one embodiment, framework 1, framework 2, framework 3, CDRL1, and CDRL2 are all derived from a human germline sequence selected from the group consisting of IGKV3-20 (e.g., IGKV3-20*01, e.g., having the amino acid sequence of SEQ ID NO: 22).

In certain embodiments, the instant disclosure provides an isolated antibody that specifically binds to CTLA-4 (e.g., human CTLA-4), comprising a heavy chain variable region having an amino acid sequence derived from a human IGHV3-21 germline sequence (e.g., IGHV3-21*01, e.g., having the amino acid sequence of SEQ ID NO: 21), and a light chain variable region having an amino acid sequence derived from a human germline sequence selected from the group consisting of IGKV3-20 (e.g., IGKV3-20*01, e.g., having the amino acid sequence of SEQ ID NO: 22).

In certain embodiments, the instant disclosure provides an isolated antibody that cross-competes for binding to CTLA-4 (e.g., human CTLA-4) with an antibody comprising the heavy and light chain variable region amino acid sequences set forth in SEQ ID NOs: 2 and 9; 4 and 9; 5 and 9; 6 and 9; 7 and 9; or 8 and 9, respectively. In certain embodiments, the instant disclosure provides an isolated antibody that cross-competes for binding to CTLA-4 (e.g., human CTLA-4) with an antibody comprising the heavy and light chain variable region amino acid sequences set forth in SEQ ID NOs: 3 and 9, respectively.

In certain embodiments, the instant disclosure provides an isolated antibody that binds to the same or an overlapping epitope of CTLA-4 (e.g., an epitope of human CTLA-4) as an antibody described herein, e.g., an antibody comprising the heavy and light chain variable region amino acid sequences set forth in SEQ ID NOs: 2 and 9; 4 and 9; 5 and 9; 6 and 9; 7 and 9; or 8 and 9, respectively. In certain embodiments, the instant disclosure provides an isolated antibody that binds to the same or an overlapping epitope of CTLA-4 (e.g., an epitope of human CTLA-4) as an antibody described herein, e.g., an antibody comprising the heavy and light chain variable region amino acid sequences set forth in SEQ ID NOs: 3 and 9, respectively. In certain embodiments, the epitope of an antibody can be determined by, e.g., NMR spectroscopy, surface plasmon resonance (BIAcore®)), X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, all of which are herein incorporated by reference in their entireties). Antibody:antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323, all of which are herein incorporated by reference in their entireties). Mutagenesis mapping studies may be accomplished using any method known to one of skill in the art. See, e.g., Champe M et al., (1995) supra and Cunningham B C & Wells J A (1989) supra for a description of mutagenesis techniques, including alanine scanning mutagenesis techniques. In a specific embodiment, the epitope of an antibody is determined using alanine scanning mutagenesis studies. In addition, antibodies that recognize and bind to the same or overlapping epitopes of CTLA-4 (e.g., human CTLA-4) can be identified using routine techniques such as an immunoassay, for example, by showing the ability of one antibody to block the binding of another antibody to a target antigen, i.e., a competitive binding assay. Competition binding assays also can be used to determine whether two antibodies have similar binding specificity for an epitope. Competitive binding can be determined in an assay in which the immunoglobulin under test inhibits specific binding of a reference antibody to a common antigen, such as CTLA-4 (e.g., human CTLA-4). Numerous types of competitive binding assays are known, for example: solid phase direct or indirect radioimmunoassay (MA), solid phase direct or indirect enzyme immunoassay (EIA), sandwich competition assay (see Stahli C et al., (1983) Methods Enzymol 9: 242-253); solid phase direct biotin-avidin EIA (see Kirkland T N et al., (1986) J Immunol 137: 3614-9); solid phase direct labeled assay, solid phase direct labeled sandwich assay (see Harlow E & Lane D, (1988) Antibodies: A Laboratory Manual, Cold Spring Harbor Press); solid phase direct label MA using I-125 label (see Morel G A et al., (1988) Mol Immunol 25(1): 7-15); solid phase direct biotin-avidin EIA (see Cheung R C et al., (1990) Virology 176: 546-52); and direct labeled MA (see Moldenhauer G et al., (1990) Scand J Immunol 32: 77-82), all of which are herein incorporated by reference in their entireties. Typically, such an assay involves the use of purified antigen (e.g., CTLA-4 such as human CTLA-4) bound to a solid surface or cells bearing either of these, an unlabeled test immunoglobulin and a labeled reference immunoglobulin. Competitive inhibition can be measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75% or more. A competition binding assay can be configured in a large number of different formats using either labeled antigen or labeled antibody. In a common version of this assay, the antigen is immobilized on a 96-well plate. The ability of unlabeled antibodies to block the binding of labeled antibodies to the antigen is then measured using radioactive or enzyme labels. For further details see, for example, Wagener C et al., (1983) J Immunol 130: 2308-2315; Wagener C et al., (1984) J Immunol Methods 68: 269-274; Kuroki M et al., (1990) Cancer Res 50: 4872-4879; Kuroki M et al., (1992) Immunol Invest 21: 523-538; Kuroki M et al., (1992) Hybridoma 11: 391-407 and Antibodies: A Laboratory Manual, Ed Harlow E & Lane D editors supra, pp. 386-389, all of which are herein incorporated by reference in their entireties.

In certain embodiments, the instant disclosure provides an isolated antibody that specifically binds to CTLA-4 (e.g., human CTLA-4), the antibody comprising a heavy chain comprising the amino acid sequence set forth in SEQ ID NO: 23, 24, 25, or 26. In certain embodiments, the antibody comprises a heavy chain comprising the amino acid sequence set forth in SEQ ID NO: 23. In certain embodiments, the antibody comprises a heavy chain comprising the amino acid sequence set forth in SEQ ID NO: 24. In certain embodiments, the antibody comprises a heavy chain comprising the amino acid sequence set forth in SEQ ID NO: 25. In certain embodiments, the antibody comprises a heavy chain comprising the amino acid sequence set forth in SEQ ID NO: 26.

In certain embodiments, the instant disclosure provides an isolated antibody that specifically binds to CTLA-4 (e.g., human CTLA-4), the antibody comprising a light chain comprising the amino acid sequence set forth in SEQ ID NO: 27.

In certain embodiments, the instant disclosure provides an isolated antibody that specifically binds to CTLA-4 (e.g., human CTLA-4), the antibody comprising a heavy chain comprising the amino acid sequence of SEQ ID NO: 23 and a light chain comprising the amino acid sequence of SEQ ID NO: 27. In certain embodiments, the instant disclosure provides an isolated antibody that specifically binds to CTLA-4 (e.g., human CTLA-4), the antibody comprising a heavy chain comprising the amino acid sequence of SEQ ID NO: 24 and a light chain comprising the amino acid sequence of SEQ ID NO: 27. In certain embodiments, the instant disclosure provides an isolated antibody that specifically binds to CTLA-4 (e.g., human CTLA-4), the antibody comprising a heavy chain comprising the amino acid sequence of SEQ ID NO: 25 and a light chain comprising the amino acid sequence of SEQ ID NO: 27. In certain embodiments, the instant disclosure provides an isolated antibody that specifically binds to CTLA-4 (e.g., human CTLA-4), the antibody comprising a heavy chain comprising the amino acid sequence of SEQ ID NO: 26 and a light chain comprising the amino acid sequence of SEQ ID NO: 27.

Any Ig constant region can be used in the antibodies described herein. In certain embodiments, the Ig region is a human IgG, IgE, IgM, IgD, IgA, or IgY immunoglobulin molecule, any class (e.g., $IgG_1$, $IgG_2$, $IgG_3$, $IgG_4$, $IgA_1$, and $IgA_2$), or any subclass (e.g., $IgG_{2a}$ and $IgG_{2b}$) of immunoglobulin molecule.

In certain embodiments, the instant disclosure provides an isolated antibody that specifically binds to CTLA-4 (e.g., human CTLA-4), the antibody comprising a heavy chain constant region comprising the amino acid sequence of SEQ ID NO: 28, 29, 30, or 31. In certain embodiments, the instant disclosure provides an isolated antibody that specifically binds to CTLA-4 (e.g., human CTLA-4), the antibody comprising a light chain constant region comprising the amino acid sequence of SEQ ID NO: 32.

In certain embodiments, the instant disclosure provides an isolated antibody that specifically binds to CTLA-4 (e.g., human CTLA-4), the antibody comprising a heavy chain constant region, e.g., an $IgG_1$ constant region, or fragment thereof comprising a mutation selected from the group consisting of: S239D, I332E, and a combination thereof, numbered according to the EU numbering system. In certain embodiments, the antibody comprises an $IgG_1$ heavy chain constant region comprising S239D and I332E mutations, numbered according to the EU numbering system. In certain embodiments, the antibody comprises a heavy chain constant region comprising the amino acid sequence of SEQ ID NO: 29.

In certain embodiments, the instant disclosure provides an isolated antibody that specifically binds to CTLA-4 (e.g., human CTLA-4), the antibody comprising a heavy chain constant region, e.g., an $IgG_1$ constant region, or fragment thereof comprising a mutation selected from the group consisting of: S239D, A330L, I332E, and combinations thereof, numbered according to the EU numbering system. In certain embodiments, the antibody comprises an $IgG_1$ heavy chain constant region comprising S239D, A330L, and I332E mutations, numbered according to the EU numbering system. In certain embodiments, the antibody comprises a heavy chain constant region comprising the amino acid sequence of SEQ ID NO: 30.

In certain embodiments, the instant disclosure provides an isolated antibody that specifically binds to CTLA-4 (e.g., human CTLA-4), the antibody comprising a heavy chain constant region, e.g., an $IgG_1$ constant region, or fragment thereof comprising a mutation selected from the group consisting of: L235V, F243L, R292P, Y300L, P396L, and combinations thereof, numbered according to the EU numbering system. In certain embodiments, the antibody comprises an $IgG_1$ heavy chain constant region comprising L235V, F243L, R292P, Y300L, and P396L mutations, numbered according to the EU numbering system. In certain embodiments, the antibody comprises a heavy chain constant region comprising the amino acid sequence of SEQ ID NO: 31.

In certain embodiments, the IgG regions of the antibodies described herein have an increased affinity for FcγRIIIA, e.g., as compared with an antibody with a wild-type Fc region, e.g., an $IgG_1$ Fc. Sequence alterations that result in increased affinity for FcγRIIIA are known in the art, for example, in Kellner et al., *Methods* 65: 105-113 (2014), Lazar et al., *Proc Natl Acad Sci* 103: 4005-4010 (2006), Shields et al., *J Biol Chem.* 276(9):6591-6604 (2001), each of which is herein incorporated by reference in its entirety. In certain embodiments, the antibody comprises a heavy chain constant region, e.g., an $IgG_1$ constant region, or fragment thereof comprising a mutation selected from the group consisting of: G236A, S239D, F243L, T256A, K290A, R292P, S298A, Y300L, V305I, A330L, I332E, E333A, K334A, A339T, and P396L, and combinations thereof, numbered according to the EU numbering system. In certain embodiments, the antibody comprises a heavy chain constant region, e.g., an $IgG_1$ constant region, or fragment thereof comprising S239D, numbered according to the EU numbering system. In certain embodiments, the antibody comprises a heavy chain constant region, e.g., an $IgG_1$ constant region, or fragment thereof comprising T256A, numbered according to the EU numbering system. In certain embodiments, the antibody comprises a heavy chain constant region, e.g., an $IgG_1$ constant region, or fragment thereof comprising K290A, numbered according to the EU numbering system. In certain embodiments, the antibody comprises a heavy chain constant region, e.g., an $IgG_1$ constant region, or fragment thereof comprising S298A, numbered according to the EU numbering system. In certain embodiments, the antibody comprises a heavy chain constant region, e.g., an $IgG_1$ constant region, or fragment thereof comprising I332E, numbered according to the EU numbering system. In certain embodiments, the antibody comprises a heavy chain constant region, e.g., an $IgG_1$ constant region, or fragment thereof comprising E333A, numbered according to the EU numbering system. In certain embodiments, the antibody comprises a heavy chain constant region, e.g., an $IgG_1$ constant region, or fragment thereof comprising K334A, numbered according to the EU numbering system. In certain embodiments, the antibody comprises a heavy chain constant region, e.g., an $IgG_1$ constant region, or fragment thereof comprising A339T, numbered according to the EU numbering system.

In certain embodiments, the antibody comprises a heavy chain constant region, e.g., an $IgG_1$ constant region, or fragment thereof comprising S239D and I332E, numbered according to the EU numbering system. In certain embodiments, the antibody comprises a heavy chain constant region, e.g., an $IgG_1$ constant region, or fragment thereof comprising S239D, A330L, and I332E, numbered according to the EU numbering system. In certain embodiments, the antibody comprises a heavy chain constant region, e.g., an $IgG_1$ constant region, or fragment thereof comprising S298A, E333A, and K334A, numbered according to the EU numbering system. In certain embodiments, the antibody comprises a heavy chain constant region, e.g., an $IgG_1$ constant region, or fragment thereof comprising G236A, S239D, and I332E, numbered according to the EU numbering system. In certain embodiments, the antibody comprises a heavy chain constant region, e.g., an $IgG_1$ constant region, or fragment thereof comprising F243L, R292P, Y300L, V305I, and P396L, numbered according to the EU numbering system.

In certain embodiments, the antibodies described herein exhibit antibody-dependent cellular cytotoxicity (ADCC) activity. In certain embodiments, the antibodies described herein initiate natural killer cell mediated cell depletion. In certain embodiments, the antibodies described herein are used for treating tumor infiltrated with natural killer cells. In certain embodiments, the antibodies described herein exhibit antibody-dependent cellular phagocytosis (ADCP) activity. In certain embodiments, the antibodies described herein initiate macrophage mediated cell depletion. In certain embodiments, the antibodies described herein are used for treating tumor infiltrated with macrophages. In certain embodiments, the antibodies described herein selectively deplete intratumoral regulatory T cells.

In certain embodiments, an antibody described herein is an activatable antibody that in an activated state binds human CTLA-4 protein. In certain embodiments, the activatable antibody comprises a masking moiety that inhibits the binding of the antibody in an uncleaved state to human CTLA-4 protein, and at least one cleavable moiety coupled to the antibody, e.g., wherein the cleavable moiety is a polypeptide that functions as a substrate for a protease that is enriched in the tumor microenvironment. Exemplary activatable antibodies are described, e.g., in U.S. Pat. Nos. 8,513,390 and 8,518,404, and U.S. Patent Application Publication Nos. US 2014/0255313, US 2014/0010810, US 2014/0023664, which are incorporated herein by reference. In certain embodiments, the activatable antibody comprises a human IgG heavy chain constant region that is a variant of a wild type human IgG heavy chain constant region, wherein the variant human IgG heavy chain constant region binds to human FcγRIIIA with higher affinity than the wild type human IgG heavy chain constant region binds to human FcγRIIIA In certain embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to alter one or more functional properties of the antibody, such as serum half-life, complement fixation, Fc receptor binding and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375 and 6,165,745, all of which are herein incorporated by reference in their entireties, for examples of mutations that will alter (e.g., decrease or increase) the half-life of an antibody in vivo. In some embodiments, one, two or more amino acid mutations (e.g., substitutions, insertions, or deletions) are introduced into an IgG constant domain, or FcRn-binding fragment thereof (preferably an Fc or hinge-Fc domain fragment) to decrease the half-life of the antibody in vivo. In other embodiments, one, two or more amino acid mutations (e.g., substitutions, insertions or deletions) are introduced into an IgG constant domain, or FcRn-binding fragment thereof (preferably an Fc or hinge-Fc domain fragment) to increase the half-life of the antibody in vivo. In a specific embodiment, the antibodies may have one or more amino acid mutations (e.g., substitutions) in the second constant (CH2) domain (residues 231-340 of human $IgG_1$) and/or the third constant (CH3) domain (residues 341-447 of human $IgG_1$), numbered according to the EU numbering system. In a specific embodiment, the constant region of the $IgG_1$ of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See U.S. Pat. No. 7,658,921, which is herein incorporated by reference in its entirety. This type of mutant IgG, referred to as "YTE mutant" has been shown to display fourfold increased half-life as compared to wild-type versions of the same antibody (see Dall'Acqua W F et al., (2006) J Biol Chem 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In some embodiments, one, two, or more mutations (e.g., amino acid substitutions) are introduced into the Fc region of an antibody described herein (e.g., CH2 domain (residues 231-340 of human $IgG_1$) and/or CH3 domain (residues 341-447 of human $IgG_1$) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) PNAS 109: 6181-6186, U.S. Pat. No. 6,737,056, and International Publication Nos. WO 02/060919; WO 98/23289; and WO 97/34631, all of which are herein incorporated by reference in their entireties.

In a further embodiment, one, two, or more amino acid substitutions are introduced into an IgG constant domain Fc region to alter the effector function(s) of the antibody. For example, one or more amino acids selected from amino acid residues 234, 235, 236, 237, 297, 318, 320 and 322, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In some embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on Fc region, which may reduce Fc receptor binding (see, e.g., Shields R L et al., (2001) J Biol Chem 276: 6591-604, which is herein incorporated by reference in its entirety). In various embodiments, one or more of the following mutations in the constant region of an antibody described herein may be made: an N297A substitution; an N297Q substitution; a L235A substitution and a L237A substitution; a L234A substitution and a L235A substitution; a E233P substitution; a L234V substitution; a L235A substitution; a C236 deletion; a P238A substitution; a D265A substitution; a A327Q substitution; or a P329A substitution, numbered according to the EU numbering system. In certain embodiments, a mutation selected from the group consisting of D265A, P329A, and a combination thereof, numbered according to the EU numbering system, may be made in the constant region of an antibody described herein.

In a specific embodiment, an antibody described herein comprises the constant domain of an $IgG_1$ with an N297Q or N297A amino acid substitution, numbered according to the EU numbering system. In one embodiment, an antibody described herein comprises the constant domain of an $IgG_1$ with a mutation selected from the group consisting of D265A, P329A, and a combination thereof, numbered according to the EU numbering system. In another embodiment, an antibody described herein comprises the constant domain of an $IgG_1$ with a mutation selected from the group consisting of L234A, L235A, and a combination thereof, numbered according to the EU numbering system. In certain embodiments, amino acid residues in the constant region of an antibody described herein in the positions corresponding to positions L234, L235, and D265 in a human $IgG_1$ heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human $IgG_1$ heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In some embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In certain embodiments, an antibody described herein comprises the constant region of an IgG$_4$ antibody and the serine at amino acid residue 228 of the heavy chain, numbered according to the EU numbering system, is substituted for proline.

In certain embodiments, any of the constant region mutations or modifications described herein can be introduced into one or both heavy chain constant regions of an antibody described herein having two heavy chain constant regions.

In certain embodiments, the instant disclosure provides an isolated antibody that specifically binds to CTLA-4 (e.g., human CTLA-4) and functions as an antagonist.

In certain embodiments, the instant disclosure provides an isolated antibody that specifically binds to CTLA-4 (e.g., human CTLA-4) and decreases CTLA-4 (e.g., human CTLA-4) activity by at least 5%, 10%, 15%, 20%, 25%, 30%, 35%, 40%, 45%, 50%, 55%, 60%, 65%, 70%, 75%, 80%, 85%, 90%, 95%, 98%, or 99% as assessed by methods described herein and/or known to one of skill in the art, relative to CTLA-4 (e.g., human CTLA-4) activity without any antibody or with an unrelated antibody (e.g., an antibody that does not specifically bind to CTLA-4 (e.g., human CTLA-4)). In certain embodiments, the instant disclosure provides an isolated antibody that specifically binds to CTLA-4 (e.g., human CTLA-4) and decreases CTLA-4 (e.g., human CTLA-4) activity by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold as assessed by methods described herein and/or known to one of skill in the art, relative to CTLA-4 (e.g., human CTLA-4) activity without any antibody or with an unrelated antibody (e.g., an antibody that does not specifically bind to CTLA-4 (e.g., human CTLA-4)). Non-limiting examples of CTLA-4 (e.g., human CTLA-4) activity can include CTLA-4 (e.g., human CTLA-4) signaling, CTLA-4 (e.g., human CTLA-4) binding to CTLA-4 (e.g., human CTLA-4) ligand (e.g., CD80 or CD86), and inhibition of cytokine production (e.g., IL-2, IFN-γ, or TNF-α). In certain embodiments, the instant disclosure provides an isolated antibody that specifically binds to CTLA-4 (e.g., human CTLA-4) and deactivates, reduces, or inhibits a CTLA-4 (e.g., human CTLA-4) activity. In specific embodiments, a decrease in a CTLA-4 (e.g., human CTLA-4) activity is assessed as described in the Examples, infra.

In specific embodiments, the instant disclosure provides an isolated antibody that specifically binds to CTLA-4 (e.g., human CTLA-4) and reduces CTLA-4 (e.g., human CTLA-4) binding to its ligand (e.g., CD80 or CD86) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods known to one of skill in the art, relative to CTLA-4 (e.g., human CTLA-4) binding to its ligand (e.g., CD80 or CD86) without any antibody or with an unrelated antibody (e.g., an antibody that does not specifically bind to CTLA-4 (e.g., human CTLA-4)). In specific embodiments, the instant disclosure provides an isolated antibody that specifically binds to CTLA-4 (e.g., human CTLA-4) and reduces CTLA-4 (e.g., human CTLA-4) binding to its ligand (e.g., CD80 or CD86) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods known to one of skill in the art, relative to CTLA-4 (e.g., human CTLA-4) binding to its ligand (e.g., CD80 or CD86) without any antibody or with an unrelated antibody (e.g., an antibody that does not specifically bind to CTLA-4 (e.g., human CTLA-4)).

In specific embodiments, the instant disclosure provides an isolated antibody that specifically binds to CTLA-4 (e.g., human CTLA-4) and increases cytokine production (e.g., IL-2, IFN-γ, or TNF-α) by at least about 5%, 10%, 15%, 20%, 25%, 30%, 35%, 40%, 45%, 50%, 55%, 60%, 65%, 70%, 75%, 80%, 85%, 90%, 95%, 98%, or 99%, as assessed by methods described herein (see the Examples, infra) or known to one of skill in the art, relative to cytokine production without any antibody or with an unrelated antibody (e.g., an antibody that does not specifically bind to CTLA-4 (e.g., human CTLA-4)). In specific embodiments, the instant disclosure provides an isolated antibody that specifically binds to CTLA-4 (e.g., human CTLA-4) and increases cytokine production (e.g., IL-2, IFN-γ, or TNF-α) by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold, as assessed by methods described herein (see the Examples, infra) or known to one of skill in the art, relative to cytokine production without any antibody or with an unrelated antibody (e.g., an antibody that does not specifically bind to CTLA-4 (e.g., human CTLA-4)).

In certain embodiments, human peripheral blood mononuclear cells (PBMCs) stimulated with *Staphylococcus* Enterotoxin A (SEA) in the presence of an antibody described herein, which specifically binds to CTLA-4 (e.g., human CTLA-4), have increased IL-2 production by at least about 1.2 fold, 1.3 fold, 1.4 fold, 1.5 fold, 2 fold, 2.5 fold, 3 fold, 3.5 fold, 4 fold, 4.5 fold, 5 fold, 6 fold, 7 fold, 8 fold, 9 fold, 10 fold, 15 fold, 20 fold, 30 fold, 40 fold, 50 fold, 60 fold, 70 fold, 80 fold, 90 fold, or 100 fold relative to PBMCs only stimulated with SEA without any antibody or with an unrelated antibody (e.g., an antibody that does not specifically bind to CTLA-4 (e.g., human CTLA-4)), as assessed by methods described herein (see the Examples, infra) or known to one of skill in the art.

6.3 Pharmaceutical Compositions

Provided herein are compositions comprising an anti-CTLA-4 antibody described herein having the desired degree of purity in a physiologically acceptable carrier, excipient or stabilizer (Remington's Pharmaceutical Sciences (1990) Mack Publishing Co., Easton, Pa.). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In a specific embodiment, pharmaceutical compositions comprise an anti-CTLA-4 antibody described herein, and optionally one or more additional prophylactic or therapeutic agents, in a pharmaceutically acceptable carrier. In a specific embodiment, pharmaceutical compositions comprise an effective amount of an antibody or antigen-binding fragment thereof described herein, and optionally one or more additional prophylactic or therapeutic agents, in a pharmaceutically acceptable carrier. In some embodiments, the antibody is the only active ingredient included in the pharmaceutical composition. Pharmaceutical compositions described herein can be useful in inhibiting, CTLA-4 activity and treating a condition, such as cancer or an infectious disease.

In one aspect, provided herein is a pharmaceutical composition comprising an anti-CTLA-4 antibody of the invention and a pharmaceutically acceptable carrier or excipient, for use as a medicament.

In one aspect, provided herein is a pharmaceutical composition comprising an anti-CTLA-4 antibody of the invention and a pharmaceutically acceptable carrier or excipient, for use in a method for the treatment of cancer.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances. Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

A pharmaceutical composition may be formulated for any route of administration to a subject. Specific examples of routes of administration include intranasal, oral, pulmonary, transdermal, intradermal, and parenteral. Parenteral administration, characterized by either subcutaneous, intramuscular or intravenous injection, is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Preparations for parenteral administration of an antibody include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Topical mixtures comprising an antibody are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

An anti-CTLA-4 antibody described herein can be formulated as an aerosol for topical application, such as by inhalation (see, e.g., U.S. Pat. Nos. 4,044,126, 4,414,209 and 4,364,923, which describe aerosols for delivery of a steroid useful for treatment of inflammatory diseases, particularly asthma and are herein incorporated by reference in their entireties). These formulations for administration to the respiratory tract can be in the form of an aerosol or solution for a nebulizer, or as a microtine powder for insufflations, alone or in combination with an inert carrier such as lactose. In such a case, the particles of the formulation will, in one embodiment, have diameters of less than 50 microns, in one embodiment less than 10 microns.

An anti-CTLA-4 antibody described herein can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the antibody alone or in combination with other pharmaceutically acceptable excipients can also be administered.

Transdermal patches, including iontophoretic and electrophoretic devices, are well known to those of skill in the art, and can be used to administer an antibody. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957, all of which are herein incorporated by reference in their entireties.

In certain embodiments, a pharmaceutical composition comprising an antibody or antigen-binding fragment thereof described herein is a lyophilized powder, which can be reconstituted for administration as solutions, emulsions and other mixtures. It may also be reconstituted and formulated as solids or gels. The lyophilized powder is prepared by dissolving an antibody or antigen-binding fragment thereof described herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbitol, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature. Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

The anti-CTLA-4 antibodies described herein and other compositions provided herein can also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874, all of which are herein incorporated by reference in their entireties. In a specific embodiment, an antibody or antigen-binding fragment thereof described herein is targeted to a tumor.

The compositions to be used for in vivo administration can be sterile. This is readily accomplished by filtration through, e.g., sterile filtration membranes.

6.4 Methods of Use and Uses

In another aspect, the instant disclosure provides a method of treating a subject using the anti-CTLA-4 antibodies described herein. Any disease or disorder in a subject that would benefit from inhibition of CTLA-4 function can be treated using the anti-CTLA-4 antibodies described herein. The anti-CTLA-4 antibodies described herein are particularly useful for inhibiting immune system tolerance to tumors, and accordingly can be used as an immunotherapy for subjects with cancer. For example, in certain embodiments, the instant disclosure provides a method of increasing T-cell activation in response to an antigen in a subject, the method comprising administering to the subject an effective amount of an anti-CTLA-4 antibody or pharmaceutical composition thereof, as described herein. In certain embodiments, the instant disclosure provides a method of treating cancer in a subject, the method comprising administering to the subject an effective amount of the antibody or pharmaceutical composition, as described herein.

Cancers that can be treated with the antibodies, therapeutic combinations, or pharmaceutical compositions described herein include, without limitation, solid cancer (e.g., relapsed or refractory solid cancer, and advanced or metastatic solid cancer), carcinoma, sarcoma, melanoma (e.g., stage III or stage IV melanoma), small cell lung cancer, non-small cell lung cancer, urothelial cancer, ovarian cancer, prostate cancer (e.g., metastatic hormone-refractory prostate cancer and progressive metastatic prostate cancer), pancreatic cancer, breast cancer (e.g., $HER2^-$ breast cancer (e.g., relapsed/refractory $HER2^-$ breast cancer)), head and neck cancer (e.g., relapsed/refractory head and neck squamous cell carcinoma (HNSCC)), glioma, malignant glioma, glioblastoma multiforme, brain metastasis, merkel cancer, gastric cancer, gastroesophageal cancer, renal cell carcinoma, uveal melanoma, colon cancer, cervical cancer, lymphoma (e.g., relapsed or refractory lymphoma), non-Hodgkin's lymphoma, Hodgkin's lymphoma, leukemia, and multiple myeloma. In certain embodiments, the cancer is treated with intratumoral administration of an antibody, therapeutic combination, or pharmaceutical composition described herein. Cancers that can be treated with intratumoral administration of the antibodies, therapeutic combinations, or pharmaceutical compositions described herein include, without limitation, solid tumors (e.g., advanced or metastatic solid tumors), head and neck cancer (e.g., relapsed/refractory head and neck squamous cell carcinoma (HNSCC)), and breast cancer (e.g., $HER2^-$ breast cancer (e.g., relapsed/refractory $HER2^-$ breast cancer)).

In certain embodiments, the cancer treated in accordance with the methods described herein is a solid tumor. In certain embodiments, the cancer treated in accordance with the methods described herein is a metastatic or locally advanced cancer (e.g., a metastatic or locally advanced solid tumor). In certain embodiments, the cancer is treated in accordance with a method described herein as a first cancer therapy after diagnosis of the metastatic or locally advanced tumor (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cancer is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the tumor with a different cancer therapy, optionally wherein the method described herein is provided as the second cancer therapy administered. In certain embodiments, the cancer is treated in accordance with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered. In certain embodiments, the cancer treated in accordance with the methods described herein is a metastatic or locally advanced cancer (e.g., solid tumor) for which no standard therapy is available. In other embodiments, the cancer treated in accordance with the methods described herein is a metastatic or locally advanced cancer (e.g., solid tumor) for which a standard therapy has failed (i.e., the cancer has progressed after the standard therapy). In certain embodiments, a therapy fails if the cancer is refractory to the therapy. In certain embodiments, a therapy fails if the cancer relapses after responding, fully or partially, to the therapy. In certain embodiments, metastatic or locally advanced cancer (e.g., solid tumor) has been confirmed histologically or cytologically.

In certain embodiments, the cancer is a solid tumor. In certain embodiments, the cancer (e.g., solid tumor) expresses PD-L1. In certain embodiments, the percentage of tumor cells in a sample of the cancer (e.g., solid tumor) that exhibit detectable expression (e.g., partial or complete expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the cancer (e.g., solid tumor) that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the cancer (e.g., solid tumor) that exhibit detectable membrane expression (e.g., partial or complete membrane expression) of PD-L1 is at least 1%. In certain embodiments, the percentage of tumor cells in a sample of the cancer (e.g., solid tumor) that exhibit detectable membrane expression (e.g., partial or complete membrane expression) of PD-L1 is at least 5%. In certain embodiments, the percentage of tumor cells in a sample of the cancer (e.g., solid tumor) that exhibit detectable membrane expression (e.g., partial or complete membrane expression) of PD-L1 is at least 25%. In certain embodiments, the percentage of tumor cells in a sample of the cancer (e.g., solid tumor) that exhibit detectable membrane expression (e.g., partial or complete membrane expression) of PD-L1 is at least 50%.

In certain embodiments, the metastatic or locally advanced cancer (e.g., solid tumor) expresses PD-L1. In certain embodiments, the percentage of tumor cells in a sample of the metastatic or locally advanced cancer (e.g., solid tumor) that exhibit detectable expression (e.g., partial or complete expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced cancer (e.g., solid tumor) that exhibit detectable membrane expression (e.g., partial or complete membrane expression) of PD-L1 is at least 1% (e.g., at least 2%, 3%, 4%, 5%, 10%, 15%, 20%, 25%, 30%, 35%, 40%, 45%, 50%, 60%, 70%, 80%, or 90%). In certain embodiments, the percentage of tumor cells in a sample of the metastatic or locally advanced cancer (e.g., solid tumor) that exhibit detectable membrane expression (e.g., partial or complete membrane expression) of PD-L1 is at least 1%. In certain embodiments, the percentage of tumor cells in a sample of the metastatic or locally advanced cancer (e.g., solid tumor) that exhibit detectable membrane expression (e.g., partial or complete membrane expression) of PD-L1 is at least 5%. In certain embodiments, the percentage of tumor cells in a sample of the metastatic or locally advanced cancer (e.g., solid tumor) that exhibit detectable membrane expression (e.g., partial or complete membrane expression) of PD-L1 is at least 25%. In certain embodiments, the percentage of tumor cells in a sample of the metastatic or locally advanced cancer (e.g., solid tumor) that exhibit detectable membrane expression (e.g., partial or complete membrane expression) of PD-L1 is at least 50%.

For each and every one of the methods described herein that requires a certain percentage of cells in a sample exhibit detectable expression (e.g., membrane expression, partial or complete membrane expression) of PD-L1, the expression of PD-L1 can be detected by any method well known in the art, including but not limited to immunohistochemistry. Exemplary immunohistochemistry assays for measuring PD-L1 expression in tumor cells are provided in Hirsch et al. (2017, J. Thoracic Oncol. 12(2): 208-222), Rimm et al. (2017, JAMA Oncol. 3(8): 1051-1058), and Diggs and Hsueh (2017, Biomarker Res. 5:12), which are incorporated by reference herein in their entirety.

In certain embodiments, the cancer treated in accordance with a method described herein is a metastatic or locally advanced non-small cell lung cancer (NSCLC). In certain embodiments, the cancer treated in accordance with a method described herein is a metastatic non-small cell lung cancer (NSCLC). In certain embodiments, the cancer treated in accordance with a method described herein is a Stage IV, metastatic or locally advanced NSCLC. In certain embodiments, the cancer treated in accordance with a method described herein is a Stage IV, metastatic NSCLC. In certain embodiments, the percentage of tumor cells in a sample of the metastatic or locally advanced NSCLC that exhibit detectable expression (e.g., partial or complete expression) of PD-L1 is at least 1%, 2%, 3%, 4%, 5%, 10%, 15%, 20%, 25%, 30%, 35%, 40%, 45%, 50%, 60%, 70%, 80%, or 90%. In certain embodiments, the percentage of tumor cells in a sample of the metastatic or locally advanced NSCLC that exhibit detectable membrane expression (e.g., partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%. In certain embodiments, the percentage of tumor cells in a sample of the metastatic or locally advanced NSCLC that exhibit detectable membrane expression (e.g., partial or complete membrane expression) of PD-L1 is at least 1%. In certain embodiments, the percentage of tumor cells in a sample of the metastatic or locally advanced NSCLC that exhibit detectable membrane expression (e.g., partial or complete membrane expression) of PD-L1 is at least 5%. In certain embodiments, the percentage of tumor cells in a sample of the metastatic or locally advanced NSCLC that exhibit detectable membrane expression (e.g., partial or complete membrane expression) of PD-L1 is at least 25%. In certain embodiments, the percentage of tumor cells in a sample of the metastatic or locally advanced NSCLC that exhibit detectable membrane expression (e.g., partial or complete membrane expression) of PD-L1 is at least 50%. In certain embodiments, the metastatic or locally advanced NSCLC has no EGFR or ALK genomic tumor aberrations. In certain embodiments, the metastatic or locally advanced NSCLC has no EGFR sensitizing mutation (e.g., mutation that is amenable to treatment with a tyrosine kinase inhibitor including erlotinib, gefitinib, or afatanib) or ALK translocation. In certain embodiments, the subject having the metastatic or locally advanced NSCLC has received no prior systemic chemotherapy treatment for metastatic or locally advanced NSCLC. In certain embodiments, the metastatic or locally advanced NSCLC is treated in accordance with a method described herein as a first cancer therapy after diagnosis (e.g., within 1, 2, 3, 4, 5, or 6 days; 1, 2, 3, 4, 6, 8, or 12 weeks; or, 1, 2, 3, 4, 6, 8, or 12 months after diagnosis) of the metastatic or locally advanced NSCLC. In certain embodiments, the method comprises treating a subject having NSCLC (e.g., Stage IV, metastatic, or locally advanced NSCLC) using an anti-CTLA-4 antibody described herein, e.g., AGEN1884.H3 (IgG$_1$ S239D/A330L/I332E), or pharmaceutical composition comprising such anti-CTLA-4 antibody, wherein the percentage of tumor cells in a sample of the NSCLC that exhibit detectable membrane expression (e.g., partial or complete membrane expression) of PD-L1 is at least 1%, 2%, 3%, 4%, 5%, 10%, 15%, 20%, 25%, 30%, 35%, 40%, 45%, 50%, 60%, 70%, 80%, or 90%, and wherein the method is provided as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis).

In certain embodiments, the cancer treated in accordance with the methods described herein is a cervical cancer. In certain embodiments, the cancer treated in accordance with the methods described herein is a metastatic or locally advanced, unresectable squamous cell carcinoma, adenosquamous carcinoma, or adenocarcinoma of the cervix. In certain embodiments, the cancer treated in accordance with the methods described herein is an unresectable or metastatic cervical cancer. In certain embodiments, the cervical cancer has progressed after a standard therapy (e.g., has relapsed after the standard therapy, or is refractory to the standard therapy). In certain embodiments, the standard therapy comprises a platinum-containing chemotherapy. In certain embodiments, the platinum-containing chemotherapy is selected from the group consisting of cisplatin, carboplatin, oxaliplatin, nedaplatin, satraplatin, picoplatin, triplatin, phenanthriplatin, iproplatin, lobaplatin, heptaplatin, lipoplatin, and a combination thereof. In certain embodiments, the standard therapy further comprises a second chemotherapy. In certain embodiments, the second chemotherapy is selected from the group consisting of a nucleotide analog (e.g., gemcitabine), a folate antimetabolite (e.g., pemetrexed), and a taxane (e.g., paclitaxel). In certain embodiments, the standard therapy is any platinum-based doublet chemotherapy (PT-DC) (also known as platinum-containing doublet) known in the art. In certain embodiments, the PT-DC comprises cisplatin and gemcitabine, cisplatin and pemetrexed, cisplatin and paclitaxel, carboplatin and paclitaxel, or cisplatin and topotecan. The standard therapy (e.g., one comprising a PT-DC) can optionally further comprise one or more additional therapies, such as bevacizumab. In certain embodiments, the standard therapy comprises paclitaxel and topotecan. In certain embodiments, the cervical cancer is HPV positive. In certain embodiments, the cervical cancer is associated with microsatellite instability. In certain embodiments, the cancer treated in accordance with the methods described herein is a metastatic or locally advanced, unresectable squamous cell carcinoma, adenosquamous carcinoma, or adenocarcinoma of the cervix that has relapsed after a platinum-containing doublet administered for treatment of advanced (recurrent, unresectable, or metastatic) disease. In certain embodiments, the cancer of the cervix is treated in accordance with a method described herein as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cancer of the cervix is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cancer of the cervix with a different cancer therapy, optionally wherein the method described herein is provided as the second cancer therapy administered. In certain embodiments, the cancer of the cervix is treated in accordance with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered. In certain embodiments, the method comprises treating a subject having cervical cancer (e.g., a metastatic or locally advanced, unresectable squamous cell carcinoma, adenosquamous carcinoma, or adenocarcinoma of the cervix) using an anti-CTLA-4 antibody described herein, e.g., AGEN1884.H3 (IgG$_1$ S239D/A330L/I332E), or pharmaceutical composition comprising such anti-CTLA-4 antibody, wherein the method is provided as a first cancer therapy after diagnosis of the cervical cancer (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the method comprises treating a subject having cervical cancer (e.g., a metastatic or locally advanced, unresectable squamous cell carcinoma, adenosquamous carcinoma, or adenocarcinoma of the cervix) using an anti-CTLA-4 antibody described herein, e.g., AGEN1884.H3 (IgG$_1$ S239D/A330L/I332E), or pharmaceutical composition comprising such anti-CTLA-4 antibody, wherein the method is provided after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cervical cancer with a different cancer therapy, or provided after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), and wherein the method described herein is provided as the second cancer therapy administered.

In certain embodiments, the cancer treated in accordance with the methods described herein is a cutaneous squamous-cell carcinoma (cSCC). In certain embodiments, the cancer treated in accordance with the methods described herein is a Stage IV cutaneous squamous-cell carcinoma (cSCC). In certain embodiments, the cSCC (e.g., Stage IV cSCC) is not curable with radiation therapy. In certain embodiments, the Stage IV cSCC is diagnosed histologically or cytologically according to the eighth edition of the American Joint Committee on Cancer staging manual (AJCC-8). In certain embodiments, the cSCC (e.g., Stage IV cSCC) is treated in accordance with a method described herein as a first cancer therapy after diagnosis of the cSCC (e.g., Stage IV cSCC) (e.g., within 1, 2, 3, 4, 5, or 6 days; 1, 2, 3, 4, 6, 8, or 12 weeks; or, 1, 2, 3, 4, 6, 8, or 12 months after diagnosis). In certain embodiments, the cSCC (e.g., Stage IV cSCC) is treated in accordance with a method described herein as the first cancer therapy after diagnosis of tumor progression (e.g., within 1, 2, 3, 4, 5, or 6 days; 1, 2, 3, 4, 6, 8, or 12 weeks; or, 1, 2, 3, 4, 6, 8, or 12 months after diagnosis of tumor progression) that has occurred despite previous treatment of the cSCC (e.g., Stage IV cSCC) with a different cancer therapy, optionally wherein the method described herein is provided as the second cancer therapy administered. In certain embodiments, the cSCC (e.g., Stage IV cSCC) is treated in according with a method described herein as the first cancer therapy after diagnosis of toxicity of a different cancer therapy (e.g., within 1, 2, 3, 4, 5, or 6 days; 1, 2, 3, 4, 6, 8, or 12 weeks; or, 1, 2, 3, 4, 6, 8, or 12 months after diagnosis of toxicity of the different cancer therapy), optionally wherein the method described herein is provided as the second cancer therapy administered.

In certain embodiments, the cancer treated in accordance with the methods described herein is B cell lymphoma (e.g., B cell chronic lymphocytic leukemia, B cell non-Hodgkin lymphoma, cutaneous B cell lymphoma, diffuse large B cell lymphoma), basal cell carcinoma, bladder cancer, blastoma, brain metastasis, breast cancer, Burkitt lymphoma, carcinoma (e.g., adenocarcinoma (e.g., of the gastroesophageal junction)), cervical cancer, colon cancer, colorectal cancer (colon cancer and rectal cancer), endometrial carcinoma, esophageal cancer, Ewing sarcoma, follicular lymphoma, gastric cancer, gastroesophageal junction carcinoma, gastrointestinal cancer, glioblastoma (e.g., glioblastoma multiforme, e.g., newly diagnosed or recurrent), glioma, head and neck cancer (e.g., head and neck squamous cell carcinoma), hepatic metastasis, Hodgkin's and non-Hodgkin's lymphoma, kidney cancer (e.g., renal cell carcinoma and Wilms' tumors), laryngeal cancer, leukemia (e.g., chronic myelocytic leukemia, hairy cell leukemia), liver cancer (e.g., hepatic carcinoma and hepatoma), lung cancer (e.g., non-small cell lung cancer and small-cell lung cancer), lymphblastic lymphoma, lymphoma, mantle cell lymphoma, metastatic brain tumor, metastatic cancer, myeloma (e.g., multiple myeloma), neuroblastoma, ocular melanoma, oropharyngeal cancer, osteosarcoma, ovarian cancer, pancreatic cancer (e.g., pancreatis ductal adenocarcinoma), prostate cancer (e.g., hormone refractory (e.g., castration resistant), metastatic, metastatic hormone refractory (e.g., castration resistant, androgen independent)), renal cell carcinoma (e.g., metastatic), salivary gland carcinoma, sarcoma (e.g., rhabdomyosarcoma), skin cancer (e.g., melanoma (e.g., metastatic melanoma)), soft tissue sarcoma, solid tumor, squamous cell carcinoma, synovia sarcoma, testicular cancer, thyroid cancer, transitional cell cancer (urothelial cell cancer), uveal melanoma (e.g., metastatic), verrucous carcinoma, vulval cancer, and Waldenstrom macroglobulinemia.

In certain embodiments, the cancer treated in accordance with the methods described herein is human sarcoma or carcinoma, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (e.g., metastatic), hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, melanoma, neuroblastoma, or retinoblastoma.

In certain embodiments, the cancer treated in accordance with the methods described herein is angiosarcoma.

In certain embodiments, the cancer treated in accordance with the methods described herein is an acute lymphocytic leukemia or acute myelocytic leukemia (e.g., myeloblastic, promyelocytic, myelomonocytic, monocytic and erythroleukemia); chronic leukemia (chronic myelocytic (granulocytic) leukemia or chronic lymphocytic leukemia); Hodgkin's disease; non-Hodgkin's disease; acute myeloid leukemia; B-cell lymphoma; T-cell lymphoma; anaplastic large cell lymphoma; intraocular lymphoma; follicular lymphoma; small intestine lymphoma; or orsplenic marginal zone lymphoma.

In certain embodiments, the cancer treated in accordance with the methods described herein is multiple myeloma, Waldenstrom's macroglobulinemia, heavy chain disease, gastrointestinal stromal tumors, head and/or neck cancer (e.g., squamous cell carcinoma of the hypopharynx, squamous cell carcinoma of the larynx, cell carcinoma of the oropharynx, or verrucous carcinoma of the larynx), endometrial stromal sarcoma, mast cell sarcoma, adult soft tissue sarcoma, uterine sarcoma, merkel cell carcinoma, urothelial carcinoma, melanoma with brain metastases, uveal melanoma, uveal melanoma with liver metastases, non-small cell lung cancer, rectal cancer, or myelodysplastic syndrome. In some embodiments, the cancer treated in accordance with the methods is metastatic.

In certain embodiments, the cancer treated in accordance with the methods described herein is prostate cancer, breast cancer, lung cancer, colorectal cancer, melanoma, bronchial cancer, bladder cancer, brain or central nervous system cancer, peripheral nervous system cancer, uterine or endometrial cancer, cancer of the oral cavity or pharynx, non-Hodgkin's lymphoma, thyroid cancer, kidney cancer, biliary tract cancer, small bowel or appendix cancer, salivary gland cancer, thyroid gland cancer, adrenal gland cancer, squamous cell cancer, mesothelioma, osteocarcinoma, thyoma/thymic carcinoma, glioblastoma, myelodysplastic syndrome, soft tissue sarcoma, DIPG, adenocarcinoma, osteosarcoma, chondrosarcoma, leukemia, or pancreatic cancer. In some embodiments, the cancer treated in accordance with the methods described herein includes a carcinoma (e.g., an adenocarcinoma), lymphoma, blastoma, melanoma, sarcoma, or leukemia.

In certain embodiments, the cancer treated in accordance with the methods described herein is squamous cell cancer, small-cell lung cancer, non-small cell lung cancer, gastrointestinal cancer, Hodgkin's lymphoma, non-Hodgkin's lymphoma, pancreatic cancer, glioblastoma, glioma, cervical cancer, ovarian cancer, liver cancer (e.g., hepatic carcinoma and hepatoma), bladder cancer, breast cancer, inflammatory breast cancer, Merkel cell carcinoma, colon cancer, colorectal cancer, stomach cancer, urinary bladder cancer, endometrial carcinoma, myeloma (e.g., multiple myeloma), salivary gland, carcinoma, kidney cancer (e.g., renal cell carcinoma and Wilms' tumors), basal cell carcinoma, melanoma, prostate cancer, vulval cancer, thyroid cancer, testicular cancer, esophageal cancer, serous adenocarcinoma or various types of head and neck cancer. In certain embodiments, the cancer treated in accordance with the methods described herein includes desmoplastic melanoma, inflammatory breast cancer, thymoma, rectal cancer, anal cancer, or surgically treatable or non-surgically treatable brain stem glioma. In a specific embodiment, the cancer is a solid tumor. In another specific embodiment, the cancer is glioblastoma multiforme. In some embodiments, the glioblastoma multiforme is recurrent. In some embodiments, the glioblastoma multiforme is newly diagnosed. In some embodiments, the glioblastoma multiforme is in a subject having non-methylated MGMT promoters. In some embodiments, the glioblastoma multiforme is refractory to Bevacizumab therapy. In some embodiments, the glioblastoma multiforme is in a subject that has not received Bevacizumab therapy.

In certain embodiments, the cancer treated in accordance with the methods described herein is metastatic melanoma (e.g., resistant metastatic melanoma), metastatic ovarian cancer, or metastatic renal cell carcinoma. In certain embodiments, the cancer treated in accordance with the methods described herein is melanoma that is resistant to Ipilimumab. In some embodiments, the cancer treated in accordance with the methods described herein is melanoma that is resistant to Nivolumab or Pembrolizumab. In some embodiments, the cancer treated in accordance with the methods described herein is melanoma that is resistant to Ipilimumab and Nivolumab or Pembrolizumab.

In certain embodiments, the cancer treated in accordance with the methods described herein is breast cancer (e.g., herceptin resistant breast cancer and trastuzumab-DM1 (T-DM1) resistant breast cancer), prostate cancer, glioblastoma multiforme, colorectal cancer, sarcoma, bladder cancer, cervical cancer, HPV-associated cancers, cancers of the vagina, cancers of the vulva, cancers of the penis, cancer of the anus, cancer of the rectum, cancer of the oropharynx, multiple myeloma, renal cell carcinoma, ovarian cancer, hepatocellular cancer, endometrial cancer, pancreatic cancer, lymphoma, and leukemia (e.g., elderly leukemia, acute myeloid leukemia (AML), and elderly AML).

In certain embodiments, the cancer treated in accordance with the methods described herein is metastatic malignant melanoma (e.g., cutaneous or intraocular malignant melanoma), renal cancer (e.g., clear cell carcinoma), prostate cancer (e.g., hormone refractory prostate adenocarcinoma), breast cancer, colon cancer, lung cancer (e.g., non-small cell lung cancer), bone cancer, pancreatic cancer, skin cancer, cancer of the head or neck, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, glioma, pituitary adenoma, Kaposi's sarcoma, epidermoid cancer, squamous cell cancer, T-cell lymphoma, environmentally induced cancers including those induced by asbestos, esophageal cancer, liver cancer, refractory or recurrent malignancies, metastatic cancers, cancers that express PD-L1, and combinations of said cancers.

In certain embodiments, the subject has previously received an immunotherapy. In certain embodiments, the subject has not previously received any immunotherapy. In certain embodiments, the cancer is an advanced or metastatic cancer.

In certain embodiments, the instant disclosure provides a method of preventing or treating an infectious disease in a subject, the method comprising administering to the subject an effective amount of an anti-CTLA-4 antibody or pharmaceutical composition thereof, as described herein. In one embodiment, provided herein are methods for preventing and/or treating an infection (e.g., a viral infection, a bacterial infection, a fungal infection, a protozoal infection, or a parasitic infection). The infection prevented and/or treated in accordance with the methods can be caused by an infectious agent identified herein. In a specific embodiment, an anti-CTLA-4 antibody described herein or a composition thereof is the only active agent administered to a subject. In some embodiments, an anti-CTLA-4 antibody described herein or a composition thereof is used in combination with anti-infective interventions (e.g., antivirals, antibacterials, antifungals, or anti-helminthics) for the treatment of infectious diseases.

Infectious diseases that can be treated and/or prevented by anti-CTLA-4 antibodies or pharmaceutical compositions described herein are caused by infectious agents including but not limited to bacteria, parasites, fungi, protozae, and viruses. In a specific embodiment, the infectious disease treated and/or prevented by anti-CTLA-4 antibodies or pharmaceutical compositions described herein is caused by a virus. Viral diseases or viral infections that can be prevented and/or treated in accordance with the methods described herein include, but are not limited to, those caused by hepatitis type A, hepatitis type B, hepatitis type C, influenza (e.g., influenza A or influenza B), varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial infections that can be prevented and/or treated include infections caused by *Escherichia coli, Klebsiella pneumoniae, Staphylococcus aureus, Enterococcus faecalis, Proteus vulgaris, Staphylococcus viridans*, and *Pseudomonas aeruginosa*. Bacterial diseases caused by bacteria (e.g., *Escherichia coli, Klebsiella pneumoniae, Staphylococcus aureus, Enterococcus faecalis, Proteus vulgaris, Staphylococcus viridans*, and *Pseudomonas aeruginosa*) that can be prevented and/or treated in accordance with the methods described herein include, but are not limited to, Mycobacteria *rickettsia, Mycoplasma, Neisseria, S. pneumonia, Borrelia burgdorferi* (Lyme disease), *Bacillus antracis* (anthrax), tetanus, Streptococcus, Staphylococcus, mycobacterium, pertissus, cholera, plague, diptheria, *chlamydia, S. aureus* and *legionella*.

Protozoal diseases or protozoal infections caused by protozoa that can be prevented and/or treated in accordance with the methods described herein include, but are not limited to, *leishmania*, coccidiosis, *trypanosoma schistosoma* or malaria. Parasitic diseases or parasitic infections caused by parasites that can be prevented and/or treated in accordance with the methods described herein include, but are not limited to, *chlamydia* and *rickettsia*.

Fungal diseases or fungal infections that can be prevented and/or treated in accordance with the methods described herein include, but are not limited to, those caused by *Candida* infections, zygomycosis, *Candida* mastitis, progressive disseminated trichosporonosis with latent trichosporonemia, disseminated candidiasis, pulmonary paracoccidioidomycosis, pulmonary aspergillosis, *Pneumocystis carinii* pneumonia, cryptococcal meningitis, coccidioidal meningoencephalitis and cerebrospinal vasculitis, *Aspergillus niger* infection, *Fusarium* keratitis, paranasal sinus mycoses, *Aspergillus fumigatus* endocarditis, tibial dyschondroplasia, *Candida glabrata* vaginitis, oropharyngeal candidiasis, X-linked chronic granulomatous disease, tinea pedis, cutaneous candidiasis, mycotic placentitis, disseminated trichosporonosis, allergic bronchopulmonary aspergillosis, mycotic keratitis, *Cryptococcus neoformans* infection, fungal peritonitis, *Curvularia geniculata* infection, staphylococcal endophthalmitis, sporotrichosis, and dermatophytosis.

In certain embodiments, the infectious disease is acute. In certain embodiments, the infectious disease is chronic. In certain embodiments, the infectious disease is caused by flavivirus, e.g., West Nile virus, Saint Louis encephalitis virus, Powassan virus, tick-borne encephalitis virus, dengue virus, zika virus, Kyasanur Forest disease virus, yellow fever virus, and chikungunya virus. In certain embodiments, the infectious disease is caused by Ebola virus. In certain embodiments, the infectious disease is caused by influenza virus. In certain embodiments, the infectious disease is caused by Human Immunodeficiency Virus (HIV), Hepatitis B virus (HBV) or Hepatitis C virus (HCV). In certain embodiments, the anti-CTLA-4 antibody or pharmaceutical composition thereof, as described herein, promotes viral control. In certain embodiments, the anti-CTLA-4 antibody or pharmaceutical composition thereof, as described herein, eliminates viral reservoirs.

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use as a medicament.

The present invention relates, in one aspect, to an anti-CTLA-4 antibody of the invention, and/or its use in combination with pharmaceutically acceptable carriers or excipients, for preparing pharmaceutical compositions or medicaments for immunotherapy (e.g., an immunotherapy for increasing T-cell activation in response to an antigen in a subject, treating cancer, or treating or preventing infectious diseases).

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use in a method for the treatment of cancer.

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use in a method for inhibiting immune system tolerance to tumors and/or for immunotherapy for subjects with cancer.

The present invention relates in one aspect to an anti-CTLA-4 antibody of the invention and/or a pharmaceutical composition of the invention comprising an anti-CTLA-4 antibody of the invention and a pharmaceutically acceptable carrier or excipient, for use in a method for the treatment of an infectious disease.

In certain embodiments, the anti-CTLA-4 antibody or pharmaceutical composition described herein is administered as a monotherapy.

In certain embodiments, these methods further comprise administering an additional therapeutic agent to the subject. In certain embodiments, the additional therapeutic agent is a chemotherapeutic or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM1 antibody, an agonist anti-GITR antibody, an agonist anti-OX40 antibody, an agonist anti-CD137 antibody, an agonist anti-DR3 antibody, an agonist anti-TNFSF14 antibody, and an agonist anti-CD27 antibody. In certain embodiments, the checkpoint targeting agent is an antagonist anti-PD-1 antibody. In certain embodiments, the checkpoint targeting agent is an antagonist anti-PD-L1 antibody. In certain embodiments, the checkpoint targeting agent is an antagonist anti-LAG-3 antibody. In certain embodiments, the additional therapeutic agent is an agonist to a tumor necrosis factor receptor superfamily member or a tumor necrosis factor superfamily member.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) an additional therapeutic agent, for use as a medicament. In a preferred embodiment, the additional therapeutic agent is a chemotherapeutic or a checkpoint targeting agent.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) an additional therapeutic agent, for use in a method for the treatment of cancer.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) an additional therapeutic agent, for use in a method for the treatment of an infectious disease.

In certain embodiments, an anti-CTLA-4 antibody described herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., WO 2010/005958 which is incorporated by reference herein in its entirety), F001287 (Flexus Biosciences), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a compound that targets an immunomodulatory enzyme, for use as a medicament. In a preferred embodiment, the compound targets IDO and/or TDO.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a compound that targets an immunomodulatory enzyme, for use in a method for the treatment of cancer. In a preferred embodiment, the compound targets IDO and/or TDO.

In certain embodiments, an anti-CTLA-4 antibody described herein is administered to a subject in combination with a vaccine. In certain embodiments, the vaccine is a heat shock protein based tumor vaccine or a heat shock protein based pathogen vaccine. In a specific embodiment, an anti-CTLA-4 antibody described herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes and Th1 and Th-2-mediated immune responses. In certain embodiments, HSPPCs used in methods described herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, an anti-CTLA-4 antibody described herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference herein in their entireties, U.S. Pat. Nos. 6,391,306, 6,383,492, 6,403,095, 6,410,026, 6,436,404, 6,447,780, 6,447,781 and 6,610,659, all of which are herein incorporated by reference in their entireties.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a vaccine, for use as a medicament. In a preferred embodiment, the vaccine is a heat shock protein based tumor vaccine or a heat shock protein based pathogen vaccine. In a preferred embodiment, the vaccine is a heat shock protein based viral vaccine.

In certain embodiments, the present invention relates to (a) an anti-CTLA-4 antibody of the invention and/or a pharmaceutical composition of the invention comprising an anti-CTLA-4 antibody of the invention and a pharmaceutically acceptable carrier or excipient and (b) a vaccine, for use in a method for the treatment of cancer. In a preferred embodiment, the vaccine is a heat shock protein based tumor vaccine.

The anti-CTLA-4 antibody and the additional therapeutic agent (e.g., chemotherapeutic, checkpoint targeting agent, IDO inhibitor, and/or vaccine) can be administered separately, sequentially or concurrently as separate dosage forms. In one embodiment, an anti-CTLA-4 antibody is administered parenterally, and an IDO inhibitor is administered orally.

In certain embodiments, an anti-CTLA-4 antibody described herein is administered to a subject intratumorally. In certain embodiments, an anti-CTLA-4 antibody described herein is administered to a subject intratumorally in combination with an additional therapeutic agent. In certain embodiments, the additional therapeutic agent is administered systemically. In certain embodiments, the subject has solid tumors. In certain embodiments, the subject has head and neck squamous cell carcinoma (HNSCC). In certain embodiments, the subject has HER2⁺ breast cancer. In certain embodiments, the additional therapeutic agent that is administered systemically is an anti-PD-1 antibody (e.g., pembrolizumab or nivolumab). In certain embodiments, the additional therapeutic agent that is administered systemically is an anti-EGFR antibody (e.g., cetuximab). In certain embodiments, the additional therapeutic agent that is administered systemically is an anti-HER2 antibody (e.g., trastuzumab). In certain embodiments, the additional therapeutic agent that is administered systemically is a chemotherapeutic agent (e.g., gemcitabine). In certain embodiments, the subject has solid tumors and the additional therapeutic agent that is administered systemically is an anti-PD-1 antibody (e.g., pembrolizumab or nivolumab). In certain embodiments, the anti-PD-1 antibody is pembrolizumab administered at 200 mg every three weeks. In certain embodiments, the subject has head and neck squamous cell carcinoma (HNSCC) and the additional therapeutic agent that is administered systemically is an anti-EGFR antibody (e.g., cetuximab). In certain embodiments, the subject has HER2⁻ breast cancer and the additional therapeutic agent that is administered systemically is an anti-HER2 antibody (e.g., trastuzumab). In certain embodiments, the subject further received a chemotherapeutic agent (e.g., gemcitabine). In one aspect, the present invention relates to an anti-CTLA-4 antibody and/or pharmaceutical composition of the present invention, and optionally an additional therapeutic agent, for use in a method for the treatment of cancer, wherein the anti-CTLA-4 antibody and/or pharmaceutical composition of the present invention is administered intratumorally to the subject. In one preferred embodiment, an additional therapeutic agent is administered to the subject, more preferably, an additional therapeutic agent is administered systemically to the subject.

In certain embodiments, an anti-PD-1 antibody is used in methods described herein. In certain embodiments, the anti-PD-1 antibody is Nivolumab, also known as BMS-936558 or MDX1106, developed by Bristol-Myers Squibb. In certain embodiments, the anti-PD-1 antibody is Pembrolizumab, also known as Lambrolizumab or MK-3475, developed by Merck & Co. In certain embodiments, the anti-PD-1 antibody is Pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods described herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods described herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods described herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, an anti-LAG-3 antibody is used in methods described herein. In certain embodiments, the anti-LAG-3 antibody is BMS-986016 developed by Bristol-Myers Squibb. In certain embodiments, the anti-LAG-3 antibody is LAG525 developed by Novartis. In certain embodiments, the anti-LAG-3 antibody is GSK2831781 developed by GSK.

Non-limiting examples of anti-LAG-3 antibodies that may be used in treatment methods described herein are disclosed in the following patents and patent applications, which are incorporated herein by reference in their entireties for all purposes: U.S. Pat. No. 9,244,059; U.S. Publication No. US 2011/0150892 A1; U.S. Publication No. US 2014/0093511 A1; U.S. Publication No. US 2014/0286935 A1; U.S. Publication No. US 2015/0259420 A1; and PCT Publication No. WO 2015/042246 A1; PCT Publication No. WO 2015/116539 A1; PCT Publication No. WO 2015/200119 A1; and PCT Publication No. WO 2016/028672 A1.

In certain embodiments, an anti-EGFR antibody is used in methods described herein. In certain embodiments, the anti-EGFR antibody is cetuximab developed by Bristol-Myers Squibb and ImClone, panitumumab developed by Abgenix and Amgen, nimotuzumab developed by CMI Cuba and YM BioSciences, necitumumab developed by ImClone, zalutumumab developed by Genmab, matuzumab developed by Takeda, Sym004 developed by Merck Serono and Symphogen, imgatuzumab developed by Glycart and Roche, duligotumab developed by Genentech and Roche, depatuxizumab developed by Abbott, depatuxizumab mafodotin developed by Abbvie, MM-151 developed by Adimab and Merrimack, GC1118 developed by Green Cross, AMG 595 developed by Amgen and ImmunoGen, CetuGEX developed by Glycotope, laprituximab emtansine developed by ImmunoGen, JNJ-61186372 developed by Genmab and Janssen Biotech, SCT200 developed by Sinocelltech, LY3164530 developed by Lilly, HLX07 developed by Shanghai Henlius, or SYN004 developed by Synermore.

In certain embodiments, an anti-HER2 antibody is used in methods described herein. In certain embodiments, the anti-HER2 antibody is trastuzumab developed by Genentech and Roche, trastuzumab emtansine developed by Genentech and Roche, pertuzumab developed by Genentech, ertumaxomab developed by Fresenius, margetuximab developed by MacroGenics, MM-111 developed by Merrimack, CT-P06 developed by Celltrion, PF-05280014 developed by Pfizer, MM-302 developed by Merrimack, SB3 developed by Merck & Co, CMAB302 developed by Shanghai CP Guojian, TrasGEX developed by Glycotope, ARX788 developed by Ambrx and Zhejiang Medicine, SYD985 developed by Synthon, FS102 developed by Bristol-Myers Squibb and f-star, BCD-022 developed by Biocad, ABP 980 developed by Amgen, DS-8201a developed by Daiichi Sankyo, HLX02 developed by Shanghai Henlius, or CANMAb developed by Biocon and Mylan.

An antibody or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival and subcutaneous routes. Pulmonary administration can also be employed, e.g., by use of an inhaler or nebulizer, and formulation with an aerosolizing agent for use as a spray. In certain embodiments, the antibody or pharmaceutical composition described herein is delivered subcutaneously or intravenously. In certain embodiments, the antibody or pharmaceutical composition described herein is delivered intratumorally. In certain embodiments, the anti-CTLA-4 antibody or pharmaceutical composition described herein is delivered to a tumor draining lymph node. In certain embodiments, the antibody or pharmaceutical composition described herein is delivered via a localized administration (e.g., subcutaneous administration). In certain embodiments, the anti-CTLA-4 antibody or pharmaceutical composition described herein is delivered systemically. In certain embodiments, the anti-CTLA-4 antibody or pharmaceutical composition described herein is delivered locally.

In one aspect, the present invention relates to an anti-CTLA-4 antibody and/or pharmaceutical composition of the present invention, and optionally an additional therapeutic agent, for use in a method for the treatment of cancer, wherein the anti-CTLA-4 antibody and/or pharmaceutical composition of the present invention is delivered intratumorally to the subject, is delivered to a tumor draining lymph node of a subject, or is delivered via a localized administration (e.g., subcutaneous administration) to a subject.

The amount of an antibody or composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an anti-CTLA-4 antibody or pharmaceutical composition described herein is administered to a subject (e.g., via intravenous injection) at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg. In certain embodiments, an anti-CTLA-4 antibody or pharmaceutical composition described herein is administered to a subject (e.g., via intravenous injection) every week, every two weeks, every three weeks, every four weeks, every six weeks, every eight weeks, every twelve weeks, every month, every two months, every three months, every four months, every five months, every six months, every eight months, and every year, e.g., at the doses described above. In certain embodiments, an anti-CTLA-4 antibody or pharmaceutical composition described herein is administered to a subject (e.g., via intravenous injection) every three weeks at the doses described above.

In one aspect, the present invention relates to an anti-CTLA-4 antibody and/or pharmaceutical composition of the present invention, and optionally an additional therapeutic agent, for use in a method for the treatment of cancer, wherein the anti-CTLA-4 antibody and/or pharmaceutical composition of the present invention is administered to a subject at 0.01 mg/kg, 0.03 mg/kg, 0.1 mg/kg, 0.3 mg/kg, 1 mg/kg, 3 mg/kg, 6 mg/kg, 10 mg/kg, about 0.1 mg/kg, about 0.3 mg/kg, about 1 mg/kg, about 3 mg/kg, about 6 mg/kg, or about 10 mg/kg, more preferably every two weeks, every three weeks, every four weeks, every six weeks, or every twelve weeks.

In certain embodiments, an anti-CTLA-4 antibody or pharmaceutical composition described herein is administered to a subject (e.g., via intravenous injection) at 0.1 mg/kg every two weeks, every three weeks, every four weeks, every six weeks, or every twelve weeks. In certain embodiments, an anti-CTLA-4 antibody or pharmaceutical composition described herein is administered to a subject (e.g., via intravenous injection) at 0.3 mg/kg every two weeks, every three weeks, every four weeks, every six weeks, or every twelve weeks. In certain embodiments, an anti-CTLA-4 antibody or pharmaceutical composition described herein is administered to a subject (e.g., via intravenous injection) at 1 mg/kg every two weeks, every three weeks, every four weeks, every six weeks, or every twelve weeks. In certain embodiments, an anti-CTLA-4 antibody or pharmaceutical composition described herein is administered to a subject (e.g., via intravenous injection) at 3 mg/kg every two weeks, every three weeks, every four weeks, every six weeks, or every twelve weeks. In certain embodiments, an anti-CTLA-4 antibody or pharmaceutical composition described herein is administered to a subject (e.g., via intravenous injection) at 6 mg/kg every two weeks, every three weeks, every four weeks, every six weeks, or every twelve weeks. In certain embodiments, an anti-CTLA-4 antibody or pharmaceutical composition described herein is administered to a subject (e.g., via intravenous injection) at 10 mg/kg every two weeks, every three weeks, every four weeks, every six weeks, or every twelve weeks.

In certain embodiments, an anti-CTLA-4 antibody or pharmaceutical composition described herein is administered to a subject (e.g., via intravenous injection) at 0.1 mg/kg or about 0.1 mg/kg every three weeks. In certain embodiments, an anti-CTLA-4 antibody or pharmaceutical composition described herein is administered to a subject (e.g., via intravenous injection) at 0.3 mg/kg or about 0.3 mg/kg every three weeks. In certain embodiments, an anti-CTLA-4 antibody or pharmaceutical composition described herein is administered to a subject (e.g., via intravenous injection) at 1 mg/kg or about 1 mg/kg every three weeks. In certain embodiments, an anti-CTLA-4 antibody or pharmaceutical composition described herein is administered to a subject (e.g., via intravenous injection) at 3 mg/kg or about 3 mg/kg every three weeks. In certain embodiments, an anti-CTLA-4 antibody or pharmaceutical composition described herein is administered to a subject (e.g., via intravenous injection) at 6 mg/kg or about 6 mg/kg every three weeks. In certain embodiments, an anti-CTLA-4 antibody or pharmaceutical composition described herein is administered to a subject (e.g., via intravenous injection) at 10 mg/kg or about 10 mg/kg every three weeks.

In certain embodiments, an anti-CTLA-4 antibody or pharmaceutical composition described herein is administered to a subject via intratumoral injection at 0.01 mg/kg, 0.03 mg/kg, 0.1 mg/kg, 0.3 mg/kg, 1 mg/kg, 3 mg/kg, about 0.01 mg/kg, about 0.03 mg/kg, about 0.1 mg/kg, about 0.3 mg/kg, about 1 mg/kg, or about 3 mg/kg. In certain embodiments, an anti-CTLA-4 antibody or pharmaceutical composition described herein is administered to a subject via intratumoral injection every week, every two weeks, every three weeks, every four weeks, every six weeks, every eight weeks, every twelve weeks, every month, every two months, every three months, every four months, every five months, every six months, every eight months, and every year, e.g., at the doses described above. In certain embodiments, an anti-CTLA-4 antibody or pharmaceutical composition described herein is administered to a subject via intratumoral injection every three weeks at the doses described above.

In certain embodiments, an anti-CTLA-4 antibody or pharmaceutical composition described herein is administered to a subject via intratumoral injection at 0.01 mg/kg or about 0.01 mg/kg every three weeks. In certain embodiments, an anti-CTLA-4 antibody or pharmaceutical composition described herein is administered to a subject via intratumoral injection at 0.03 mg/kg or about 0.03 mg/kg every three weeks. In certain embodiments, an anti-CTLA-4 antibody or pharmaceutical composition described herein is administered to a subject via intratumoral injection at 0.1 mg/kg or about 0.1 mg/kg every three weeks. In certain embodiments, an anti-CTLA-4 antibody or pharmaceutical composition described herein is administered to a subject via intratumoral injection at 0.3 mg/kg or about 0.3 mg/kg every three weeks. In certain embodiments, an anti-CTLA-4 antibody or pharmaceutical composition described herein is administered to a subject via intratumoral injection at 1 mg/kg or about 1 mg/kg every three weeks. In certain embodiments, an anti-CTLA-4 antibody or pharmaceutical composition described herein is administered to a subject via intratumoral injection at 3 mg/kg or about 3 mg/kg every three weeks.

In certain embodiments, an anti-CTLA-4 antibody or pharmaceutical composition described herein is administered to a subject via a localized administration (e.g., subcutaneous administration) at 0.01 mg/kg, 0.03 mg/kg, 0.1 mg/kg, 0.3 mg/kg, 1 mg/kg, 3 mg/kg, about 0.01 mg/kg, about 0.03 mg/kg, about 0.1 mg/kg, about 0.3 mg/kg, about 1 mg/kg, or about 3 mg/kg. In certain embodiments, an anti-CTLA-4 antibody or pharmaceutical composition described herein is administered to a subject via a localized administration (e.g., subcutaneous administration) every week, every two weeks, every three weeks, every four weeks, every six weeks, every eight weeks, every twelve weeks, every month, every two months, every three months, every four months, every five months, every six months, every eight months, and every year, e.g., at the doses described above.

In certain embodiments, the therapeutic combination is administered to a subject for at least 3, 6, 9, 12, 18, or 24 months. In certain embodiments, the therapeutic combination is administered to a subject for up to 3, 6, 9, 12, 18, or 24 months.

In certain embodiments, the instant disclosure provides a method of treating a subject having angiosarcoma, the method comprising administering to the subject (e.g., intravenously, intratumorally, or subcutaneously) an effective amount of an anti-CTLA-4 antibody or pharmaceutical composition described herein. In certain embodiments, the instant disclosure provides a method of treating a subject having angiosarcoma, the method comprising administering to the subject intravenously an antibody that specifically binds to human CTLA-4 at 0.01 mg/kg, 0.03 mg/kg, 0.1 mg/kg, 0.3 mg/kg, 1 mg/kg, 3 mg/kg, about 0.01 mg/kg, about 0.03 mg/kg, about 0.1 mg/kg, about 0.3 mg/kg, about 1 mg/kg, or about 3 mg/kg, optionally every one, two or three weeks. In certain embodiments, the instant disclosure provides a method of treating a subject having angiosarcoma, the method comprising administering to the subject intravenously an antibody that specifically binds to human CTLA-4 at 0.1 mg/kg once every three weeks. In certain embodiments, the antibody comprises a heavy chain variable region comprising the amino acid sequence of SEQ ID NO: 8 and a light chain variable region comprising the amino acid sequence of SEQ ID NO: 9. In certain embodiments, the antibody comprises a heavy chain comprising the amino acid sequence of SEQ ID NO: 23; and a light chain comprising the amino acid sequence of SEQ ID NO: 27. In certain embodiments, the antibody comprises a heavy chain comprising the amino acid sequence of SEQ ID NO: 24; and a light chain comprising the amino acid sequence of SEQ ID NO: 27. In certain embodiments, the antibody comprises a heavy chain comprising the amino acid sequence of SEQ ID NO: 25; and a light chain comprising the amino acid sequence of SEQ ID NO: 27. In certain embodiments, the antibody comprises a heavy chain comprising the amino acid sequence of SEQ ID NO: 26; and a light chain comprising the amino acid sequence of SEQ ID NO: 27.

An anti-CTLA-4 antibody described herein can also be used to assay CTLA-4 protein levels in a biological sample using classical immunohistological methods known to those of skill in the art, including immunoassays, such as the enzyme linked immunosorbent assay (ELISA), immunoprecipitation, or Western blotting. Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label an antibody or an antigen-binding fragment thereof described herein. Alternatively, a second antibody that recognizes an anti-CTLA-4 antibody or antigen-binding fragment thereof described herein can be labeled and used in combination with an anti-CTLA-4 antibody or antigen-binding fragment thereof to detect CTLA-4 protein levels. In one embodiment, the present invention relates to the use of an anti-CTLA-4 antibody of the invention, for assaying and/or detecting CTLA-4 protein levels in a biological sample in vitro.

Assaying for the expression level of CTLA-4 protein is intended to include qualitatively or quantitatively measuring or estimating the level of a CTLA-4 protein in a first biological sample either directly (e.g., by determining or estimating absolute protein level) or relatively (e.g., by comparing to the disease associated protein level in a second biological sample). CTLA-4 polypeptide expression level in the first biological sample can be measured or estimated and compared to a standard CTLA-4 protein level, the standard being taken from a second biological sample obtained from an individual not having the disorder or being determined by averaging levels from a population of individuals not having the disorder. As will be appreciated in the art, once the "standard" CTLA-4 polypeptide level is known, it can be used repeatedly as a standard for comparison.

As used herein, the term "biological sample" refers to any biological sample obtained from a subject, cell line, tissue, or other source of cells potentially expressing CTLA-4. Methods for obtaining tissue biopsies and body fluids from animals (e.g., humans) are well known in the art. Biological samples include peripheral mononuclear blood cells.

An anti-CTLA-4 antibody or antigen-binding fragment thereof described herein can be used for prognostic, diagnostic, monitoring and screening applications, including in vitro and in vivo applications well known and standard to the skilled artisan and based on the present description. Prognostic, diagnostic, monitoring and screening assays and kits for in vitro assessment and evaluation of immune system status and/or immune response may be utilized to predict, diagnose and monitor to evaluate patient samples including those known to have or suspected of having an immune system-dysfunction or with regard to an anticipated or desired immune system response, antigen response or vaccine response. The assessment and evaluation of immune system status and/or immune response is also useful in determining the suitability of a patient for a clinical trial of a drug or for the administration of a particular chemotherapeutic agent or an antibody or antigen-binding fragment thereof, including combinations thereof, versus a different agent or antibody or antigen-binding fragment thereof. This type of prognostic and diagnostic monitoring and assessment is already in practice utilizing antibodies against the HER2 protein in breast cancer (HercepTest™, Dako) where the assay is also used to evaluate patients for antibody therapy using Herceptin®. In vivo applications include directed cell therapy and immune system modulation and radio imaging of immune responses.

In one aspect, the present invention relates to an anti-CTLA-4 antibody and/or pharmaceutical composition of the present invention for use as a diagnostic.

In one aspect, the present invention relates to an anti-CTLA-4 antibody and/or pharmaceutical composition of the present invention for use in a method for the prediction, diagnosis and/or monitoring of an immune system-dysfunction and/or cancer.

In one embodiment, the present invention relates to the use of an anti-CTLA-4 antibody of the invention, for predicting, diagnosing and/or monitoring an immune system-dysfunction and/or cancer in a subject by assaying and/or detecting CTLA-4 protein levels in a biological sample of the subject of in vitro.

In one embodiment, an anti-CTLA-4 antibody or antigen-binding fragment thereof can be used in immunohistochemistry of biopsy samples. In another embodiment, an anti-CTLA-4 antibody or antigen-binding fragment thereof can be used to detect levels of CTLA-4, or levels of cells which contain CTLA-4 on their membrane surface, which levels can then be linked to certain disease symptoms. Anti-CTLA-4 antibodies or antigen-binding fragments thereof described herein may carry a detectable or functional label. When fluorescence labels are used, currently available microscopy and fluorescence-activated cell sorter analysis (FACS) or combination of both methods procedures known in the art may be utilized to identify and to quantitate the specific binding members. Anti-CTLA-4 antibodies or antigen-binding fragments thereof described herein may carry a fluorescence label. Exemplary fluorescence labels include, for example, reactive and conjugated probes e.g. Aminocoumarin, Fluorescein and Texas red, Alexa Fluor dyes, Cy dyes and DyLight dyes. An anti-CTLA-4 antibody or antigen-binding fragment thereof may carry a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of anti-CTLA-4 antibody or antigen-binding fragment thereof to CTLA-4 (e.g., human CTLA-4). In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-CTLA-4 antibody or antigen-binding fragment thereof under conditions that allow for the formation of a complex between the antibody or antigen-binding fragment thereof and CTLA-4. Any complexes formed between the antibody or antigen-binding fragment thereof and CTLA-4 are detected and compared in the sample and the control. In light of the specific binding of the antibodies described herein for CTLA-4, the antibodies or antigen-binding fragments thereof can be used to specifically detect CTLA-4 expression on the surface of cells. The antibodies or antigen-binding fragments thereof described herein can also be used to purify CTLA-4 via immunoaffinity purification. Also included herein is an assay system which may be prepared in the form of a test kit for the quantitative analysis of the extent of the presence of, for instance, CTLA-4 or CTLA-4/CTLA-4 ligand complexes. The system or test kit may comprise a labeled component, e.g., a labeled antibody, and one or more additional immunochemical reagents.

In one embodiment, the present invention relates to an in vitro method for assaying and/or detecting CTLA-4 protein levels in a biological sample comprising (1) contacting a sample and optionally a control sample with an anti-CTLA-4 antibody or antigen-binding fragment thereof of the invention under conditions that allow for the formation of a complex between the antibody or antigen-binding fragment thereof and CTLA-4, and (2) detecting and comparing the complexes formed in the sample and optionally the control.

6.5 Polynucleotides, Vectors and Methods of Producing Anti-CTLA-4 Antibodies In another aspect, provided herein are polynucleotides comprising a nucleotide sequence encoding an antibody described herein or a fragment thereof (e.g., a light chain variable region and/or heavy chain variable region) that specifically binds to a CTLA-4 (e.g., human CTLA-4) antigen, and vectors, e.g., vectors comprising such polynucleotides for recombinant expression in host cells (e.g., E. coli and mammalian cells). Provided herein are polynucleotides comprising nucleotide sequences encoding any of the antibodies provided herein, as well as vectors comprising such polynucleotide sequences, e.g., expression vectors for their efficient expression in host cells, e.g., mammalian cells.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody described herein is isolated or purified.

In particular aspects, provided herein are polynucleotides comprising nucleotide sequences encoding antibodies or antigen-binding fragments thereof, which specifically bind to a CTLA-4 polypeptide (e.g., human CTLA-4) and comprises an amino acid sequence as described herein, as well as antibodies which compete with such antibodies for binding to a CTLA-4 polypeptide (e.g., in a dose-dependent manner), or which binds to the same epitope as that of such antibodies.

In certain aspects, provided herein are polynucleotides comprising a nucleotide sequence encoding the light chain or heavy chain of an antibody described herein. The polynucleotides can comprise nucleotide sequences encoding a light chain comprising the VL FRs and CDRs of antibodies described herein (see, e.g., Table 1).

Also provided herein are polynucleotides encoding an anti-CTLA-4 antibody that are optimized, e.g., by codon/RNA optimization, replacement with heterologous signal sequences, and elimination of mRNA instability elements. Methods to generate optimized nucleic acids encoding an anti-CTLA-4 antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly, all of which are herein incorporated by reference in their entireties. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of an anti-CTLA-4 antibody or fragment thereof by at least 1 fold, 2 fold, 3 fold, 4 fold, 5 fold, 10 fold, 20 fold, 30 fold, 40 fold, 50 fold, 60 fold, 70 fold, 80 fold, 90 fold, or 100 fold or more relative to the expression of an anti-CTLA-4 antibody encoded by polynucleotides that have not been optimized.

In certain embodiments, an optimized polynucleotide sequence encoding an anti-CTLA-4 antibody described herein or a fragment thereof (e.g., VL domain and/or VH domain) can hybridize to an antisense (e.g., complementary) polynucleotide of an unoptimized polynucleotide sequence encoding an anti-CTLA-4 antibody described herein or a fragment thereof (e.g., VL domain and/or VH domain). In specific embodiments, an optimized nucleotide sequence encoding an anti-CTLA-4 antibody described herein or a fragment hybridizes under high stringency conditions to antisense polynucleotide of an unoptimized polynucleotide sequence encoding an anti-CTLA-4 antibody described herein or a fragment thereof. In a specific embodiment, an optimized nucleotide sequence encoding an anti-CTLA-4 antibody described herein or a fragment thereof hybridizes under high stringency, intermediate or lower stringency hybridization conditions to an antisense polynucleotide of an unoptimized nucleotide sequence encoding an anti-CTLA-4 antibody described herein or a fragment thereof. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, e.g., antibodies described in Table 1, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), BioTechniques 17: 242-6, incorporated by reference in its entirety), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody described herein can be generated from nucleic acid from a suitable source (e.g., a hybridoma) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody is not available, but the sequence of the antibody molecule is known, a nucleic acid encoding the immunoglobulin can be chemically synthesized or obtained from a suitable source (e.g., an antibody cDNA library or a cDNA library generated from, or nucleic acid, preferably poly A+ RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody.

Amplified nucleic acids generated by PCR can then be cloned into replicable cloning vectors using any method well known in the art.

DNA encoding anti-CTLA-4 antibodies described herein can be readily isolated and sequenced using conventional procedures (e.g., by using oligonucleotide probes that are capable of binding specifically to genes encoding the heavy and light chains of the anti-CTLA-4 antibodies). Hybridoma cells can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-CTLA-4 antibodies in the recombinant host cells.

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a heavy chain constant region, e.g., the human gamma 4 constant region, and the PCR amplified VL domains can be cloned into vectors expressing a light chain constant region, e.g., human kappa or lambda constant regions. In certain embodiments, the vectors for expressing the VH or VL domains comprise an EF-1α promoter, a secretion signal, a cloning site for the variable region, constant domains, and a selection marker such as neomycin. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

The DNA also can be modified, for example, by substituting the coding sequence for human heavy and light chain constant domains in place of the murine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) Current Protocols in Molecular Biology, Vol. I, Green Publishing Associates, Inc. and John Wiley & Sons, Inc., New York at pages 6.3.1-6.3.6 and 2.10.3, incorporated by reference in its entirety.

In certain aspects, provided herein are cells (e.g., host cells) expressing (e.g., recombinantly) antibodies described herein (or an antigen-binding fragment thereof) which specifically bind to CTLA-4 (e.g., human CTLA-4) and related polynucleotides and expression vectors. Provided herein are vectors (e.g., expression vectors) comprising polynucleotides comprising nucleotide sequences encoding anti-CTLA-4 antibodies or a fragment for recombinant expression in host cells, preferably in mammalian cells. Also provided herein are host cells comprising such vectors for recombinantly expressing anti-CTLA-4 antibodies described herein (e.g., human or humanized antibody). In a particular aspect, provided herein are methods for producing an antibody described herein, comprising expressing such antibody from a host cell.

Recombinant expression of an antibody described herein (e.g., a full-length antibody, heavy and/or light chain of an antibody, or a single chain antibody described herein) that specifically binds to CTLA-4 (e.g., human CTLA-4) involves construction of an expression vector containing a polynucleotide that encodes the antibody. Once a polynucleotide encoding an antibody molecule, heavy and/or light chain of an antibody, or a fragment thereof (e.g., heavy and/or light chain variable regions) described herein has been obtained, the vector for the production of the antibody molecule can be produced by recombinant DNA technology using techniques well known in the art. Thus, methods for preparing a protein by expressing a polynucleotide containing an antibody or antibody fragment (e.g., light chain or heavy chain) encoding nucleotide sequence are described herein. Methods which are well known to those skilled in the art can be used to construct expression vectors containing antibody or antibody fragment (e.g., light chain or heavy chain) coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable region of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464, which are herein incorporated by reference in their entireties) and variable regions of the antibody can be cloned into such a vector for expression of the entire heavy, the entire light chain, or both the entire heavy and light chains.

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or fragment thereof, or a single chain antibody described herein, operably linked to a promoter for expression of such sequences in the host cell. In certain embodiments, for the expression of double-chained antibodies, vectors encoding both the heavy and light chains, individually, can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain or a heavy chain variable region of an antibody described herein, or a fragment thereof, and a second vector comprising a polynucleotide encoding a light chain or a light chain variable region of an antibody described herein, or a fragment thereof. In other embodiments, a first host cell comprises a first vector comprising a polynucleotide encoding a heavy chain or a heavy chain variable region of an antibody described herein, or a fragment thereof, and a second host cell comprises a second vector comprising a polynucleotide encoding a light chain or a light chain variable region of an antibody described herein. In specific embodiments, a heavy chain/heavy chain variable region expressed by a first cell associated with a light chain/light chain variable region of a second cell to form an anti-CTLA-4 antibody described herein or an antigen-binding fragment thereof. In certain embodiments, provided herein is a population of host cells comprising such first host cell and such second host cell.

In a particular embodiment, provided herein is a population of vectors comprising a first vector comprising a polynucleotide encoding a light chain/light chain variable region of an anti-CTLA-4 antibody described herein, and a second vector comprising a polynucleotide encoding a heavy chain/heavy chain variable region of an anti-CTLA-4 antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies described herein or an antigen-binding fragment thereof are CHO cells, for example CHO cells from the CHO GS System™ (Lonza). In a particular embodiment, cells for expressing antibodies described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking M K & Hofstetter H (1986) Gene 45: 101-5; and Cockett M I et al., (1990) Biotechnology 8(7): 662-7, which are herein incorporated by reference in their entireties). In certain embodiments, antibodies described herein are produced by CHO cells or NS0 cells. In a specific embodiment, the expression of nucleotide sequences encoding antibodies described herein which specifically bind CTLA-4 (e.g., human CTLA-4) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794, herein incorporated by reference in its entirety), in which the antibody coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509, which are herein incorporated by reference in their entireties); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan J & Shenk T (1984) PNAS 81(12): 3655-9, herein incorporated by reference in its entirety). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544, herein incorporated by reference in its entirety).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, anti-CTLA-4 antibodies described herein are produced in mammalian cells, such as CHO cells.

In a specific embodiment, the antibodies described herein or antigen-binding fragments thereof have reduced fucose content or no fucose content. Such antibodies can be produced using techniques known one skilled in the art. For example, the antibodies can be expressed in cells deficient or lacking the ability of to fucosylate. In a specific example, cell lines with a knockout of both alleles of $\alpha 1,6$-fucosyltransferase can be used to produce antibodies or antigen-binding fragments thereof with reduced fucose content. The Potelligent® system (Lonza) is an example of such a system that can be used to produce antibodies or antigen-binding fragments thereof with reduced fucose content.

For long-term, high-yield production of recombinant proteins, stable expression cells can be generated. For example, cell lines which stably express an anti-CTLA-4 antibody described herein or an antigen-binding fragment thereof can be engineered. In specific embodiments, a cell provided herein stably expresses a light chain/light chain variable region and a heavy chain/heavy chain variable region which associate to form an antibody described herein or an antigen-binding fragment thereof.

In certain aspects, rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express an anti-CTLA-4 antibody described herein or a fragment thereof. Such engineered cell lines can be particularly useful in screening and evaluation of compositions that interact directly or indirectly with the antibody molecule.

A number of selection systems can be used, including but not limited to the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034, herein incorporated by reference in its entirety) and adenine phosphoribosyltransferase (Lowy I et al., (1980) Cell 22(3): 817-23, herein incorporated by reference in its entirety) genes in tk-, hgprt- or aprt-cells, respectively. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), all of which are herein incorporated by reference in their entireties. Methods commonly known in the art of recombinant DNA technology can be routinely applied to select the desired recombinant clone and such methods are described, for example, in Ausubel F M et al., (eds.), Current Protocols in Molecular Biology, John Wiley & Sons, N Y (1993); Kriegler M, Gene Transfer and Expression, A Laboratory Manual, Stockton Press, N Y (1990); and in Chapters 12 and 13, Dracopoli N C et al., (eds.), Current Protocols in Human Genetics, John Wiley & Sons, N Y (1994); Colbère-Garapin F et al., (1981) J Mol Biol 150: 1-14, which are incorporated by reference herein in their entireties.

The expression levels of an antibody molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), herein incorporated by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse G F et al., (1983) Mol Cell Biol 3: 257-66, herein incorporated by reference in its entirety).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides. The host cells can be co-transfected with different amounts of the two or more expression vectors. For example, host cells can be transfected with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50.

Alternatively, a single vector can be used which encodes, and is capable of expressing, both heavy and light chain polypeptides. In such situations, the light chain should be placed before the heavy chain to avoid an excess of toxic free heavy chain (Proudfoot N J (1986) Nature 322: 562-565; and Köhler G (1980) PNAS 77: 2197-2199, which are herein incorporated by reference in their entireties). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody or an antigen-binding fragment thereof described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly, such preparations of the antibody have less than about 30%, 20%, 10%, or 5% (by dry weight) of chemical precursors or compounds other than the antibody of interest. In a specific embodiment, antibodies described herein are isolated or purified.

Antibodies or fragments thereof that specifically bind to CTLA-4 (e.g., human CTLA-4) can be produced by any method known in the art for the synthesis of antibodies, for example, by chemical synthesis or by recombinant expression techniques. The methods described herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) Molecular Cloning: A Laboratory Manual, Cold Spring Harbor Laboratory Press; Sambrook J et al., (1989), Molecular Cloning: A Laboratory Manual, Second Edition, Cold Spring Harbor Laboratory Press; Sambrook J et al., (2001) Molecular Cloning: A Laboratory Manual, Cold Spring Harbor Laboratory Press, Cold Spring Harbor, N.Y.; Ausubel F M et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren B et al., (eds.) (1999) Genome Analysis: A Laboratory Manual, Cold Spring Harbor Laboratory Press, all of which are herein incorporated by reference in their entireties.

In a specific embodiment, an antibody described herein is an antibody (e.g., recombinant antibody) prepared, expressed, created or isolated by any means that involves creation, e.g., via synthesis, genetic engineering of DNA sequences. In certain embodiments, such antibody comprises sequences (e.g., DNA sequences or amino acid sequences) that do not naturally exist within the antibody germline repertoire of an animal or mammal (e.g., human) in vivo.

In one aspect, provided herein is a method of making an antibody or an antigen-binding fragment thereof which specifically binds to CTLA-4 (e.g., human CTLA-4) comprising culturing a cell or host cell described herein. In a certain aspect, provided herein is a method of making an antibody or an antigen-binding fragment thereof which specifically binds to CTLA-4 (e.g., human CTLA-4) comprising expressing (e.g., recombinantly expressing) the antibody or antigen-binding fragment thereof using a cell or host cell described herein (e.g., a cell or a host cell comprising polynucleotides encoding an antibody described herein). In a particular embodiment, the cell is an isolated cell. In a particular embodiment, the exogenous polynucleotides have been introduced into the cell. In a particular embodiment, the method further comprises the step of purifying the antibody or antigen-binding fragment thereof obtained from the cell or host cell. Preferably, the method is performed in vitro.

Methods for producing polyclonal antibodies are known in the art (see, for example, Chapter 11 in: Short Protocols in Molecular Biology, (2002) 5th Ed., Ausubel F M et al., eds., John Wiley and Sons, New York, herein incorporated by reference in its entirety).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow E & Lane D, Antibodies: A Laboratory Manual, (Cold Spring Harbor Laboratory Press, 2nd ed. 1988); Hammerling G J et al., in: Monoclonal Antibodies and T-Cell Hybridomas 563 681 (Elsevier, N.Y., 1981), which are herein incorporated by reference in their entireties. The term "monoclonal antibody" as used herein is not limited to antibodies produced through hybridoma technology. For example, monoclonal antibodies can be produced recombinantly from host cells exogenously expressing an antibody described herein or a fragment thereof, for example, light chain and/or heavy chain of such antibody.

In specific embodiments, a "monoclonal antibody," as used herein, is an antibody produced by a single cell (e.g., hybridoma or host cell producing a recombinant antibody), wherein the antibody specifically binds to CTLA-4 (e.g., human CTLA-4) as determined, e.g., by ELISA or other antigen-binding or competitive binding assay known in the art or in the examples provided herein. In particular embodiments, a monoclonal antibody can be a chimeric antibody or a humanized antibody. In certain embodiments, a monoclonal antibody is a monovalent antibody or multivalent (e.g., bivalent) antibody. In particular embodiments, a monoclonal antibody is a monospecific or multispecific antibody (e.g., bispecific antibody). Monoclonal antibodies described herein can, for example, be made by the hybridoma method as described in Kohler G & Milstein C (1975) Nature 256: 495, herein incorporated by reference in its entirety, or can, e.g., be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel F M et al., supra).

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will specifically bind to the protein (e.g., CTLA-4 (e.g., human CTLA-4)) used for immunization. Alternatively, lymphocytes may be immunized in vitro. Lymphocytes then are fused with myeloma cells using a suitable fusing agent, such as polyethylene glycol, to form a hybridoma cell (Goding J W (Ed), Monoclonal Antibodies: Principles and Practice, pp. 59-103 (Academic Press, 1986), herein incorporated by reference in its entirety). Additionally, a RIMMS (repetitive immunization multiple sites) technique can be used to immunize an animal (Kilpatrick K E et al., (1997) Hybridoma 16:381-9, herein incorporated by reference in its entirety).

In some embodiments, mice (or other animals, such as rats, monkeys, donkeys, pigs, sheep, hamster, or dogs) can be immunized with an antigen (e.g., CTLA-4 (e.g., human CTLA-4)) and once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the American Type Culture Collection (ATCC®) (Manassas, Va.), to form hybridomas. Hybridomas are selected and cloned by limited dilution. In certain embodiments, lymph nodes of the immunized mice are harvested and fused with NS0 myeloma cells.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as NS0 cell line or those derived from MOPC-21 and MPC-11 mouse tumors available from the Salk Institute Cell Distribution Center, San Diego, Calif., USA, and SP-2 or X63-Ag8.653 cells available from the American Type Culture Collection, Rockville, Md., USA. Human myeloma and mouse-human heteromyeloma cell lines also have been described for the production of human monoclonal antibodies (Kozbor D (1984) J Immunol 133: 3001-5; Brodeur et al., Monoclonal Antibody Production Techniques and Applications, pp. 51-63 (Marcel Dekker, Inc., New York, 1987), which are herein incorporated by reference in their entireties).

Culture medium in which hybridoma cells are growing is assayed for production of monoclonal antibodies directed against CTLA-4 (e.g., human CTLA-4). The binding specificity of monoclonal antibodies produced by hybridoma cells is determined by methods known in the art, for example, immunoprecipitation or by an in vitro binding assay, such as radioimmunoassay (MA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding J W (Ed), Monoclonal Antibodies: Principles and Practice, supra). Suitable culture media for this purpose include, for example, D-MEM or RPMI 1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Antibodies described herein include antibody fragments which recognize specific CTLA-4 (e.g., human CTLA-4) and can be generated by any technique known to those of skill in the art. For example, Fab and F(ab')2 fragments described herein can be produced by proteolytic cleavage of immunoglobulin molecules, using enzymes such as papain (to produce Fab fragments) or pepsin (to produce F(ab')2 fragments). A Fab fragment corresponds to one of the two identical arms of an antibody molecule and contains the complete light chain paired with the VH and CH1 domains of the heavy chain. A F(ab')2 fragment contains the two antigen-binding arms of an antibody molecule linked by disulfide bonds in the hinge region.

Further, the antibodies described herein or antigen-binding fragments thereof can also be generated using various phage display methods known in the art. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with a scFv linker by PCR and cloned into a phagemid vector. The vector is electroporated in E. coli and the E. coli is infected with helper phage. Phage used in these methods are typically filamentous phage including fd and M13, and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkonan U et al., (1995) J Immunol Methods 182: 41-50; Ames R S et al., (1995) J Immunol Methods 184: 177-186; Kettleborough C A et al., (1994) Eur J Immunol 24: 952-958; Persic L et al., (1997) Gene 187: 9-18; Burton D R & Barbas C F (1994) Advan Immunol 57: 191-280; PCT Application No. PCT/GB91/001134; International Publication Nos. WO 90/02809, WO 91/10737, WO 92/01047, WO 92/18619, WO 93/1 1236, WO 95/15982, WO 95/20401, and WO 97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108, all of which are herein incorporated by reference in their entireties.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and F(ab')$_2$ fragments can also be employed using methods known in the art such as those disclosed in PCT publication No. WO 92/22324; Mullinax R L et al., (1992) BioTechniques 12(6): 864-9; Sawai H et al., (1995) Am J Reprod Immunol 34: 26-34; and Better M et al., (1988) Science 240: 1041-1043, all of which are herein incorporated by reference in their entireties.

In certain embodiments, to generate whole antibodies, PCR primers including VH or VL nucleotide sequences, a restriction site, and a flanking sequence to protect the restriction site can be used to amplify the VH or VL sequences from a template, e.g., scFv clones. Utilizing cloning techniques known to those of skill in the art, the PCR amplified VH domains can be cloned into vectors expressing a VH constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

A chimeric antibody is a molecule in which different portions of the antibody are derived from different immunoglobulin molecules. For example, a chimeric antibody can contain a variable region of a mouse or rat monoclonal antibody fused to a constant region of a human antibody. Methods for producing chimeric antibodies are known in the art. See, e.g., Morrison S L (1985) Science 229: 1202-7; Oi V T & Morrison S L (1986) BioTechniques 4: 214-221; Gillies S D et al., (1989) J Immunol Methods 125: 191-202; and U.S. Pat. Nos. 5,807,715, 4,816,567, 4,816,397, and 6,331,415, all of which are herein incorporated by reference in their entireties.

A humanized antibody is capable of binding to a predetermined antigen and which comprises a framework region having substantially the amino acid sequence of a human immunoglobulin and CDRs having substantially the amino acid sequence of a non-human immunoglobulin (e.g., a murine immunoglobulin). In particular embodiments, a humanized antibody also comprises at least a portion of an immunoglobulin constant region (Fc), typically that of a human immunoglobulin. The antibody also can include the CH1, hinge, CH2, CH3, and CH4 regions of the heavy chain. A humanized antibody can be selected from any class of immunoglobulins, including IgM, IgG, IgD, IgA and IgE, and any isotype, including IgG$_1$, IgG$_3$ and IgG$_4$. Humanized antibodies can be produced using a variety of techniques known in the art, including but not limited to, CDR-grafting (European Patent No. EP 239400; International Publication No. WO 91/09967; and U.S. Pat. Nos. 5,225,539, 5,530,101, and 5,585,089), veneering or resurfacing (European Patent Nos. EP 592106 and EP 519596; Padlan E A (1991) Mol Immunol 28(4/5): 489-498; Studnicka G M et al., (1994) Prot Engineering 7(6): 805-814; and Roguska M A et al., (1994) PNAS 91: 969-973), chain shuffling (U.S. Pat. No. 5,565,332), and techniques disclosed in, e.g., U.S. Pat. Nos. 6,407,213, 5,766,886, International Publication No. WO 93/17105; Tan P et al., (2002) J Immunol 169: 1119-25; Caldas C et al., (2000) Protein Eng. 13(5): 353-60; Morea V et al., (2000) Methods 20(3): 267-79; Baca M et al., (1997) J Biol Chem 272(16): 10678-84; Roguska M A et al., (1996) Protein Eng 9(10): 895 904; Couto J R et al., (1995) Cancer Res. 55 (23 Supp): 5973s-5977s; Couto J R et al., (1995) Cancer Res 55(8): 1717-22; Sandhu J S (1994) Gene 150(2): 409-10 and Pedersen J T et al., (1994) J Mol Biol 235(3): 959-73, all of which are herein incorporated by reference in their entireties. See also U.S. Application Publication No. US 2005/0042664 A1 (Feb. 24, 2005), which is incorporated by reference herein in its entirety.

Methods for making multispecific (e.g., bispecific antibodies) have been described, see, for example, U.S. Pat. Nos. 7,951,917; 7,183,076; 8,227,577; 5,837,242; 5,989,830; 5,869,620; 6,132,992 and 8,586,713, all of which are herein incorporated by reference in their entireties.

Single domain antibodies, for example, antibodies lacking the light chains, can be produced by methods well known in the art. See Riechmann L & Muyldermans S (1999) J Immunol 231: 25-38; Nuttall S D et al., (2000) Curr Pharm Biotechnol 1(3): 253-263; Muyldermans S, (2001) J Biotechnol 74(4): 277-302; U.S. Pat. No. 6,005,079; and International Publication Nos. WO 94/04678, WO 94/25591 and WO 01/44301, all of which are herein incorporated by reference in their entireties.

Further, antibodies that specifically bind to a CTLA-4 antigen can, in turn, be utilized to generate anti-idiotype antibodies that "mimic" an antigen using techniques well known to those skilled in the art. (See, e.g., Greenspan N S & Bona C A (1989) FASEB J 7(5): 437-444; and Nissinoff A (1991) J Immunol 147(8): 2429-2438, which are herein incorporated by reference in their entireties).

In particular embodiments, an antibody described herein, which binds to the same epitope of CTLA-4 (e.g., human CTLA-4) as an anti-CTLA-4 antibody described herein, is a human antibody or an antigen-binding fragment thereof. In particular embodiments, an antibody described herein, which competitively blocks (e.g., in a dose-dependent manner) any one of the antibodies described herein, from binding to CTLA-4 (e.g., human CTLA-4), is a human antibody or an antigen-binding fragment thereof. Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., CTLA-4). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg N & Huszar D (1995) Int Rev Immunol 13:65-93, which is herein incorporated by reference in its entirety. For a detailed discussion of this technology for producing human antibodies and human monoclonal antibodies and protocols for producing such antibodies, see, e.g., International Publication Nos. WO 98/24893, WO 96/34096 and WO 96/33735; and U.S. Pat. Nos. 5,413,923, 5,625,126, 5,633,425, 5,569,825, 5,661,016, 5,545,806, 5,814,318 and 5,939,598. Examples of mice capable of producing human antibodies include the Xenomouse™ (Abgenix, Inc.; U.S. Pat. Nos. 6,075,181 and 6,150,184), the HuAb-Mouse™ (Mederex, Inc./Gen Pharm; U.S. Pat. Nos. 5,545,806 and 5,569,825), the Trans Chromo Mouse™ (Kirin) and the KM Mouse™ (Medarex/Kirin), all of which are herein incorporated by reference in their entireties.

Human antibodies which specifically bind to CTLA-4 (e.g., human CTLA-4) can be made by a variety of methods known in the art including phage display methods described above using antibody libraries derived from human immunoglobulin sequences. See also U.S. Pat. Nos. 4,444,887, 4,716,111, and 5,885,793; and International Publication Nos. WO 98/46645, WO 98/50433, WO 98/24893, WO 98/16654, WO 96/34096, WO 96/33735, and WO 91/10741, all of which are herein incorporated by reference in their entireties.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that specifically bind to a target antigen (e.g., CTLA-4 (e.g., human CTLA-4)). Such methods are known and are described in the art, see, e.g., Shinmoto H et al., (2004) Cytotechnology 46: 19-23; Naganawa Y et al., (2005) Human Antibodies 14: 27-31, which are herein incorporated by reference in their entireties.

6.6 Kits

Also provided, are kits comprising one or more antibodies described herein, or pharmaceutical composition or conjugates thereof. In a specific embodiment, provided herein is a pharmaceutical pack or kit comprising one or more containers filled with one or more of the ingredients of the pharmaceutical compositions described herein, such as one or more antibodies provided herein or an antigen-binding fragment thereof. In some embodiments, the kits contain a pharmaceutical composition described herein and any prophylactic or therapeutic agent, such as those described herein. In certain embodiments, the kits may contain a T-cell mitogen, such as, e.g., phytohaemagglutinin (PHA) and/or phorbol myristate acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises an antibody described herein, preferably a purified antibody, in one or more containers. In a specific embodiment, kits described herein contain a substantially isolated CTLA-4 antigen (e.g., human CTLA-4) as a control. In another specific embodiment, the kits described herein further comprise a control antibody which does not react with a CTLA-4 antigen. In another specific embodiment, kits described herein contain one or more elements for detecting the binding of an antibody to a CTLA-4 antigen (e.g., the antibody can be conjugated to a detectable substrate such as a fluorescent compound, an enzymatic substrate, a radioactive compound or a luminescent compound, or a second antibody which recognizes the first antibody can be conjugated to a detectable substrate). In specific embodiments, a kit provided herein can include a recombinantly produced or chemically synthesized CTLA-4 antigen. The CTLA-4 antigen provided in the kit can also be attached to a solid support. In a more specific embodiment, the detecting means of the above described kit includes a solid support to which a CTLA-4 antigen is attached. Such a kit can also include a non-attached reporter-labeled anti-human antibody or anti-mouse/rat antibody. In this embodiment, binding of the antibody to the CTLA-4 antigen can be detected by binding of the said reporter-labeled antibody.

In one embodiment, the present invention relates to the use of a kit of the present invention for in vitro assaying and/or detection of human CTLA-4 in a biological sample.

7. EXAMPLES

The examples in this Section (i.e., Section 6) are offered by way of illustration, and not by way of limitation.

7.1 Example 1: Characterization of Novel Anti-CTLA-4 Antibodies

This example describes the characterization of antibodies that bind to human CTLA-4. In particular, this example describes the characterization of antibodies that specifically bind to human CTLA-4 and inhibit the function of CTLA-4. The sequence information of the variable regions of these antibodies is provided in Table 4. All the antibodies were expressed as $IgG_1$ antibodies and analyzed in the assays described below. 7.1.1 Binding of Anti-CTLA-4 Antibodies to CTLA-4-Expressing Cells Jurkat cells engineered to constitutively express human CTLA-4 (Promega) were used to analyze the binding of anti-CTLA-4 antibodies. Briefly, the cells were stained at 5×10⁵ cells/well using 2 μg/ml of antibody in a 96-well plate for 30 minutes at 4° C. The cells were washed twice and incubated for 20 minutes at 4° C. with an anti-human IgG secondary antibody (Thermo Scientific, Cat #31529). The cells were washed and suspended in 50 μl of 2% paraformaldehyde (Alfa Aesar, Cat #43368) prepared in PBS. Data were collected with BD FACS Canto II.

As shown in FIGS. 1A-1G, all the anti-CTLA-4 antibodies tested bound to CTLA-4-expressing cells.

7.1.2 Effect of Anti-CTLA-4 Antibody on Human PBMCs Following Staphylococcal Enterotoxin A (SEA) Stimulation The functional activities of the anti-CTLA-4 antibody AGEN1884.H3 (IgG$_1$) on primary human PBMCs were assessed following Staphylococcal Enterotoxin A (SEA) stimulation. Briefly, cryopreserved PBMCs were stimulated with 100 ng/ml of the SEA superantigen (Toxin Technologies, Cat #at101red) in the absence or presence of 10 μg/ml of an anti-CTLA-4 antibody or an isotype control antibody (IgG$_1$) for 5 days at 37° C. and 5% $CO_2$. IL-2 concentrations in the culture supernatant were analyzed by AlphaLISA (Perkin Elmer, Cat #AL221F).

The anti-CTLA-4 antibody AGEN1884.H3 (IgG$_1$) increased IL-2 production in human PBMCs stimulated with the SEA superantigen (FIG. 2).

7.1.3 Effect of Anti-CTLA-4 Antibody on IL-2-Luciferase Reporter Cell Line

Next, the functional activities of the anti-CTLA-4 antibody AGEN1884.H3 (IgG$_1$) were further analyzed using an IL-2-luciferase reporter assay. Briefly, a human T cell line (Jurkat) that endogenously expressed CD3 and CD28 was engineered to constitutively express cell surface CTLA-4 and a luciferase reporter gene driven by an IL-2 promoter. The Jurkat reporter cell line was co-cultured with an antigen presenting cell line (Raji) that endogenously expressed CD80 and CD86 and was engineered to express a proprietary T cell activator (Promega). T cell receptor (TCR) triggering (signal 1) was achieved by the T cell activator; and costimulatory signaling (signal 2) was provided in trans by CD80 and CD86 expressed on Raji cells. TCR signaling in the Jurkat T cell line triggered IL-2 expression, leading to luciferase production, a surrogate marker for T cell activation. Co-culture of these two cell lines resulted in engagement of the inhibitory co-receptor CTLA-4 (expressed on Jurkat cells) with its natural ligands CD80 and CD86 (expressed on Raji cells) inhibiting T cell activation, demonstrated by a lack of luciferase expression. This inhibition was relieved upon addition of increasing concentrations of anti-CTLA-4 blocking antibodies. Luciferase expression was quantified using Bio-Glo™ reagent and the resulting data were used to determine fold response values (fold increase with AGEN1884.H3 (IgG$_1$) compared with an isotype control antibody (IgG$_1$)).

As shown in FIG. 3, the anti-CTLA-4 antibody AGEN1884.H3 (IgG$_1$) dose-dependently released CTLA-4 mediated inhibition of T cells in this IL-2-luciferase reporter assay.

7.1.4 Effect of Anti-CTLA-4 Antibody on Fc Gamma Receptor IIIA Reporter Cell Line The ability of anti-CTLA-4 antibody to co-engage CTLA-4 and signal via activating Fc gamma receptors was evaluated using a reporter cell line expressing Fc gamma receptor IIIA (FcγRIIIA) (Promega). Briefly, Jurkat cells were engineered to constitutively express human CTLA-4 on the cell surface. These target cells were co-cultured with an effector cell line (Jurkat) engineered to express FcγRIIIA (the V158 variant) upstream of an NFAT response element (RE) driving expression of firefly luciferase. A titrated dose of AGEN1884.H3 (IgG$_1$) or an isotype control antibody (IgG$_1$) was added to the co-culture and incubated at 37° C. overnight. Simultaneous engagement of AGEN1884.H3 by the target cell line (binding to CTLA-4 by the Fab region) and effector cell line (binding to FcγRIIIA by the Fc region) triggers NFAT RE reporter gene activation and luciferase expression. The next day, Bio-Glo reagent (Promega) was added to the co-culture, luminescence was measured by EnVison Multimode Plate Reader (Perkin Elmer), and relative light units (RLU) were recorded to calculate fold response values (fold increase with AGEN1884.H3 (IgG$_1$) compared with an isotype control antibody (IgG$_1$)).

When bound to target cells expressing human CTLA-4 on the cell surface, the IgG$_1$ antibody AGEN1884.H3 activated FcγRIIIA signaling in the effector cells (FIG. 4).

7.2 Example 2: Characterization of Anti-CTLA-4 Antibodies with Different Fc Regions This example analyzes the impact of Fc/Fc receptor interaction on the functional activity of anti-CTLA-4 antibodies. AGEN1884.H3 was expressed as antibodies in which the IgG$_1$ Fc region comprises the S239D/I332E, S239D/A330L/I332E, or L235V/F243L/R292P/Y300L/P396L mutations, numbered according to the EU numbering system, and tested in functional assays described below. The antibody AGEN1884.H3 (IgG$_1$ S239D/I332E) comprises a heavy chain comprising the amino acid sequence of SEQ ID NO: 24 and a light chain comprising the amino acid sequence of SEQ ID NO: 27. The antibody AGEN1884.H3 (IgG$_1$ S239D/A330L/I332E) comprises a heavy chain comprising the amino acid sequence of SEQ ID NO: 25 and a light chain comprising the amino acid sequence of SEQ ID NO: 27. The antibody AGEN1884.H3 (IgG$_1$ L235V/F243L/R292P/Y300L/P396L) comprises a heavy chain comprising the amino acid sequence of SEQ ID NO: 26 and a light chain comprising the amino acid sequence of SEQ ID NO: 27. For comparison, AGEN1884 was also expressed as a wild type IgG$_1$ antibody, an IgG$_1$ antibody comprising S239D/I332E or S239D/A330L/I332E mutations, numbered according to the EU numbering system, or an afucosylated IgG$_1$ antibody, and tested in some functional assays.

7.2.1 Binding of Anti-CTLA-4 Antibodies to CTLA-4-Expressing Cells

The binding of anit-CTLA-4 antibodies AGEN1884.H3 (IgG$_1$ S239D/I332E), AGEN1884.H3 (IgG$_1$ S239D/A330L/I332E), and AGEN1884.H3 (IgG$_1$ L235V/F243L/R292P/Y300L/P396L) to CTLA-4-expressing cells was characterized similarly as described above. Briefly, Jurkat cells engineered to express human CTLA-4 (Promega) were stained first with 5 μg/ml of an anti-CTLA-4 antibody or an isotype control antibody and then with an anti-human IgG secondary antibody (Thermo Scientific, Cat #31529). The cells were analyzed using BD FACS Canto II.

As shown in FIGS. 5A-5D, AGEN1884.H3 antibodies with different Fc regions all bound to cells expressing human CTLA-4.

7.2.2 Effect of Anti-CTLA-4 Antibody on Ligand Binding to Human CTLA-4

In this example, the ability of an Fc variant anti-CTLA-4 antibody AGEN1884.H3 (IgG$_1$-S239D/A330E/I332E) to block binding between human CTLA-4 and its ligands, CD80 and CD86, was tested.

Briefly, recombinant CD80-Fc and CD86-Fc proteins were conjugated to the fluorochrome Alexa Fluor 647 (Invitrogen, A20186). Jurkat cells were transduced with trCTLA4 (truncated intracellular domain) under the control of the EF1α promoter, as described in Nakaseko et al. (J Exp Med. 1999 Sep. 20; 190(6): 765-774), thus producing a cell line that constitutively expressed human CTLA-4 on the cell surface. CTLA-4-expressing cells were incubated with a dose titration of anti-CTLA-4 antibody AGEN1884.H3 (IgG$_1$-S239D/A330E/I332E), a reference anti-CTLA-4 antibody, or an isotype control antibody (IgG$_1$). The cells were then stained with fluorescently labelled CD80-Fc or CD86-Fc protein. Following staining, fluorescence was analyzed using the LSRFortessa flow cytometer (BD Biosciences). FACS plots were analyzed using a combination of FACS DIVA and WEHI Weasel software. Values were plotted using Graphpad Prism software.

As shown in FIG. 6A, AGEN1884.H3 (IgG$_1$-S239D/A330E/I332E) and the reference anti-CTLA-4 antibody each blocked binding between human CTLA-4 and CD80 in a dose-dependent manner, whereas isotype control antibody (IgG$_1$) had no effect. As shown in FIG. 6B, AGEN1884.H3 (IgG$_1$-S239D/A330E/I332E) and the reference anti-CTLA-4 antibody each also blocked binding between human CTLA-4 and CD86 in a dose-dependent manner, whereas isotype control antibody (IgG$_1$) had no effect. These data show that AGEN1884.H3 (IgG$_1$-S239D/A330E/I332E) functions as a ligand-blocking antibody for CTLA-4.

7.2.3 Effect of Anti-CTLA-4 Antibodies on Human PBMCs Following Staphylococcal Enterotoxin A (SEA) Stimulation In this example, the impact of Fc regions on the functional activity of anti-CTLA-4 antibodies was analyzed using the SEA stimulation assay described above. In brief, human PBMCs were cultured in vitro with 100 ng/ml of the SEA peptide (Toxin Technologies, Cat #at101red) in the absence or presence of anti-CTLA-4 antibodies with different Fc regions or an isotype control antibody. After five days, concentrations of IL-2 in the culture supernatant, a marker of T cell activation, were measured using AlphaLISA (Perkin Elmer, Cat #AL221F).

As shown in FIG. 7A, the three AGEN1884.H3 antibodies containing mutations in the IgG$_1$ Fc regions, all of which enhanced binding to FcγRIIIA, stimulated more IL-2 secretion than AGEN1884.H3 with a wild type IgG$_1$ Fc region.

In similar studies, AGEN1884.H3 or AGEN1884 antibodies with different Fc regions were tested in the SEA stimulation assay. Introducing S239D/I332E, S239D/A330L/I332E, or L235V/F243L/R292P/Y300L/P396L substitutions in the IgG$_1$ Fc region significantly enhanced the functional activity of AGEN1884.H3 (FIG. 7B). Similarly, AGEN1884 (IgG$_1$ S239D/I332E), AGEN1884 (IgG$_1$ S239D/A330L/I332E), and afucosylated AGEN1884 (IgG$_1$) enhanced IL-2 production at substantially lower concentrations compared to AGEN1884 with a wild type IgG$_1$ Fc region (FIG. 7C).

7.2.4 Effect of Anti-CTLA-4 Antibodies on ZAP70 Phosphorylation

In this example, the impact of Fc regions on the functional activity of anti-CTLA-4 antibodies in the T cell-antigen presenting cell (APC) synapse was analyzed using an assay that measures extent of phosphorylation of the protein tyrosine kinase ZAP70, which is recruited to the TCR following TCR engagement, where it becomes phosphorylated and facilitates downstream signaling events.

Briefly, human PBMCs were incubated with a suboptimal concentration of SEA peptide and 10 µg/mL of isotype control antibody (IgG$_1$) or the anti-CTLA-4 antibodies AGEN1884.H3 (Ig AGEN1884.H3 (IgG$_1$ S239D/A330L/I332E), or AGEN1884.H3 (IgG$_1$ N297A). Cells were then incubated at 37° C. for 0 (pre) 1, 5, 10, 30, or 60 minutes. At the end of the incubation, cells were lysed with cold 1×RIPA buffer supplemented with a phosphatase/protease inhibitor cocktail (Cell Signaling Technologies). Following supernatant clarification, protein concentration was quantified using bicinchoninic acid (BCA) analysis (Pierce Biotechnology). Cell lysates (20 µg/lane) were prepared in Bolt LDS sample buffer diluted and heated for 10 minutes at 70° C. before being loaded onto a 4-12% Bolt Bis Tris gels (Novex). Proteins were separated in 1× Bolt MOPS-buffer (ThermoFisher) and then blotted onto a PVDF membrane. Following blockade with 5% bovine serum albumin (BSA, 1 hour), samples were incubated with primary anti-human rabbit phospho-ZAP70 (Tyr493)/Syk (Tyr526) antibody (Cell Signaling Technologies) in blocking buffer overnight at 4° C. Membranes were probed with goat anti-rabbit secondary HRP-conjugate and visualized with SignalFire ECL reagent (Cell Signaling Technology). Images were captured using the Chemidoc imaging system (BioRad). As a control, total ZAP70 protein was evaluated following membrane stripping with Restore™ PLUS Western Blot Stripping Buffer. Densitometric analysis of phospho-ZAP70 normalized to that of total ZAP70 was performed using Image J (Wayne Rasband; National Institute of Mental Health, Bethesda, Md., USA) and expressed as the fold change relative to the isotype control treated samples that was incubated for 1 minute.

As shown in FIGS. 8A-8B, in the isotype control antibody sample, ZAP70 phosphorylation was transiently increased within ten minutes after stimulation and rapidly diminished with no detectable levels after 15 minutes. In contrast, the addition of anti-CTLA-4 antibodies AGEN1884.H3 (IgG$_1$) or AGEN1884.H3 (IgG$_1$ S239D/A330L/I332E) extended detectable ZAP70 activation to 30 minutes, with the most pronounced activity and relative abundance observed with AGEN1884.H3 (IgG$_1$ S239D/A330L/I332E).

7.2.5 Effect of Murine Anti-CTLA-4 Antibodies on Tumor Growth and Intratumoral Regulatory T Cell Depletion in a Mouse Model In this example, the impact of Fc regions on the antitumor and intratumoral regulatory T cell (Treg) depletion activities of anti-CTLA-4 antibodies was analyzed using a mouse model for colon cancer (CT26 tumor-bearing mice).

Briefly, $5 \times 10^4$ CT26 tumor cells were suspended in 100 ml PBS and injected subcutaneously into 6-8 week old female BALB/cJ mice (Jackson Laboratories). Following engraftment to a tumor volume of 50-80 mm$^3$, mice were treated with a single 100 µg dose of murine anti-CTLA-4 antibody 9D9 (mIgG2a), an Fc-silent variant of anti-CTLA-4 antibody 9D9 (mIgG2a-N297A), an Fc variant of anti-CTLA-4 antibody 9D9 (mIgG2a-S239D/A330L/I332E), or an isotype control antibody (mIgG2a). Amino acid sequences for the murine antibodies tested are shown in Table 7.

TABLE 7

Amino acid sequences of murine anti-CTLA-4 antibodies

| Description | Sequence | SEQ ID NO |
|---|---|---|
| Murine anti-CTLA-4 antibody (mIgG2a) heavy chain | EAKLQESGPVLVKPGASVKMSCKASGYTFTDY YMNWVKQSHGKSLEWIGVINPYNGDTSYNQKF KGKATLTVDKSSSTAYMELNSLTSEDSAVYYC ARYYGSWFAYWGQGTLVTVSSAKTTAPSVYPL APVCGDTTGSSVTLGCLVKGYFPEPVTLTWNSG SLSSGVHTFPAVLQSDLYTLSSSVTVTSSTWPSQ SITCNVAHPASSTKVDKKIEPRGPTIKPCPPCKCP APNLLGGPSVFIFPPKIKDVLMISLSPIVTCVVVD VSEDDPDVQISWFVNNVEVHTAQTQTHREDYN STLRVVSALPIQHQDWMSGKEFKCKVNNKDLP APIERTISKPKGSVRAPQVYVLPPPEEEMTKKQV TLTCMVTDFMPEDIYVEWTNNGKTELNYKNTE PVLDSDGSYFMYSKLRVEKKNWVERNSYSCSV VHEGLHNHHTTKSFSRTPG | 49 |
| Murine anti-CTLA-4 antibody (mIgG2a-S239D/A330L/I332E) heavy chain | EAKLQESGPVLVKPGASVKMSCKASGYTFTDY YMNWVKQSHGKSLEWIGVINPYNGDTSYNQKF KGKATLTVDKSSSTAYMELNSLTSEDSAVYYC ARYYGSWFAYWGQGTLVTVSSAKTTAPSVYPL APVCGDTTGSSVTLGCLVKGYFPEPVTLTWNSG SLSSGVHTFPAVLQSDLYTLSSSVTVTSSTWPSQ SITCNVAHPASSTKVDKKIEPRGPTIKPCPPCKCP APNLLGGPDVFIFPPKIKDVLMISLSPIVTCVVVD VSEDDPDVQISWFVNNVEVHTAQTQTHREDYN STLRVVSALPIQHQDWMSGKEFKCKVNNKDLP LPEERTISKPKGSVRAPQVYVLPPPEEEMTKKQ VTLTCMVTDFMPEDIYVEWTNNGKTELNYKNT EPVLDSDGSYFMYSKLRVEKKNWVERNSYSCS VVHEGLHNHHTTKSFSRTPG | 50 |
| Murine anti-CTLA-4 antibody (mIgG2a-N297A) heavy chain | EAKLQESGPVLVKPGASVKMSCKASGYTFTDY YMNWVKQSHGKSLEWIGVINPYNGDTSYNQKF KGKATLTVDKSSSTAYMELNSLTSEDSAVYYC ARYYGSWFAYWGQGTLVTVSSAKTTAPSVYPL APVCGDTTGSSVTLGCLVKGYFPEPVTLTWNSG SLSSGVHTFPAVLQSDLYTLSSSVTVTSSTWPSQ SITCNVAHPASSTKVDKKIEPRGPTIKPCPPCKCP APNLLGGPSVFIFPPKIKDVLMISLSPIVTCVVVD VSEDDPDVQISWFVNNVEVHTAQTQTHREDYA STLRVVSALPIQHQDWMSGKEFKCKVNNKDLP APIERTISKPKGSVRAPQVYVLPPPEEEMTKKQV TLTCMVTDFMPEDIYVEWTNNGKTELNYKNTE PVLDSDGSYFMYSKLRVEKKNWVERNSYSCSV VHEGLHNHHTTKSFSRTPG | 51 |
| Murine anti-CTLA-4 antibody (mIgG2a) light chain | DIVMTQTTLSLPVSLGDQASISCRSSQSIVHSNG NTYLEWYLQKPGQSPKLLIYKVSNRFSGVPDRF SGSGSGTDFTLKISRVEAEDLGVYYCFQGSHVP YTFGGGTKLEIKRADAAPTVSIFPPSSEQLTSGG ASVVCFLNNFYPKDINVKWKIDGSERQNGVLNS WTDQDSKDSTYSMSSTLTLTKDEYERHNSYTC EATHKTSTSPIVKSFNRNEC | 52 |

In a first experiment, mice treated with antibodies were then measured biweekly for tumor growth. As shown in FIG. 9A, an Fc variant of anti-CTLA-4 antibody 9D9 (shown as mIgG2a-S239D/A330L/I332E) induced complete regression in all CT26 tumor-bearing mice (eight out of eight mice tested). In contrast, other variants of antibody 9D9 failed to elicit the same efficacy: antibody 9D9 (mIgG2a) itself induced complete regressions in three out of nine mice tested, and the Fc-silent variant of antibody 9D9 (mIgG2a-N297A) failed to induce regression in any of the nine mice tested.

In a second experiment, CT26 tumor-bearing mice were treated as described above and then sacrificed at 0, 24, 72, or 240 hours post-treatment for collection of tumor tissue, tumor draining lymph nodes, and spleens. Collected tissues were evaluated for FoxP3+ Treg expansion by flow cytometry. Single cell suspensions were obtained by mechanical dissociation followed by filtration (70 μM cell strainer). To reduce non-specific binding, the cells were incubated with an FcγR blocking antibody (Biolegend) in FACS buffer (PBS, 2 mM EDTA, 0.5% BSA, pH 7.2) for 15 minutes at ambient temperature. Samples were then washed twice in FACS buffer and stained for a lineage panel of CD3, CD4, CD8, and CD25, as well as a fixable live/dead marker, for 30 minutes at 4° C. For Treg delineation, samples were then washed twice, fixed, permeabilized, and then incubated with an anti-FoxP3 antibody (FJK-16s) for 30 minutes at 4° C. Samples were analyzed using the LSRFortessa flow cytometer (BD Biosciences). FACS plots were analyzed using a combination of FACS DIVA and WEHI Weasel software. As shown in FIG. 9B, the anti-CTLA-4 antibody 9D9 (mIgG2a) and the Fc variant anti-CTLA-4 antibody 9D9 (mIgG2a-S239D/A330L/I332E) each reduced the quantities of intratumoral FoxP3+ Tregs compared to the isotype control antibody, with the Fc variant anti-CTLA-4 antibody 9D9 (mIgG2a-S239D/A330L/I332E) decreasing the quantity of intratumoral FoxP3+ Tregs most significantly. The Fc-silent variant of anti-CTLA-4 antibody 9D9 (mIgG2a-N297A) did not substantially reduce the quantity of intratumoral FoxP3+ Tregs relative to the isotype control antibody. None of the treatment groups showed substantial changes in the quantities of intratumoral CD45+ leukocytes or CD4+ non-Tregs. The Fc variant anti-CTLA-4 antibody 9D9 (mIgG2a-S239D/A330L/I332E) induced the largest increase in intratumoral CD8/Treg ratio over time, followed by antibody 9D9 (mIgG2a), and then by the Fc-silent variant antibody 9D9 (mIgG2a-N297A) and the isotype control antibody (mIgG2a).

As shown in FIG. 9C, the anti-CTLA-4 antibody 9D9 (mIgG2a), the Fc variant anti-CTLA-4 antibody 9D9 (mIgG2a-S239D/A330L/I332E) and the Fc-silent variant of anti-CTLA-4 antibody 9D9 (mIgG2a-N297A) had no substantial effect on the quantities of tumor draining lymph node (TDLN) FoxP3+ Tregs compared to the isotype control antibody. Similarly, as shown in FIG. 9D, the anti-CTLA-4 antibody 9D9 (mIgG2a), the Fc variant anti-CTLA-4 antibody 9D9 (mIgG2a-S239D/A330L/I332E) and Fc-silent variant of anti-CTLA-4 antibody 9D9 (mIgG2a-N297A) had no substantial effect on the quantities of splenic FoxP3+ Tregs compared to the isotype control antibody.

7.2.6 Effect of Murine Anti-CTLA-4 Antibodies in Combination with a Tumor Vaccine on Tumor Growth In this example, the effect on tumor growth of a combination of murine anti-CTLA-4 antibodies and an HPV tumor vaccine was tested in the HPV+ TC-1 syngeneic tumor mouse model.

The TC-1 cell line was developed by co-transformation of primary lung epithelial cells (C57BL/6) with c-Ha-ras and HPV-16 (E6/E7) oncogenes, as described in Lin et al. (1996, Cancer Res. 56(1): 21-26). For tumor implantation, $2 \times 10^5$ TC-1 cells were injected subcutaneously into 6-8 week old female C57BL/6 mice (Jackson Laboratories). At each of days day 5, 10 and 15 post-tumor implantation, mice were administered 100 µg of anti-CTLA-4 antibody 9D9 (mIgG2a), an Fc variant anti-CTLA-4 antibody 9D9 (mIgG2a-S239D/A330L/I332E), or an isotype control antibody (mIgG2a), in combination with a dose of HPV vaccine (HPV+ tumor, viral antigens E6/E7) or no additional treatment. Each dose of HPV vaccine contained 30 µg of HSP protein (0.4 nM) complexed with HPV pool peptide (1.2 nM) and was supplemented with 10 µg QS-21 Stimulon® adjuvant. After treatment, mice were assessed biweekly for tumor growth and were sacrificed when tumors reached 2000 mm³ or upon ulceration.

As shown in FIG. 10, the antitumor efficacy of anti-CTLA-4 antibody 9D9 (mIgG2a) and the Fc variant anti-CTLA-4 antibody 9D9 (mIgG2a-S239D/A330L/I332E) each showed improvement when administered in combination with HPV tumor vaccine. This effect was greater for the Fc variant anti-CTLA-4 antibody (mIgG2a-S239D/A330L/I332E). In particular, the Fc variant anti-CTLA-4 antibody 9D9 (mIgG2a-S239D/A330L/I332E) induced a noticeable additional decrease in TC-1 tumor growth when combined with the HPV tumor vaccine, relative to when the antibody was administered as a single agent. This additional decrease in tumor growth was greater than that observed for the combinations of antibody 9D9 (mIgG2a) or the isotype control antibody (mIgG2a) with the HPV tumor vaccine.

7.2.7 Characterization of Expanded and Activated T Cell Populations

In this example, expanded and activated T cell populations were characterized for gene expression and CpG methylation. In brief, natural CD4$^+$ CD25$^+$ FOXP3$^+$ regulatory T cells or CD4$^+$ CD25$^{+/-}$ FOXP3$^-$ non-regulatory T cells were isolated from peripheral blood of a healthy human donor, expanded, and activated. The T cells were then characterized for expression of FOXP3 and CTLA-4 by flow cytometry, and assessed for lineage stability by examining DNA CpG methylation at CpG regions within the FOXP3 and CTLA4 loci. As known in the art, hypomethylation at these CpG sites can be used to accurately delineate effector versus regulatory T cell lineages (Waight et al., 2015, J. Immunol. 194(3): 878-882).

PBMCs were isolated via Ficoll gradient from healthy donor buffy coats (Research Blood Components, LLC) and were then enriched for effector T cells (Teffs) or natural regulatory T cells (Tregs) using magnetic bead isolation (MACS, Miltenyi). The enriched Teffs or Tregs were activated with CD3-CD28 microbeads (1:1 bead:cell ratio; Invitrogen) and with recombinant human IL-2 for seven days in RPMI media supplemented with 10% heat-inactivated FBS at 37° C. and 5% $CO_2$. Following stimulation, the cells were evaluated for FOXP3 and CTLA-4 expression via flow cytometry. To reduce non-specific binding, the cells were pre-incubated with an FcγR blocking antibody (Biolegend) in FACS buffer (PBS, 2 mM EDTA, 0.5% BSA, pH 7.2) for 15 minutes at ambient temperature. Samples were then washed twice in FACS buffer and stained with a lineage panel of CD3, CD4, CD8, CD25, as well as a fixable cell death marker, for 30 minutes at 4° C. To assess membrane CTLA-4 expression, CTLA-4 staining was conducted at 37° C. For intracellular FOXP3 and CTLA-4 staining, samples were washed twice, fixed, permeabilized, and incubated with an anti-FOXP3 antibody (PCH101) and anti-CTLA-4 antibody (BNI3), respectively, for 30 minutes at 4° C. Samples were then washed twice and analyzed using the LSRFortessa flow cytometer (BD Biosciences). FACS plots were analyzed using a combination of FACS DIVA and WEHI Weasel software. For CpG methylation analysis, total DNA was isolated from approximately $1 \times 10^5$ naïve CD4$^+$ T cells, activated Teffs, or activated Tregs and subjected to pyrosequencing.

As shown in FIG. 11A, a high level of FOXP3 expression was detected on activated Tregs, as well as high levels of both intracellular and membrane CTLA-4 expression. In contrast, activated Teffs showed reduced levels of FOXP3, intracellular CTLA-4, and membrane CTLA-4 relative to activated Tregs. In particular, substantially less membrane CTLA-4 expression was observed for activated Teffs compared to activated Tregs. FIG. 11B further shows that activated Tregs also exhibited hypomethylated FOXP3 and CTLA4 CpG regions compared to naïve and activated Teffs from the same donor.

7.2.8 Effect of Anti-CTLA-4 Antibodies on Antibody Dependent Cellular Cytotoxicity of CTLA-4-Expressing Human T Cells In this example, the effect of anti-CTLA-4 antibody AGEN1884.H3 (IgG$_1$) or Fc variants thereof on antibody dependent cellular cytotoxicity (ADCC) of human CTLA-4-expressing T cells was assessed using high content microscopy of caspase 3/7 activation to quantify ADCC activity.

Briefly, CTLA-4-expressing target cells were co-cultured with NK-92 cells expressing FcγRIIIA, following opsonization with 10 µg/ml of anti-CTLA-4 antibody or Fc variants thereof, as described below. In a first experiment, Jurkat cells engineered to constitutively express cell-surface human CTLA-4 were used as target cells. CTLA-4-expressing Jurkat cells were generated by transducing the Jurkat cell line with trCTLA4 (intracellular domain removed) under the control of the EF1α promoter, as described in Nakaseko et al. (1999, J. Exp. Med. 190(6): 765-774). In a second experiment, primary human activated effector and regulatory T cells were used as target cells. CTLA-4-expressing target cells and FcγRIIIA-158V-expressing NK-92 cells were differentially stained using red and blue live-cell tracers (Thermo Fisher) and co-cultured at a 1:1 cell ratio ($1.5 \times 10^3$ cells/well in 384-well plates). Samples were treated with 10 μg/ml of AGEN1884.H3 (IgG$_1$), AGEN1884.H3 (IgG$_1$ N297A), AGEN1884.H3 (IgG$_1$ S239D/A330L/I332E), AGEN1884.H3 (IgG$_1$ S267E/L328F), afucosylated AGEN1884.H3 (IgG$_1$), or an isotype control antibody (IgG$_1$). Samples were then evaluated for the induction of apoptosis over time by live confocal imaging of caspase 3/7 substrate, which fluoresces following cleavage by activated caspase. Sample images were acquired every 20 minutes for six hours. Percentage ADCC activity is measured as the number of apoptotic cells relative to the total cell count under each condition.

As shown in FIG. 12A, the Fc variant AGEN1884.H3 (IgG$_1$ S239D/A330L/I332E) antibody, the afucosylated AGEN1884.H3 antibody, and the AGEN1884.H3 (IgG$_1$) antibody each induced substantially greater ADCC activity in Jurkat cells engineered to express cell-surface CTLA-4 relative to the AGEN1884.H3 (IgG$_1$ N297A) variant, the AGEN1884.H3 (IgG$_1$ S267E/L328F) variant, and isotype control antibody (IgG$_1$). The AGEN1884.H3 (IgG$_1$ S239D/A330L/I332E) Fc variant antibody and the afucosylated AGEN1884.H3 antibody induced greater increases in ADCC activity compared to the AGEN1884.H3 (IgG$_1$) antibody. As shown in FIG. 12B, the AGEN1884.H3 (IgG$_1$ S239D/A330L/I332E) Fc variant antibody induced the highest levels of ADCC in both primary human activated effector T cells (left panel) and primary human activated regulatory T cells (right panel), followed by afucosylated AGEN1884.H3 antibody. The AGEN1884.H3 (IgG$_1$) antibody also induced slightly higher levels of ADCC compared to controls. The remaining antibodies tested induced little to no ADCC activity in either effector or regulatory T cells. Notably, the AGEN1884.H3 (IgG$_1$ S239D/A330L/I332E) Fc variant antibody and the afucosylated AGEN1884.H3 antibody each induced substantially greater ADCC in regulatory T cells compared to effector T cells.

7.2.9 Effect of Anti-CTLA-4 Antibodies in Combination with an Anti-PD-1 Antibody on T Cell Functionality In this example, the effect of anti-CTLA-4 antibodies in combination with an anti-PD-1 antibody on primary human T cell function was examined.

Briefly, PBMCs were isolated via Ficoll gradient from healthy donor buffy coats (Research Blood Components, LLC) of two human donors. This experiment was performed twice on PBMCs collected from each donor, for a total of two replicates per donor. For each replicate, isolated PBMCs were incubated for four days under stimulatory culture conditions with a dosage titration of anti-CTLA-4 antibody AGEN1884.H3 (IgG$_1$), an Fc variant anti-CTLA-4 antibody AGEN1884.H3 (IgG$_1$ S239D/A330L/I332E), or an isotype control antibody (IgG$_1$), in combination with a fixed dosage (5 μg/ml) of a reference anti-PD-1 antagonist antibody or an isotype control antibody (IgG$_4$). Stimulatory culture conditions were defined as cells suspended in RPMI media, supplemented with 100 ng/ml SEA superantigen (Sigma-Aldrich), 10% heat-inactivated FBS at 37° C., and 5% $CO_2$. Following incubation, cell-free supernatants were assayed for IL-2 production using an AlphaLISA immunoassay (Perkin-Elmer). Data was collected using the EnVision® Multilabel Plate Reader (Perkin-Elmer), and the concentration of IL-2 was determined using an IL-2 standard curve. Values were interpolated and plotted using Graphpad Prism software.

As shown in FIGS. 13A-13D, the anti-CTLA-4 antibody AGEN1884.H3 (IgG$_1$) and the Fc variant anti-CTLA-4 antibody AGEN1884.H3 (IgG$_1$ S239D/A330L/I332E) each induced increased IL-2 production relative to isotype controls or reference anti-PD-1 antibody alone. IL-2 production was further enhanced when AGEN1884.H3 or AGEN1884.H3 (IgG$_1$ S239D/A330L/I332E) was combined with reference anti-PD-1 antibody. Whether administered with isotype control antibody or in combination with anti-PD-1 reference antibody, the Fc variant anti-CTLA-4 antibody AGEN1884.H3 (IgG$_1$ S239D/A330L/I332E) induced a greater increase in IL-2 production compared to AGEN1884.H3 (IgG$_1$). This effect was consistent in replicates for the first donor (FIGS. 13A and 13B) and the second donor (FIGS. 13C and 13D).

7.3 Example 3: Epitope Mapping of Anti-CTLA-4 Antibody

The interaction of the Fab fragment of AGEN1884 (AGEN1884-Fab) with the extracellular domain of human CTLA-4 was studied by hydrogen-deuterium exchange (HDX) mass spectrometry. CTLA-4 extracellular domain alone or in combination with AGEN1884-Fab, in phosphate buffered saline solution at pH 7.4, was diluted with a ten-fold volume of deuterium oxide labeling buffer and incubated for varying periods of time (0, 60, 300, 1800, and 7200 seconds) at room temperature. Exchange of deuterium for hydrogen was quenched by adding one volume of 4 M guanidine hydrochloride, 0.85 M TCEP (tris(2-carboxyethyl)phosphine) buffer and the final pH was 2.5. Samples were then subjected to on-column pepsin/protease type XIII digestion and LC-MS analysis. Mass spectra were recorded in MS only mode. For the calculation of deuterium incorporation, the mass spectra for a given peptide were combined across the extracted ion chromatogram peak and the weighted average m/z was calculated. The mass increase from the mass of the native peptide (0 minute) to the weighted averaged mass corresponds to the level of deuterium incorporation. The deuterium buildup curves over exchange time for all the peptides were plotted for further analysis and were compared with HDExaminer software.

Most of the CTLA-4 peptides displayed identical or similar deuterium levels with and without the anti-human CTLA-4 Fab present. Several peptide segments, however, were found to have significantly decreased deuterium incorporation upon Fab binding. All the residues in this paragraph are numbered according to SEQ ID NO: 33. Two regions, residues 80-82 (QVT, SEQ ID NO: 39) and residues 135-149 (YPPPYYLGIGNGTQI, SEQ ID NO: 37), experienced strong deuterium protection when human CTLA-4 was bound to Fab. The strongest decrease in deuterium uptake was observed at residues 140-141 (YL) which thus appeared to be a main feature of the epitope of AGEN1884 on CTLA-4. Inspection of the sequences of human and cynomolgus monkey CTLA-4, both of which AGEN1884 binds strongly (data not shown), reveals almost complete sequence identity in the two regions described above, except for a methionine substitution for leucine at position 141 (FIG. 14A). In contrast, AGEN1884 does not bind to any significant extent to either mouse or rat CTLA-4 (data not shown) which differ from human CTLA-4 at residues 140-143 (YLGI, SEQ ID NO: 34) at three out of four positions (FIG. 14A). Further selectivity data show that AGEN1884 binds with high specificity to human and cynomolgus monkey CTLA-4 and not to other related CD28 family members including CD28, ICOS, BTLA, and PD-1 (data not shown). Sequence comparison among these related proteins shows that the non-CTLA-4 proteins all differ at residues 140-143 (YLGI, SEQ ID NO: 34) (FIG. 14B), further supporting the importance of this epitope to the binding of AGEN1884.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. A method of increasing T cell activation in response to an antigen in a subject, the method comprising administering to the subject an effective amount of an isolated antibody that specifically binds to human CTLA-4, the antibody comprising a heavy chain variable region (VH) comprising complementarity determining regions CDRH1, CDRH2, and CDRH3 and a light chain variable region (VL) comprising complementarity determining regions CDRL1, CDRL2, and CDRL3, wherein:
   (a) CDRH1 comprises the amino acid sequence of SYSMN (SEQ ID NO: 10);
   (b) CDRH2 comprises the amino acid sequence of SISSSSSYIYYAXSVKG (SEQ ID NO: 18), wherein X is E or D;
   (c) CDRH3 comprises the amino acid sequence of VGLXGPFDI (SEQ ID NO: 19), wherein X is F or M;
   (d) CDRL1 comprises the amino acid sequence of RASQSVSRYLG (SEQ ID NO: 15);
   (e) CDRL2 comprises the amino acid sequence of GASTRAT (SEQ ID NO: 16); and
   (f) CDRL3 comprises the amino acid sequence of QQYGSSPWT (SEQ ID NO: 17),
and wherein the CDRH1, CDRH2, and CDRH3 sequences of the antibody are not SEQ ID NOs: 10, 11, and 13, respectively.

2. The method of claim 1, wherein the CDRH1, CDRH2, CDRH3, CDRL1, CDRL2, and CDRL3 sequences of the antibody are SEQ ID NOs: 10, 12, 14, 15, 16, and 17, respectively.

3. The method of claim 1, wherein
   (a) the VH comprises an amino acid sequence selected from the group consisting of SEQ ID NOs: 2, 4, 5, 6, 7 and 8; and/or
   (b) the VL comprises the amino acid sequence of SEQ ID NO: 9.

4. The method of claim 1, wherein the VH and the VL comprise the amino acid sequences set forth in SEQ ID NOs: 2 and 9; 4 and 9; 5 and 9; 6 and 9; 7 and 9; or 8 and 9, respectively.

5. The method of claim 1, wherein
   (a) the antibody comprises a heavy chain comprising an amino acid sequence selected from the group consisting of SEQ ID NOs: 23, 24, 25, and 26; and/or
   (b) the antibody comprises a light chain comprising the amino acid sequence of SEQ ID NO: 27.

6. The method of claim 1, wherein the antibody comprises a heavy chain and a light chain comprising the amino acid sequences set forth in SEQ ID NOs: 23 and 27; 24 and 27; 25 and 27; or 26 and 27, respectively.

7. A method of treating cancer in a subject, the method comprising administering to the subject an effective amount of an isolated antibody that specifically binds to human CTLA-4, the antibody comprising a heavy chain variable region comprising complementarity determining regions CDRH1, CDRH2, and CDRH3 and a light chain variable region comprising complementarity determining regions CDRL1, CDRL2, and CDRL3, wherein:
   (a) CDRH1 comprises the amino acid sequence of SYSMN (SEQ ID NO: 10);
   (b) CDRH2 comprises the amino acid sequence of SISSSSSYIYYAXSVKG (SEQ ID NO: 18), wherein X is E or D;
   (c) CDRH3 comprises the amino acid sequence of VGLXGPFDI (SEQ ID NO: 19), wherein X is F or M;
   (d) CDRL1 comprises the amino acid sequence of RASQSVSRYLG (SEQ ID NO: 15);
   (e) CDRL2 comprises the amino acid sequence of GASTRAT (SEQ ID NO: 16); and
   (f) CDRL3 comprises the amino acid sequence of QQYGSSPWT (SEQ ID NO: 17),
and wherein the CDRH1, CDRH2, and CDRH3 sequences of the antibody are not SEQ ID NOs: 10, 11, and 13, respectively.

8. The method of claim 7, wherein the CDRH1, CDRH2, CDRH3, CDRL1, CDRL2, and CDRL3 sequences of the antibody are SEQ ID NOs: 10, 12, 14, 15, 16, and 17, respectively.

9. The method of claim 7, wherein
   (a) the VH comprises an amino acid sequence selected from the group consisting of SEQ ID NOs: 2, 4, 5, 6, 7 and 8; and/or
   (b) the VL comprises the amino acid sequence of SEQ ID NO: 9.

10. The method of claim 7, wherein the VH and the VL comprise the amino acid sequences set forth in SEQ ID NOs: 2 and 9; 4 and 9; 5 and 9; 6 and 9; 7 and 9; or 8 and 9, respectively.

11. The method of claim 7, wherein
(a) the antibody comprises a heavy chain comprising an amino acid sequence selected from the group consisting of SEQ ID NOs: 23, 24, 25, and 26; and/or
(b) the antibody comprises a light chain comprising the amino acid sequence of SEQ ID NO: 27.

12. The method of claim 7, wherein the antibody comprises a heavy chain and a light chain comprising the amino acid sequences set forth in SEQ ID NOs: 23 and 27; 24 and 27; 25 and 27; or 26 and 27, respectively.

13. The method of claim 7, wherein the cancer is
(a) a metastatic or locally advanced tumor;
(b) a solid tumor; and/or
(c) refractory to a standard therapy.

14. The method of claim 7, wherein the cancer is selected from the group consisting of B cell lymphoma, basal cell carcinoma, bladder cancer, blastoma, brain metastasis, breast cancer, Burkitt lymphoma, cervical cancer, colon cancer, colorectal cancer, cutaneous squamous cell carcinoma, endometrial carcinoma, esophageal cancer, Ewing sarcoma, follicular lymphoma, gastric cancer, gastroesophageal junction carcinoma, gastrointestinal cancer, glioblastoma, glioma, head and neck cancer, hepatic metastasis, Hodgkin's lymphoma, non-Hodgkin's lymphoma, kidney cancer, laryngeal cancer, leukemia, liver cancer, small cell lung cancer, non-small cell lung cancer, lymphoblastic lymphoma, lymphoma, mantle cell lymphoma, metastatic cancer, myeloma, neuroblastoma, ocular melanoma, oropharyngeal cancer, osteosarcoma, ovarian cancer, pancreatic cancer, prostate cancer, metastatic hormone refractory cancer, renal cell carcinoma, salivary gland carcinoma, sarcoma, skin cancer, soft tissue sarcoma, solid tumor, squamous cell carcinoma, synovia sarcoma, testicular cancer, thyroid cancer, transitional cell cancer, uveal melanoma, verrucous carcinoma, vulval cancer, and Waldenstrom macroglobulinemia.

15. The method of claim 7, wherein the antibody is administered as the first cancer therapy after:
(a) diagnosis of tumor progression that has occurred despite previous treatment of the cancer with a different cancer therapy; or
(b) diagnosis of toxicity of a different cancer therapy.

16. The method of claim 7, wherein the antibody is administered at a dose of 0.01 mg/kg, 0.03 mg/kg, 0.1 mg/kg, 0.3 mg/kg, 1 mg/kg, 3 mg/kg, 6 mg/kg, or 10 mg/kg.

17. The method of claim 7, wherein the antibody is administered at an interval of once every two weeks, once every three weeks, once every four weeks, once every six weeks, or once every twelve weeks.

18. The method of claim 7, further comprising administering an additional therapeutic agent to the subject.

19. The method of claim 18, wherein the additional therapeutic agent is selected from the group consisting of a chemotherapeutic, a checkpoint targeting agent, an inhibitor of indoleamine-2,3-dioxygenase (IDO), and a vaccine.

20. The method of claim 19, wherein the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist anti-CEACAM 1 antibody, an agonist anti-GITR antibody, an agonist anti-OX40 antibody, and an agonist anti-CD 137 antibody.

* * * * *

SEQUENCE LISTING

```
<160> NUMBER OF SEQ ID NOS: 52

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115

<210> SEQ ID NO 2
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Met Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Leu Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Met Val Thr Val Ser Ser
        115
```

<210> SEQ ID NO 5
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Leu Val Thr Val Ser Ser
        115

<210> SEQ ID NO 6
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Met Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Met Gly Pro Phe Asp Ile Trp Gly Gln Gly Thr
            100                 105                 110

Leu Val Thr Val Ser Ser
        115

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Leu Val Thr Val Ser Ser
        115

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

```
Leu Gly Trp Tyr Gln Gln Lys Pro Gly Gln Ala Pro Arg Leu Leu Ile
            35                  40                  45

Tyr Gly Ala Ser Thr Arg Ala Thr Gly Ile Pro Asp Arg Phe Ser Gly
    50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys
                100                 105

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Ser Met Asn
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Ile Ser Ser Ser Ser Ser Tyr Ile Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Ile Ser Ser Ser Ser Ser Tyr Ile Tyr Tyr Ala Glu Ser Val Lys
1               5                   10                  15

Gly

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Gly Leu Met Gly Pro Phe Asp Ile
1               5

<210> SEQ ID NO 14
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 14

Val Gly Leu Phe Gly Pro Phe Asp Ile
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ala Ser Gln Ser Val Ser Arg Tyr Leu Gly
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Ala Ser Thr Arg Ala Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Gln Tyr Gly Ser Ser Pro Trp Thr
1               5

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Glu or Asp

<400> SEQUENCE: 18

Ser Ile Ser Ser Ser Ser Ser Tyr Ile Tyr Tyr Ala Xaa Ser Val Lys
1               5                   10                  15

Gly

<210> SEQ ID NO 19
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Met

<400> SEQUENCE: 19

Val Gly Leu Xaa Gly Pro Phe Asp Ile
1               5

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(62)
<223> OTHER INFORMATION: Glu or Asp
<220> FEATURE:
<221> NAME/KEY: MOD_RES
<222> LOCATION: (102)..(102)
<223> OTHER INFORMATION: Phe or Met
<220> FEATURE:
<221> NAME/KEY: MOD_RES
<222> LOCATION: (113)..(113)
<223> OTHER INFORMATION: Leu or Met

<400> SEQUENCE: 20

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Xaa Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Xaa Gly Pro Phe Asp Ile Trp Gly Gln Gly Thr
            100                 105                 110

Xaa Val Thr Val Ser Ser
        115

<210> SEQ ID NO 21
<211> LENGTH: 98
<212> TYPE: PRT
<213> ORGANISM: Homo sapiens

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg

<210> SEQ ID NO 22
<211> LENGTH: 96
<212> TYPE: PRT
<213> ORGANISM: Homo sapiens

<400> SEQUENCE: 22

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 23
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Ser Tyr
                 20                  25                  30

Ser Met Asn Trp Val Arg Gln Ala Pro Gly Lys Gly Leu Glu Trp Val
             35                  40                  45

Ser Ser Ile Ser Ser Ser Ser Tyr Ile Tyr Tyr Ala Glu Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Val Gly Leu Phe Gly Pro Phe Asp Ile Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 24
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 25
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Leu Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 26
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
            85                  90                  95

Ala Arg Val Gly Leu Phe Gly Pro Phe Asp Ile Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145             150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Val Gly Gly Pro Ser
225             230                 235                 240

Val Phe Leu Leu Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Leu Arg Val Val
        290                 295                 300

Ser Val Leu Thr Val Leu His Gln Asp Trp Leu Asn Gly Lys Glu Tyr
305             310                 315                 320
```

```
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Leu Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 27
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Arg Tyr
                20                  25                  30

Leu Gly Trp Tyr Gln Gln Lys Pro Gly Gln Ala Pro Arg Leu Leu Ile
            35                  40                  45

Tyr Gly Ala Ser Thr Arg Ala Thr Gly Ile Pro Asp Arg Phe Ser Gly
50                  55                  60

Ser Gly Ser Gly Thr Asp Phe Thr Leu Thr Ile Thr Arg Leu Glu Pro
65                  70                  75                  80

Glu Asp Phe Ala Val Tyr Tyr Cys Gln Gln Tyr Gly Ser Ser Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
                195                 200                 205

Phe Asn Arg Gly Glu Cys
            210
```

<210> SEQ ID NO 28
<211> LENGTH: 329
<212> TYPE: PRT
<213> ORGANISM: Homo sapiens

<400> SEQUENCE: 28

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 29
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 30
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Leu Pro Glu Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 31
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Val Gly Gly Pro Ser Val Phe Leu Leu Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Leu Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Leu Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 33
<211> LENGTH: 223
<212> TYPE: PRT
<213> ORGANISM: Homo sapiens

<400> SEQUENCE: 33

```
Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
                20                  25                  30

Val Phe Cys Lys Ala Met His Val Ala Gln Pro Ala Val Val Leu Ala
                35                  40                  45

Ser Ser Arg Gly Ile Ala Ser Phe Val Cys Glu Tyr Ala Ser Pro Gly
 50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Leu Gly Ile Gly
130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
            210                 215                 220
```

<210> SEQ ID NO 34
<211> LENGTH: 4
<212> TYPE: PRT
<213> ORGANISM: Homo sapiens

<400> SEQUENCE: 34

```
Tyr Leu Gly Ile
 1
```

<210> SEQ ID NO 35
<211> LENGTH: 9
<212> TYPE: PRT
<213> ORGANISM: Homo sapiens

```
<400> SEQUENCE: 35

Tyr Pro Pro Pro Tyr Tyr Leu Gly Ile
1               5

<210> SEQ ID NO 36
<211> LENGTH: 10
<212> TYPE: PRT
<213> ORGANISM: Homo sapiens

<400> SEQUENCE: 36

Tyr Leu Gly Ile Gly Asn Gly Thr Gln Ile
1               5                   10

<210> SEQ ID NO 37
<211> LENGTH: 15
<212> TYPE: PRT
<213> ORGANISM: Homo sapiens

<400> SEQUENCE: 37

Tyr Pro Pro Pro Tyr Tyr Leu Gly Ile Gly Asn Gly Thr Gln Ile
1               5                   10                  15

<210> SEQ ID NO 38
<211> LENGTH: 7
<212> TYPE: PRT
<213> ORGANISM: Homo sapiens

<400> SEQUENCE: 38

Met Tyr Pro Pro Pro Tyr Tyr
1               5

<210> SEQ ID NO 39
<211> LENGTH: 3
<212> TYPE: PRT
<213> ORGANISM: Homo sapiens

<400> SEQUENCE: 39

Gln Val Thr
1

<210> SEQ ID NO 40
<211> LENGTH: 223
<212> TYPE: PRT
<213> ORGANISM: Macaca fascicularis

<400> SEQUENCE: 40

Met Ala Cys Leu Gly Phe Gln Arg His Lys Ala Arg Leu Asn Leu Ala
1               5                   10                  15

Thr Arg Thr Arg Pro Tyr Thr Leu Leu Phe Ser Leu Leu Phe Ile Pro
                20                  25                  30

Val Phe Ser Lys Ala Met His Val Ala Gln Pro Ala Val Val Leu Ala
            35                  40                  45

Asn Ser Arg Gly Ile Ala Ser Phe Val Cys Glu Tyr Ala Ser Pro Gly
        50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
                100                 105                 110
```

Asn Leu Thr Ile Gln Gly Leu Arg Ala Met Asp Thr Gly Leu Tyr Ile
            115                 120                 125

Cys Lys Val Glu Leu Met Tyr Pro Pro Tyr Tyr Met Gly Ile Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
        210                 215                 220

<210> SEQ ID NO 41
<211> LENGTH: 223
<212> TYPE: PRT
<213> ORGANISM: Mus musculus

<400> SEQUENCE: 41

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
                20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
        50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Tyr Phe Val Gly Met Gly
        130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Ser Ala Val Ser Leu Ser Lys Met Leu Lys Lys
                180                 185                 190

Arg Ser Pro Leu Thr Thr Gly Val Tyr Val Lys Met Pro Pro Thr Glu
                195                 200                 205

Pro Glu Cys Glu Lys Gln Phe Gln Pro Tyr Phe Ile Pro Ile Asn
        210                 215                 220

<210> SEQ ID NO 42
<211> LENGTH: 223
<212> TYPE: PRT
<213> ORGANISM: Rattus norvegicus -continued

```
<400> SEQUENCE: 42

Met Ala Cys Leu Gly Leu Gln Arg Tyr Lys Thr His Leu Gln Leu Pro
1               5                   10                  15

Ser Arg Thr Trp Pro Phe Gly Val Leu Leu Ser Leu Leu Phe Ile Pro
            20                  25                  30

Ile Phe Ser Glu Ala Ile Gln Val Thr Gln Pro Ser Val Val Leu Ala
        35                  40                  45

Ser Ser His Gly Val Ala Ser Phe Pro Cys Glu Tyr Ala Ser Ser His
    50                  55                  60

Asn Thr Asp Glu Val Arg Val Thr Val Leu Arg Gln Thr Asn Asp Gln
65                  70                  75                  80

Val Thr Glu Val Cys Ala Thr Thr Phe Thr Val Lys Asn Thr Leu Gly
                85                  90                  95

Phe Leu Asp Asp Pro Phe Cys Ser Gly Thr Phe Asn Glu Ser Arg Val
            100                 105                 110

Asn Leu Thr Ile Gln Gly Leu Arg Ala Ala Asp Thr Gly Leu Tyr Phe
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Val Thr Ala Val Ser Leu Asn Arg Thr Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 43
<211> LENGTH: 220
<212> TYPE: PRT
<213> ORGANISM: Homo sapiens

<400> SEQUENCE: 43

Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Val Asn Leu Ser Cys Lys Tyr Ser Tyr Asn Leu Phe Ser
        35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140
```

```
Leu Phe Pro Gly Pro Ser Lys Pro Phe Trp Val Leu Val Val Gly
145                 150                 155                 160

Gly Val Leu Ala Cys Tyr Ser Leu Leu Val Thr Val Ala Phe Ile Ile
            165                 170                 175

Phe Trp Val Arg Ser Lys Arg Ser Arg Leu Leu His Ser Asp Tyr Met
        180                 185                 190

Asn Met Thr Pro Arg Arg Pro Gly Pro Thr Arg Lys His Tyr Gln Pro
            195                 200                 205

Tyr Ala Pro Pro Arg Asp Phe Ala Ala Tyr Arg Ser
        210                 215                 220

<210> SEQ ID NO 44
<211> LENGTH: 199
<212> TYPE: PRT
<213> ORGANISM: Homo sapiens

<400> SEQUENCE: 44

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
        195

<210> SEQ ID NO 45
<211> LENGTH: 289
<212> TYPE: PRT
<213> ORGANISM: Homo sapiens

<400> SEQUENCE: 45

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45
```

```
Leu Ala Gly Asp Pro Phe Glu Leu Glu Cys Pro Val Lys Tyr Cys Ala
     50                  55                  60

Asn Arg Pro His Val Thr Trp Cys Lys Leu Asn Gly Thr Thr Cys Val
 65                  70                  75                  80

Lys Leu Glu Asp Arg Gln Thr Ser Trp Lys Glu Lys Asn Ile Ser
                 85                  90                  95

Phe Phe Ile Leu His Phe Glu Pro Val Leu Pro Asn Asp Asn Gly Ser
             100                 105                 110

Tyr Arg Cys Ser Ala Asn Phe Gln Ser Asn Leu Ile Glu Ser His Ser
         115                 120                 125

Thr Thr Leu Tyr Val Thr Asp Val Lys Ser Ala Ser Glu Arg Pro Ser
     130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                 165                 170                 175

Cys Leu Arg Arg His Gln Gly Lys Gln Asn Glu Leu Ser Asp Thr Ala
             180                 185                 190

Gly Arg Glu Ile Asn Leu Val Asp Ala His Leu Lys Ser Glu Gln Thr
         195                 200                 205

Glu Ala Ser Thr Arg Gln Asn Ser Gln Val Leu Leu Ser Glu Thr Gly
     210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                 245                 250                 255

Tyr Ala Ser Leu Asn His Ser Val Ile Gly Pro Asn Ser Arg Leu Ala
             260                 265                 270

Arg Asn Val Lys Glu Ala Pro Thr Glu Tyr Ala Ser Ile Cys Val Arg
         275                 280                 285

Ser

<210> SEQ ID NO 46
<211> LENGTH: 288
<212> TYPE: PRT
<213> ORGANISM: Homo sapiens

<400> SEQUENCE: 46

Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
                 20                  25                  30

Asn Pro Pro Thr Phe Ser Pro Ala Leu Leu Val Val Thr Glu Gly Asp
             35                  40                  45

Asn Ala Thr Phe Thr Cys Ser Phe Ser Asn Thr Ser Glu Ser Phe Val
         50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
             100                 105                 110

Ala Arg Arg Asn Asp Ser Gly Thr Tyr Leu Cys Gly Ala Ile Ser Leu
         115                 120                 125
```

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 47
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Val Gly Leu Phe Gly Pro Phe Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

```
Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 48
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Glu Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

```
Ala Arg Val Gly Leu Phe Gly Pro Phe Asp Ile Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Phe Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 49
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 49

```
Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Val Thr Val Ser Ser Ala Lys Thr Thr Ala Pro Ser Val Tyr Pro Leu
            115                 120                 125

Ala Pro Val Cys Gly Asp Thr Thr Gly Ser Ser Val Thr Leu Gly Cys
130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
            195                 200                 205

Lys Val Asp Lys Lys Ile Glu Pro Arg Gly Pro Thr Ile Lys Pro Cys
210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
            275                 280                 285

Thr Gln Thr His Arg Glu Asp Tyr Asn Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
            355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400
```

```
Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly
        435                 440                 445

<210> SEQ ID NO 50
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

Lys Val Asp Lys Lys Ile Glu Pro Arg Gly Pro Thr Ile Lys Pro Cys
    210                 215                 220

Pro Pro Cys Lys Cys Pro Ala Pro Asn Leu Leu Gly Gly Pro Asp Val
225                 230                 235                 240

Phe Ile Phe Pro Pro Lys Ile Lys Asp Val Leu Met Ile Ser Leu Ser
                245                 250                 255

Pro Ile Val Thr Cys Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Asn Ser Thr Leu Arg Val Val Ser
    290                 295                 300
```

-continued

Ala Leu Pro Ile Gln His Gln Asp Trp Met Ser Gly Lys Glu Phe Lys
305                 310                 315                 320

Cys Lys Val Asn Asn Lys Asp Leu Pro Leu Pro Glu Glu Arg Thr Ile
            325                 330                 335

Ser Lys Pro Lys Gly Ser Val Arg Ala Pro Gln Val Tyr Val Leu Pro
        340                 345                 350

Pro Pro Glu Glu Glu Met Thr Lys Lys Gln Val Thr Leu Thr Cys Met
    355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
            405                 410                 415

Trp Val Glu Arg Asn Ser Tyr Ser Cys Ser Val Val His Glu Gly Leu
        420                 425                 430

His Asn His His Thr Thr Lys Ser Phe Ser Arg Thr Pro Gly
    435                 440                 445

<210> SEQ ID NO 51
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Val Thr Val Ser Ser Ala Lys Thr Thr Ala Pro Ser Val Tyr Pro Leu
        115                 120                 125

Ala Pro Val Cys Gly Asp Thr Thr Gly Ser Ser Val Thr Leu Gly Cys
    130                 135                 140

Leu Val Lys Gly Tyr Phe Pro Glu Pro Val Thr Leu Thr Trp Asn Ser
145                 150                 155                 160

Gly Ser Leu Ser Ser Gly Val His Thr Phe Pro Ala Val Leu Gln Ser
                165                 170                 175

Asp Leu Tyr Thr Leu Ser Ser Ser Val Thr Val Thr Ser Ser Thr Trp
            180                 185                 190

Pro Ser Gln Ser Ile Thr Cys Asn Val Ala His Pro Ala Ser Ser Thr
        195                 200                 205

```
Lys Val Asp Lys Lys Ile Glu Pro Arg Gly Pro Thr Ile Lys Pro Cys
            210                 215                 220

Pro Pro Cys Lys Cys Pro Ala Pro Asn Leu Leu Gly Gly Pro Ser Val
225                 230                 235                 240

Phe Ile Phe Pro Pro Lys Ile Lys Asp Val Leu Met Ile Ser Leu Ser
                245                 250                 255

Pro Ile Val Thr Cys Val Val Val Asp Val Ser Glu Asp Asp Pro Asp
            260                 265                 270

Val Gln Ile Ser Trp Phe Val Asn Asn Val Glu Val His Thr Ala Gln
        275                 280                 285

Thr Gln Thr His Arg Glu Asp Tyr Ala Ser Thr Leu Arg Val Val Ser
290                 295                 300

Ala Leu Pro Ile Gln His Gln Asp Trp Met Ser Gly Lys Glu Phe Lys
305                 310                 315                 320

Cys Lys Val Asn Asn Lys Asp Leu Pro Ala Pro Ile Glu Arg Thr Ile
                325                 330                 335

Ser Lys Pro Lys Gly Ser Val Arg Ala Pro Gln Val Tyr Val Leu Pro
            340                 345                 350

Pro Pro Glu Glu Glu Met Thr Lys Lys Gln Val Thr Leu Thr Cys Met
        355                 360                 365

Val Thr Asp Phe Met Pro Glu Asp Ile Tyr Val Glu Trp Thr Asn Asn
370                 375                 380

Gly Lys Thr Glu Leu Asn Tyr Lys Asn Thr Glu Pro Val Leu Asp Ser
385                 390                 395                 400

Asp Gly Ser Tyr Phe Met Tyr Ser Lys Leu Arg Val Glu Lys Lys Asn
                405                 410                 415

Trp Val Glu Arg Asn Ser Tyr Ser Cys Ser Val Val His Glu Gly Leu
            420                 425                 430

His Asn His His Thr Thr Lys Ser Phe Ser Arg Thr Pro Gly
        435                 440                 445

<210> SEQ ID NO 52
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

```
Arg Ala Asp Ala Ala Pro Thr Val Ser Ile Phe Pro Pro Ser Ser Glu
        115             120             125

Gln Leu Thr Ser Gly Gly Ala Ser Val Val Cys Phe Leu Asn Asn Phe
        130             135             140

Tyr Pro Lys Asp Ile Asn Val Lys Trp Lys Ile Asp Gly Ser Glu Arg
145             150             155             160

Gln Asn Gly Val Leu Asn Ser Trp Thr Asp Gln Asp Ser Lys Asp Ser
            165             170             175

Thr Tyr Ser Met Ser Ser Thr Leu Thr Leu Thr Lys Asp Glu Tyr Glu
            180             185             190

Arg His Asn Ser Tyr Thr Cys Glu Ala Thr His Lys Thr Ser Thr Ser
        195             200             205

Pro Ile Val Lys Ser Phe Asn Arg Asn Glu Cys
210             215
```